(12) United States Patent
Drasler et al.

(10) Patent No.: US 10,959,843 B2
(45) Date of Patent: Mar. 30, 2021

(54) STRADDLE ANNULAR MITRAL VALVE

(71) Applicants: William Joseph Drasler, Minnetonka, MN (US); William Joseph Drasler, II, Minnetonka, MN (US)

(72) Inventors: William Joseph Drasler, Minnetonka, MN (US); William Joseph Drasler, II, Minnetonka, MN (US)

(*) Notice: Subject to any disclaimer, the term of this patent is extended or adjusted under 35 U.S.C. 154(b) by 191 days.

(21) Appl. No.: 16/147,823

(22) Filed: Sep. 30, 2018

(65) Prior Publication Data

US 2019/0142582 A1 May 16, 2019

Related U.S. Application Data

(60) Provisional application No. 62/622,874, filed on Jan. 27, 2018, provisional application No. 62/614,451, filed on Jan. 7, 2018, provisional application No. 62/597,013, filed on Dec. 11, 2017, provisional application No. 62/587,153, filed on Nov. 16, 2017, provisional application No. 62/584,583, filed on Nov. 12, 2017.

(51) Int. Cl.
*A61F 2/24* (2006.01)

(52) U.S. Cl.
CPC .............. *A61F 2/2418* (2013.01); *A61F 2/24* (2013.01); *A61F 2/2412* (2013.01); *A61F 2/2433* (2013.01); *A61F 2/2436* (2013.01); *A61F 2220/0008* (2013.01); *A61F 2220/0016* (2013.01); *A61F 2220/0025* (2013.01); *A61F 2230/0008* (2013.01); *A61F 2230/0065* (2013.01); *A61F 2230/0069* (2013.01); *A61F 2230/0078* (2013.01); *A61F 2250/0003* (2013.01)

(58) Field of Classification Search
CPC .. A61F 2/2418; A61F 2/24; A61F 2/07; A61F 2/2412
See application file for complete search history.

(56) References Cited

U.S. PATENT DOCUMENTS

| | | | | |
|---|---|---|---|---|
| 2011/0172765 A1* | 7/2011 | Nguyen | ................ | A61F 2/2418 623/2.18 |
| 2015/0173898 A1* | 6/2015 | Drasler | ................. | A61F 2/2433 623/2.18 |
| 2016/0270910 A1* | 9/2016 | Birmingham | ......... | A61F 2/2418 |
| 2017/0231756 A1* | 8/2017 | Armer | ................... | A61F 2/2436 623/2.18 |

\* cited by examiner

*Primary Examiner* — Dinah Baria

(57) ABSTRACT

A two component system for replacing mitral valves using a transcatheter approach. The first component uses a torus balloon to activate barbs into the mitral annulus after the first component stent frame has been delivered. A closed ring in the first component provides a landing site for delivery of a second component that contains replacement leaflets. The second component straddles the mitral annulus such that impingement upon the left ventricular outflow track does not occur. The second component frame contains open regions that help to prevent blood stagnation.

19 Claims, 72 Drawing Sheets

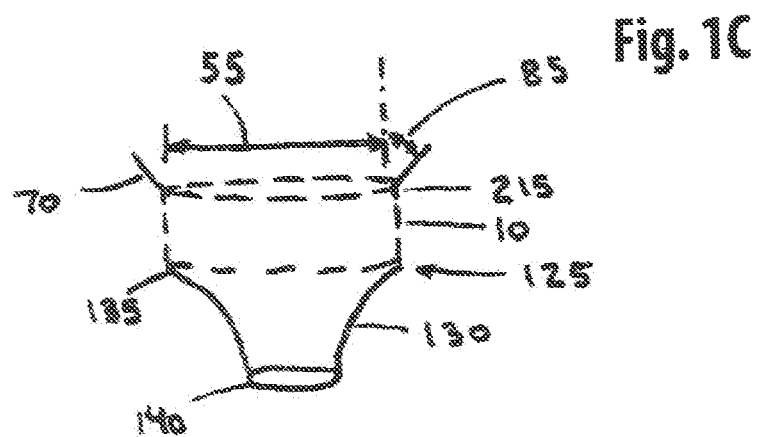
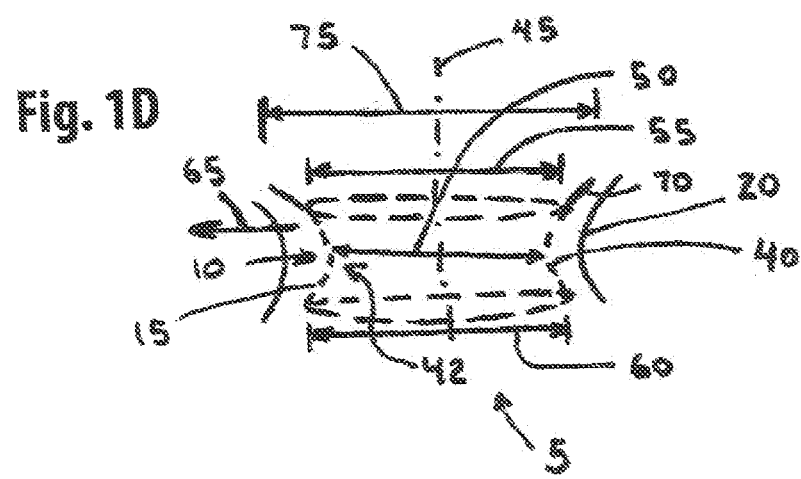
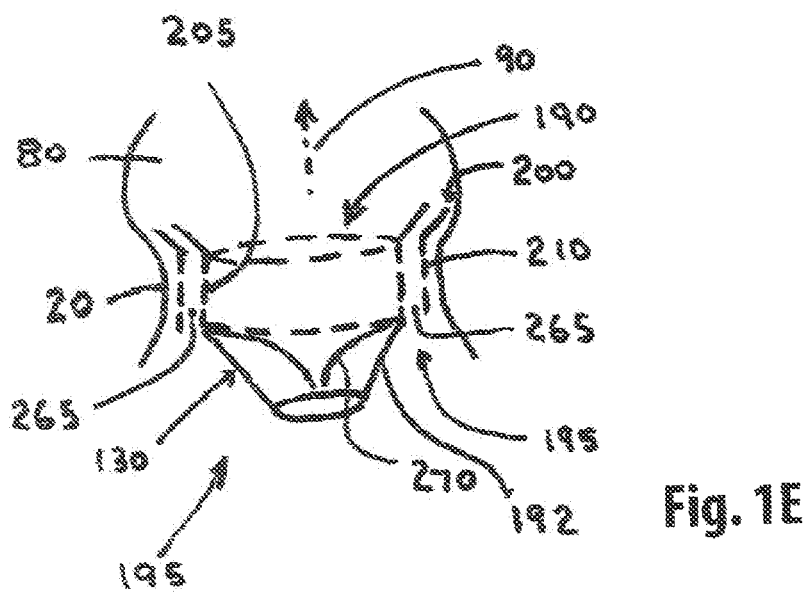

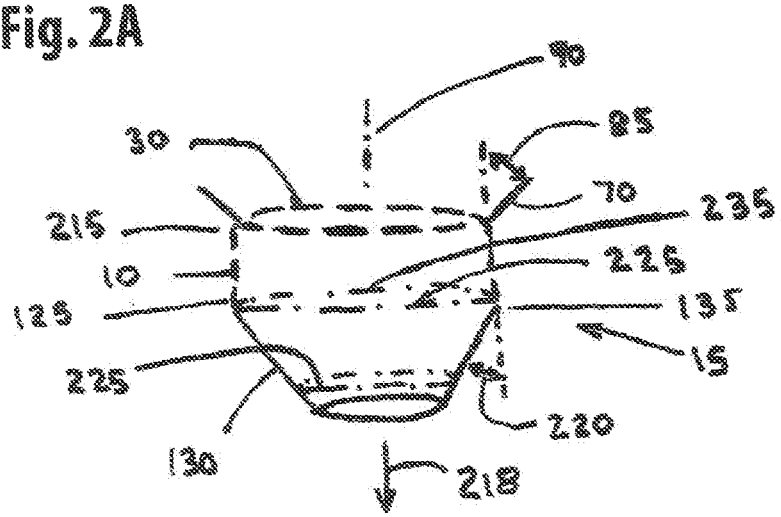
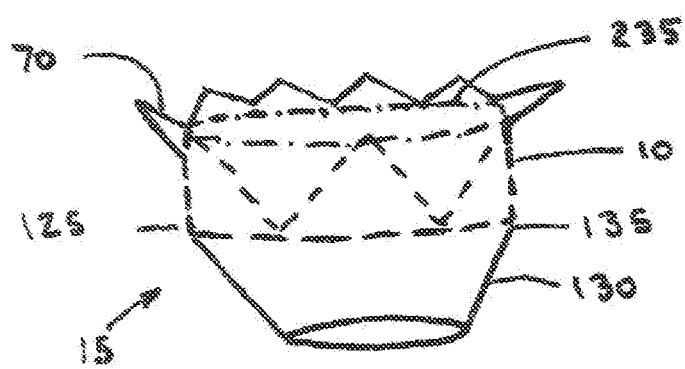

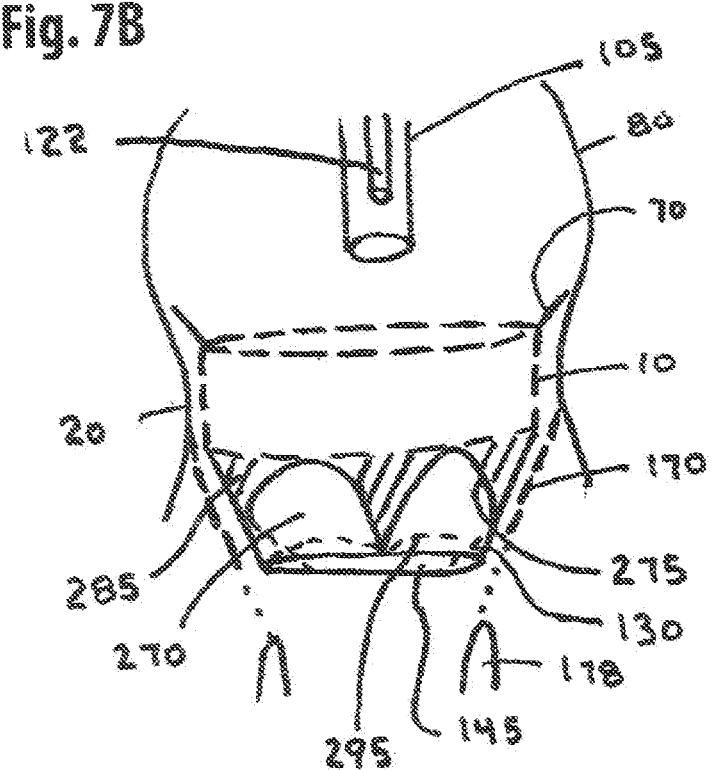
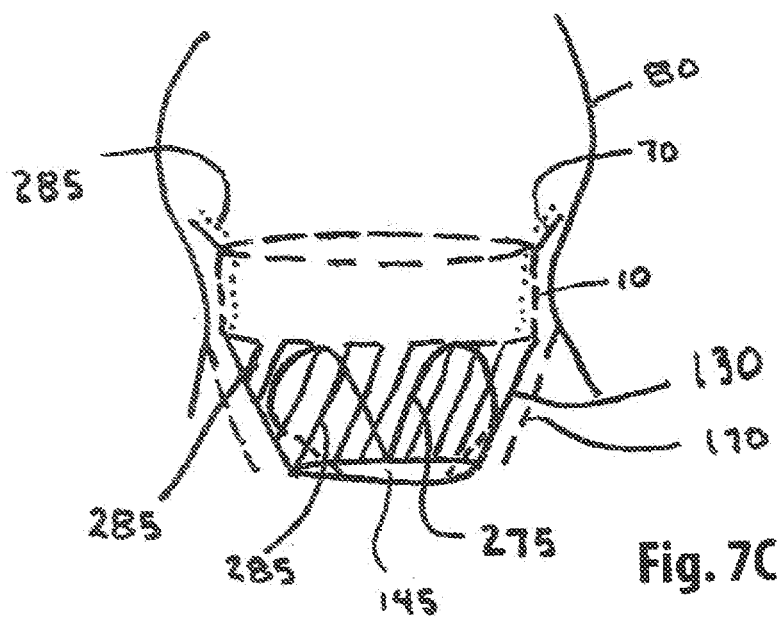

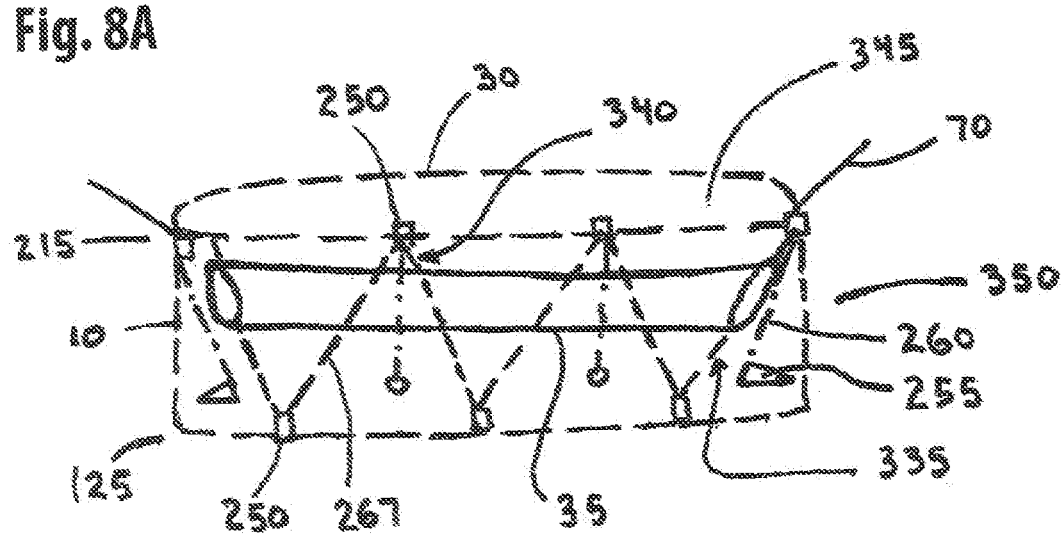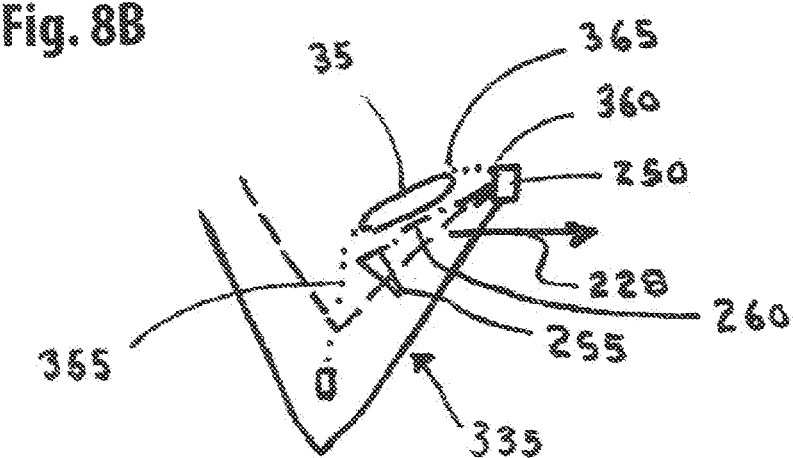

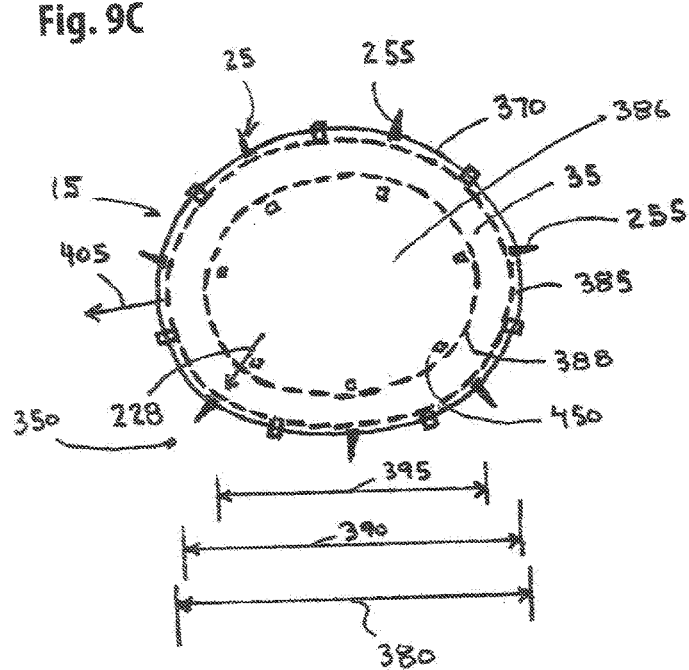
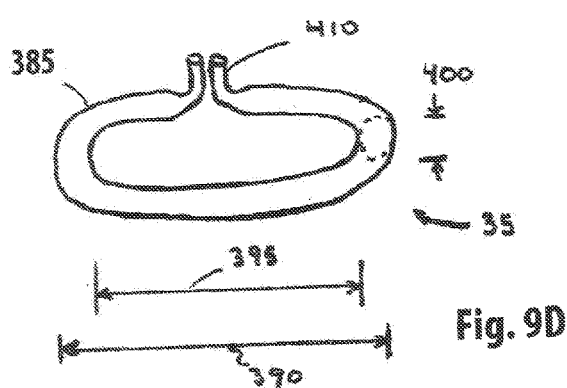

Fig. 10A
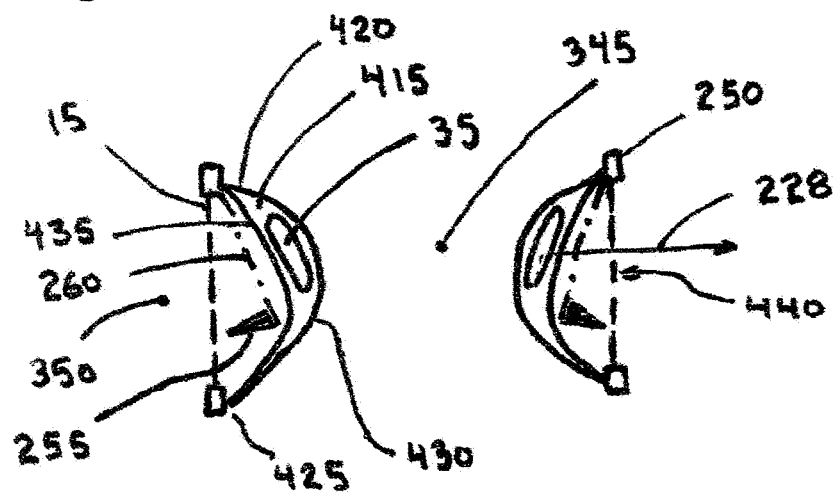
Fig. 10B
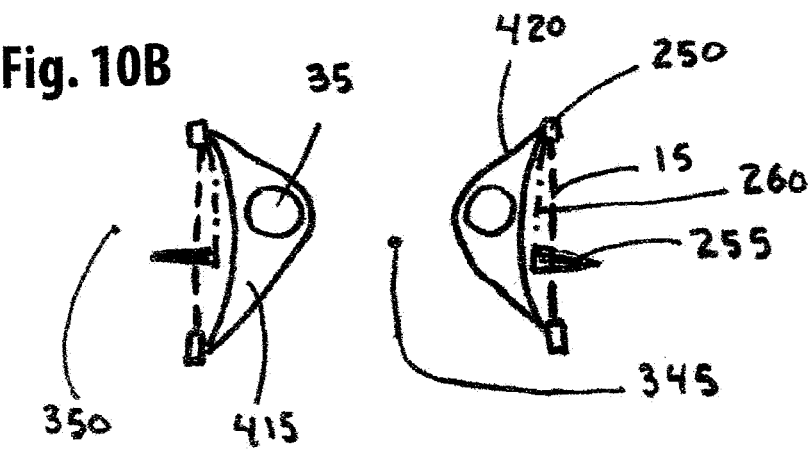
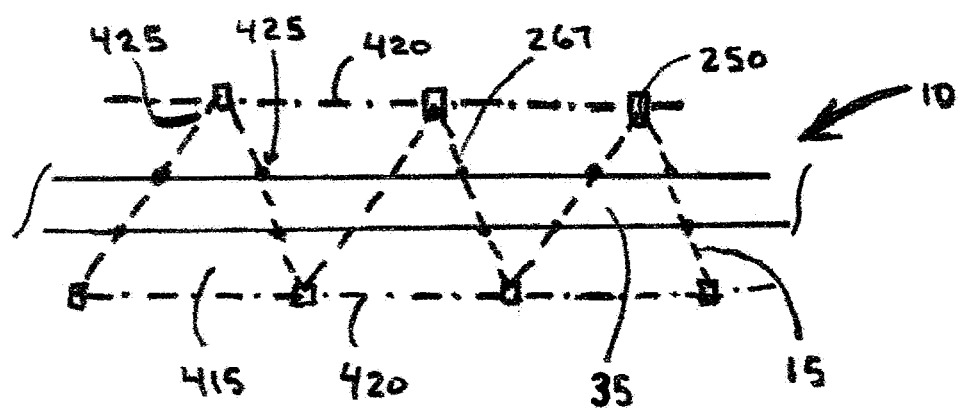
Fig. 10C

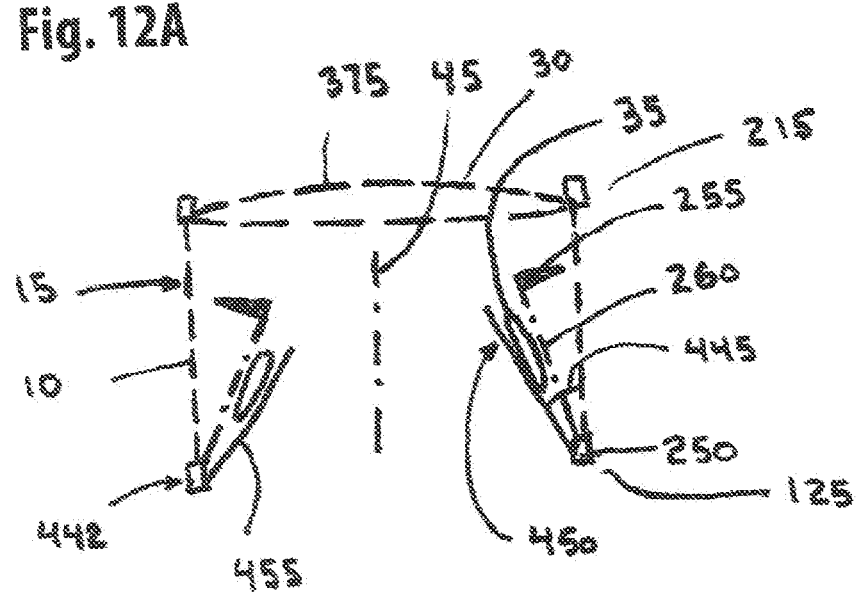
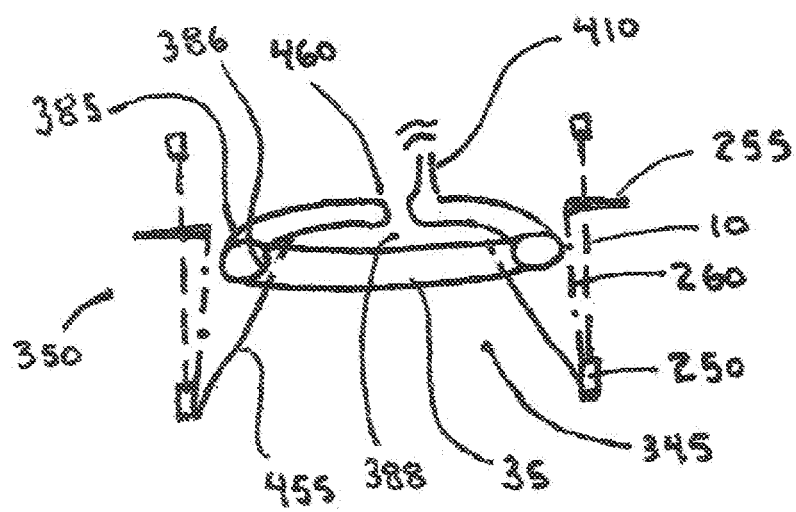

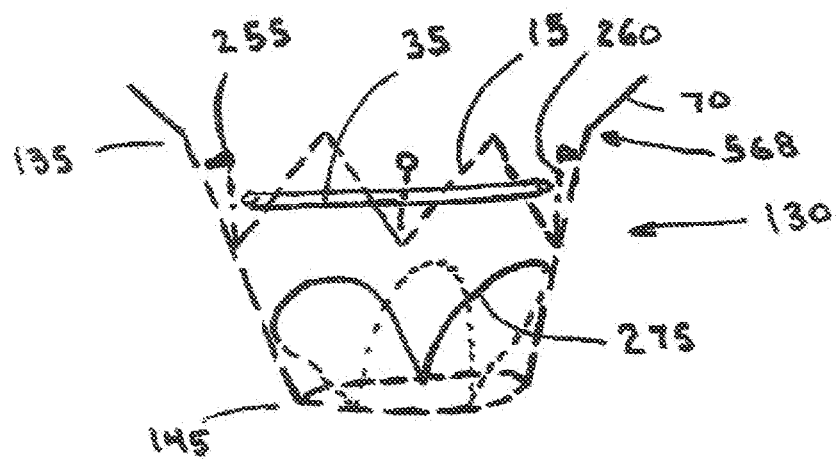
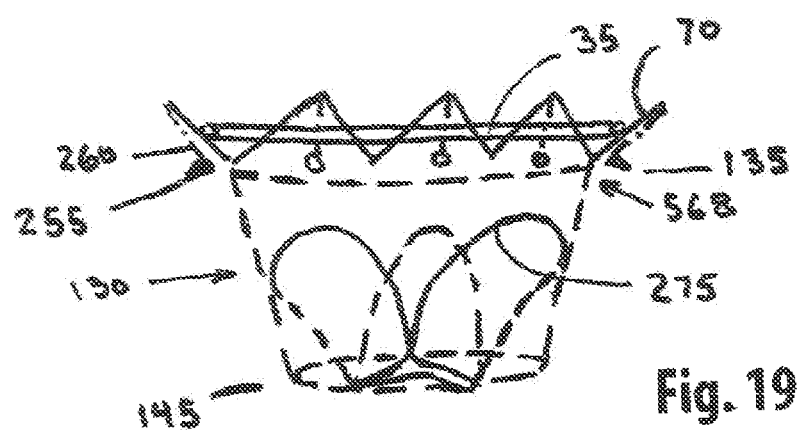

Fig. 36A
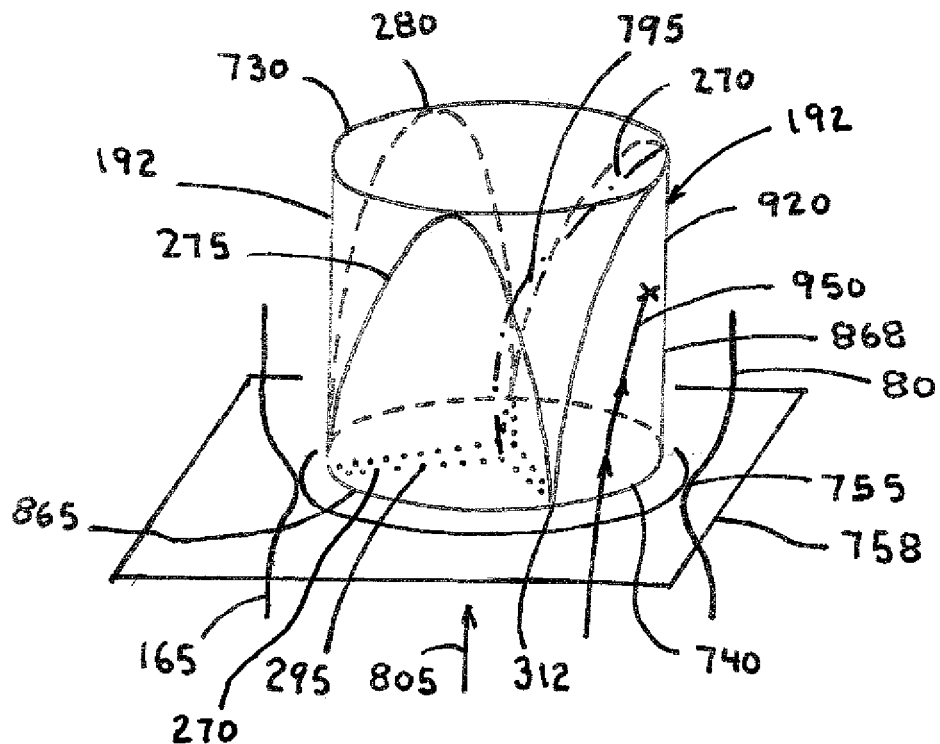
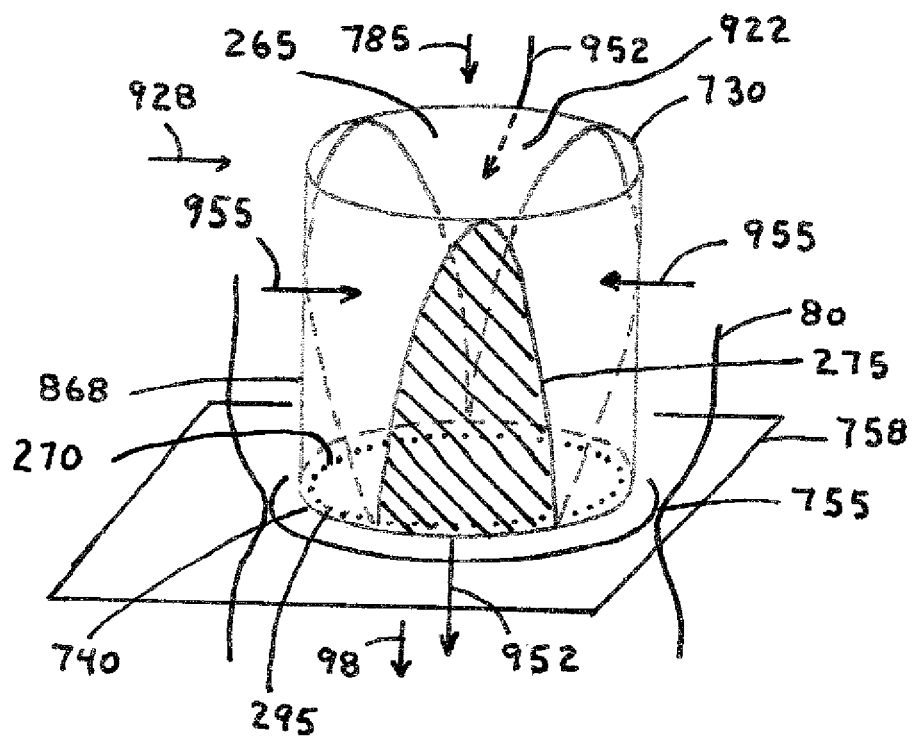
Fig. 36B

Fig. 37A
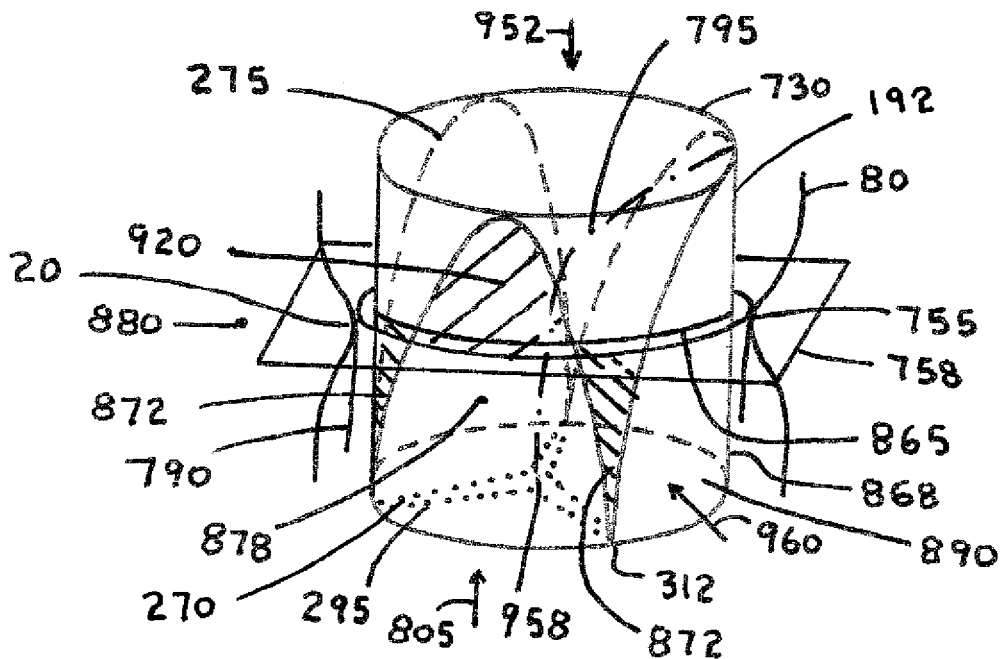
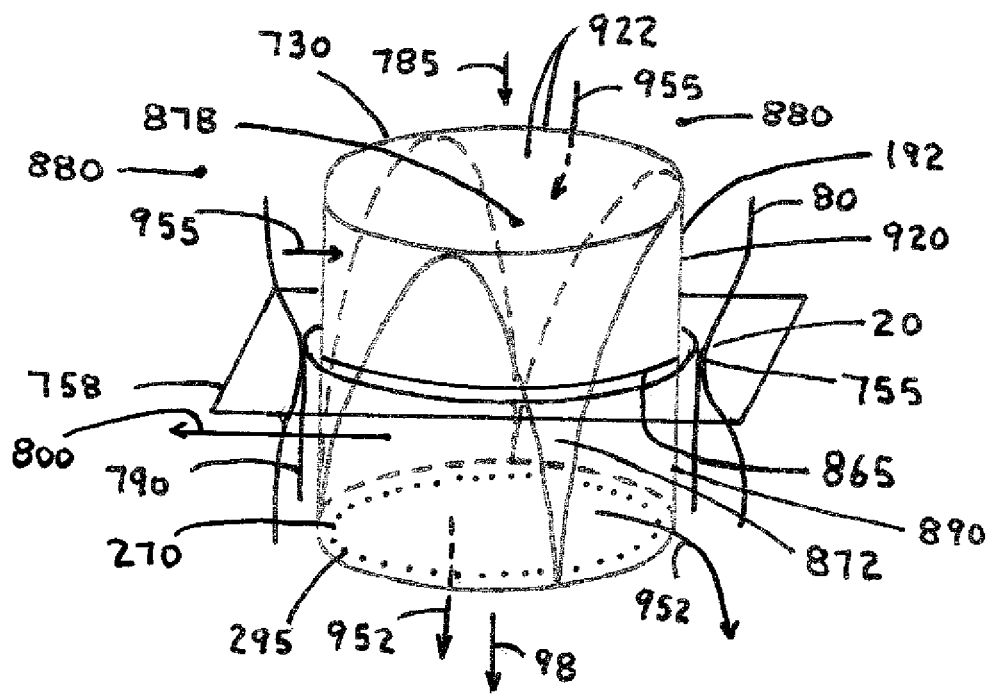
Fig. 37B

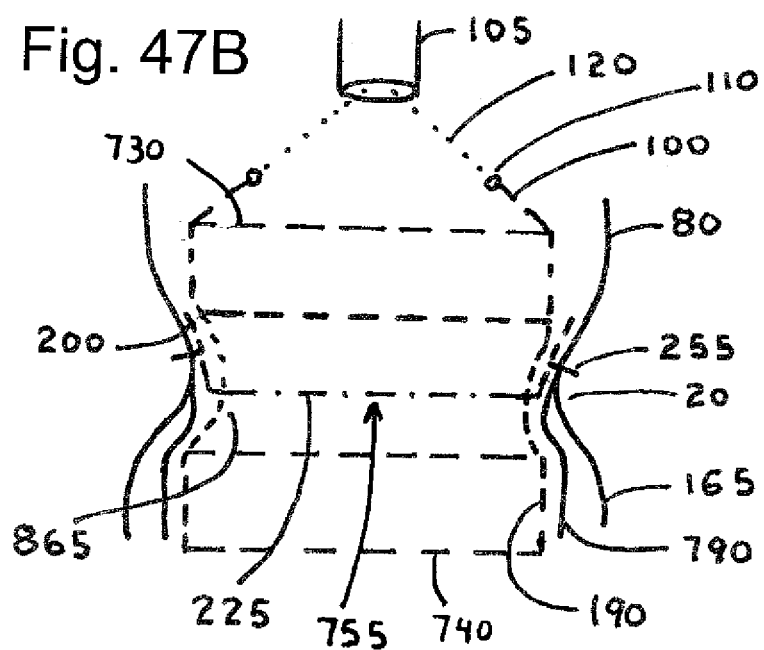
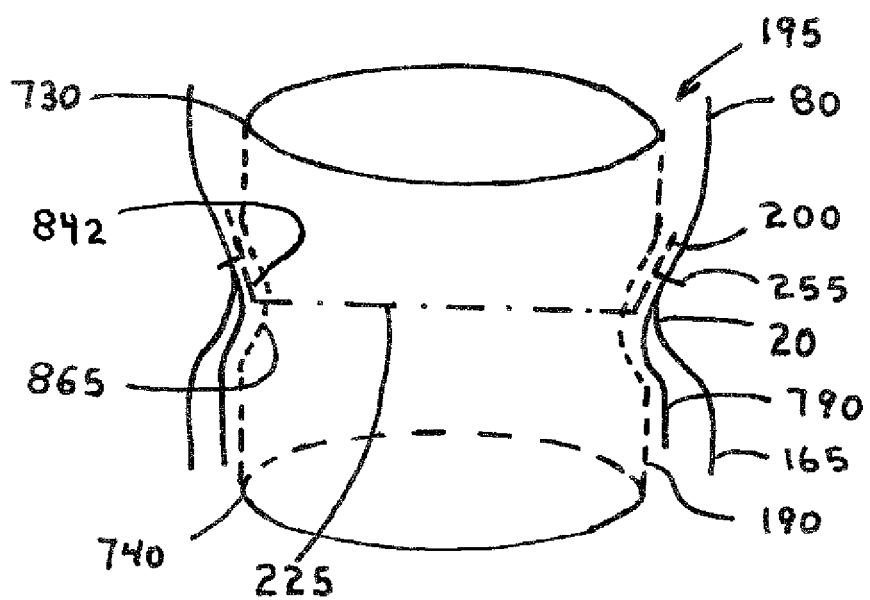

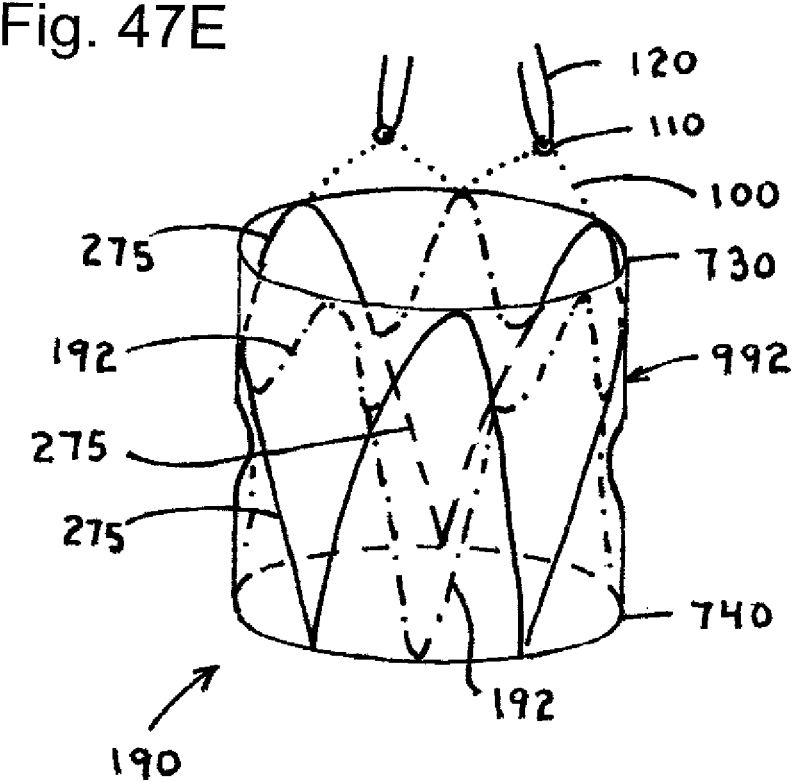

Fig. 49A
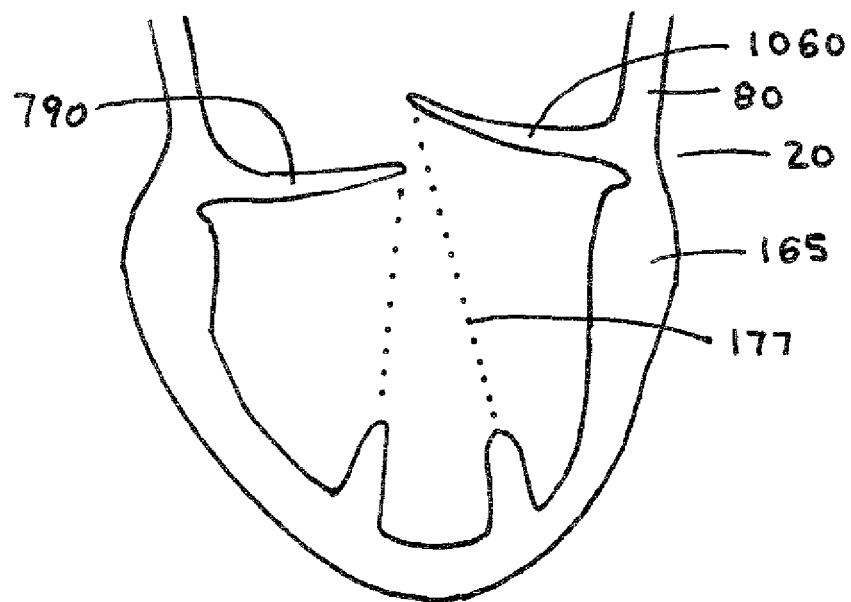
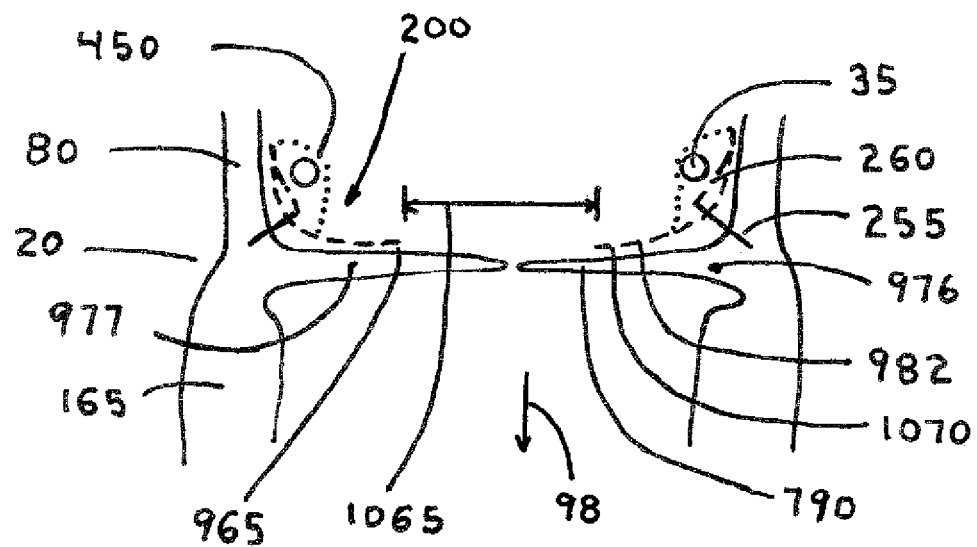
Fig. 49B

STRADDLE ANNULAR MITRAL VALVE

CROSS REFERENCE TO RELATED APPLICATIONS

This patent application makes reference to and thereby incorporates all information found in provisional patent application No. 62/584,853 filed 12 Nov. 2017 entitled Supra-Annular Mitral Valve by William J. Drasler, et. al., provisional patent application No. 62/587,153 filed 16 Nov. 2017 entitled Straddle-Annular Mitral Valve by William J. Drasler et. al., provisional patent application No. 62/597,013 filed 11 Dec. 2017 entitled Straddle Positionable Mitral Valve by William J. Drasler et. al., provisional patent application No. 62/614,451 filed 7 Jan. 2018 entitled Retractable Barb Straddle Mitral Valve by William J. Drasler, provisional patent application No. 62/622,874 filed 27 Jan. 2018 entitled Securement Mitral Valve by William J. Drasler and nonprovisional patent application Ser. No. 15/457,626 entitled Two Component Mitral Valve filed 13 Mar. 2017 by William J. Drasler, et. al.

BACKGROUND OF THE INVENTION

Valves of the heart including the aortic valve, mitral valve, and tricuspid valve can become hardened from atherosclerotic plaque and calcium and no longer function normally. Alternately these valve can prolapse and allow blood to pass through the valve in a retrograde manner that is opposite to the normal direction of flow through the valve. Such regurgitant flow can require repair or replacement of the valve. Surgical repair or replacement of such valve is often the gold standard at present for those patients able to withstand the rigors of surgery. An alternate and less invasive approach would be desirable via access to the valve from the femoral vasculature, vasculature of the arms, the apex of the heart, aortic access, or via other less invasive sites.

Transcatheter aortic valve replacement (TAVR) has evolved to become an accepted less invasive procedure for replacing diseased or incompetent aortic valves in high risk patients. Such less invasive surgical procedures are not as well developed for replacing abnormally functioning mitral valves.

Often the regurgitant mitral valve is a result of excessive expansion of the left ventricle (LV) leading to abnormal tension and angulation imposed on the mitral valve leaflet. The mitral valve leaflet is often unable to coapt properly with its neighboring leaflet and will therein allow retrograde blood flow to occur through the valve. The mitral valve annulus is more elastic, in part, than the aortic annulus and can expand in diameter reducing the ability of the mitral valve leaflets to coapt properly; one should not expand a stent into the mitral annulus to push it further outwards as is done with TAVR procedures onto the aortic valve annulus.

The mitral anatomy also provides that the anterior mitral leaflet not only helps close the mitral annulus during systole, but also provides one surface of the left ventricular outflow track (LVOT) during systolic pumping of blood out of the LV. It is therefore not acceptable to expand a stent indiscriminately outwards as is done in TAVR due to the potential for blockage of the LVOT by the anterior mitral valve leaflet.

The use of barbs or other fixation members to hold the TMVR device securely to the native mitral apparatus can create a set of potential clinical issues that are problematic to the patient. Expansion of barbs prior to full apposition of the TMVR stent against the mitral annulus, for example, can obviate the ability of the barbs to position themselves and the stent-valve frame uniformly around the perimeter of the mitral annulus. Furthermore, activation of barbs via a standard dilation balloon can block blood flow through the mitral annulus during balloon inflation causing the patient to temporarily go without oxygen supply to the brain with its ensuing consequences. Additionally, inflation of a standard balloon can cause the positioning of the stent-valve to become instantaneously displaced and hence inappropriately located across the mitral annulus due to blood pressure and blood flow generated by the LV.

The delivery profile of TMVR devices is generally greater than those for TAVR due to the larger diameter of the mitral annulus in comparison to the aortic annulus. This profile limitation has forced many of the TMVR devices to be delivered via the apex of the heart rather than through a more favorable transvascular and transseptal delivery approach. The apical approach is not well suited to patients that are older in age or are of higher risk. What is needed is a TMVR device that is of a lower profile such that it can be delivered via a transvascular and transseptal approach. The device should be easily positioned across the mitral annulus and secured to the native mitral apparatus without chance for device migration. The TMVR device should eliminate regions for blood stagnation that can lead to thromboemboli that could potentially result in stroke and should not restrict blood flow out of the LVOT.

Due to the potential for the replacement leaflets or frame of a TMVR device impeding blood flow through the LVOT, or impingement of the TMVR frame onto the native leaflets causing them to impede blood flow through the LVOT an advantage exists for locating the TMVR device in part in the LD and in part in the LV, or totally within the left atrium (LA). When locating a portion the TMVR above (i.e., toward the LA) the mitral annulus care must be taken to ensure that blood flow from the LA cannot form regions of stagnation that can lead to the formation of thromboemboli which can embolize to the brain and can lead to stroke. Locating other replacement valves of the heart at locations that are more upstream of the valve annulus can also provide benefits that are provided by the present invention. An advantage exists for positioning at least a portion of the stent-valve frame upstream of the native heart valve annulus; such positioning can reduce the stent-valve frame portion of the that is downstream of the annulus from impingement upon the LVOT or pushing the native valve leaflets into the LVOT. Locating the TMVR device substantially within the LA without having an extension of several millimeters of the stent-valve frame into the LV can also present negative sequellae. Without the stent-valve frame extending into the LV, the native leaflets can overhang into the replacement stent-valve and can interfere with stent-valve function. Stent-valves that are placed across the mitral annulus should reduce regions of blood stagnation that can occur upstream of the native annulus and downstream of the native annulus. What is needed is a stent-valve that does not cause impingement onto the LVOT and does not allow the native leaflets to interfere with the function of the replacement leaflets. Blood stagnation should be eliminated in the LA and in the LV such that thrombus formation and release of thromboemboli have been prevented.

SUMMARY

Embodiments of the present invention contain a stent that is expanded via a mechanical means such as a balloon; other embodiments are formed from a self-expanding material and are released via withdrawal of a sheath in a manner similar to that taken with current TAVR devices. The stent-valve devices of the present invention are intended for use in the mitral valve, aortic valve, tricuspid valve, and pulmonary valve of the heart; the devices can also be used in other applications to secure an implanted devices within a vessel or lumen of the body where blockage of blood flow through the lumen or vessel is not desired during the implantation of the stent-valve device or other implanted device in the vessel or lumen. Although much of the discussion presented in this application is directed toward implantation of a stent-valve device in the mitral position, it is understood that the stent-valve device or other device suitable for implantation within the body can equally be applied to other valvular positions, vascular positions, or luminal positions of the body with consideration given to adjust the size or profile of the device and the access location into the vasculature or lumen of the tissue that is undergoing the implantation of the device.

In one embodiment the device is a single member stent-valve that is able to be used for Transcatheter Mitral Valve Replacement (TMVR) has a SE stent frame with a cylindrically-shaped or a curved waist portion and an upper bulb that is attached to the waist. This waist portion makes direct contact with the mitral annulus and ensures a tight seal against the mitral annulus; the upper stent bulb extends into the left atrium (LA) and outwards against the wall of the into the LA to provide additional seal against the LA to mitral annulus junction and to heal into the tissues above the mitral annulus to ensure that the mitral annulus does not expand further over time. The waist of the SE stent frame can have a limiting cable attached around its perimeter to ensure that the waist cannot expand further beyond a prescribed perimeter upon release from an delivery sheath that can ensure that an outward force is not being continuously applied to the mitral annulus. The outward force exerted by the SE waist to reach its full perimeter and expand the mitral annulus outward to a round shape can also be increased beyond the forces normally applied by a standard SE stent frame due to the presence of a limiting cable.

In one embodiment a stent frame housing is attached to the waist of the stent frame and extends into the left ventricle (LV) to provide a housing for the replacement leaflets. The replacement leaflets are formed from a tissue material, a synthetic polymeric material, or a composite material which can include a metal such as Nitinol (NiTi); the replacement leaflets are formed from a material that can be implanted within the body for periods of years without degradation or causing an adverse reaction to the body. The housing of this invention can have a shape of a cone that has its top cut off forming a frustum; the top of the frustum extending on the downstream or outflow end of the housing that is closest to the apex of the heart. The smaller diameter of the outflow end provides two major advantages. First, the frustum-like shape does not push the native anterior leaflet of the mitral valve outwards into the LVOT which can impede blood flow out of the LV. Second, the frustum-shaped housing also allows the native mitral leaflets to be adequately exposed to blood flow across the native mitral leaflet surfaces (the inner flow surfaces that contact the blood flow from the LA to the LV and the outer surfaces that faces the myocardial wall) such that thrombosis is not generated and thromboemboli are not released with potential migration to the brain and resultant stroke.

The leaflets contained within the frustum-shaped housing can have a frustum-like shape. The replacement leaflets form a crown-like shaped attachment to the frustum-shaped housing; the nadirs of the crown-shaped attachment at the base of the leaflets forms a perimeter at the base of the housing that is significantly larger than the perimeter of the housing at the outflow end of the housing. The free edges of the replacement leaflets do not come into direct contact with the top of the frustum-shaped housing at the outflow end; the spacing between the free edges of the replacement leaflets from the housing allows blood flow to rinse the leaflets during diastole and prevent thrombosis from occurring.

A fabric or covering is attached to some or all of the SE stent portion of the housing to prevent regurgitant flow through the TMVR; the covering can extend throughout the entire stent structure, including the waist, upper bulb, and housing portions to ensure that retrograde blood leakage is not obtained. The covering can be formed from a fabric material such as a woven or knitted fabric or a polymeric sheet material; the material for the fabric can be nondistendable fabric such as PET or Nylon that resists expansion of the covering upon exposure to expansion forces. Alternately, the covering can be formed in some embodiments from an expandable material such as polyurethane or spandex that will allow expansion of the covering; the restraining forces from a limiting cable attached along a perimeter of the waist or housing can serve to limit excessive expansion of the housing beyond a specified diameter and is necessary to maintain replacement leaflet coaptation.

The replacement leaflets contained within and attached to the housing portion of the stent can form a bileaflet valve similar to that found in the venous system or native mitral valve of the body, or the replacement leaflets can form a trileaflet valve similar to that found in a native aortic valve. The material for the valve leaflets can be bovine, porcine, or other animal pericardium or other tissue, collagen, fibrin, or other valve material including polymeric or composite materials used or anticipated for use in replacement valves. Alternately, a synthetic valve material can be used including material such as polyurethane, ePTFE, NiTi, or composite materials used in implanted devices. Attachment of the leaflets to the housing portion of the stent follows a curved or crown-shaped path that is similar to that found in the attachment of aortic valve leaflets or venous valve leaflets to their respective conduit. Polymeric or metal fibers or members can be contained within the leaflet structure or attached to the leaflet structure to provide both structural strength and provide flexing characteristics to the leaflets and also assist as members that can be directly attached to the stent frame. The crown-shaped attachment of the leaflets of the present invention can have a frustum-like shape in the respect that the base of the leaflets follows a perimeter that is larger than the perimeter of the free edge of the leaflets by at least 30%. Bileaflet replacement mitral valve leaflets are also anticipated for use with the present invention, a bileaflet valve can be oriented such that the major axis of the native mitral annulus is oriented with the commissures of the bileaflet valve to allow for improved coaptation of the leaflets over a greater range of ovality of the mitral annulus and result in less regurgitation and improved durability for the replacement leaflets.

The waist, upper bulb, and housing portion of the stent frame can be formed from any stent geometry such as open-cell or closed-cell stent wall construction. An additional expansion limitation element—such as a limiting cable may be placed into the stent geometric structure that limits the amount of radial expansion that the waist portion or the housing can attain. The upper bulb portion of the frame on the LA side of the waist is able to expand freely and extend in diameter further than the waist.

Balloon expandable (BE) or self-expanding (SE) barbs are located along the perimeter of the waist of embodiments of the present invention to provide fixation of the stent frame to the mitral annulus. In one embodiment, the barbs are formed from a BE material such as stainless steel, for example. The BE barbs remain in an inactive configuration until the waist is expanded into contact with the mitral annulus. A post-dilation step is then performed using an expandable or dilation balloon to push against the BE barbs and activate them into a configuration that engages the tip of the barb with the tissues of the mitral annulus. The barbs, when activated, provide stability to the stent frame against migration toward the LA due to blood pressure and flow generated by the LV.

A dilation balloon used for delivery or expansion of specific embodiments of the present invention can be formed from a shape having a diameter approximately equal to that of the mitral annulus in the waist portion and an alternate diameter that matches the shape and diameter of the stent frame and tissue structure in another portion. The balloon can have a torus or doughnut shape to allow blood flow across the annulus with the balloon inflated. The delivery system for some specific embodiments may include such a balloon to dilate various components of the present invention.

In another embodiment for fixation of the stent frame to the annulus the barbs are formed from a SE material; the SE barbs (formed from NiTi, for example) are held by a control fiber in an inactive position until the waist has been positioned against the annulus and has been fully expanded to its final diameter. The barbs can be released or activated by applying tension to the control fiber once the waist of the stent frame has been determined to be positioned accurately adjacent the annulus.

In yet another embodiment the valve of the present invention consists of a dual member stent-valve formed from two components that are delivered separately. The first component or support member contains a waist that forms a portion of the stent frame that is firmly attached to the mitral annulus (via barbs) and forms an outer ring structure into which a smaller diameter stent-valve can be placed; the outer ring structure can be formed by a limiting cable that is placed along the perimeter of the stent frame. The first component provides a fixed perimeter that holds a second component stent-valve via a frictional fit or via geometric locking of the first and second components. The first component forms an adapter that allows a second component (containing the replacement leaflets) to be implanted within its open central lumen as a second step. The embodiment for the first component that is comprised of a waist or waist frame is intended to allow complete unobstructed function of the native valve leaflets (by locating the stent frame waist across the mitral annulus and above the native mitral leaflets, for example) until the second component is inserted into and attached to the first component. Alternately, an upper bulb and/or a housing can be attached to the waist to form the first component. The stent frame is delivered to the location requiring a replacement valve contained in a small diameter non-deployed configuration within a sheath. The SE waist is released from the sheath and allowed to expand adjacent the mitral annulus; the stent frame has an upper bulb located above the waist in the LA to assist with positioning the stent frame waist across the annulus. The upper bulb has a larger diameter than the waist to prevent migration of the valve toward the LV and to provide a seal between the stent frame and the wall of the LA and mitral annulus. The equilibrium waist diameter is sized to be slightly larger (approximately 2 mm larger) than the effective diameter of the annulus to ensure that it makes direct contact along the entire perimeter of the mitral annulus and prevents leakage between the stent frame and the mitral annulus.

The second component of this embodiment is a stent-valve; the stent-valve having an expandable stent frame and replacement leaflets attached to the stent frame. In one embodiment the stent-valve has a frustum-like shape frame body that houses the replacement leaflets and having a smaller diameter at the outflow end of the frustum-shaped body by 30% (range 25-35%) than the diameter of the mitral valve annulus or the diameter of the inflow end of its frustum-shaped body. The stent-valve can be a modified TAVR device or a stent-valve with a frustum-like or hyperboloid-like shape for its frame. A TAVR device can be modified to form a frustum-like second component that is inserted and placed into the housing of the first component of the present invention. For example, the skirt or covering of a stent-valve device could be removed such that the covering of the first component housing serves to provide the function of preventing leakage of blood past the valve leaflets of the stent-valve device. The second component is delivered after the first component has been successfully positioned and attached across the mitral annulus.

In another embodiment the second component can be a cylindrically shaped stent-valve similar to some stent-valves used for TAVR implantation. The cylindrically shaped stent-valve can be held into contact with the first component via friction, geometric, or locking members to the waist of the first component. In one embodiment the SE waist of the second component is positioned adjacent to the waist of the first component. Release of the frustum-shaped stent-valve body of the second component is accomplished by removal of an external sheath that was holding the SE stent-valve and its contained replacement leaflets in a collapsed configuration. In another embodiment the second component could be formed instead from a BE stent body and delivered to the first component housing via mounting onto a dilation balloon that is shaped to fit within the first component housing.

The diameter of a mitral valve annulus is typically 35 mm and ranges from 28-40 mm in most patients; some patients could have an enlarged mitral valve annulus that is larger than 48 mm; some mitral annulus can be as small as 25 mm. The stent frame of the first component of the present embodiment has a waist that is located adjacent the mitral annulus and is approximately 35 mm for an average diameter to match the diameter of the mitral annulus. The aortic valve annulus is significantly smaller than the mitral valve annulus with an average diameter of approximately 24 mm and ranging from 19-29 mm. The use of a limiting cable located within a curved waist of the first component; the curved waist having a convex shape that extends into the open lumen of the first component provides a locking member for frictional or geometrical locking of the first component with the second component; the second component having a small 25 mm stent frame diameter that is similar to the diameter of a TAVR device The activation of BE fixation elements such as BE barbs to hold the stent frame from migration can be accomplished using a torus-shaped balloon (i.e., torus balloon) rather than a standard large diameter cylindrically-shaped dilation balloon. The torus balloon has a central opening similar to the opening of a doughnut that allows blood flow to cross the balloon without impeding flow through the mitral annulus. The central opening of the torus balloon allows the BE barbs to be activated while blood flow through the mitral annulus is maintained without blockage as would be imposed by a cylindrical or conically shaped balloon without a central opening.

The torus balloon of one embodiment of the present invention is attached to the waist or other region of the stent frame and saline is used to inflate the torus balloon after the waist portion of the stent frame is positioned properly adjacent to the mitral annulus. The inflated torus balloon pushes the fixation elements or fixation barbs outward into penetration within the mitral annulus. Prior to inflation of the balloon, the stent frame can be withdrawn into the delivery tube and repositioned across the mitral annulus, if necessary. Upon activation of the BE barbs, the inflation fluid delivery tube is detached from the torus balloon and the inflation tube is removed from the device. The saline inflation fluid is allowed to leak out of the torus balloon allowing the torus balloon to return to a flattened deflated configuration and the torus balloon can be implanted along with the stent frame.

In one embodiment the torus balloon is intended to be attached to the stent frame and is implanted along with the stent frame into the tissues of the heart. In another embodiment, the torus balloon is removable from the stent frame such that the torus balloon can first be inflated to activate the BE barbs and then be removed from the tissues of the body thereby leaving the other portions of the stent valve implanted adjacent the mitral annulus of the heart.

In another embodiment of the mitral valve device SE fixation elements are held in an inactive configuration toward the inside or luminal side of the stent frame. A feature that is formed onto the barb is designed to interface with a control fiber that holds the SE barb in an inactive configuration. Upon release of the control fiber via application of a tension force in the control fiber, the SE barb springs back to its equilibrium configuration with the barb extending outwards to the outside of the stent frame and into the mitral annulus. The bards extend into the mitral annulus along a perimeter of the mitral annulus. Their depth of penetration into the mitral annulus is less than the depth that would allow penetration into the circumflex artery that could otherwise cause negative sequellae.

In another embodiment the torus balloon can be formed with a segmented configuration formed from a series of larger diameter spherical segments separated by a series of smaller diameter cylindrical segments. The larger diameter spherical segments are placed adjacent to the inside of the barb struts to push the barbs outwards upon inflation of the segmented torus balloon. The smaller diameter cylindrical segments connect each spherical segment to each other and also the balloon port to provide an inflation lumen through which each of the spherical segments can be inflated. The smaller diameter cylindrical segments maintain a lower profile for the torus balloon in both its delivery configuration as well as during inflation and as the balloon is implanted. In one embodiment positioning for the cylindrical segments on the outside surface of the stent frame provides the stent-valve with an advantage by not pushing the stent frame further away from the mitral annulus as the torus balloon is inflated. In another embodiment with the cylindrical segments positioned on the inside of the stent frame a greater area for blood flow through the central lumen of the torus balloon will be provided.

Heart valves formed from biological tissues have been used for replacement of native heart valves in the aortic, mitral, pulmonary, and tricuspid positions. Such replacement valve have been used in surgical procedures and have recently been modified for use in TAVR and other transcatheter heart valve procedures. The surgical replacement heart valves typically have an attachment ring that is sewn or otherwise attached to the annulus of the native heart valve tissue. The replacement leaflets are attached to two or three posts that extend downstream from the attachment ring. For TAVR and other transcatheter replacement valves, the leaflets are attached to the stent frame and follow a crown-shaped attachment of the leaflets to the stent frame. The transcatheter stent frame is covered by an impervious covering that does not allow blood flow to pass across the wall of the stent frame such that the replacement heart valve can provide unidirectional flow of blood from the upstream side to the downstream side of the stent-valve and prevention of perivalvular leakage of blood between the stent-valve and the native valve tissues surrounding the stent-valve.

Locating a covered transcatheter stent-valve upstream of the annulus of the native heart valve can lead to formation of a stagnation region between the stent valve and the surrounding native tissue that forms the native channel or lumen for blood flow. The presence of a covering on the stent-valve frame can prevent blood from forming a linear hemodynamic path from the lumen of the native blood vessel or chamber in a direction downstream and into the stent-valve. This nonlinear path can result in the formation of a stagnation region between the native chamber wall and the covered stent-valve leading to thrombosis and the formation of thromboemboli that can be detrimental to the patient. If a portion of the stent-valve extends downstream of the securement and seal of the stent-valve to the annulus of the native heart valve it is important to ensure that antegrade blood flow into the stent-valve from the left atrium (LA) is maximized during diastolic heart relaxation, and that stagnation of blood between the native leaflets and the stent-valve frame in the left ventricle (LV) has been minimized. Also it is important to ensure that during the initiation of systolic LV heart contraction that blood can flow momentarily in a retrograde direction to assist in closing the replacement leaflets and prevent stagnation of blood between the native leaflets and the stent-valve frame. The stent-valve frame should be positioned across the valve annulus such that the potential for native valve leaflet prolapse cannot allow for entry or overhang of the native leaflet into the downstream end of the stent-valve and interfering with stent-valve function.

The stent-valve of the present invention extends in an axial direction for a distance below (i.e., toward the LV) the annulus to prevent native leaflet overhang into the stent-valve but does not extend to an axial distance that results in LVOT obstruction. The stent-valve also extends into the LA, but provides for blood flow from the LA to the LV without regions of blood stagnation. The present invention is a stent-valve that allows for direct blood flow from the blood vessel lumen or chamber in a direction downstream from the LA and into the stent-valve without causing regions of potential blood stagnation in the left atrium (LA); the stent valve also allows for blood flow between the native leaflets and the stent-valve frame in the LV to prevent blood stagnation, thrombosis, and formation of thromboemboli.

During delivery of the first component of a two component mitral valve system, the barbs that attach or hold the first component to the mitral annulus or mitral surrounding tissue are activated by an activating torus balloon. The torus balloon causes hinge regions of the barbs to become plastically deformed such that the barb assumes an activated configuration with the barb tip extending into the surrounding mitral tissues located outside of the first component frame. Following activation of the barbs the first component is held adjacent to the mitral tissue via the SE stent frame and is unable to migrate toward the LA or the LV due to the extension of the barb tips into the mitral surrounding tissues.

During delivery of the first component to the mitral annulus and after release of the first component from the delivery sheath, the first component is held by either control fibers or recapture struts that extend into the delivery sheath. The first component can be fully retracted into the delivery sheath even after the first component has been allowed to expand via SE expansion energy into contact with the mitral annulus. The first component can also be held via the control fibers or recapture struts even after the activating torus balloon has been inflated to activate the barbs in a radially outward direction into the mitral annulus or surrounding mitral tissues.

In one embodiment, the first component has a second torus balloon or deactivating torus balloon is located along the perimeter of the stent-valve frame between the stent-valve frame and the barb strut. Following the deflation of the activating torus balloon, the deactivating balloon can be inflated if necessary to cause the barb to become deactivated by moving the barb tips radially inward such that they no longer extend into the surrounding mitral tissues. The first component can then be fully retracted into the delivery sheath or can be repositioned as required by the physician to an alternate location adjacent to the mitral surrounding tissues.

BRIEF DESCRIPTION OF THE DRAWINGS

FIG. 1C is a perspective view of a frame having a housing with a shape of a hyperboloid of revolution.

FIG. 1D is a perspective view of a frame having a curved or concave waist.

FIG. 1E is a perspective view of a dual component stent valve having a first component or support frame located against the annulus and a second component or valve frame positioned within the first component.

FIG. 2A is a perspective view of frame for a single member heart valve or a frame for a first component having two limiting cables located along a perimeter of the waist and the frustum housing.

FIG. 2B is a perspective view of the frame showing the upper bulb in a perspective view.

FIG. 7B is a perspective view of single member stent valve having a covering over a portion of the housing and providing an open area for blood flow through the spacing between the frame and the free edges and through the open frame housing during systole.

FIG. 7C is a perspective view of single member stent valve having a covering over the entire housing and providing an open area for blood flow through the spacing between the frame and the free edges during systole.

FIG. 8A is a perspective view of a waist region of a frame having barbs attached along a perimeter of the frame and a torus balloon attached along a perimeter of the frame, the torus balloon is not inflated and the barbs are not activated and hence are on the inside or luminal side of the frame.

FIG. 8B shows a perspective side view of two frame stent struts and the attachment of the balloon to the frame and attachment of the barb struts to the frame via ferrules; the torus balloon is not inflated.

FIG. 9C is a top plan view of the torus balloon in an inflated configuration showing the barb tips extending to the outside of the frame perimeter.

FIG. 9D is a perspective view of the torus balloon showing the inner and outer diameters and showing the balloon ports for inflation.

FIG. 10A is a sectional plan view through the waist showing a torus balloon in a deflated configuration located adjacent to the barb struts and contained within a pocket of a balloon holder that is attached to the frame.

FIG. 10B is a sectional plan view through the waist showing a torus balloon in an inflated configuration located adjacent to the barb struts and the barb tips being activated to extend outside of the frame.

FIG. 10C is a plan view of a torus balloon attached to stent struts of the frame waist.

FIG. 12A is a sectional view of a frame waist having a backing arm attached to the frame and supporting the torus balloon on the inside perimeter of the torus balloon.

FIG. 12B is a perspective view of the frame waist having a backing arm located on the inside perimeter of the torus balloon; the torus balloon is inflated and activates the barb strut moving the barb tip to the frame outside.

FIG. 18 is a perspective view of a single member stent valve having a torus balloon in a deflated configuration along the perimeter of the frame waist and located adjacent to the barb struts.

FIG. 19 is a perspective view of a single member stent valve having a torus balloon located along the perimeter of the upper bulb and located adjacent to the barb struts.

FIG. 36A is a perspective view of a second component frame positioned above the annular plane and showing one-way valvular function of the replacement leaflets during systole.

FIG. 36B is a perspective view of a second component frame positioned above the annular plane and showing open stent-valve frame surface providing for blood flow across the stent-valve frame surface during diastole.

FIG. 37A is a perspective view of a stent-valve frame that straddles the annular plane providing washing of the outside surface of the native leaflet surface below the annular plane during the initiation of systole.

FIG. 37B is a perspective view of a stent-valve frame that straddles the annular plane providing washing of the inside surface of the native leaflet surface below the annular plane during diastole.

FIG. 44A is a plan view of the first component having both an activating torus balloon and a deactivating torus balloon; the barbs have not yet been activated.

FIG. 44B is a plan view of the first component having both an activating torus balloon and a deactivating torus balloon; the barbs have been activated into the surrounding annular tissues by the activating torus balloon.

FIG. 44C is a plan view of the first component having both an activating torus balloon and a deactivating torus balloon; the barbs have been deactivated by the deactivating torus balloon.

FIG. 45 is a perspective view of a first component frame having a supra securement locking feature and an infra securement locking feature that can lock onto an annular plane or onto a first component frame.

FIG. 46A is a perspective view of a dual member stent-valve system having a first component frame with a supra securement locking feature and an infra securement locking feature that locks onto the first component frame; the first component is still being held by the control fibers and recapture struts.

FIG. 46B is a perspective view of a dual member stent-valve system having a first component frame with a supra securement locking feature and an infra securement locking feature that locks onto the first component frame and has been released from the delivery catheter.

FIG. 46C is a plan view of a second stent-valve component frame having frame extensions along all or a portion of its perimeter.

FIG. 46D shows a plan view of a second component having frame extensions being locked into a first component to form a dual member stent-valve system.

FIG. 47A is a perspective view of a second component stent-valve frame having a concave region that is able to lock with a concave region of a first component or lock around a native valve annulus.

FIG. 47B is a plan dual member stent-valve system having a second component stent-valve frame with a concave region that is locked onto a smaller diameter region of the first component created by a limiting cable; the second component is being held by the delivery catheter.

FIG. 47C is a perspective view of a dual member stent-valve system having a second component stent-valve frame with a concave region that is locked onto a smaller diameter region of the first component created by a limiting cable; the second component has been released from the delivery catheter.

FIG. 47D is a plan view of the dual member stent-valve having a second component with a concave region that forms a locking attachment around the limiting cable of the first component.

FIG. 47E is a perspective view of the second component stent-valve showing the stent frame structure and showing the recapture struts.

Figure 48:
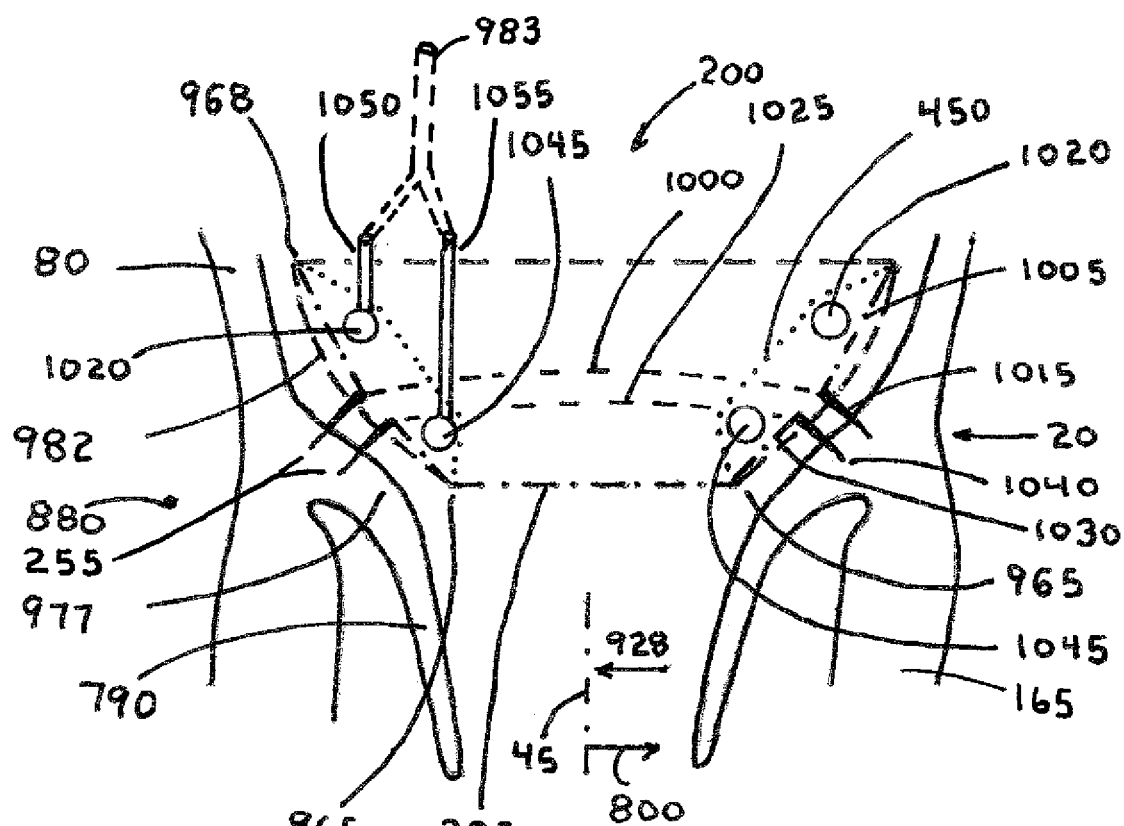

FIG. 48 is a sectional view of a first component having two rows of barbs, each row being activated by a separate torus balloon.

FIG. 49A is a sectional view of a heart showing a flail leaflet that extends toward the left atrium.

FIG. 49B is a plan view of a first component frame used without the second component to treat flail leaflet.

Figure 50A:
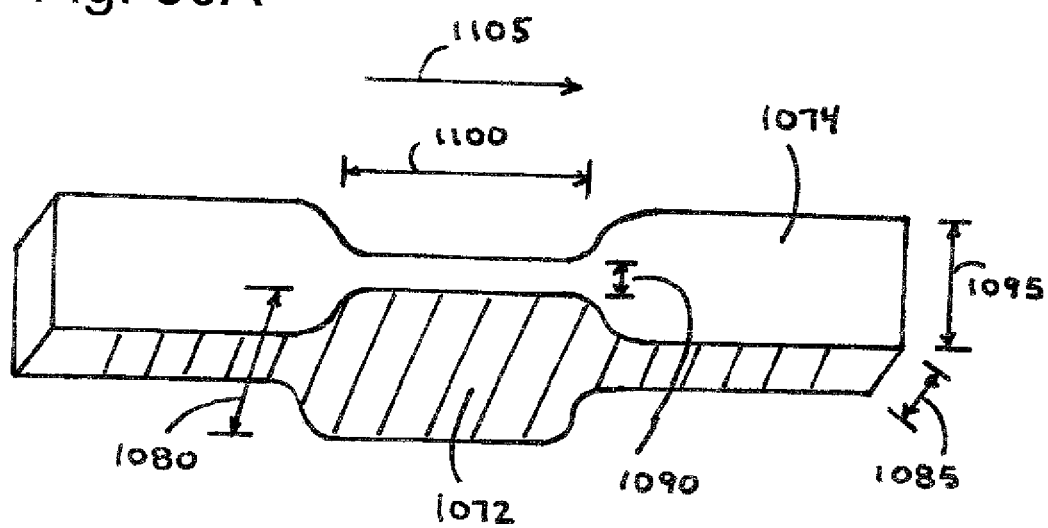

FIG. 50A is a perspective view of a hinge and strut structure that can be used to form the first component frame or the second stent-valve frame.

Figure 50B:
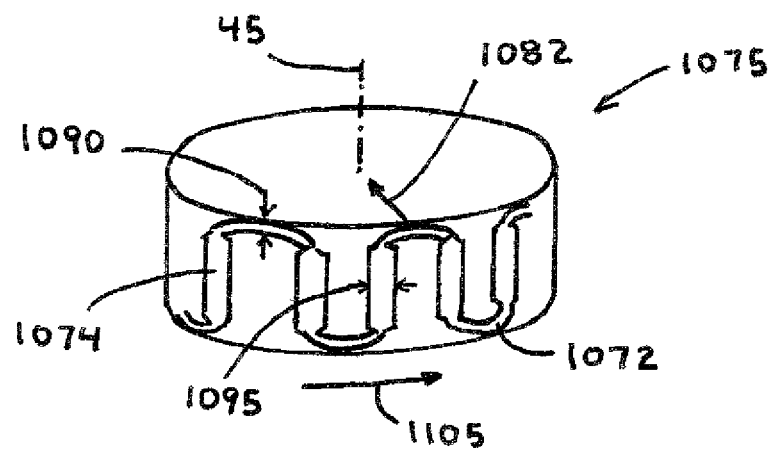

FIG. 50B is a perspective view of the hinge and struts structure of FIG. 50A applied to the first component frame or the second component frame structure in a unexpanded configuration during delivery within the delivery catheter.

Figure 50C:
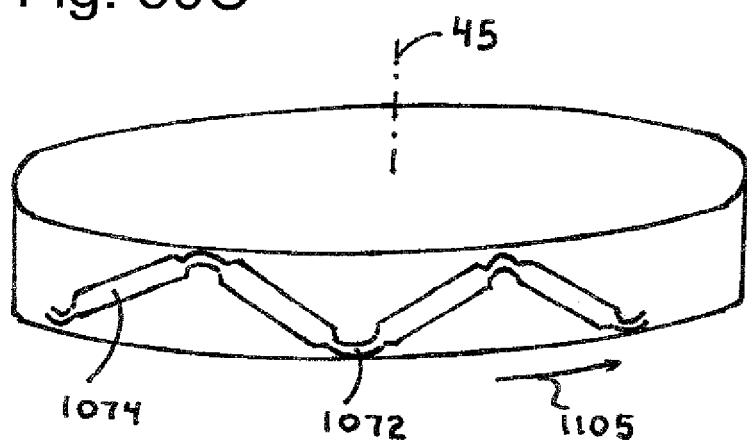

FIG. 50C is a perspective view of the hinge and struts structure of FIG. 50A applied to the first component frame or the second component frame structure in an expanded configuration after release from a delivery catheter.

Figure 51A:
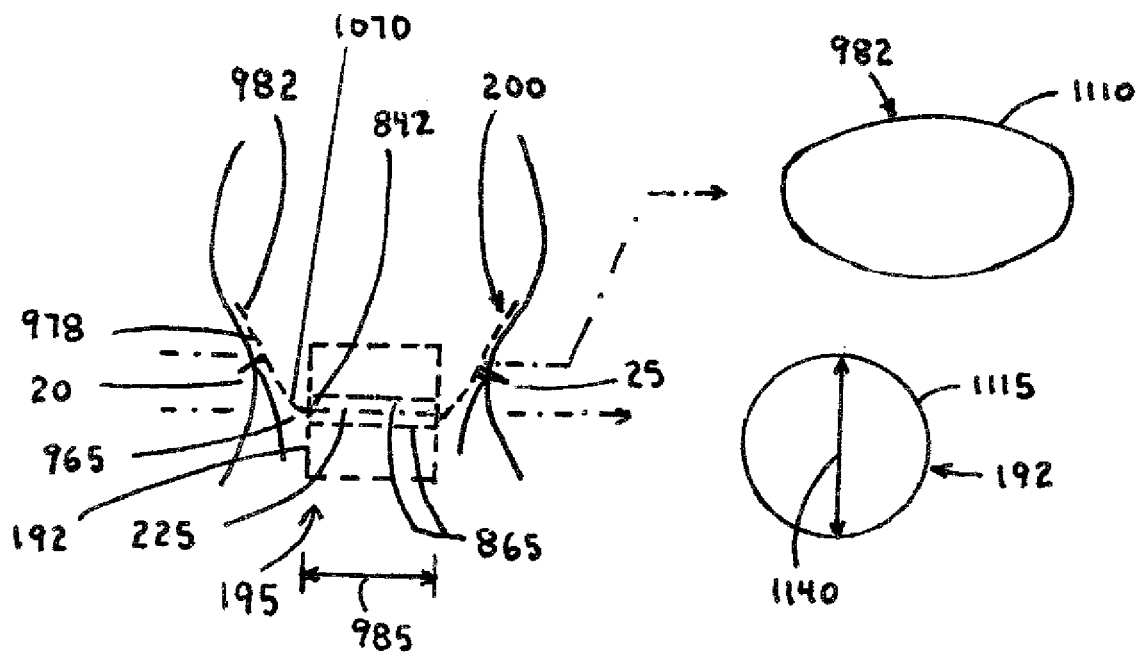

FIG. 51A is a plan view of first component frame that conforms to an oval heart annulus and a round second component positioned within the lumen of the first component downstream of the annulus.

Figure 51B:
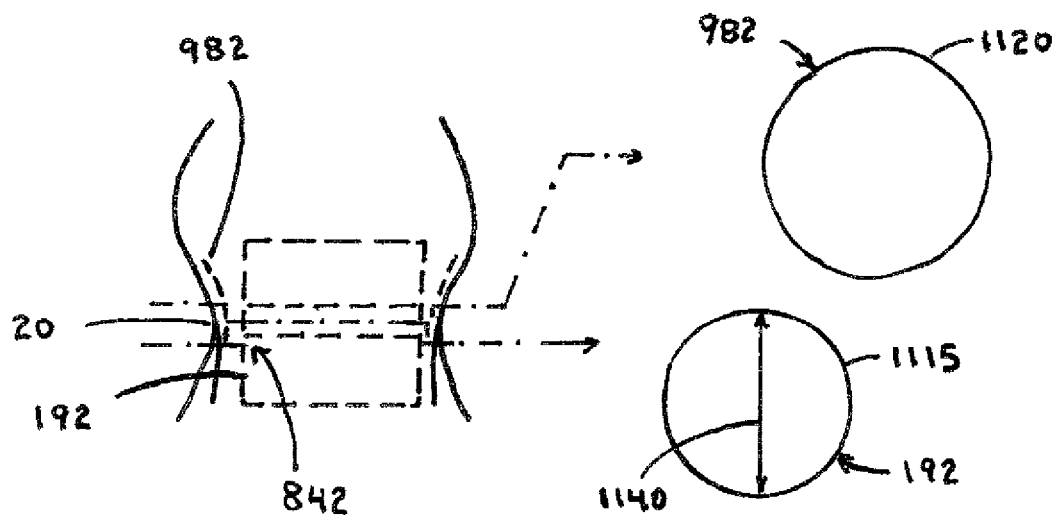

FIG. 51B is a plan view of first component frame that forms an oval heart annulus into a round cross section and a round second component positioned within the lumen of the first component downstream of the annulus.

Figure 51C:
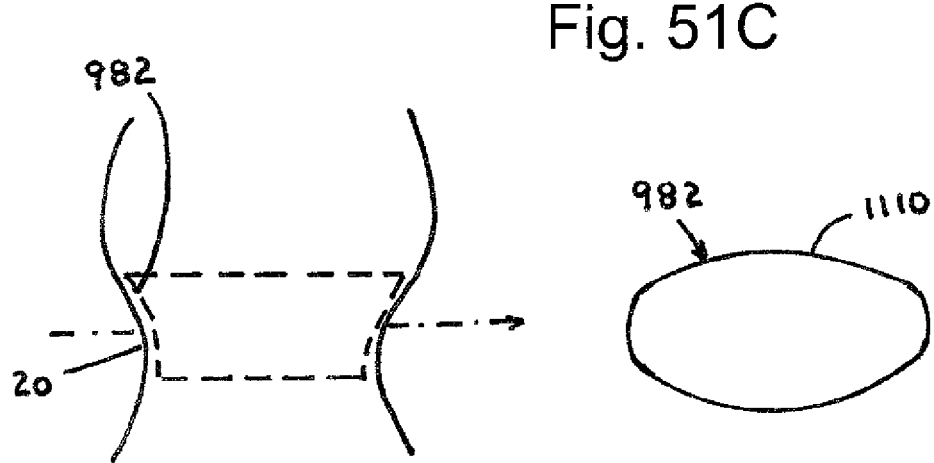

FIG. 51C is a plan view of first component frame that conforms to an oval heart annulus.

Figure 51D:
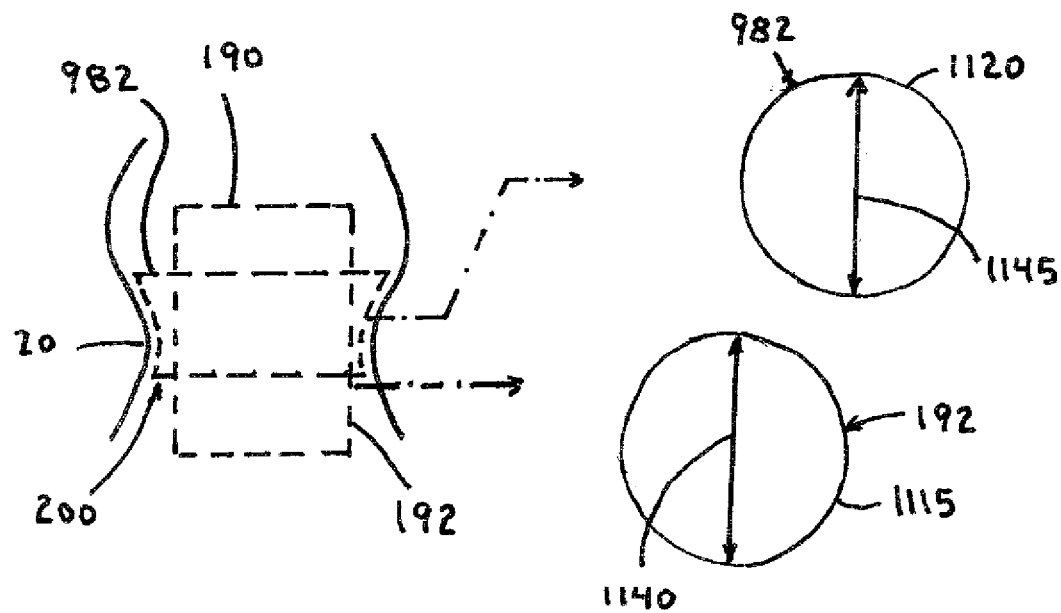

FIG. 51D is a plan view of first component frame that conforms to an oval heart annulus and a round second component positioned within the lumen of the first component at the annulus and forming the first component into a round cross-sectional shape.

Figure 51E:
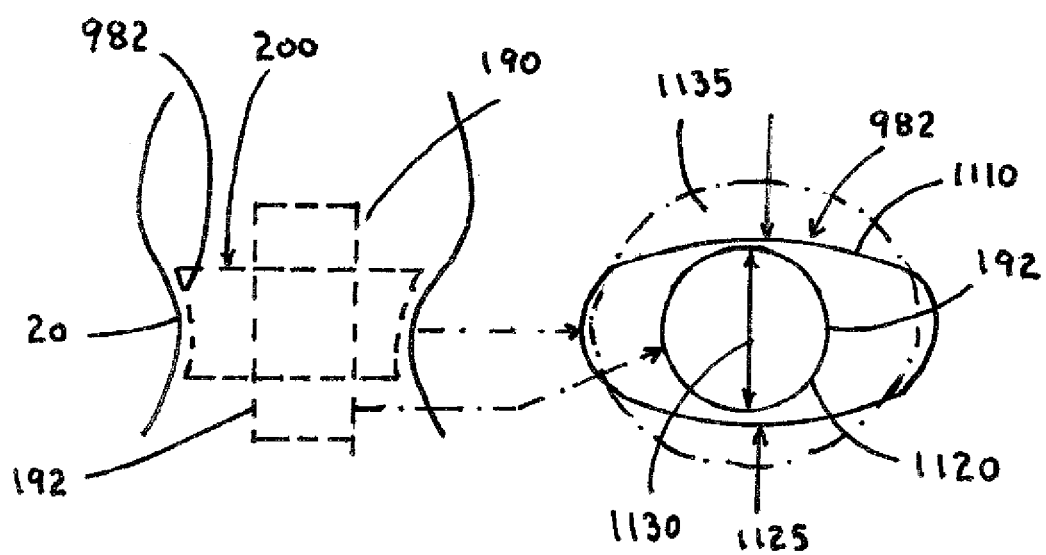

FIG. 51E is a plan view of first component frame that conforms to an oval heart annulus and a round second component positioned at the annulus with a round cross-sectional diameter equal to the minor axis of the first component.

DETAILED DESCRIPTION

One embodiment of the present invention comprises a single member stent-valve that is intended as a transcatheter replacement valve for a valve of the heart; the single member stent-valve (5) is intended to be delivered within the lumen of the native heart valve and expanded outwards forming a functioning valve device having replacement leaflets. The valve device will be described in an application for its use as a transcatheter mitral valve replacement (TMVR) although it is understood that the invention can be applied to other valves found within the heart. The invention further comprises a dual member stent valve comprised of two components, a first component or support member and a second component or valve member. The first component is delivered across the annulus of the heart and affixed to the annulus or other native tissues of the heart; the first component does not interfere with function of native valve leaflets such that the mitral valve is fully functional while awaiting the delivery and implant of a second component. The first component does not itself contain any replacement leaflets, and has an open lumen that allows unimpeded blood flow in both the upstream and downstream direction such that it can be positioned accurately across the mitral annulus without hemodynamic forces imposed on the first component. The second component or stent-valve component or valve member of the dual member stent-valve is delivered subsequent to the first component and is placed within the open central lumen of the expanded first component; the second component contains the replacement leaflets that control blood flow in an antegrade or downstream direction from the left atrium (LA) to the left ventricle (LV). In describing various embodiments of the invention, it is understood that the single member stent-valve can have a fixation elements or barbs that function to hold or attach the frame of the single member stent-valve against the annulus tissues of the native heart valve to prevent migration of the frame; the same fixation elements can be found in the first component of a dual member stent-valve. Additionally, it is understood that the replacement valve leaflets found in the single member stent-valve are attached to the stent frame to direct blood flow in a downstream direction; the leaflets can be attached to the stent frame of the second component of the dual member stent-valve in the same manner as that found in the single member stent-valve.

The first component or support member of the dual member stent-valve provides, in itself an invention that functions as an adapter that can be implanted within the tissues of a native heart valve. Following implantation of the first component or adapter, a second device such as a stent-valve already available on the market can be implanted into the open central lumen of the first component. The second component can be, for example, a balloon expandable (BE) stent-valve or a self-expanding (SE) stent-valve used for transcatheter aortic valve replacement (TAVR) or other similarly sized stent valve device application. Alternately, the second component can comprise one of the embodiments of the second component that are presented in the present application. The reference numerals and reference names from each embodiment of this specification can be applied to other embodiments bearing the same reference numerals or reference names found in this specification.

Figure 1A:
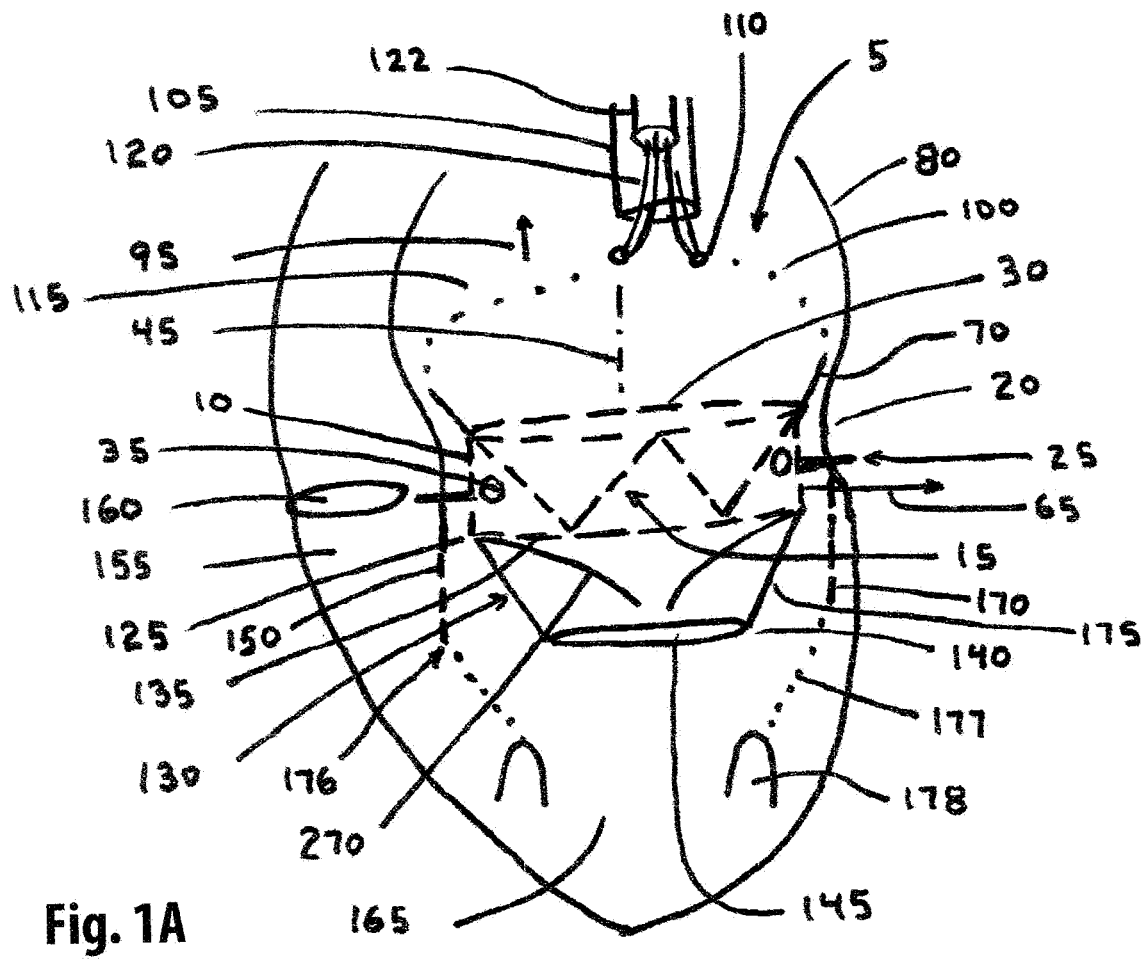
FIG. 1A is a perspective view of a single member heart valve in an expanded configuration positioned across the native mitral valve annulus.

One embodiment for the frame of the single member stent-valve (5) of the present invention is shown in FIGS. 1A-1D; the waist (10) of the frame (15) or stent-valve frame (15) of the single member stent-valve (5) can be implanted adjacent to the annulus (20) of the native mitral valve as shown in FIG. 1A. The waist (10) of the single member stent-valve (5) can have barbs (25) located along the waist perimeter (30) as shown in FIG. 1A and further described in other embodiments of the invention; the barbs (25) can be activated by dilation of a torus balloon (35). The frame (5) of the single member stent-valve (5) holds the replacement leaflets; the frame (15) is formed from an elastically deformable material such as Nitinol, Elgiloy, or other elastic, metal, plastic, or composite material. The wall structure of the portions of the frame (15) can be an open cell zig-zag structure, a closed cell structure, a combination of open and closed cell or any other wall structure geometry that has been used or proposed for use in stents or stent-valves for vascular therapy.

The frame (15) is comprised of a cylindrical stent or a curved stent that forms the waist (10) of the present embodiment; the waist (10) is located adjacent to the valve annulus (20) (20) such as the mitral valve annulus (20). The waist (10) can have a non-cylindrical or curved shape that forms a curved waist (40) along its perimeter that is in contact with the native valve annulus (20) as shown in FIG. 1D and extends with a concave region (42) radially inward toward the central axis (45) of the frame. For the curved waist (40) the waist central diameter (50) has a smaller diameter than either the waist inlet diameter (55) or the waist outlet diameter (60). The waist central diameter (50) is 5 mm smaller (range 2-10 mm smaller) than the waist inlet diameter (55) or waist outlet diameter (60). The waist (10) is formed with a stored energy that exerts a frame outward force (65) onto an average sized annulus (20) of 35 mm diameter (range 25-48 mm) that is equivalent to the force provided by a 5 atm balloon (range 4-7 atm) of the same diameter. The large outward force of the waist (10) pushes the waist (10) into the mitral annulus (20) and forms a seal between the waist (10) and the mitral annulus (20). The waist (10) is attached to or contiguous with the upper bulb (70) which extends outwards from its attachment to the waist; the upper bulb (70) extending into the LA (80) with an upper bulb inlet diameter (75) that is larger than the waist inlet diameter (55). The upper bulb (70) extends outwards with an upper bulb angle (85) that can be at a 90 degree angle with respect to the waist (10) axial direction (90) or at a 45 degree angle or at an intermediate upper bulb angle. The upper bulb (70) serves to provide an improved seal between the upper bulb (70) and the annulus (20) and wall of the LA (80) as the upper bulb (70) undergoes healing with the mitral annulus (20) and surrounding tissues will serve to hold the mitral annulus (20) from further dilation; also, the upper bulb (70) serves to locate the waist (10) such that it is positioned adjacent to the annulus (20). Attached to or contiguous with the upper bulb (70) and extending upstream (95) into the left atrium (LA) are recapture struts (100); these struts are somewhat weaker in outward force than the waist outward force and have a larger overall equilibrium diameter and shape that matches the larger and curved or rounded surface found in the left atrium (LA). The recapture struts (100) allow the waist (10) and frame (15) of the present invention to be released from a delivery sheath (105) and placed into contact with the mitral annulus (20) and recaptured back into the delivery sheath (105) if the position of the waist (10) with respect to the mitral valve annulus (20) is not in position along the length of the axial direction (90) of the frame. The recapture struts (100) can be retained within a delivery sheath (105), for example, while the stent waist (10) has been released into contact with the mitral annulus (20). The frame (15) can be repositioned, if necessary, a second time across the mitral annulus (20). A holding feature (110) located at the proximal end (115) of the frame (15) allows the recapture struts (100) to be held by one or more control fibers (120) that extends through the delivery sheath (105) to a location outside of the body. A pusher member (122) is used to push the stent valve frame (15) out of the delivery sheath (105).

Attached to or contiguous with the distal or waist outlet end (125) (toward the distal end of the waist) is the housing (130). The housing (130) has the shape of a conical surface having its tip cut off at its top forming a frustum and provides a housing in one embodiment for replacement leaflets (270) which will serve to direct antegrade blood flow downstream from the LA to the LV and restrict retrograde blood flow from the LV to the LA. The larger housing base (135) of the frustum is attached to the waist, and the housing top (140) of the frustum-shaped housing (130) is located at the housing outlet end (145). Alternately, the housing (130) can have the shape of a one-sheeted hyperboloid of revolution that has been truncated as shown in FIG. 1C; the base of the hyperboloid is located adjacent to and attached to the waist (10) and the truncated portion that forms the top of the hyperboloid is located at the outlet end or outflow end of the housing (130). Both the frustum and the truncated hyperboloid are shapes that get continuously larger in diameter as they extend along their axial direction (90) from the housing top (140) to the housing base (135) of the frustum-shaped housing (130); the housing (130) for this embodiment does not contain a cylindrical region.

Figure 1B:
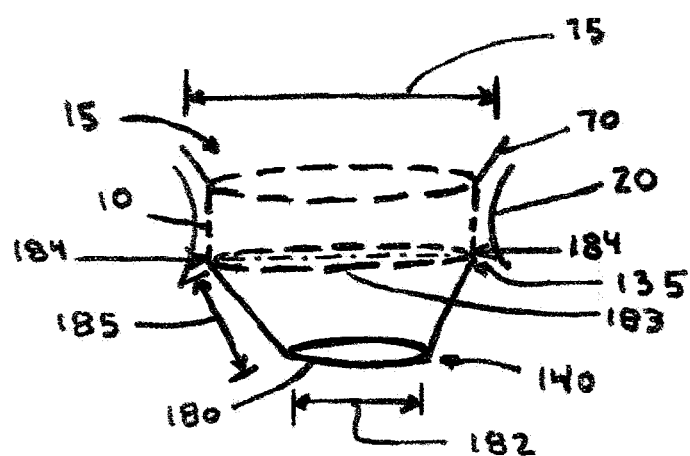
FIG. 1B is a perspective view of the frame of a single member valve with a frustum-shaped housing.

With the frame (15) implanted across the mitral annulus (20) as shown in FIGS. 1A and 1B the frustum-like shaped housing (130) (including the hyperbolic-shaped housing (130)) does not impinge upon the native anterior mitral leaflet (150); the left ventricular outflow tract (LVOT) (155) is not restricted from flow of blood out of the aortic valve (160) due to systolic contractions of the left ventricle, LV (165). As shown in FIG. 1B, the native anterior mitral leaflet and native posterior mitral leaflet (170) are able to approximate the housing outer surface (175) and prevent the formation of a low blood flow region that would be susceptible for formation of thrombus or thromboemboli that could lead to the formation of a stroke. The native free edges (176) of the native anterior mitral leaflet (150) and native posterior mitral leaflet (170) are attached via cordae tendineae (177) to papillary muscles (178) to prevent leaflet eversion during the cardiac systolic cycle. The housing base (135) of the frustum-like housing (130) is expanded outward to a perimeter that is equal to the perimeter of the mitral annulus (20); the effective diameter of the mitral annulus (20) (i.e., diameter of a circle have a specified perimeter) is an average of 35 mm (range of 25-48 mm); the housing top (140) of the frustum-like housing (130) has a housing top perimeter (180) and housing top diameter (182) that is 30% smaller (range 25-35% smaller) than the housing base perimeter (183) and housing base diameter (184) of the housing base (135) in its expanded configuration; the diameter of the top of the frustum is 25 mm (range 18-30 mm). The housing length (185) of the frustum-like housing (130) from the housing top (140) to the housing base (135) is 20 mm (range 10-30 mm).

The stent-valve frame (15) as described in FIGS. 1A-1D can also be used as an embodiment for a second component (190) of a dual member stent valve (195) as shown in FIG. 1E. The second component (190) can have a valve frame (192) similar to the stent frame (15) structure as described for the single component stent-valve; the second component (190) is delivered into the open central lumen (265) of the first component or support frame (200). The second component waist (205) would, however, be delivered adjacent the first component waist (210) as shown in FIG. 1E; the first component waist (210) would be located adjacent and in contact with the native valve annulus (20). Also, the second component (190) may not contain the barbs (25) as described for the single component stent-valve; the) would contain barbs (25) for fixation of the dual member stent-valve as described in other embodiments of this patent application.

FIGS. 2A and 2B show a side and perspective view of waist, upper bulb (70) and housing (130) of the frame (15) comprising the single member stent-valve (5) or the second component (190) of the dual member stent valve (195) of the present invention; replacement leaflets would be attached to the frame as described in other embodiments. The upper bulb (70) extends from the waist inlet end (215) with a bulb angle (85) of 45 degrees off of the axial direction (90) (range 20-90 degrees). The housing base (135) is attached to the waist outlet end (125); the housing (130) extends in a distal direction (218) toward the housing top (140) with a housing angle (220) (measured with respect to the axial direction (90)) of 11 degrees for a frustum (range 6 to 22 degrees); the housing angle (220) is 30 degrees (range 10-45 degrees) for a hyperboloid-shaped housing (130). A limiting cable (225) can be attached to the stent frame (15) or can be contiguous with the stent frame (15) along the waist perimeter (30) to limit the amount of radial expansion that the waist (10) is allowed to extend; the limiting cable (225) can also be attached along a perimeter of the housing (130). The cable can be formed from multifilament materials such as stainless steel, polyethylene terephthalate, Nitinol, and other polymer or metal materials, alloys, or composites. The cable is very soft in its ability to bend due to the multifilament strands of very small diameter filaments, typically having a filament diameter of 10 microns (range 5 microns to 100 microns). The cable is able to be easily folded back upon itself by application of a bending force equal to 50 grams (in earth gravitation). The limiting cable perimeter (235) is set to be 3 mm larger (range zero to 9 mm larger) than the perimeter of the annulus (20) such that the waist (10) of the stent with it large outward force is able to make direct contact around the perimeter of the annulus (20) without influence of the cable constraint; the cable prevents any further force to be exerted against the annulus (20) once the cable has reached its full perimeter. For a 35 mm annulus (20) effective diameter, for example, a 35-37 mm effective diameter of the cable would be used having a cable perimeter that is zero to 6 mm larger than the perimeter of the annulus (20) and a cable effective diameter (i.e., diameter of a circle with the perimeter of the cable) that is zero to 2 mm larger than the effective diameter of the annulus (20). The housing (130)

gets continuously smaller as it extends in the axial direction (90) from the base to the top of the housing (130).

Figure 3A:
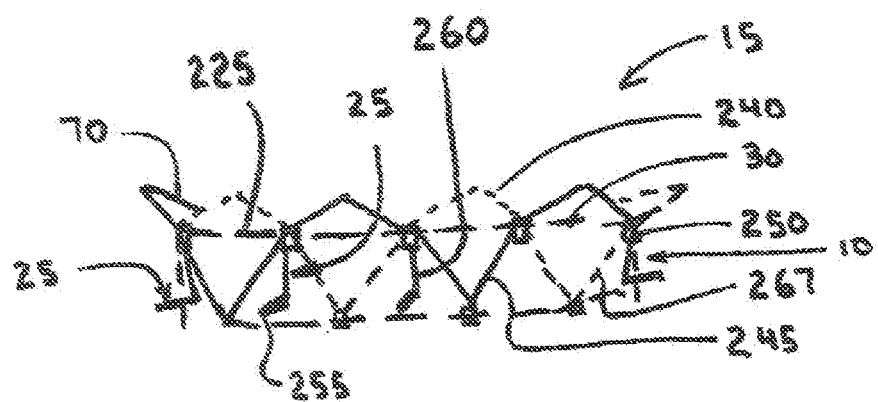
FIG. 3A is a plan view of the waist region of a frame having barbs attached via ferrules to the frame.
Figure 3B:
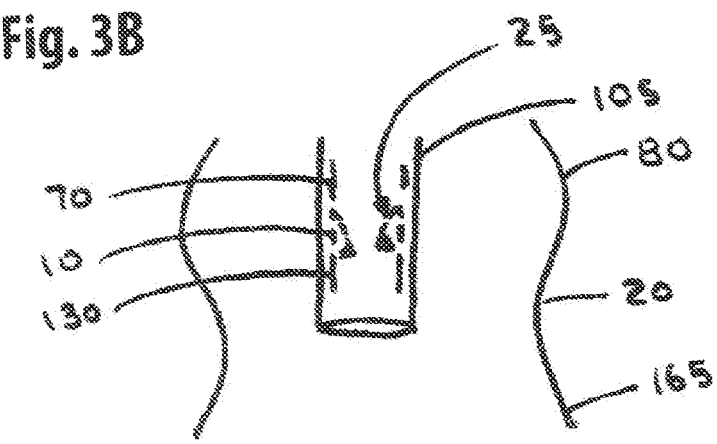
FIG. 3B is a plan view of a stent valve in a smaller diameter configuration positioned within a delivery catheter.
Figure 3C:
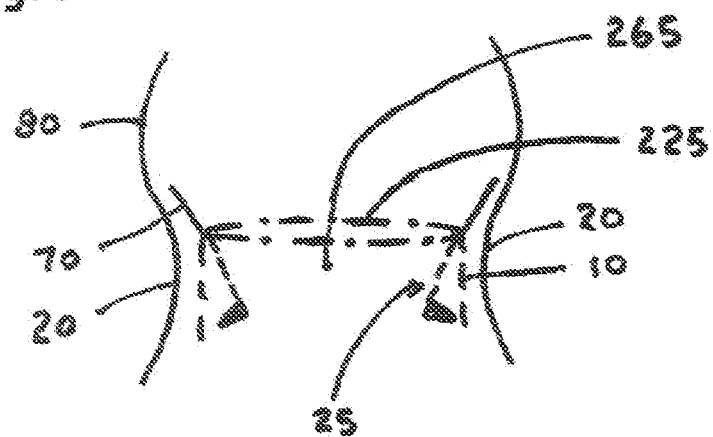
FIG. 3C is a perspective view of the waist and upper bulb of a frame having barbs attached and found in an inactive configuration with barb tips on the inside of the frame.
Figure 3D:
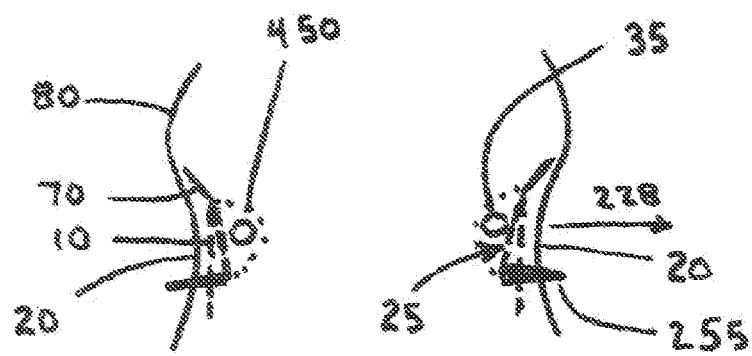
FIG. 3D is a perspective view of the waist and upper bulb of a frame having barbs attached and found in an active configuration with barb tips on the outside of the frame.

FIGS. 3A-3D show one embodiment of the waist (10) and upper bulb (70) portions of the frame (15) that can be applied to the single member stent-valve (5) and also to the first component (200) of the dual member stent-valve (195). In this embodiment a balloon expandable (BE) set of barbs (25) are located around the waist perimeter (30). The waist (10) is constructed by interleaving a first zig-zag stent (240) with a second zig-zag stent (245) such that first and second zig-zag stents are held together by ferrules (250) placed along the frame or waist perimeter (30). The upper portions of the zig-zag stents form the upper bulb (70) and the lower portions of the zig-zag stents form the waist. A multiplicity of barbs (25) (range 8-40) are attached to the ferrules (250) such that the barb tip (255) does not extend to the outside of a circle formed by the waist (10) when the stent frame (15) is located within the delivery sheath (105) to reach its expanded configuration as shown in FIG. 3B or after release from the delivery sheath (105) as shown in FIG. 3C. The barb strut (260) is formed from a BE material such that upon exposure to a dilation balloon such as a torus balloon (35) as shown in FIG. 3D (or other shaped dilation balloon), the barb is forced outwards into the annulus (20) via a balloon outward force (228) of the torus balloon (35) onto the barb (25).

Figure 4A:
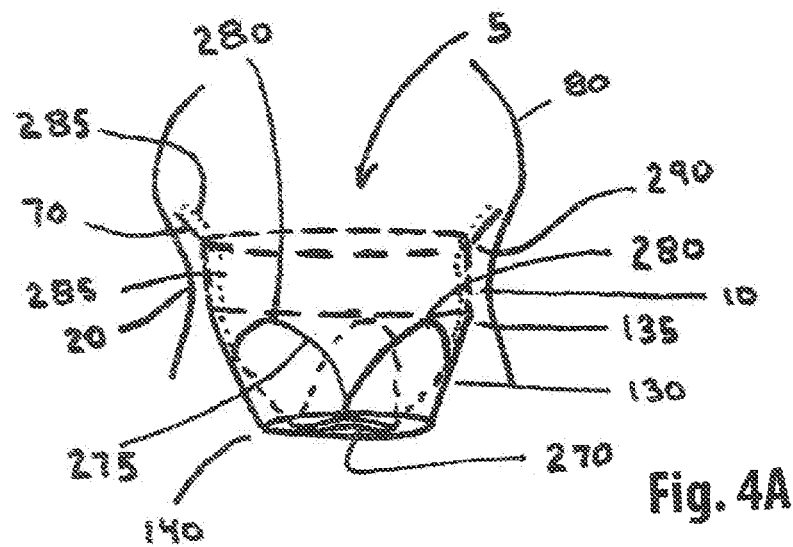
FIG. 4A is a perspective view of a single member frame having replacement leaflets attached within a frustum shaped housing and having a waist located adjacent to the native valve annulus.
Figure 4B:
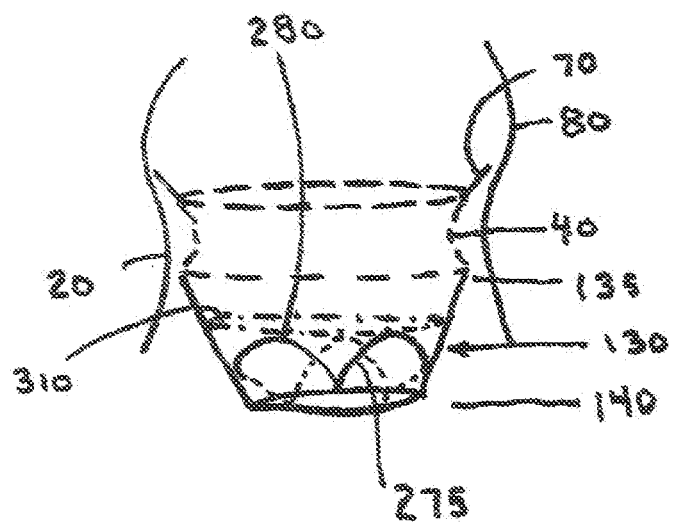
FIG. 4B is a perspective view of a single member frame having replacement leaflets attached within a portion of the frustum-shaped housing and a curved or concave waist located adjacent to the native valve annulus.
Figure 4C:
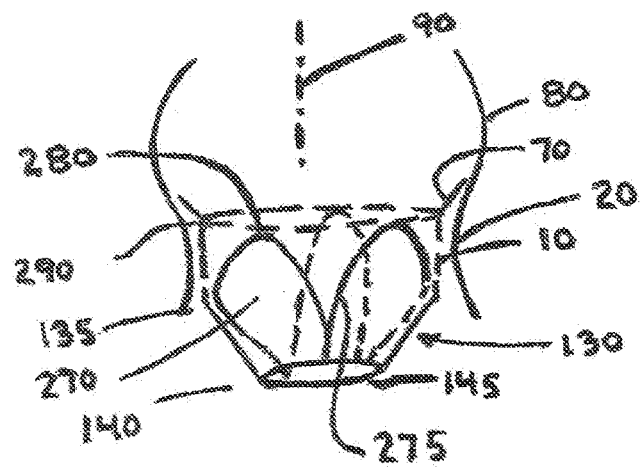
FIG. 4C is a perspective view of a single member frame having replacement leaflets attached within a frustum shaped housing and within the cylindrically-shaped waist located adjacent to the native valve annulus.

The frame waist (10) as shown in FIGS. 3C, 3D, and 4C can be a portion of a single member stent-valve frame (15) that contains replacement leaflets; alternately the frame waist (10) can be a portion of the first component (200) of a dual member stent-valve (195); the first component (200) of the dual member stent valve (195) does not contain replacement leaflets and serves as an adapter into which a second component (190) that contains replacement leaflets can be positioned and implanted into the central lumen (265) of the adapter.

The barb strut (260) of this embodiment can be formed from stainless steel or plastically deformable metal, polymer, or biodegradable material. The barb tip (255) is formed with a pointed shape that extends in a direction perpendicular to the barb strut (260) and directed toward the tissue of the mitral annulus (20) when it is activated to expand into the annulus via inflation of the torus balloon (35). The barb strut (260) can have a diameter of 0.003 inches (range 0.002-0.006 inches).

The barb tip (255) can be formed from a metal, polymer, or from a biodegradable material such as polylactic acid, for example. The barb tip (255) extends outwards for a distance of 2 mm (range 1 to 4 mm) such that the barb tip (255) will not be able to reach outwards beyond the mitral annulus (20) and extend into the circumflex artery or other inappropriate tissue. The barb should have adequate surface area to ensure that the stent frame (15) does not migrate toward the LA (80) due to pressure and force applied by the LV (165) onto the stent frame; the barb strut (260) can be formed with a flattened shape (see FIG. 20B), for example, to maximized the area of the barb tip (255) that is resisting the migration force imposed by the LV (165) blood pressure. The flattened barb tip (255) can have a dimension ranging from 0.003-0.010 inches in each perpendicular direction forming the barb tip area. Each structural element of the waist (10) (i.e., a zig-zag repeat segments, for example) can contain one or more barbs (25) such that the number of barbs (25) along the perimeter of the waist (10) can range from as few as 8 to 40 or more barbs (25). Under the condition that over 40 barbs (25) are placed along the waist (10) of the present stent frame, the length of the barb tip (255) can be reduced to less than 2 mm; for a smaller number of barbs (25), the barb length would extend out at length nearer the upper tip distance range. Approximately 16 barb tips (255) (range 8-40 barb tips) are positioned equally along the perimeter of the waist (10) and extend radially into the native heart tissue for a distance of 3 mm (range 2-5 mm) to hold the stent-frame waist (10) from migrating toward the LA (80) due to LV (165) pressures of 200 mm Hg.

The barbs (25) ensure that the frame (15) of the present invention along with the frictional forces provided by the waist (10) and upper bulb (70) will not migrate towards the LA (80) during the systolic cycle of the heart and also assist in preventing migration into the LV (165) during diastole. It is understood that the barb struts (260) can be formed to be contiguous with the waist (10) portion of the frame (15) or can be attached to the waist (10) portion of the frame (15) via alternate attachment methods including adhesives, brazing, welding, thermal bonding, swaging, crimping with ferrules, and other attachment methods.

Found along the waist perimeter (30) of the single member stent-valve (5) or the first component (200) of the dual member stent-valve (195) embodiment is a limiting cable (225); additional limiting cables (210) can also be located along other perimeters of the frame. The limiting cable (225) can extend through each of the ferrules (250) that are located along a perimeter of the frame; the ferrules (250) can be crimped closed to prevent the stent frame struts (267) of the waist (10) portion of the stent frame (15) from extending outwards beyond a specified preset perimeter. The limiting cable (225) is formed from multiple filaments or other construction and construction materials described previously that are very flexible. The presence of the limiting cable (225) allows the waist (10) portion of the frame (15) of a single member stent-valve (5) to exert a larger (larger than a standard stent of the same diameter) frame outward force (65) prior to being limited by the limiting cable (225) (i.e., equal to a 6 atm (range 2-20 atm) dilation balloon of 35 mm diameter) to ensure that the annulus (20) is formed into a round shape and that direct contact is made between the waist (10) and the annulus (20) along the entire perimeter such that a good seal is created to prevent leakage of blood between the frame (15) and the annulus (20). For a dual member stent-valve assembly the presence of a limiting cable (225) in the waist (10) of the support component or first component (200) that is positioned adjacent to the annulus (20) to provide a defined perimeter ring into which a second component (190) (or valve component) can be delivered to form a frictional or geometric lock between the first component (200) and second component (190); this is further described in later embodiments. The limiting cable (225) prevents the waist (10) from continuing to exert an outward force onto the annulus (20) that can result in unwanted dilation of the annulus (20) which is often times already too large in diameter and is the cause of the mitral regurgitation that is being addressed by the present mitral valve replacement device. A torus shaped dilation balloon (35) (described further in later embodiments) can be dilated to generate a balloon outward force (228) to push the barb tips (255) outwards into the native mitral valve annulus (20) or adjacent tissue to fixate the stent-valve and prevent migration of the stent-valve. Backing member or backing element (450) provides the support for the torus balloon (35) to push against to generate the outward force (228) to move the barb (25) outwards during balloon inflation. The dilation balloon can alternately be replaced by a cylindrically shaped braided expansion member or other expansion member that allows blood flow to pass freely across the expansion member while in an expanded configuration.

FIGS. 4A to 4B show the frustum-shaped or hyperboloid-shaped housing (130) (i.e., frustum-like housing (130)) attached downstream to the cylindrically-shaped waist or curved-shape waist (40) that is located adjacent to the annulus (20). The device as shown in FIGS. 4A-4C can be a single member stent-valve (5) that contains replacement leaflets (270) and is delivered with the frame waist (10) adjacent to the mitral annulus (20). In this embodiment three leaflets are located within the housing (130), however, the present invention can instead include only two leaflets or up to four leaflets. The leaflets are attached to the wall of the housing (130) in a crown-shaped leaflet attachment (275) having the nadirs (280) of the leaflets located at the base of the housing (130) as shown in FIG. 4A, the nadirs can alternately be located between the housing base (135) and the housing top as shown in FIG. 4B or can be located in the waist. The attachment of the leaflets to the housing (130) can be via direct attachment of the leaflets to the struts (267) of the housing frame (130) or to the fabric or covering (285) that is attached to all or part of the housing frame (130). Various forms of attachment of the leaflets can be used including suturing, adhesives, polymer bonding, thermal bonding, and other forms of attachment. In an alternate embodiment the leaflets can be attached to both the housing (130) and the waist (10) as shown in FIG. 4C where the nadirs of the leaflet attachments (275) are located at the junction (290) of the waist (10) and the upper bulb (70) such that the housing length (185) extending in an axial direction (90) from the waist (10) to upper bulb junction (290) to the housing outlet end (145) is reduced, thereby reducing the likelihood for impingement of the housing (130) onto the anterior native mitral leaflet.

In an alternate embodiment, the device shown in FIGS. 4A-4C can be a second member or second component (190) of a dual member stent-valve (195); the second member that contains replacement leaflets (270) would be implanted within the lumen of a first member (or support member) that is initially implanted across the mitral annulus (20) and attached to the native heart tissue via barbs (25) as described in other embodiments.

Figure 5A:
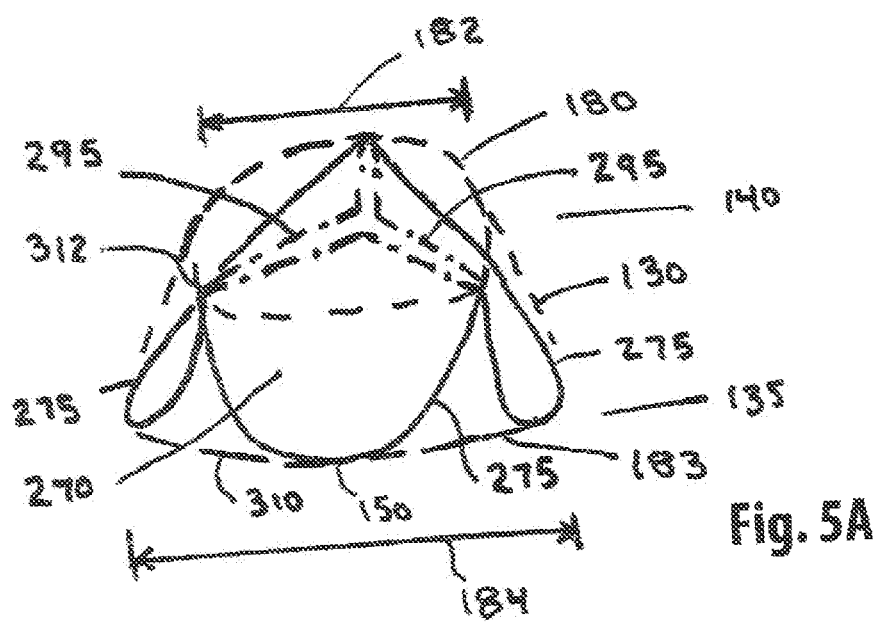
FIG. 5A is a perspective view of frustum shaped leaflets having a free edge perimeter that is smaller than the leaflet base perimeter located at the nadirs of the leaflets.
Figure 5B:
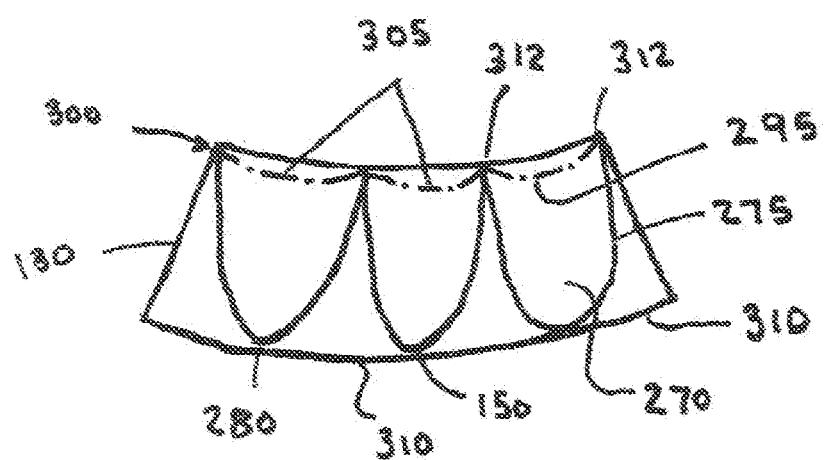
FIG. 5B is a plan view of frustum-shaped leaflets that have been splayed out onto a flat surface showing a smaller free edge perimeter than the leaflet base perimeter.

As shown in FIGS. 5A and 5B the leaflets themselves form a frustum-like shape or hyperboloid-like shape that fits precisely within the frustum-shaped or hyperboloid-shaped housing (130). Each leaflet has a free edge (295) that forms a leaflet top (300) and that resides at or near the level of the housing top (or downstream end) of the housing (130); the leaflet free edge (295) has a smaller leaflet free edge perimeter (305) than the housing top perimeter (180); the nadirs (150) of the leaflet attachment (275) to the housing (130) follow a leaflet base perimeter (310) that coincides with the larger housing base perimeter (183) located at the housing base (135). The pressure forces from the LV acting on the free edges (295) of the leaflets and the leaflet regions nearest the free edges (295) are lower due to the reduced area of exposure at the smaller downstream end of the frustum; the leaflets are less likely to undergo stress fracture failure. The housing base perimeter (183) is equal to Pi*D where D is the housing base diameter (184); the housing top perimeter (180) is Pi*d where d is the housing top diameter (182). FIG. 5A shows a perspective view of the free edges (295) of the leaflets coaptation with each other to prevent flow of blood during systole from the housing top toward the housing base. Upon cutting the frustum-shaped housing (130) along one side and splaying it open as seen in FIG. 5B, one can view the free edges (295) of the three leaflets and the crown-shaped attachment of the leaflets to the frustum-shaped housing (130). The replacement leaflets (270) are attached to the housing top at three commissures (312); the free edges (295) of the leaflets also join to their neighboring leaflet at the commissures (312). The replacement leaflets (270) are attached to the housing (130) along the frustum-like shape of the housing (130) and thereby themselves have a frustum-like shape when the cut edge is closed as shown in FIG. 5A.

The replacement leaflets (270) can be formed from various types of tissues including pericardial tissue or tissues taken from a variety of animal sources. The tissues are often treated via a crosslinking process including glutaraldehyde processing, for example. Other leaflet material include polymer film, ePTFE, Dacron fabric, polyethylene terephthalate film or fabric, polyurethane, composite materials Including Nitinol formed as a composite thin leaflet, or other thin and strong materials that are suitable for implant. A metal frame such as Nitinol, for example, or alternately, fibers can be sandwiched between or contained between polymeric film or tissue film members to provide strength and proper flex characteristics to the replacement leaflets (270); leaflet axial strain of up to 15% is attained during the systolic portion of the heart contraction cycle in comparison to diastole; circumferential strain is limited to less than 10% during systole.

Figure 6A:
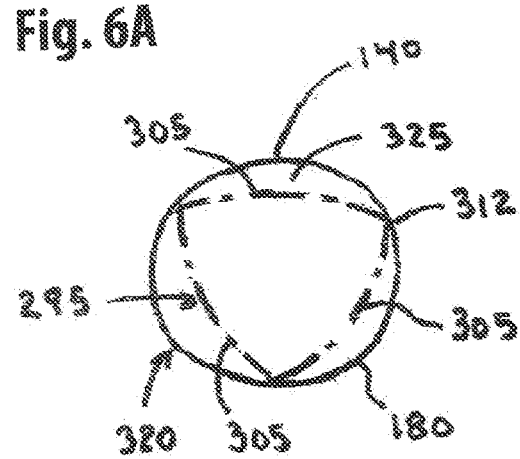
FIG. 6A is a plan view of the cross-section of the housing top viewing the leaflet free edges in an open configuration and having a spacing between the leaflet free edges and the housing top of the frame.
Figure 6B:
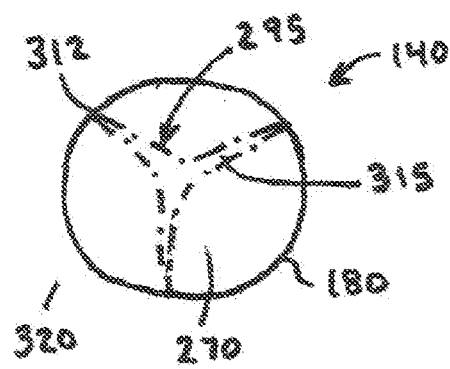
FIG. 6B is a plan view of the cross-section of the housing top viewing the leaflet free edges in a closed configuration.

FIGS. 6A and 6B show an end view of the housing top (140). FIG. 6A shows the leaflets in an open condition as found during diastole; the free edges (295) of the leaflets do not make contact with the housing wall (320) at the housing top (140). The leaflet free edge perimeter is 10% (range 5-20%) less than the housing top perimeter (180). This perimeter difference provides a gap or spacing (325) between the free edges (295) of the leaflets and the housing top between respective commissures (312) to allow for blood flow to the back side or LV (165) side of the replacement leaflets (270) during systole to ensure that the leaflet is properly cleansed by blood flow and reduce thrombus formation, and also provide direct access for blood pressure to assist in closing the leaflets during systole when the native leaflets can be pushed via blood pressure into contact with the housing (130). The leaflet free edge can be seen to be attached to the housing top at each of the three commissures (312). FIG. 6B shows the free edge of the leaflets at the level of the housing top in a closed configuration as found during systole. Here the free edges (295) are seen coapting or touching the free edge of a neighboring leaflet forming a leaflet coaptation (315) to prevent blood flow from the LV (165) to the LA. In an alternate embodiment the spacing (325) can be eliminated allowing the leaflet free edge (295) to come into direct contact with the housing top (140) or other surface of the housing (130).

Figure 7D:
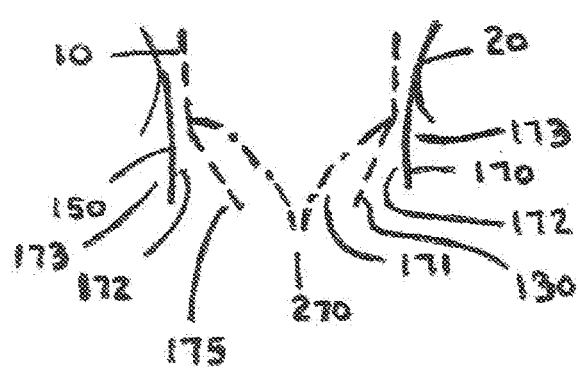
FIG. 7D is a plan view of the single member stent valve identifying the surfaces of the replacement leaflets and the native valve leaflets and flow features of the present design intended to prevent thromboemboli from forming.
Figure 7A:
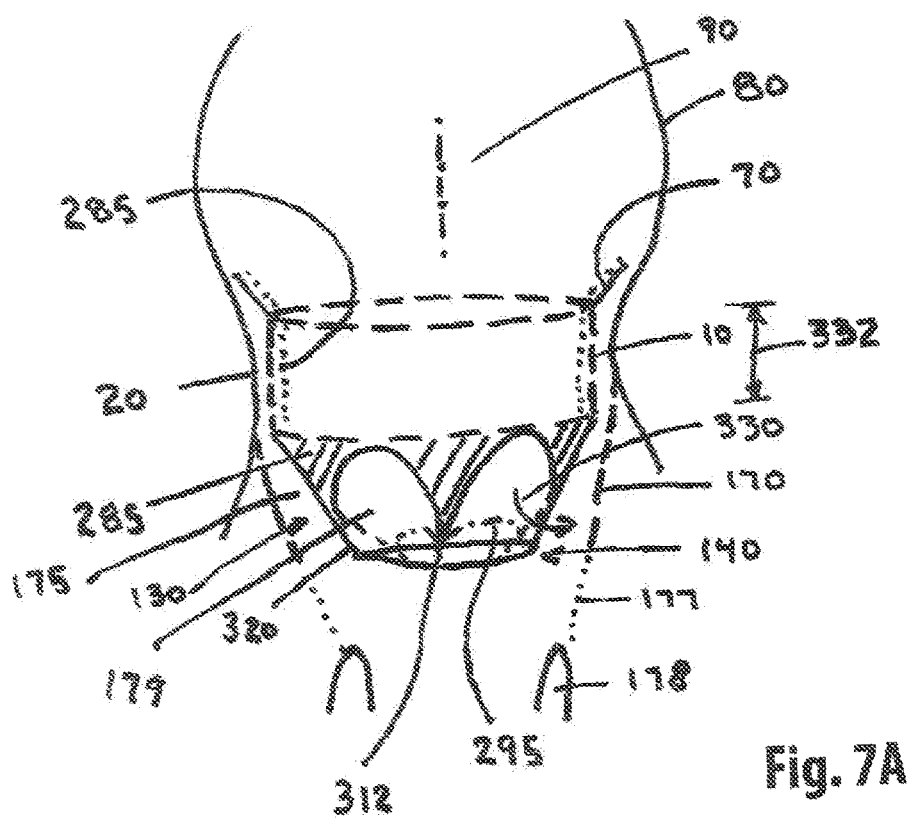
FIG. 7A is a perspective view of single member stent valve having a covering over a portion of the housing and providing an open area for blood flow through the open frame housing during diastole.

FIGS. 7A-7C show the waist, the upper bulb (70), and housing (130) and the fabric or covering (285) that is attached to all or part of the single member stent-valve frame. The fabric can be sewn, bonded by adhesive, or otherwise attached to the frame (15) of the waist, the upper bulb (70), or the housing (130). The fabric can be formed from an expanded polytetrafluoroethylene (ePTFE), Dacron, a woven fabric, or other thin material that will not let blood flow across its wall thickness. As shown in FIGS. 7A and 7B the fabric is attached along the entire perimeter of the waist (10) and along the entire waist length (332) in the axial direction (90); the fabric extends at least to cover the surface of the housing (130) extending from the housing base (135) to crown-shaped line of attachment of the leaflets to the housing (130). The fabric can also extend to cover the surface of the upper bulb (70) to assist in preventing leakage between the frame (15) and the surrounding tissues of the annulus (20) and LA. The fabric extends to each of the three commissures (312). The remainder of the housing surface (175) is an open housing surface (179)(i.e., without a covering (285)) that allows radial blood flow (330) through the non-covered wall of the housing (130) through the open housing surface (179). As shown in FIG. 7A radial blood flow (330) can occur at the early start of systole into the outlet end of the housing and flow out of the open housing surface (179) as systolic blood flow that will keep the outer surfaces (171) of the replacement leaflets (270) clean and free of thrombotic deposition. During diastole a diastolic blood flow of blood can occur in the form of a recirculation pattern through the open housing surface (179); this blood flow can also help to keep the outer surfaces (171) of the replacement leaflets (270) clean. The native leaflets have blood flow across their inner or central surfaces (172) from the systolic radial blood flow and from the diastolic blood flow to maintain the native leaflets in a condition of pivotal movement at its attachment to the mitral annulus (20) from a leaflet location adjacent the housing outer surface (175) during middle to late systole as shown in FIG. 7B to a location that is removed or separated from the housing outer surface (175) toward the lateral wall of the LV (165) during early systole and during diastole as shown in FIG. 7A.

As shown in FIG. 7C, in an alternate embodiment the fabric or covering (285) can be attached to the entire outer surface of the housing (175). The fabric can also be attached along the waist (10) and can be attached to the upper bulb (70). In this embodiment the native leaflets would tend to position themselves against the housing outer surface (175) during early systole, late systole, and during diastole since blood cannot flow across the housing wall (320) if the housing (130) has a fabric or covering (285). The inner surface (172) of the native leaflets would tend to become attached to the fabric that is located on the housing outer surface (175). The frustum-like shape of the housing (130) allows the native leaflet to lie flat against the outer surface of the housing (175) without restriction from the chordae tendineae. Also, no aspect of the present frame (15) pushes outward on the leaflet with a radial outward component that would limit the ability of the native leaflets from moving into direct apposition with the entire housing outer surface (175). The native leaflets that are in contact with the present housing (130) tend to become healed against the housing outer surface (175) across their entire inner surface thereby eliminating any source for thrombus. Since the housing has a frustum-like shape, the native leaflets can fit snugly against the housing outer surface (175) without the presence of pockets or open areas that can result in thrombus formation. Thus, the shape of the frustum or hyperboloid housing (130) is necessary to ensure that the native leaflets can approximate the housing outer surface (175) and not be held away from the housing (130) by the chordae tendineae or by any structure of the stent-valve frame (15) that can hold the native leaflet from making full approximation with the housing outside surface (175). The outer native leaflet surface (173) would remain free of thrombus due to the direct access to blood flow during systole and the recirculation blood flow in the LV (165) during diastole thereby preventing thrombus formation on the outer surface of the native mitral valve leaflets.

The device of FIGS. 7A-7C and alternately describe a second component (190) (or valve member) of a dual member stent-valve (195). The second component (190) would be delivered into the open central lumen (265) of a first component (200) that was delivered initially across the native mitral annulus (20). The second component waist (205) of the second component (190) stent-valve frame (15) would be positioned adjacent to the waist (10) of the first component (200) as described in subsequent embodiments.

During the method of use for the single member stent-valve (5) the delivery sheath (105) enters the mitral annulus (20) with the waist (10) of the frame (15) located adjacent to the mitral annulus (20) and the sheath is withdrawn partially while holding the pusher member (122) in a fixed position (see FIG. 1A). As the delivery sheath (105) is withdrawn the waist (10) expands out into contact with the mitral annulus (20), the upper bulb (70) expands out into contact with the LA, and the housing (130) is positioned across the native leaflets of the mitral valve. The recapture struts (100) are being held by the release cords that are extending within the pusher tube. If the operator does not consider that the waist (10) is properly positioned adjacent to the mitral annulus (20), the stent-valve can be withdrawn back into the delivery sheath (105) by pulling back with tension onto the pusher while maintaining position of the delivery sheath (105); alternately the stent-valve can be withdrawn by applying tension onto the pusher while advancing the delivery sheath (105) forward under compression. If the position of the stent-valve is acceptable, the recapture struts (100) are released by the release cords such that the recapture struts (100) expand outwards with low radial force into contact with the wall of the LA. The recapture struts (100) are thinner and more flexible than the struts (267) of the waist (10) and the upper bulb (70); their purpose is to allow the frame (15) to be withdrawn into the delivery sheath (105) and the entire frame (15) can be repositioned relative to the axial position of the waist (10) with the annulus (20) or for improved axial alignment such that the device axial direction (90) is collinear with the axial direction (90) of the mitral annulus (20).

As described in earlier embodiments shown in FIGS. 3B-3D balloon expandable fixation elements such as barbs (25) can be attached to the waist portion (i.e., the waist (10)) of the stent frame (15) (i.e., the waist (10), the upper bulb (70), and the housing (130)) of the stent-valve of the present invention. A dilation balloon having a cylindrical shape, hour-glass shape, or other shape can be used as a post dilatation tool to activate the barbs (25) comprised of a barb strut (260) and barb tip (255) by pushing the barb tips (255) outwards into the tissues of the mitral annulus (20). Such a dilation balloon would also block the blood flow across the mitral annulus (20) when it was being inflated thereby negatively affecting blood flow output from the heart to critical tissues of the body including the brain. Furthermore, an inflated balloon can be pushed toward the LA (80) via LV (165) pressure during systole; interaction of the inflated balloon with the stent frame (15) can cause the stent frame (15) to also move toward the LA (80) placing the stent frame (15) in an incorrect position with the waist (10) no longer positioned appropriately adjacent the mitral annulus (20). To address these concerns a torus-shaped balloon (i.e., torus balloon (35)) is presented that activates the balloon expandable fixation elements by applying a balloon outward force (228) to pushes the barbs (25) outwards into the tissues of the mitral annulus (20) and allows blood flow through the central regions of the torus balloon (35) during balloon inflation. The torus balloon (35) in one embodiment is inflated with saline or other similar physiological fluid or solution; the saline is provided an exit opening or balloon port that is used to inflate the torus balloon (35) and also provide a leakage path for fluid to leak out of the torus balloon (35) after the barbs have been activated to an outward position into the annulus or other valve tissue. The leakage path can be via the balloon port; alternately, the fluid can leak out of the balloon via migration of the fluid through the material (such as ePTFE) used to form the wall structure of the torus balloon. The torus balloon (35) of one embodiment is permanently attached to the stent frame (15) and hence is implanted along with the stent frame (15) within the heart; in other embodiments the torus balloon (35) can be removed from the stent frame (15) after the torus balloon (35) has been inflated to activate the barbs (25) and subsequently deflated. In still another embodiment the torus balloon (35) can be filled with a curable polymer, gel, or foam and is retained within the torus balloon (35) and is not allowed to leak out of the balloon following activation of the barbs (25).

Figure 8C:
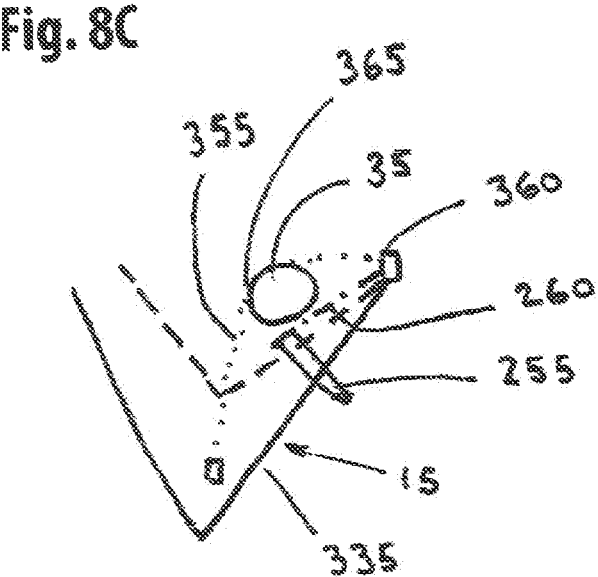
FIG. 8C shows a perspective side view of two frame stent struts and the attachment of the balloon to the frame and attachment of the barb struts to the frame via ferrules; the torus balloon is inflated and the barb tips extend to the outside of the frame.

FIGS. 8A-8D show an embodiment for the waist (10) of the stent frame (15) for a single member stent-valve (5) or for the first component (200) of a dual member stent-valve (195). The frame waist (10) is attached to the annulus (20) via barbs (25) which are activated to force the barbs (25) outward into the annulus (20). The waist (10) of a first component (200) is positioned upstream (95) of the native mitral valve leaflets to reduce interference with native mitral leaflet function. The waist (10) is shown with a torus balloon (35) attached to the waist (10) of the stent frame (15) although it is understood that the torus balloon (35) could be attached to the upper bulb (70) of the stent frame (15) or to the housing (130) of the single member stent-valve. The waist (10) in this embodiment has a frame (15) with from an open cell wall structure but it could equally be formed from a closed cell construction or other wall structures found in stent and stent-valve devices. In this embodiment the waist (10) is formed from a zig-zag structure (335) having generally straight stent struts (267) that are joined or contiguous with bent regions (340). This embodiment is shown having ferrules (250) that are located along a perimeter at the waist inlet end (215) or upstream end and waist outlet end (125) or downstream end although it is understood that other stent frame (15) structures without ferrules (250) can be used without deviating from the present invention. The ferrules (250) can be used to attach the barb strut (260) to the waist (10) as shown in FIG. 8A; alternately the barb strut (260) can be formed contiguously with the stent struts (267) or can be attached to the stent frame (15) via an attachment method such as welding, brazing, or via adhesives and not require the ferrules (250) as part of the stent frame. The barb struts (260) are formed from a balloon expandable (BE) material such as stainless steel or other plastically deformable material used in stent construction. At one end of the barb strut (260) is a barb tip (255) that is sharp and pointed outwards toward the outside (350) of the stent frame. The barb tip (255) is 2 mm long (range 1-5 mm) such that it can extend to the outside of the stent frame (15) by 2 mmm upon activation into the mitral annulus (20) to hold the stent frame (15) from migration toward the LA. The barb tip (255) can be formed into a flattened shape to enhance the area of contact with the tissue to prevent migration of the stent frame. When the barb tip (255) is inactive, it rests within the frame luminal side (345) and does not extend to the frame outside (350). Located adjacent to and in direct contact with the barb strut (260) towards the inside of the stent frame (15) is the torus balloon (35). The torus balloon (35) of this embodiment is in direct contact with the stent struts (267) and also with barb struts (260). The torus balloon (35) is adjacent to the annulus (20) but does not make contact with the mitral valve leaflet surface on the side of the leaflets that is adjacent to the LV (165) wall or adjacent to the LVOT. In some embodiments the torus balloon (35) is in direct contact with the mitral annulus (20). The torus balloon (35) can be attached directly to the frame struts (267) or the ferrules (250) of the waist (10) of the stent frame (15) via adhesives, sutures, or other bonding methods. Alternately, the torus balloon (35) can be attached to the frame (15) via balloon attachment members (355) that attach to frame attachment sites (360) located on the stent frame. The balloon attachment members (355) are aligned with the barbs (25) in a radial direction such that the balloon attachment members (355) provide a backing support to transfer the outward forces (228) of balloon inflation onto the barbs (25) to move the barbs (25) radially outwards during balloon inflation. The balloon attachment members (355) can be formed from polymer or metal fibers or sutures that can support tension of 5 lbs. (range 1-10 lbs.). The balloon attachment members (355) can be attached to the torus balloon (35) at balloon attachment sites (365); balloon attachment sites (365) for joining the attachment members (355) to the torus balloon (35) can be made via adhesives, fiber attachment, and other bonding methods.

Figure 8D:
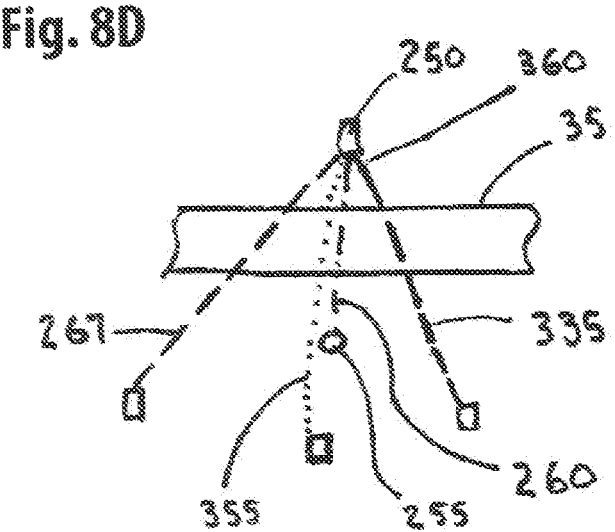
FIG. 8D shows a perspective frontal view of two frame stent struts and the attachment of the balloon to the frame and attachment of the barb struts to the frame via ferrules.

Shown in FIGS. 8B-8D are specific portions of the stent frame (15) as described in FIG. 8A. In FIG. 8B stent struts (267) located at the right side of the waist (10) in FIG. 8A are depicted along with a deflated torus balloon (35) located adjacent to the inside of the barb strut (260). The torus balloon (35) is attached to the stent frame (15) at the stent struts (267), the bent regions, or at the ferrules (250) via attachment members (355). The attachment can be made via a cable or a stent frame member that attaches directly to the torus balloon (35) or provides a support that directs the torus balloon (35) inflation radially outwards into a direction that applies a radially directed balloon outward force (228) against the barb thereby advancing the barb tip (255) into the annulus (20) located outside (350) of the perimeter of the stent frame waist. Upon inflation of the balloon as shown in FIG. 8C the barb strut (260) is pushed outwards placing the barb tip (255) extending outside (350) of the stent frame and into the tissue that surrounds the stent frame (15). A frontal view of the torus balloon (35) located behind a barb strut (260) and also behind (i.e., on the luminal side (345) of) two stent struts (267) is shown in FIG. 8D. The torus balloon (35) can be attached directly to stent struts (267); such balloon attachment sites (365) can be formed with adhesives, polymeric coatings, and other bonding methods. The barb tip (255) faces forward (i.e., toward the observer) and will be pushed further forward as the torus balloon (35) is inflated. Inflation of the torus balloon (35) will push the barb tip (255) outwards to the outside (350) of the stent frame; the torus balloon (35) of this embodiment will remain on the inside of the stent frame (15) and hence will not push the stent frame (15) away from the mitral annulus (20).

Figure 9A:
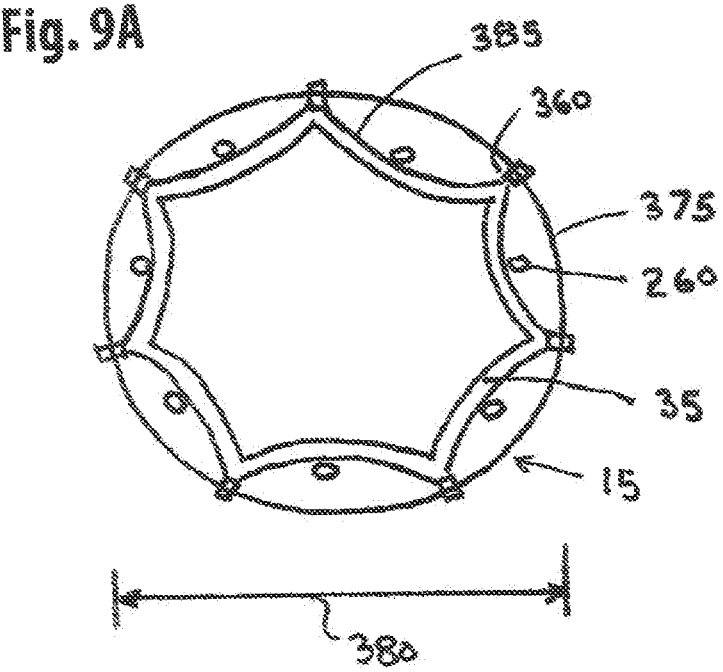
FIG. 9A is a top plan view of the torus balloon attached to the frame with barb struts located to the outside of the outer torus balloon perimeter.
Figure 9B:
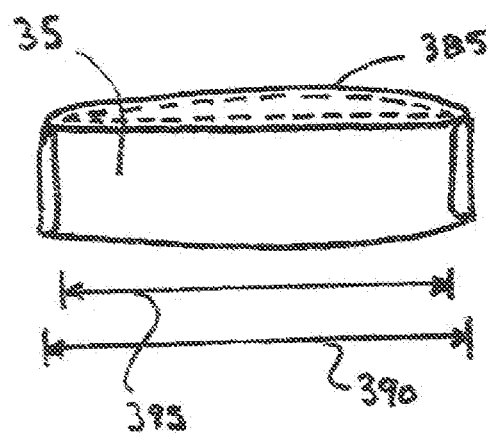
FIG. 9B is a perspective view of the torus balloon showing the balloon diameters and perimeter.

FIGS. 9A and 9C show a top view of the waist (10) region of the stent frame (15) with the torus balloon (35) having balloon attachments (365) made directly to the stent frame (15) or to the ferrules (250). The waist (10) can be a portion of a stent frame (15) of a single member stent-valve (5) or for a first component (200) (i.e., support member) of a dual member stent-valve (195). The balloon attachments of the balloon to the stent frame (15) can be via an adhesive, via thermal bonding, via encapsulation of the stent struts (267) with a polymer, via sutures, or via other attachment methods available to the medical device industry. The torus balloon (35) is attached to stent frame (15) along the stent frame perimeter (375); the torus balloon (35) extends around the inside of the barb struts (260). As shown in FIG. 9A the torus balloon (35) is in a deflated configuration, the inner perimeter and outer perimeter (385) of the torus balloon (35) in a deflated configuration having a flattened shape and similar inner and outer perimeter (385) as seen in FIGS. 9A and 9B; the torus balloon (35) extends around the inside or frame luminal side (345) of the barb struts (260) and also can be attached to the stent frame.

As shown in FIG. 9C the torus balloon (35) is inflated thereby interfacing with and applying a radially directed balloon outward force (228) to the barb strut (260) causing the barb tip (255) to extend to the outside (350) of the stent frame (15) by 3 mm (range 2-5 mm). The torus balloon outer perimeter (385) of the inflated torus balloon (35) of this embodiment has a balloon outer perimeter (385) that is equal to (range equal to 2 mm greater than) the stent frame perimeter (375) in the waist. The torus balloon inner perimeter (388) is supported by a backing element (450) to allow the inflated torus balloon (35) to push or move the barbs (25) outwards with an outward force (228) such that the barb tips (255) extend to the outside (350) of the stent frame (15). The torus balloon outer diameter (390) is equal to the stent frame diameter (380) of the waist (10) and has a diameter of 35 mm (range 28-45 mm). As shown in FIG. 9D the torus balloon inner diameter (395) in an inflated configuration is smaller than the torus balloon outer diameter (390); the torus balloon cross sectional diameter (400) is 3 mm (range 2-10 mm). The larger torus balloon cross sectional diameter obtained during balloon inflation will provide greater travel distance for the barb strut (260) to extend outwards from an inactive to an active configuration. The larger torus cross section diameter also provides a greater outward force (228) from the torus balloon (35) against the stent frame. The small torus balloon cross sectional diameter will not impact to a significant degree the profile of the stent-valve frame (15) in its delivered configuration and will allow a unrestricted blood flow through its central region in an inflated configuration. The torus balloon inner diameter (395) in an inflated configuration is 25 mm (range 15-31 mm). The torus balloon perimeter (388) provides an open central torus balloon lumen (386) that will not restrict blood flow from the LA to the LV when the torus balloon (35) is inflated.

Inflation of the torus balloon (35) not only activates the barb causing the barb tip (255) to extend into the tissues of the mitral annulus (20) but the torus balloon (35) also improves the contact of the stent frame (15) with the mitral annulus (20). Inflation of the torus balloon (35) causes the torus balloon cross section to take a circular cross sectional shape. This circular cross sectional shape counteracts the desire of the torus balloon (35) to form a kink along its perimeter and hence provide an outward frame expansion force (405) to push the stent frame (15) into intimate contact with the mitral annulus (20). The greater the inflation pressure the greater the outward frame expansion force (405) that can be applied to the stent frame. To improve the outward frame expansion force (405) as well as the balloon outward force (228) pushing on the struts the inflation pressures can exceed 10 atmospheres (range 5-20 atm), if necessary for full frame expansion and for full barb activation. A fiber winding or a braid can be contained within the wall of the torus balloon (35) to provide increased strength to the balloon and allow for higher levels of inflation pressure. Although much lower pressures of 5 atm (range 2-10 atm) are needed to push the barb struts (260) outwards, using a larger inflation pressure will provide proportionally greater outward frame expansion forces (405) by the torus balloon (35) against the waist (10) of the stent frame. In some embodiments of the present invention, portions of the torus balloon (35) makes direct contact with the tissues of the mitral annulus (20) and the inflation medium is held within the interior of the torus balloon (35) following delivery and release of the stent-valve; in these embodiments the torus balloon (35) also contributes to forming an improved seal with the mitral annulus (20) to prevent perivalvular leak.

The torus balloon (35) can be formed from a variety of polymeric materials used to form dilation balloons used in angioplasty. A noncompliant material such as polyethylene terephthalate, for example, can be used to form the torus balloon (35). Alternately, a semicompliant material such as Nylon, Pebax, or a compliant material such as polyurethane can be used; the compliance curve will dictate the inflation pressure that is used to match the perimeter (375) of the stent frame (15) in an inflated configuration. The torus balloon (35) can be formed using balloon blowing processing, for example, in a torus-shaped mold that sets the torus shape into the equilibrium shape of the torus balloon (35). The torus balloon (35) can have one balloon port (410) located at one end of the torus balloon (35) and a dead-end or leak-tight blockage at the other end of the balloon; alternately, the torus balloon (35) can be formed with two balloon ports, one at each end of the torus balloon (35) as shown in FIG. 9D. The torus balloon (35) can also be formed into a complete loop or doughnut shape but with a balloon port to allow for inflation.

FIGS. 10A-10C show an embodiment having the torus balloon (35) contained in a balloon pocket (415) of a balloon holder (420) and having the balloon holder attached to the stent frame (15) via a holder attachment (425). The stent frame (15) can be used as a portion of a single member stent-valve (5) device or as a support member (i.e., first component (200)) of a dual member stent-valve (195). The first component (200) can be an adapter that is able to provide a fixed ring structure attached to the annulus (20) into which a second component (190) (i.e., valve member) can be positioned and implanted. FIG. 10A shows the balloon holder attached to the ferrule (250) of the waist (10) or attached to the stent frame (15) wall structure on the inside of the stent frame (15) or stent frame luminal side (345). The balloon holder wraps around the barb strut (260) toward the inside surface of the barb strut (260). The torus balloon (35) is placed within a balloon pocket (415) formed from the balloon holder in a deflated configuration as shown in FIG. 10A. The balloon holder provides protection to the torus balloon (35) from accidental puncture of the balloon and allows direct attachment of the balloon holder with the stent frame (15) without potentially damaging the torus balloon (35). The balloon holder has an inner layer (430) that faces the luminal side (345) of the stent frame (15) and an outer layer (435) that faces the barb strut (260). The balloon can either float freely within the pocket of the balloon holder or it can be held in place via an adhesive, for example. Upon inflation of the torus balloon (35), the balloon assumes a circular cross sectional shape and applies an outward force (228) against the barb and pushes the barb tip (255) to the outside (350) of the stent frame (15) as shown in FIG. 10B. As shown in FIG. 10C the balloon holder can be attached to the stent frame (15) at the ferrules (250), to the stent struts (267) of the waist, to the bent regions of the stent frame. The holder attachment can be made via sutures, adhesives, thermal bonding, entrapment of the stent frame (15) by the balloon holder, or other attachment methods.

The materials for the balloon holder (420) can include woven fabric, velour, fibrous films, porous films, polymer films that are commonly used in medical device implants.

The balloon holder (420) can also serve as a skirt or fabric covering (285) that covers the stent frame (15) and prevents flow of blood across the stent frame wall (440) of the stent frame (15) from the inside or luminal side (345) to the outside (350) of the stent frame (15). The balloon holder (420) can alternately be comprised of only one layer such as the inner layer (430) that faces the luminal side (345), for example, or only the outer layer (435) that faces the outside (350). The torus balloon (35) can be attached to the inner layer (430), for example, via an adhesive, for example. The inner layer (430) or the outer layer (435) can serve as a fabric covering (285) that prevents fluid flow across the stent frame (15) from the luminal sided (345) to the outside (350) of the stent frame (15). This pocket construction to hold the torus balloon (35) or use of an inner layer (430) or use of an outer layer (435) to hold the torus balloon (35) and serve as a fabric covering (285) can be used in any of the embodiments found in the present specification of a stent frame that comprises a torus balloon (35).

Figure 11A:
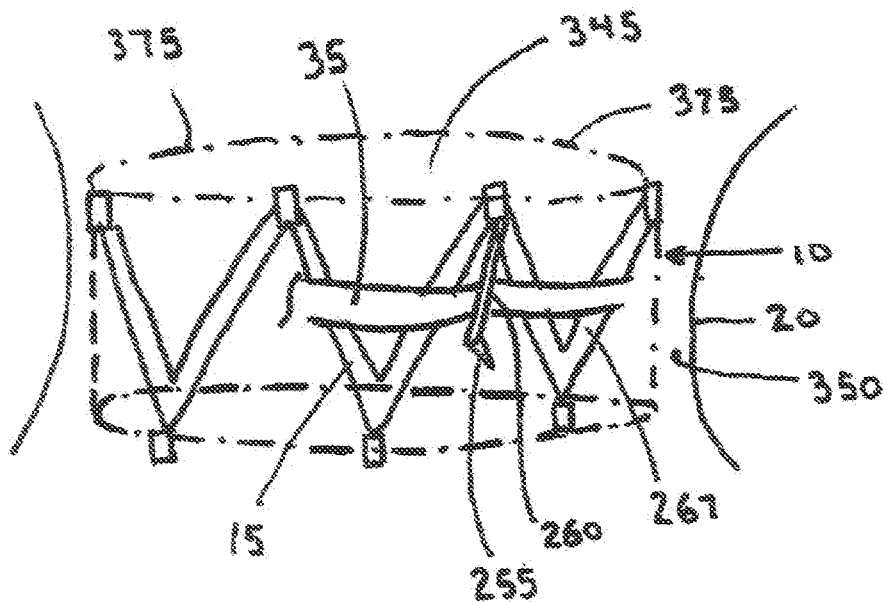
FIG. 11A is a perspective view of a torus balloon that weaves on the outside of two stent frame struts and on the inside of the barb struts as a portion of the drawing of FIG. 11A.
Figure 11B:
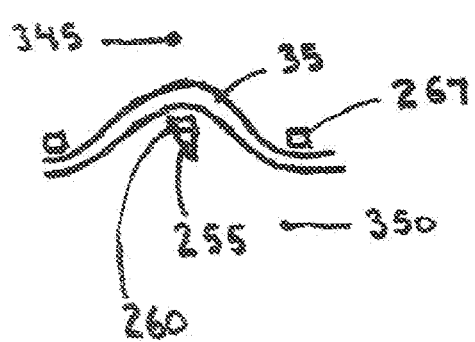
FIG. 11B is a plan view from the top of a frame waist showing the torus balloon extending on the outside of the frame struts and on the inside of the barb struts.
Figure 11C:
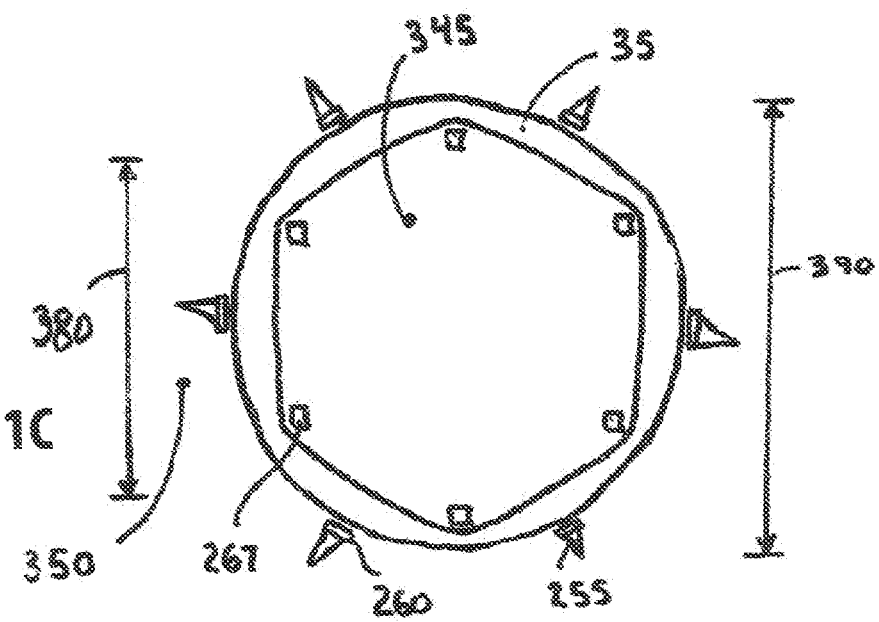
FIG. 11C is a plan view from the top showing the torus balloon weaving to the outside of the frame struts and inside of the barb struts; the balloon is inflated and the barb tips extend to the outside of the frame.

Another embodiment for placement and attachment of the torus balloon (35) within the waist (10) region of a stent frame (15) that is applicable to either a single member stent valve (5) or a first component (200) of a dual member stent-valve (195) is shown in FIGS. 11A-11C. FIG. 11A shows a waist (10) of a stent frame (15) with a deflated torus balloon (35) being placed along the outside (350) of the stent struts (267) and along the inside or luminal side (345) of the barb struts (260). The balloon can be attached to the stent struts (267) and/or the barb struts (260) via an adhesive, for example; the torus balloon (35) can alternately be allowed to move relative to the stent struts (267) and barb struts (260). FIG. 11B shows a top view of two stent struts (267) and a barb strut (260) located in between the stent struts (267); a portion of a torus balloon (35) is shown weaving to the outside of the stent struts (267) and to the inside of the barb strut (260). Upon inflation of the torus balloon (35) as shown in FIG. 11C, the barb tip (255) is pushed outwards placing the barb tip (255) to the stent frame outside (350) and outside of the stent frame perimeter (375) formed by the two stent struts (267). In this embodiment the inflated balloon outer diameter (390) is larger than the stent frame diameter (380) in the waist (10) at a location of the barb struts (260) and barb tips (255). The location of the torus balloon (35) on the outside (350) of the stent frame (15) and on the outside (350) of the stent struts (267) places the torus balloon (35) into direct contact with the tissues of the mitral annulus (20) and the torus balloon (35) forms a direct seal between the mitral annulus (20) and the stent frame. The torus balloon (35) can conform to irregularities in the shape of the mitral annulus (20) and form a continuous seal that will prevent perivalvular leaks between the stent-valve and the mitral annulus (20). The torus balloon (35) can serve as a skirt or fabric to seal the stent frame (15) from perivalvular leaks between the stent frame (15) and the mitral valve tissues. Specific embodiments that use a polymeric material as an inflation medium (i.e., a crosslinking polymeric fluid that converts to a solid or elastomeric matrix or gel or foam) for the torus balloon (35) and also have the means (such as a duckbill valve, for example) to retain the polymeric inflation medium within the torus balloon (35) are suitable candidates for forming such a seal between the torus balloon (35) and the tissues of the mitral annulus (20). Other embodiments can use saline inflation fluid that is able to leak out of the torus balloon (35) through balloon port (410) (normally used for torus balloon (35) inflation) over time as described earlier in other embodiments.

Figure 12C:
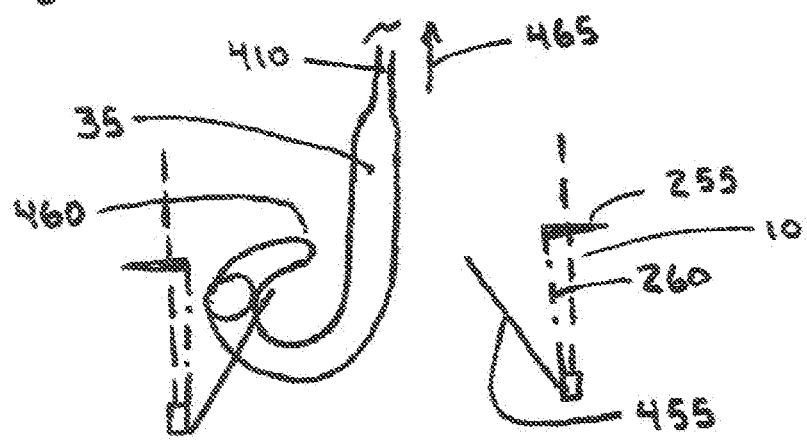
FIG. 12C is a perspective view of the torus balloon being removed from its releasable attachment to the frame following inflation of the torus balloon, activation of the barb tips, and deflation of the torus balloon.

FIGS. 12A-12C show yet another configuration for the torus balloon (35) placement along the waist perimeter (30) of the stent frame (15). The stent frame (15) can be used as a portion of a single member stent-valve (5) or as a portion of a first component (200) (or adapter) for a two-step (or dual member) stent-valve. In this embodiment the BE barb struts (260) are attached to the stent frame (15) via an frame attachment members (442) such as a ferrules (250) located at the waist outlet end (125). The BE barb strut (260) extends proximally within the inside of the stent frame (15) and has a barb tip (255) attached to the barb strut (260), the barb strut (260) extending outwards but remaining within the inside of the stent frame perimeter (375) as shown in FIG. 12A in an expanded configuration after the stent-valve has been released from the delivery sheath (105). A backing element (450) such as a stent arm (455) extends from the attachment member located at the waist outlet end (125) towards the waist inlet end (215) at a stent arm angle (445) such that the proximal end (115) of the stent arm (455) is located inwards from the barb strut (260) toward the stent frame centerline axis (45) and inward from the barb tip (255). The stent arm (455) can be a metal strut attached to the stent frame, the stent arm (455) being formed from a metal or polymeric material. The stent arm (455) is able to provide adequate support such that the barb strut (260) will bend preferentially as the stent arm (455) provides the back-up support for a torus-shaped balloon that is located between the barb strut (260) and the stent arm. The torus balloon (35) is located towards the inside of the barb strut (260) and towards the outside of the stent arm; the torus balloon (35) extends along the perimeter (375) of the stent frame (15) between stent arms and barb struts (260) located at a plurality of 16 (range 8-40) locations along the perimeter (375) of the stent frame; the torus balloon (35) is in direct contact with the stent arm (455) of the stent frame; tissue from the heart valve is not located between the stent frame (15) and the torus balloon (35).

FIG. 12A shows the torus balloon (35) in a deflated configuration with the barb tip (255) located on the inside of the stent frame; the stent frame (15) has been released from the delivery catheter and is in an expanded configuration. The torus balloon outer perimeter (385) matches approximately the expanded stent frame perimeter (375). During delivery of the stent frame (15) within the delivery sheath (105) in a nonexpanded configuration, the torus balloon (35) would be folded along its perimeter to allow for a smaller stent frame perimeter (375) and torus balloon (35) in its nonexpanded configuration within the delivery sheath (105). The torus deflated balloon is located between the barb strut (260) and the stent arm (455). One end of the torus balloon (35) is attached to a balloon port (410) that provides entry of inflation medium to inflate the torus balloon (35); the other end of the torus balloon (35) has a dead end or closed end (460) that does not allow escape of inflation medium from the torus balloon (35).

Upon inflation of the torus balloon (35) as shown in FIG. 12B, the barb strut (260) is pushed outwardly to the outside (350) of the stent frame (15) by the torus balloon (35) as the inflation forces from within the torus balloon (35) are transferred from the stent arm (455) through the torus balloon (35) to the barb strut (260) causing the barb strut (260) to extend outwards and placing the barb tip (255) to the outside (350) of the stent frame (15) and into the tissues of the mitral annulus (20). The torus balloon (35) of this embodiment is located along the perimeter on the inside or luminal side (345) of the stent frame. Following inflation of the torus balloon (35) and activation of the barbs (25) to extend outwards from the stent frame (15) and into the mitral annular tissues, the torus balloon (35) of this embodiment can be removed as shown in FIG. 12C. Upon application of tension (465) at the location of the balloon port (which extends throughout the shaft of the delivery catheter) the torus balloon (35) is pulled upwards such that it is removed from a location between the barb strut (260) and the stent arm (455) as shown in FIG. 12C. The torus balloon (35) which is formed from a soft flexible polymeric material is able to unwind (as shown in FIG. 12C) from its torus shape and be removed from its position between each of the plurality of barb struts (260) and stent arms as balloon port is placed under tension or during removal of the delivery catheter. The torus balloon (35) of this embodiment can be inflated with saline or other contrast medium to activate the barb struts (260) and barb tips (255).

Figure 12D:
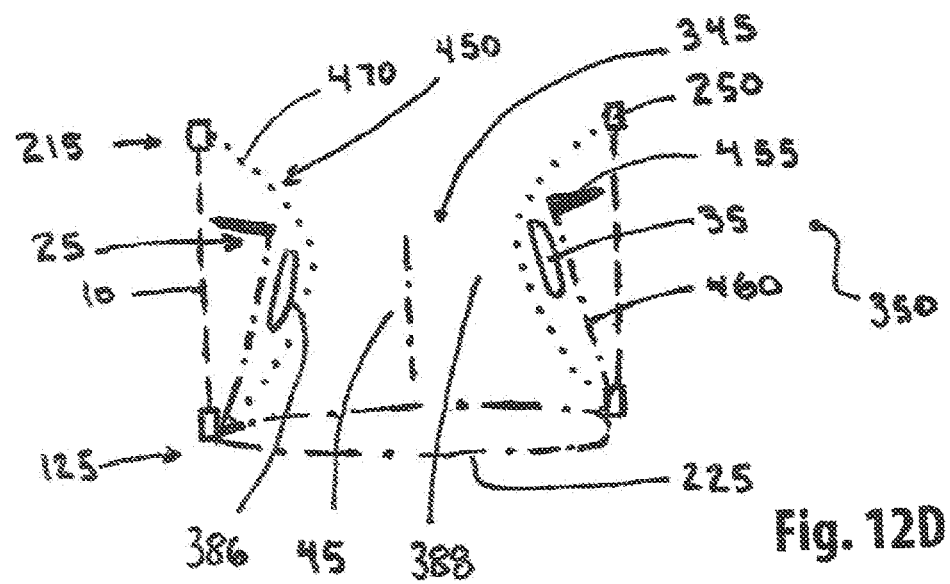
FIG. 12D is a sectional view of the frame waist showing a torus balloon in contact with a barb strut; the torus balloon is supported opposite to the barb strut by a backing fiber that is attached to the frame.

The backing element (450) can alternately be a backing fiber (470) that extends from an attachment element such as a ferrule (250) located at the waist outlet end (125) of the stent frame (15) to an attachment element located at the waist inlet end (215) of the stent frame (15) as shown in FIG. 12D. The backing member (450) resides on the inside perimeter (388) of the torus balloon (35). The backing fiber can be formed from a multifilament or monofilament strand metal or polymeric fiber that is flexible but has high tensile strength such that it will not stretch upon exposure to inflation pressures imposed upon it by the torus balloon (35). The backing fiber extends on the inside portion (i.e., nearest the stent frame (15) central axis (45)) of the torus balloon (35); the torus balloon (35) is located adjacent the inside of the barb strut (260) as shown in FIG. 12D. Upon inflation of the torus balloon (35) with contrast medium (as described in FIG. 12B), the barb strut (260) is pushed outwards such that the barb tip (255) extends outwards from the stent frame (15) and into the tissues of the mitral annulus (20). The backing element (450) provides the support such that the inflation forces from the inflated torus balloon (35) are transferred directly to the barb strut (260) causing the barb strut (260) to move outwards to the frame outside (350) during inflation of the torus balloon (35).

The torus balloon (35) is shaped like a doughnut and hence it is unable to provide significant outward force on its own (i.e., without a backing fiber (470), for example), to cause the barbs struts (260) to be deformed outwards. Rather than apply an outward force, as would be the case with a cylindrically-shaped balloon, the torus balloon would easily bend into an oval shape or form a kink when it is inflated under pressure since it is not supported in its central region. However placement of a backing fiber (470) or other backing element on the inside surface of the torus balloon as shown in FIG. 12D will allow the torus balloon internal pressure to be exerted outwards and cause the barb strut (260) to be forced outwards with a force equal to the applied outward force due to the internal pressure within the balloon.

The torus balloon (35) of this embodiment can be removed following activation of the barb tips (255) in a manner similar to that described in the embodiment of FIGS. 12A-12D by placing tension onto the balloon port and pulling proximally thereby unwinding the torus balloon (35) from its torus shape and removing it from the heart, the vasculature, and the body.

In an alternate embodiment the torus balloon (35) described in FIGS. 12A-12D can be attached to the stent frame, the barb struts (260), or the backing element (450) and can be implanted into the patient along with other portions of the stent frame (15) and stent valve. The attachment of the torus balloon (35) to a portion of the stent frame (15) can be made using an adhesive, sutures, thermal processing, or other methods available to bond polymeric or metal components together. In this alternate embodiment, the torus balloon (35) can be filled with either a saline based inflation medium which is allowed to drain or leak out of the balloon following balloon inflation. The torus balloon (35) alternately can be filled with a polymeric material that will cure or harden as described earlier; in this case, a check valve as described in earlier embodiments will be required to ensure that such polymeric material is confined to the inside of the torus balloon (35). As discussed in earlier embodiments, a limiting cable (225) can be attached anywhere along the axial length of the stent frame (15) or to the stent frame along a perimeter of the waist (10) in its expanded configuration and nonexpanded configuration.

Figure 13A:
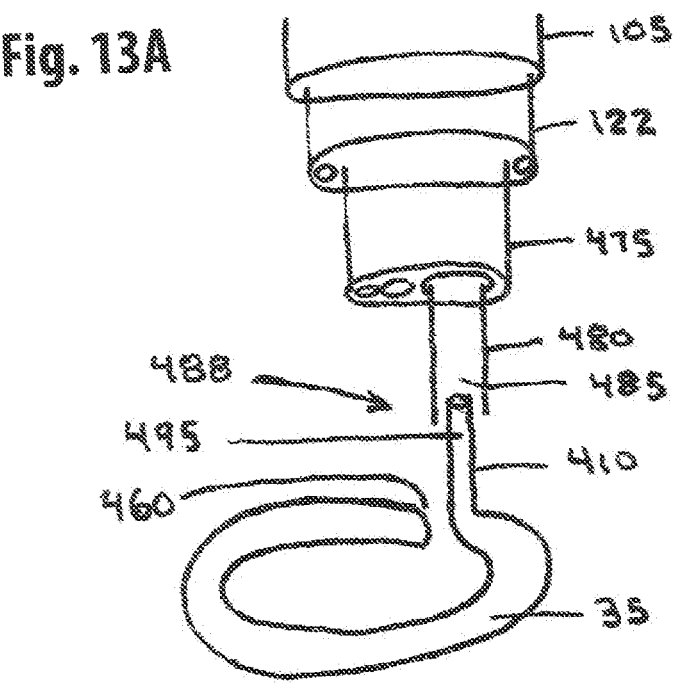
FIG. 13A is a perspective view of the delivery catheter, the pusher member, and the connection of the control shaft with the balloon port.
Figure 13B:
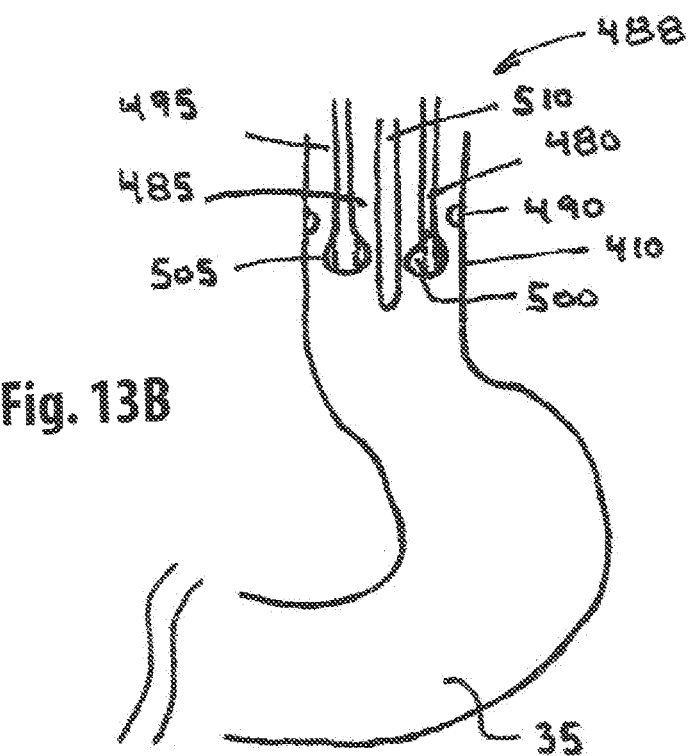
FIG. 13B is a plan view of a connection of the control shaft with the balloon port of the torus balloon using a locking intrusion.
Figure 13C:
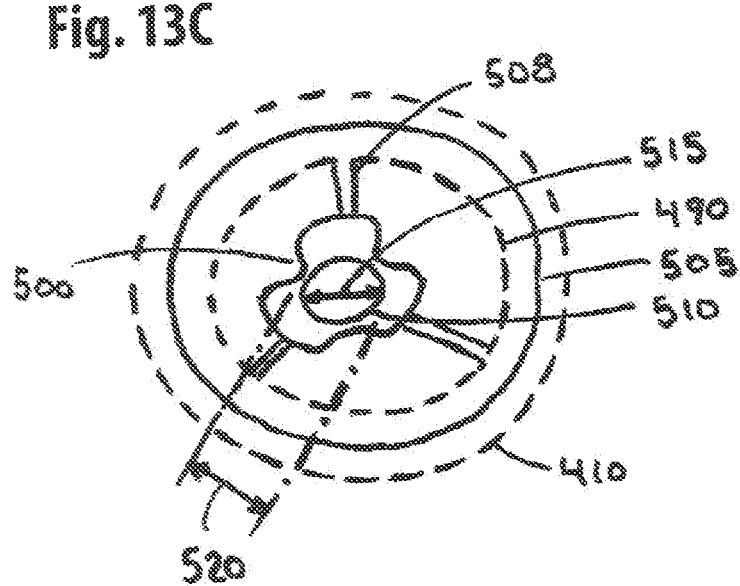
FIG. 13C is a cross-sectional view of the connection of the control shaft with the balloon port having a locking intrusion.
Figure 14:
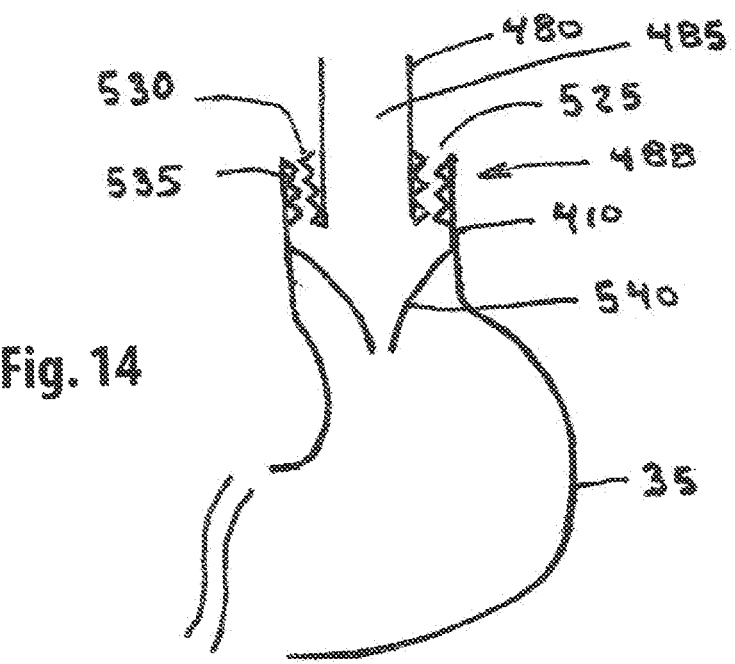
FIG. 14 is a plan view of a threaded connection of the control shaft with the balloon port.

The delivery of an inflation fluid to the torus balloon (35) and detachment of the torus balloon (35) from a control shaft is shown in FIGS. 13A-14. FIG. 13A shows the torus balloon (35) having one balloon port; the torus balloon (35) is understood to be attached to the waist (10) as shown in any of the embodiments described in FIGS. 8-12, but is shown here for clarity as only the torus balloon (35) component of the stent-valve system. A control tube (475) is located within a pusher tube (122) that is located within the delivery sheath (105) similar to that described earlier in the embodiment shown in FIG. 1A. The control tube (475) and the pusher tube (122) can be a single tube in some embodiments rather than two separate tubes. Contained within the control tube is a hollow control shaft (480) that provides a control lumen (485); the control shaft with and inner control lumen are used to provide inflation fluid to the torus balloon (35). The inflation fluid is delivered to the torus balloon (35) under pressure and hence the junction of the control shaft with the balloon port of the torus balloon (35) should not leak significant amount of inflation fluid such that inflation pressure can be attained and must be releasable by the operator at the proximal end (115) of the catheter.

FIGS. 13B and 13C shown one embodiment for a releasable attachment of the control shaft from the balloon port. The balloon port is formed with a locking intrusion (490) that extends inwards into the balloon port lumen (495). The control shaft is formed with 3 inner nubs (500) (range 2-5 nubs) that extend inward into the control lumen as shown in FIG. 13C. The control shaft also has an outer protrusion (505) that has an equilibrium diameter that is larger than the locking protrusion; control slots (508) located in the control shaft (480) allow the control shaft to expand to a larger diameter when a mandrel (510) has been inserted. The outer protrusion of the control shaft can be pushed past the locking protrusion (to engage the control shaft with the balloon port) as long as there is not a mandrel present within the control lumen of the control shaft. Once the control shaft is engaged with the balloon port, a mandrel (510) with a mandrel diameter (515) larger than an equilibrium (i.e., with no external forces impose upon it) nub diameter (520) is placed within the control lumen to form a locked nub diameter to lock the control shaft with the balloon port. Following inflation of the torus balloon (35) via the control lumen, the barb will be activated, and the torus balloon (35) is ready to be disengaged. To disengage the torus balloon (35), the mandrel is removed by applying tension to the mandrel by the operator; with the mandrel removed, the control tube can be removed from the balloon port by applying tension. The torus balloon (35) has therein been effectively inflated and released from the control shaft.

FIG. 14 shows an embodiment that provides a releasable connection (488) comprised of a threaded connection (525)

of the control shaft (480) to the balloon port (410) via a screw mechanism. The distal end of the control shaft is fitted with an outer thread (530) that fits within an inner thread (535) located within the balloon port. The control shaft lumen extends through the threaded region to allow for inflation of the torus balloon (35). The control shaft is detached from the balloon port by turning to form a threaded release. A flapper valve (540) or duck-bill valve can be placed within the balloon port to prevent the inflation fluid from draining out of the torus balloon (35) after balloon inflation. Saline can be used as an inflation fluid and allowed to drain out of the torus balloon (35) as described in earlier embodiments. Alternately a polymeric material such as a crosslinking polyurethane, epoxy, silicone, or other polymer or fluid can be used to inflate the torus balloon (35) of this or other embodiments and remain within the implanted torus balloon (35). For the embodiments that use a polymeric inflation medium, the balloon can serve to make a conformal pressure dependent seal with the mitral annulus (20) as it makes direct contact with the tissues of the mitral annulus (20).

Figure 15:
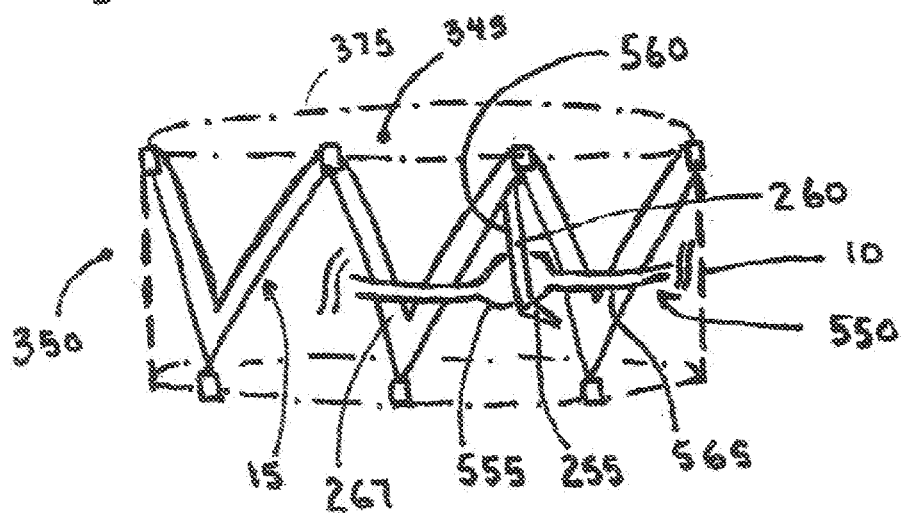
FIG. 15 is a perspective view of a torus balloon having a segmented spherical segment that makes contact with the barb strut.

FIG. 15 shows a side view of a segmented torus balloon (550) having a segmented shape that is located in the waist (10) of a stent frame (15) of the present invention used for a single member stent-valve (5) or a first member (200) of a dual member stent-valve (195). The stent frame (15) and barb struts (260) are similar to the frames and barb struts (260) shown in FIGS. 8A-12B. The stent frame (15) is formed from a SE material and the barb strut (260) is formed such that it is balloon expandable such that it can bend outwards due to an radially outward force (228) against the barb strut (260) generated by inflation of a segmented torus balloon (550). In FIG. 15 the spherical segment (555) of the segmented torus balloon (550) is located adjacent to the barb strut inside surface (560) (i.e., facing the inside (345) of the stent frame) and is inflated with inflation medium such that inflation of the spherical segment (555) will push the barb strut (260) outwards such that the barb tip (255) extends on the stent frame outside (350) of the stent frame (15) as shown for one of the plurality of barbs (25) located along the perimeter (375) of the stent frame. Each spherical segment (555) is located adjacent to an cylindrical segment (565) of a barb strut (260). Each spherical segment (555) is joined to an adjacent spherical segment (555) by a cylindrical segment (565) that retains a smaller diameter during its inflated configuration. The diameter for each inflated spherical segment (555) is 4 mm (range 3-10 mm) and the diameter of each cylindrical segment (565) is 2 mm (range 1-3 mm). The cylindrical segments do not enlarge in diameter as the segmented torus balloon (550) is inflated. At one end of the segmented torus balloon (550) is located a balloon port that is attachable to a fill tube or control shaft that provides inflation fluid to the segmented torus balloon (550). The other end of the segmented torus balloon (550) is dead-ended forming a closed end such that inflation fluid is not able to leak out of the closed end. The segmented torus balloon (550) of this embodiment provides an advantage over a uniformly cylindrical torus balloon (35) as presented in earlier embodiments. The segmented torus balloon (550) can provide a greater excursion or travel distance to the barb strut (260) due to the larger diameter spherical segment (555) while minimizing the profile for the torus balloon during delivery and during inflation of the segmented torus balloon (550) due to the smaller diameter cylindrical segments. During inflation of this segmented torus balloon (550), the cylindrical segments which are at least partially located on the outside (350) of the stent frame (15) do not provide an increased outward push against the mitral annulus (20) during inflation of the balloon since the cylindrical portions do not expand in diameter during inflation. In this embodiment, the inflation fluid is saline and the saline can be released or allowed to leak back into the patient's blood following inflation of the torus balloon in a manner described in earlier embodiments for the torus balloon (35). The balloon is implanted along with the remainder of stent frame (15) and the mitral valve device.

Figure 16:
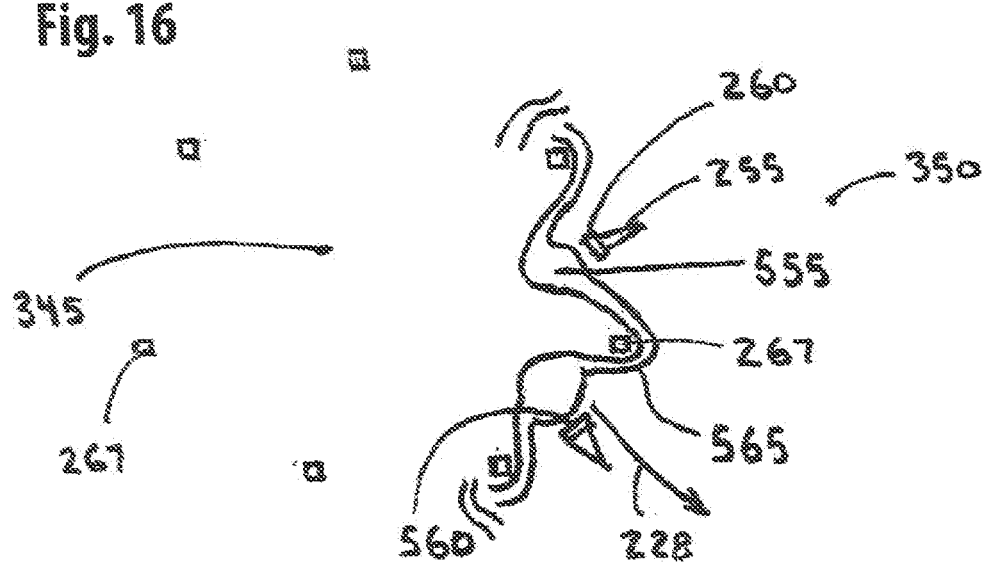
FIG. 16 is a sectional view from the top of the waist region showing the segmented torus balloon moving the barb tips to the outside of the frame during inflation of the torus balloon.

A top view of the segmented torus balloon (550) of this embodiment is shown in FIG. 16 in an inflated state. In FIG. 16 the cylindrical segment (565) is shown extending on the outside (350) of the stent frame (15) adjacent to the stent struts (267). The spherical segments (555) of the segmented torus balloon (550) are located adjacent to the cylindrical segment (565) of the barb struts (260) located facing the stent frame inside (345). During inflation the barb tip (255) is pushed outwards toward the stent frame outside (350) by the spherical segment (555) of the segmented torus balloon (550). The cylindrical portion retains its location on the outside (350) of the stent struts (267) and provides the force necessary to allow the spherical segment (555) to push the barb struts (260) outwards toward the outside (350) of the stent frame. The cylindrical segments can be attached to the stent struts (267) via balloon attachments to hold the segmented torus balloon (550) in position against the stent frame.

Figure 17:
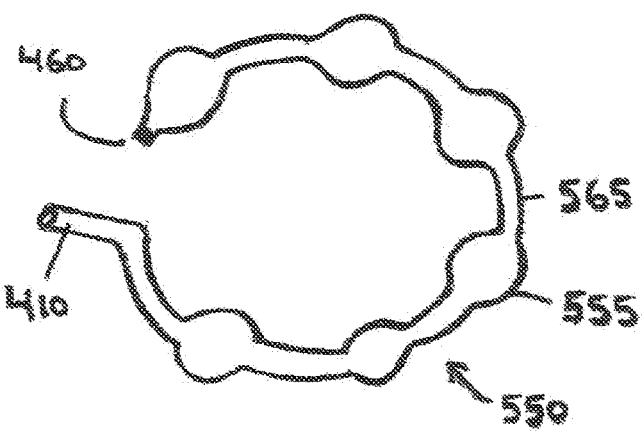
FIG. 17 is a plan view of a segmented torus balloon and a balloon inflation port.

The segmented torus balloon (550) can be formed from similar materials as described earlier for the torus balloon (35). The segmented torus balloon (550) as shown in FIG. 17 can be formed with a series of bulges or spherical segments (555) using polymeric materials and processing methods used to form current dilation balloons used in medical devices. The balloon can be formed with smaller diameter cylindrical segments in series with spherical segments (555); the balloon can have one balloon port located at one end of the balloon; the other end can be closed off and formed to be leak tight forming a closed end (460). Polymeric material for the segmented torus balloon (550) can include polyethylene terephthalate, nylon, Pebax, polyurethane, composites, copolymers, and other polymeric materials used to form dilation balloons for angioplasty and stent delivery catheters.

A shaped mold having regions with bulges can be used to form the segmented torus balloon (550) having spherical segments (555) and cylindrical segments. The mold has bulges or spherical mold segments located in series with smaller diameter cylindrical segments. Standard balloon blowing and molding techniques can be used to form the segmented torus balloon (550). The segmented torus balloon (550) can alternately be formed by bonding segments of cylindrical tubing to other segments having a spherical shape; such bonding can be accomplished via solvent bonding, adhesive bonding, thermal bonding or other suitable bonding method.

In other embodiments for the segmented torus balloon (550) of the present invention, the segmented torus balloon (550) can be inflated with a polymeric material and retained within the balloon via a valve as it is implanted as described for other embodiments for the torus balloon (35). Also, in other embodiments, the segmented torus balloon (550) can be located such that the cylindrical segments are located on the inside of the stent frame (15) and attached by balloon attachments as described in earlier embodiments for the torus balloon (35).

In further alternate embodiments of the present invention used as a single member stent-valve, the barb struts (260)

that are used to hold the stent frame (15) adjacent to the mitral annulus (20) and prevent migration of the stent valve can be attached, joined, or contiguous with the upper bulb (70) or the housing (130) rather than attached, joined, or contiguous with the waist (10) of the stent frame. In one embodiment, as shown in FIG. 18, the stent frame (15) does not have a cylindrical waist (10) portion and instead has a frustum-shaped housing (130) that is directly joined to the upper bulb (70). The barb struts (260) of this embodiment are located within or attached to the housing (130) portion and the barb tip (255) is located near the bulb/housing junction (568). The BE barb struts (260) are pushed outward due to expansion of the torus balloon (35); the torus balloon (35) can be the segmented torus balloon (550) or a torus balloon that is cylindrical throughout as discussed in earlier embodiments. The torus balloon (35) can be located on the outside (350) of the stent struts (267) and outside (350) of the stent frame (15) as shown in FIG. 18 and having a segment of the balloon located on the inside of the barb struts (260) such that inflation of the balloon pushes the barb struts (260) outwards. The torus balloon (35) can alternately be located on the inside of the stent frame (15) such that inflation of the torus balloon (35) does not push the stent frame (15) away from the mitral annulus (20). The replacement leaflets (270) are located near the outlet end (145) of the housing.

Alternately, as shown in FIG. 19 for an embodiment of a single member stent-valve, the barb struts (260) and torus balloon (35) can be joined, attached, or contiguous with the upper bulb (70). In this embodiment, the upper bulb (70) is joined directly to the housing (130) and does not contain a cylindrical waist (10) region located between the upper bulb (70) and the housing (130). The barb tips (255) are located near the bulb/housing junction (568) such that the barb tips (255) are extended outwards via inflation of the torus balloon (35) and extend the barb tips (255) into the mitral valve annulus (20). The torus balloon (35) can be located such that it weaves in an out over the outside (350) of the stent struts (267) and adjacent the inside of the barb struts (260) as described in earlier embodiments. Alternately, the torus balloon (35) can be located on the inside surface of the stent frame (15) as well as the cylindrical segment (565) of the barb struts (260) as described earlier.

Figure 20A:
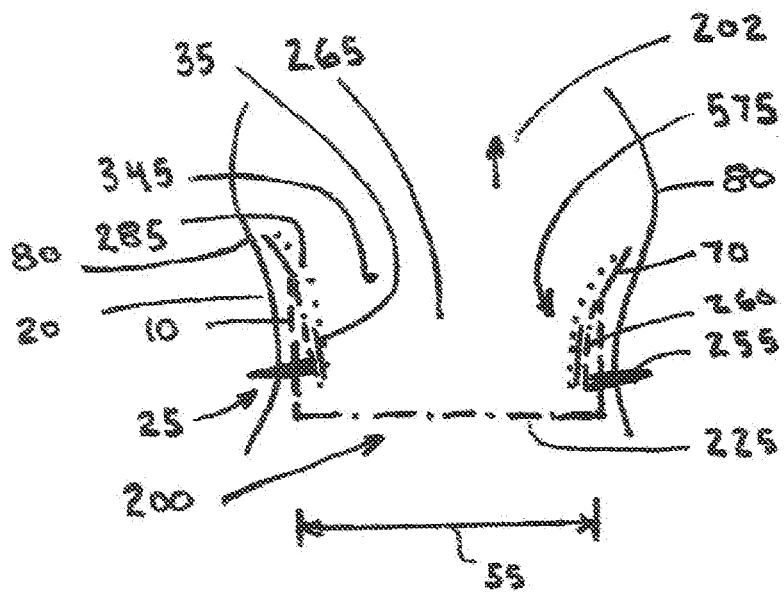
FIG. 20A is a plan view of a first component or support frame located adjacent the native valve annulus having the barbs activated by a torus balloon and extending into the annulus; a limiting cable limits further expansion of the frame.
Figure 20C:
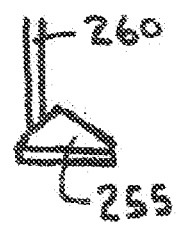
FIG. 20C is a perspective view of a barb tip having a flattened shape.
Figure 20B:
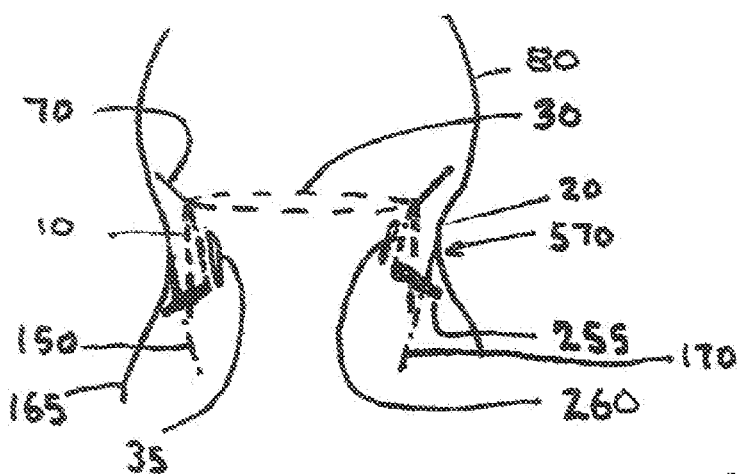
FIG. 20B is a plan view of a first component or support frame located adjacent the native valve annulus having the barbs activated by a torus balloon and extending into the base of the native valve leaflets.

FIGS. 20A and 20B show an embodiment for a first component (200) (or support member) of a two component or dual member stent-valve. The support member (200) provides a ring like structure (via the limiting cable (225)) having a defined maximum perimeter (375) for the frame (15) that is attached to the mitral annulus (20) via barbs (25), and does not interfere with the function of the native mitral valve leaflets. A valve member (or second component (190)) that contains replacement leaflets (270) provides a second component (190) that is delivered within the central lumen (265) of the first component (200) and is held in place via a friction fit or via geometrical locking of the first component (200) with the second component (190). The first component (200) can be an adapter into which the second component (190) containing the replacement leaflets (270) can be positioned and implanted. The second component (190) can be a specific stent-valve such as presented in embodiments of this patent application; the second component (190) can alternately be an existing stent-valve, such as a BE or SE stent-valve used in TAVR procedures, for example.

The first component (200) has a self-expanding (SE) stent frame (15) that is comprised of a frame waist (10) that can be attached to or contiguous with the upper bulb (70). A valve member or second component (190) which will be discussed in a later embodiment is delivered subsequent to the delivery of the first component (200) within the open central lumen (265) located of the first component (200); the second component (190) is attached to the first component (200) via friction or geometrical fit to the first component (200) that is obtained by expanding the second component (190) within the first component (200). The SE stent frame (15) of the first component (200) can be formed from Nitinol, Elgiloy, or other elastic material used in the formation of vascular stents. The waist (10) is positioned adjacent the mitral annulus (20) and the upper bulb (70) may be located in the LA (80) adjacent to the mitral annulus (20); the upper bulb (70) has a diameter at its inlet end that is larger than the waist inlet diameter (55) to assist in positioning the stent frame (15) across the mitral annulus (20) with the upper bulb (70) resting in the LA, adjacent and upstream of the mitral annulus (20). Positioning of the stent frame (15) into contact with the native mitral valve apparatus tissue is performed via release from an external sheath using a pusher member (122) as described in earlier embodiments described in the present application and patent applications that are referenced in the present application. Recapture struts (100) can be attached to the upper bulb (70) or the waist (10) of the present stent frame (15) to assist in repositioning or removal of the first component (200) in a manner consistent with the stent embodiment described in earlier embodiments. The first component (200) serves to provide a stable location that will hold a second component (190) that contains the replacement leaflets (270) for the mitral valve system of the present invention. The first component (200) allows the second component (190) to be expanded within the inside of the first component (200) and the first component (200) has a specific waist diameter that provides the necessary frictional force against the second component (190) or geometrical shape to hold the second component (190) from migrating downstream and ensuring that leakage does not occur between the first component (200) and the second component (190). A limiting cable (225) can be placed along the perimeter (375) of the stent frame (15) of the first component (200) to limit the stent frame diameter (380) and perimeter (375) of the stent frame (15) from further expansion due to outward forces from the frame of the first component (200) or second component (190) or from an inflation balloon; the limiting cable allows the second component (190) to be expanded into the first component (200) under a greater force (greater than without the limiting cable (225)) that is at least equal to a 10 atm cylindrical dilation balloon to create a tight fit between the first and second component (190). The first component (200) must also be placed within the mitral valve apparatus in a manner that will not affect the functioning of the native mitral valve leaflets during the period of time while awaiting the placement of the second component (190) into the first component (200). In the present invention the first component (200) is placed above or superior to the mitral valve leaflets and extends from the junction (570) of the native mitral valve leaflets to the mitral annulus (20) and can come into contact with the junction (570) of the native mitral valve leaflets with the annulus (20). The native mitral valve leaflets are able to function while the first component (200) is placed adjacent to the mitral annulus (20) and other native tissues of the native mitral apparatus.

The upper bulb (70) of the first component (200) serves to help prevent migration of the first component (200) toward the LV (165), to provide a seal to prevent blood leakage between the first component (200) and the mitral tissues including the LA (80) wall, mitral annulus (20), and mitral leaflets, and to assist in positioning of the first component (200) across the mitral annulus (20) with the upper bulb (70) being located in the LA just proximal to the annulus (20). As shown in FIG. 20A, the barbs (25) which are comprised of barb struts (260) (range 8-20 in number) and barb tips (255) are located along the waist perimeter (30) (see FIG. 20B); the barbs (25) can be formed from a SE elastic material such as Nitinol, for example, or can be formed from a BE material such as stainless steel, for example or from other metals or polymers. Prior to delivery of the first component (200) the barbs (25) are in an inactive configuration located toward the inside of the first component (200) in the central lumen (265) as described in earlier embodiments. Upon activation of the SE or BE barbs (25) outwards to the outside (350) of the waist, the barb tips (255) penetrate the mitral annulus (20) as shown in FIG. 20A or penetrate the base of the native mitral leaflets near the mitral leaflet junction (570) with the mitral annulus (20). Activation of the barbs (25) into the mitral tissues prevents migration of the first component (200) upstream (202) towards the LA (80) and also prevents migration downstream into the LV.

The barb tips (255) can be formed from a material with a sharp tip that can penetrate the tissues of the mitral annulus (20) or the base of the native mitral leaflets. The barb tips (255) can be formed with a flattened shape such that the surface area of the flat barb tip (255) (see FIG. 20C) is maximized in a direction facing the LA (80) or LV to resist movement of the first component (200) towards the LA (80) or LV (165). Other embodiments for the barb tip (255) are contemplated that will help to provide a greater holding force yet still allow the barb tip (255) to be withdrawn acutely under the circumstance that the operator would prefer to deactivate or remove the barb tips (255) from the surrounding tissues and reposition or remove the device. In one embodiment, for example, a fish hook that has been coated with poly L-lactic acid (PLLA) can be used as a barb tip (255). The fish hook can be coated to form a conical shape, for example, similar to those shown in FIG. 20A or 20C for delivery into the surrounding tissues. After the PLLA has had a chance to biodegrade over a time of days or weeks, the standard fish hook shape can become uncovered and can hold the surrounding tissues with greater strength and prevent deactivation of the barb tip (255) from the surrounding tissues in a manner similar to a fish hook. Other shapes can be used for the barb tip including a coiled tip such as that used, for example, on the tips of specific pacemaker leads. The coiled tip can be coated with PLLA, for example, to transform the shape of the barb tip (255) into a conical shape, for example, such as that shown in FIGS. 20A and 20C. After delivery of the PLLA-coated coiled tip to the surrounding tissues via the outward forces of the torus balloon (35), the PLLA can be degraded and leave a barb tip with greater surface area and greater potential holding power to prevent deactivation of the barb tip out of the surrounding tissues. Other tip shapes can be used to form the barb tips (255) of the present invention, and other biodegradable materials can be used to provide a coating to the barb tip (255) including biodegradable materials used in biodegradable stents and other biodegradable medical devices. Barb tips (255) can be any element or member that is able to engage the surrounding tissue and prevent the migration or embolization of the first component (200).

A covering (285) can be attached to all or a portion of the frame waist (10) and upper bulb (70) frame to prevent blood flow from crossing the wall of the waist frame or the upper bulb (70) frame; the covering (285) can be located on the inside or outside surface of the stent frame (15) and helps to ensure that perivalvular leakage around the stent frame (15) is minimized. The covering (285) material can be a thin polymeric film or weave, for example, as described in earlier embodiments. Attachment of the covering (285) to the frame (15) can be via sutures, adhesives, and various bonding methods.

One important aspect of the of the present invention is that the barbs (25) are not released or activated until the stent frame (15) has been expanded into the native mitral tissues and is in an expanded configuration. Activation of the barbs (25) after the SE stent frame (15) is expanded and placed into full contact along the entire perimeter of the waist (10) with the full perimeter of the mitral annulus (20) and other mitral tissues ensures that the barbs (25) are placed evenly around the perimeter of the mitral annulus (20) and mitral tissues. Since the mitral annulus (20) and base of the mitral valve leaflet junction (570) to the mitral annulus (20) is not actually round in shape in its native configuration, the mitral tissues will be forced into a round shape by the waist stent frame (15) prior to activation of the barbs (25). The rounding of the mitral annulus (20) by the stent frame (15) of the present invention is not restricted by undesirable premature activation of barb tips (255) into the mitral annulus (20) perimeter in an incorrect position which could occur if the barbs (25) were activated prior to full expansion of the stent frame perimeter (375) into contact with the perimeter of the annulus (20). Premature activation of the barb tips (255) would result in uneven spacing of the barbs (25) around the perimeter of the mitral annulus (20) or base of the mitral leaflet tissues and would not allow the mitral annulus (20) to fully enlarge to a round shape representative of the perimeter of the mitral annulus (20).

Another important aspect of the first component (200) of the present invention is that during activation of the barbs (25), the blood flow through the mitral annulus (20) or stent valve frame (15) should not be blocked. Blockage of mitral blood flow can result in high forces being placed onto the first component (200) during the systolic cycle of heart pumping; such forces can cause movement of the first component (200) towards the LA (80) negatively affecting the positioning of the first component (200) accurately in an axial direction (90) across the annulus (20). The use of a torus balloon (35) prevents the unwanted blockage of blood flow during delivery of the first component (200) and activation of the barbs (25) with the torus balloon (35). Additionally, mitral blood flow blockage can negatively impact oxygen transport to tissues fed by the outflow from the heart including the brain.

Figure 21A:
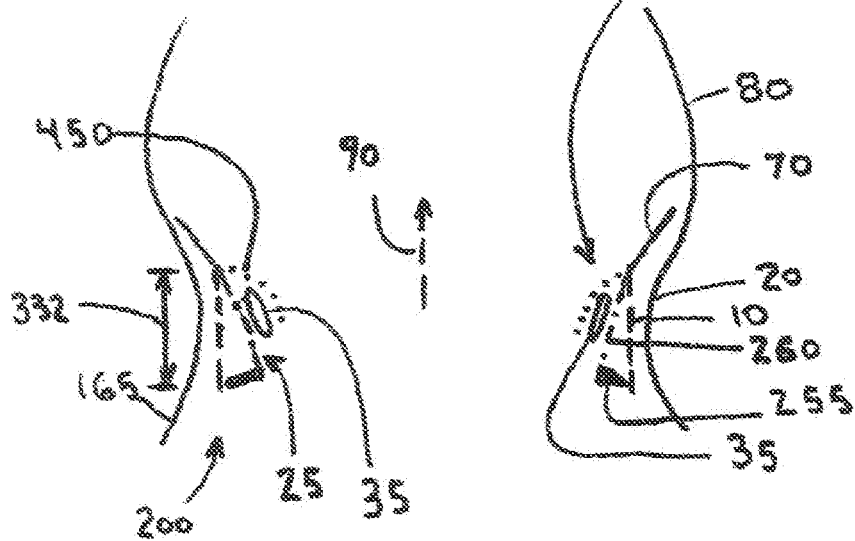
FIG. 21A is a sectional view of a first component or support frame with a backing member and having a torus balloon in a deflated configuration and barb tips inside of the frame.
Figure 21B:
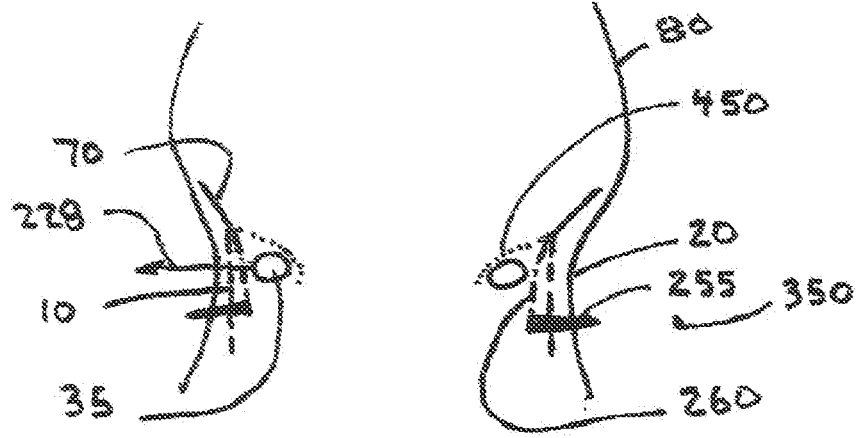
FIG. 21B is a sectional view of a first component or support frame with a backing member and having a torus balloon in an inflated configuration and barb tips outside of the frame.

FIGS. 21A and 21B show one embodiment for activation of BE barbs (25) that are located along a waist perimeter (30) of the first component (200) of the present embodiment or along the waist of the single member stent-valve (5) described earlier. The frame has been released and has expanded out to an expanded configuration (575); the barbs (25) have not been activated as shown in FIG. 21A. The first component (200) of this embodiment has an upper bulb (70) attached to the waist, the upper bulb (70) provides a benefit for proper placement of the first component (200) adjacent to the mitral annulus (20) and assisting with forming a seal between the frame (15) and the mitral annulus (20). The waist (10) of the first component (200) is similar to the waist that is described in earlier embodiments found in the present patent application. The waist can be cylindrical in shape or can have a concave or curved shape as will be described in other embodiments. The waist can have a waist length (332) in an axial direction (90) of 6 mm (range 3 mm-10 mm) and is formed from a stent structure that is open cell, closed cell, a combination of open and closed cell, or other structure found in vascular stents used in the medical device industry. The waist is placed adjacent to the mitral annulus or native mitral valve tissue such that the first component frame does not affect the movement or valvular function of the native mitral valve leaflets. In this embodiment, as described earlier for a single member stent valve (or one-step mitral valve device having the replacement leaflets (270) contained within the stent frame (15) that is attached or contiguous with a waist frame) a torus balloon (35) is inflated to apply an outward force (228) onto the barbs (25) causing the barb tips (255) to move outwards to the stent frame outside (350) and into the annulus (20) or tissue of the heart valve. In this embodiment a backing element (450) such as a stent arm (455) serves to provide a member that is attached to the stent frame (15) and provides the torus balloon (35) with a backing member of which the torus balloon (35) can be located in an uninflated configuration as shown in FIG. 21A and with the barb in an inactivated state. The inflated balloon can push against the barb strut (260) to cause the BE barb strut (260) to extend and plastically deform towards the outside (350) of the stent frame (15) and into the mitral tissues in an activated configuration as shown in FIG. 21B. The backing member (450) provides the support to allow the torus balloon (35) to push with an outward force (228) that is equal to its internal inflation pressure to extend the barb tips to the frame outside (350) and into the surrounding tissues of the heart valve. The first component (200) of the present invention can utilize any of the device mechanisms described in earlier embodiments of the present patent application to activate the barbs (25) into the mitral tissues. For example, the first component (200) can have the torus balloon (35) attached to the waist frame or the stent frame (15) as described in FIGS. 8A-8D and 9A-9D. Alternately, the torus balloon (35) for the first component (200) can be located in the waist (10) region of the first component (200) and can be located in a balloon holder and attached to the frame (15) and activated in a manner that is the same as that described in FIGS. 10A-10C. The torus balloon (35) of the first component (200) of the two step embodiment can have the torus balloon (35) located on the outside of the struts (267) of the frame waist (10) and on the inside of the barb struts (260) as shown in FIGS. 11A-11C. The torus balloon (35) of the first component (200) can be permanently attached to the first component (200) and implanted along with the first component (200) or can be removable as described in FIGS. 12A-12D. The torus balloon (35) of the first component (200) can be a segmented balloon as described in FIGS. 15 and 16.

Figure 22A:
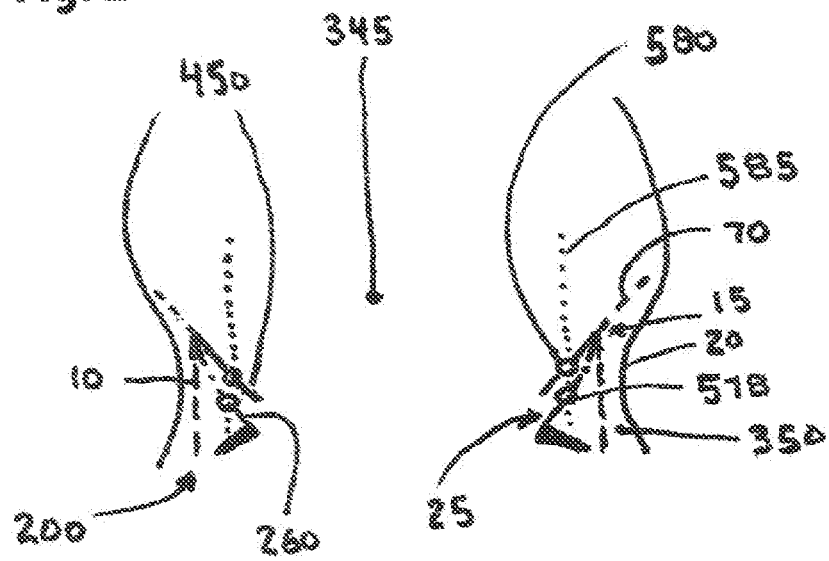
FIG. 22A is a sectional view of a first component or support frame having self-expanding barb struts held in an inactive configuration by a barb control fiber.
Figure 22B:
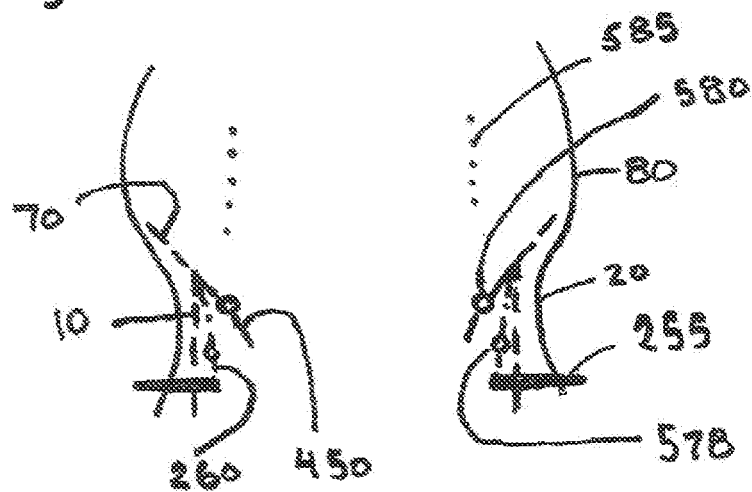
FIG. 22B is a sectional view of a first component or support frame having self-expanding barb struts that have been release by a control fiber and are in an active configuration with the barb tips outside the frame.

FIGS. 22A and 22B show another embodiment for the first component (200) for the mitral valve assembly of the present invention. This embodiment has a waist (10) and upper bulb (70) that is similar to that described in FIGS. 21A and 21B. The barb struts (260) for this embodiment are SE barb struts (260) rather than the BE barb struts (260) found in the embodiment of FIGS. 21A and 21B. This embodiment does not require the presence of a torus balloon to effect the active deployment of the barbs. The barb struts (260) are attached to the frame (15) in a manner similar to that described in earlier embodiments of the present patent application. The barb struts (260) have a barb feature (578) that allows passage of a barb control fiber (585). A backing element (450) such as a backing arm, for example, is attached to the stent frame (15) to provide a holding member that can hold the barbs (25) in an inactive configuration as shown in FIG. 22A. The backing arm has an opening feature (580) that allows passage of a barb control fiber (585). The barbs (25) are held in an inactive configuration towards the inside of the stent frame (15) via barb control fibers (585) that temporarily hold the barb struts (260) with respect to the backing elements (450) by connecting or interfacing between the opening feature of the backing arm and the barb feature of the barb strut (260). The barb struts (260) are release by applying tension via the operator to the control fibers (585) that extend to the proximal end (115) of delivery catheter located outside of the patient's body thereby releasing the barb struts (260) and placing the barb tips (255) to the outside (350) of the waist (10) stent frame (15) during barb activation as shown in FIG. 22B.

Figure 23A:
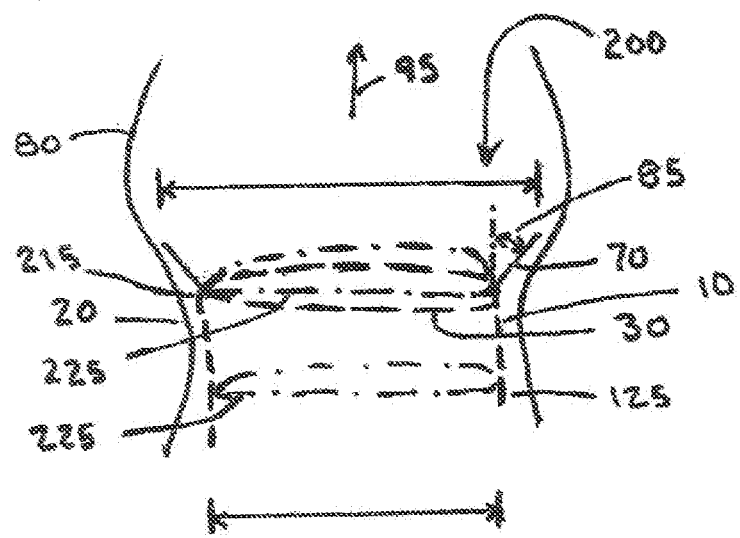
FIG. 23A is a perspective view of a frame waist for a first component or support frame having a limiting cable to limit the perimeter of the waist from further expansion.
Figure 23B:
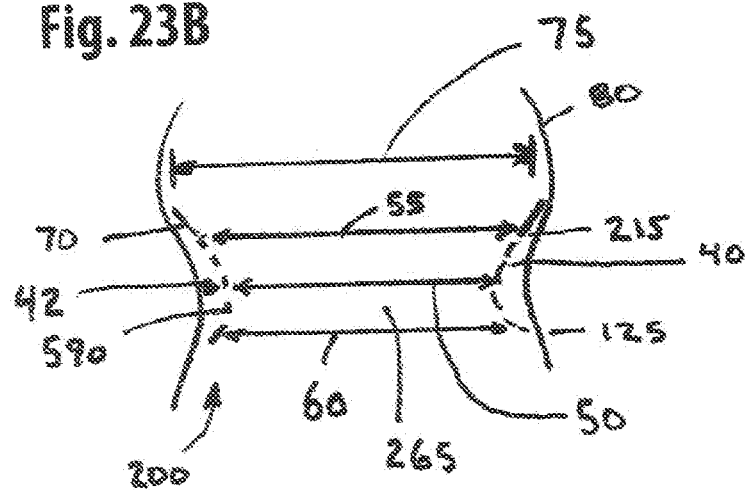
FIG. 23B is a perspective view of a frame waist of a first component having a concave region that forms a geometrical shape that can be used as a locking member for locking onto a second component or valve frame; the concave region also assists in providing a geometrical shape that fits the shape of the native valve annulus and holds onto the native valve annulus.

FIG. 23A shows a cylindrically-shaped waist (10) for the first component (200); the waist (10) being positioned adjacent the mitral annulus (20); the waist (10) can alternately be a portion of a single member stent-valve (5) as described in earlier embodiments. The upper bulb (70) is attached to the upstream end of the waist; the upper bulb (70) extends outwards to a larger upper bulb diameter (75) than the inlet waist diameter (55) as the upper bulb extends into the LA (80) at an upper bulb angle with respect to the waist of 45 degrees (range 20 to 90 degrees). One or more limiting cables (210) are attached to the waist, the limiting cables (210) extend around the perimeter (30) of the waist (10) and prevent the waist (10) from expansion to a larger perimeter than the perimeter of the limiting cables (225). As shown, one limiting cable (225) is located at the upstream end of the waist (10) near the waist inlet end (215) and one is located at the downstream end of the waist near the waist outlet end (125). The limiting cables (225) can be formed from polymeric or metal material and can be either a monofilament or multifilament strand. The limiting cable (225) is attached to the stent frame (15) via welding, brazing, adhesive bonding, swaging, or other attachment methods used in the medical device industry. The limiting cable (225) is described also in earlier embodiments found in the present patent application. FIG. 23B shows the waist (10) of the first component (200) having a curved shape or curved waist (40). The waist central diameter (50) is 3 mm (range 2-10 mm) smaller than the waist inlet diameter (55) at the upstream end (215) or the waist outlet diameter (60) at the downstream end (125) of the waist (10). The curved waist (40) shape for the first component (200) can provide a concave region (42) or hump which extend into the central lumen (265) space that would allow a groove or concave region (42) of a second component (190) to lock into position with respect to the first component (200) and would prevent the second component (190) from migrating upstream (95) toward the LA (80) or downstream toward the LV with respect to the first component (200).

Figure 24A:
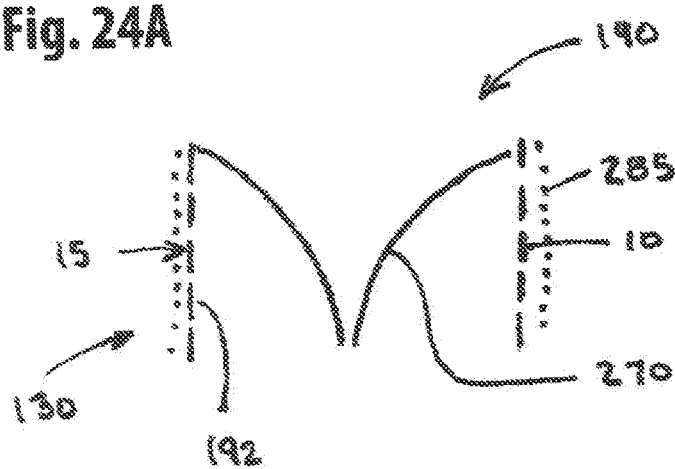
FIG. 24A is a plan view of a second component stent valve or valve frame that contains replacement leaflets.
Figure 24B:
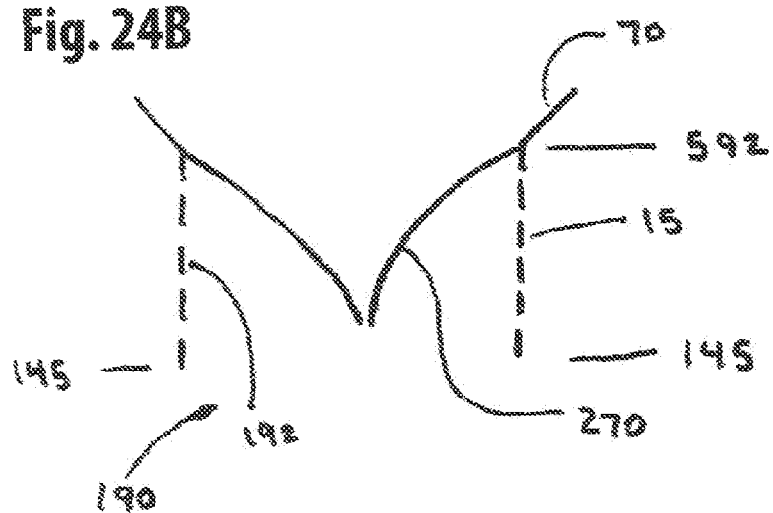
FIG. 24B is a plan view of a second component stent valve or valve frame that contains replacement leaflets; an upper bulb attached at the inlet end assists in axial placement of the second component and assists in providing a seal with a first component to prevent blood leakage between components.

Embodiments of the second component (190) of the two-step stent-valve system are shown in FIGS. 24A and 24B. FIG. 24A shows a stent-valve that could be used for a TAVR device or other stent-valve device application but instead is being applied as a second component (190) of a two-step mitral valve system. The second component (190) stent-valve has a valve frame (192) structure that contains replacement valve leaflets (270) attached to the frame (15) via crown-shaped attachments as described in earlier embodiments. The leaflet material and attachment of the leaflets to the valve frame (192) are as described in other embodiments of the present patent application. The stent-valve could have a BE stent-valve frame (192) that is formed from a BE material such as stainless steel or it can have a SE stent-valve frame (192) that is formed from Nitinol, for example. The stent valve of the second component (190) can have a cylindrically-shaped frame (15) as shown in FIG.

Figure 24C:
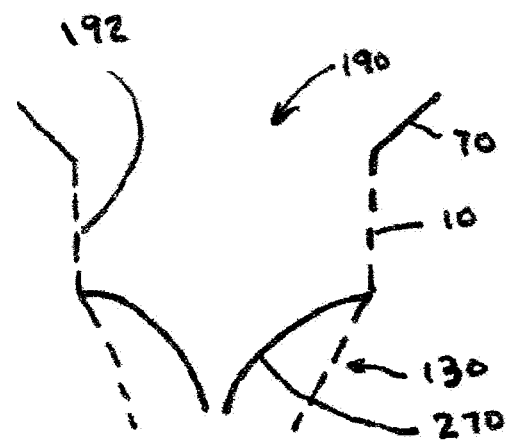
FIG. 24C is a plan view of a second component or valve frame containing replacement leaflets; the valve frame has a frustum shaped housing that houses the replacement leaflets.

24A; the stent-valve can have an upper bulb (70) extend outwards into the LA (80) as shown in FIG. 24B; the stent-valve can have a frustum-shaped housing (130) that holds the replacement valve leaflets as shown in FIG. 24C. The frustum-shaped housing (130) provides an advantage over a cylindrically shaped housing (130) in that it does not impinge upon the LVOT blood flow area; the replacement leaflets (270) can be formed with a frustum shape as described in earlier embodiments of the frustum housing (130) thereby reducing the amount of force on the leaflet free edge when the leaflets are closed during systole.

Figure 24D:
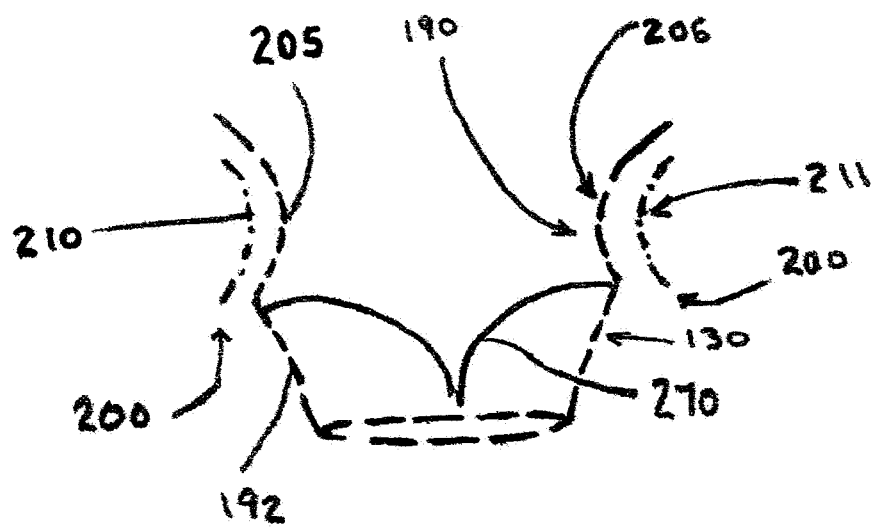
FIG. 24D is a sectional view of a dual member stent valve having a support frame having a concave waist and a valve frame located in the inside lumen of the support frame; the valve frame also having a concave waist that locks geometrically with the concave waist of the support frame.

The second component waist (205) of the second component (190) can have a second component concave region (206) that matches the curved shape of the first component concave region (211) of the first component waist (210) as shown in FIG. 24D. The second component waist (205) of the second component (190) can be delivered to a location within the mitral valve apparatus such that upon expansion of the second component (190) on the inside of the first component (200), the second component curved waist (205) tends to self-adjust itself such that the second component concave region (206) is located adjacent to the first component concave region (211). The second component concave region (206) will lock with respect to the first component concave region (211) thereby preventing migration of the second component (190) with respect to the first component (200). The first component concave region (211) is a locking region that is able to form a geometrical or locking fit with the second component concave region (206). Other locking region geometries are contemplated; the locking regions have a geometry that is distinguished from neighboring regions of the frame (15) adjacent to the locking region for the first component (200) or the second component (190).

Figure 24E:
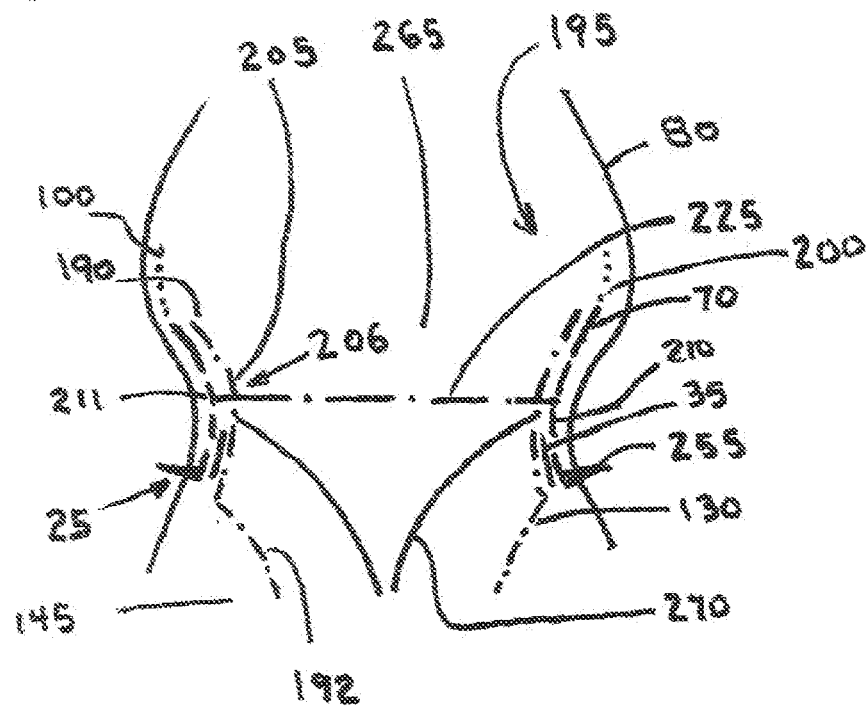
FIG. 24E is a sectional view of a dual member stent valve having a first component or support frame located adjacent to the annulus and having barb tips activated by a torus balloon; the support frame has a concave waist region; the valve frame containing replacement leaflets form the second component and is positioned on the inside of the support frame and has a concave waist that locks with the concave waist of the support frame.

FIG. 24E shows an embodiment of the dual member stent-valve (195) of the present invention having both the first component (200) and second component (190). The first component or support frame (200) was implanted initially within the lumen of the native mitral heart valve. The first component (200) has a SE stent frame (15) that was delivered via a delivery sheath (105) to a location adjacent to the mitral annulus (20) without affecting the native mitral valve function. An upper bulb (70) was extending outwards in the LA (80) to help position the frame (15) such that the waist extended across the annulus (20) and the upper bulb (70) was located in the LA. The profile of the first component or support frame (200) was very low due to the lack of replacement leaflets (270); hence the first component (200) was easily delivered by crossing the atrial septum. The first component (200) was allowed to expand out into contact with the mitral annulus (20) or other native mitral valve tissue without affecting movement of native mitral valve leaflets and not affecting their valvular function prior to activating the barbs (25) via a torus balloon (35) which is attached to the first component (200) as described in earlier embodiments. The torus balloon (35) allows blood to pass through the first component (200) and hence there is no shear forces or pressure forces that act to change the position of the first component (200). The torus balloon (35) can be inflated with saline such that leakage of inflation fluid is not of concern; detachment of the torus balloon (35) from the delivery catheter is easy since the inflation fluid is allowed to leak out of the torus balloon (35) as it is implanted. If the position of the first component (200) was not acceptable to the operator, it would have been withdrawn into the delivery sheath (105) via recapture struts (100) prior to activation of the barbs (25). The first component (200) has a limiting cable (225) around the perimeter (30) of the waist (10) to ensure that the second component (190) can be expanded into it and obtain a good frictional or geometrical fit.

Once the first component or support frame (200) has been delivered, a SE second component (190) is delivered into the open central lumen (265) provided by the first component (200). The second component waist (205) has a curved waist (40) with a second component concave region (206) that matches the first component concave region (211) of the first component (200) thereby locking the first component (200) with the second component (190). A covering on the first component concave region (211) and the second component concave region (206) assist in preventing leakage of blood from between the first component (200) and the second component (190). The second component (190) is released within the open central lumen (265) of the first component (200) and makes contact long a continuous perimeter with the first component (200) in the locking region or the concave regions such that blood flow is not allowed to leak between the first component (200) and the second component (190). The second component (190) can have a cylindrical housing (130) for the replacement leaflets (270) or the downstream end (145) of the housing (130) can be smaller in diameter than the housing inlet end (592) to ensure that the LVOT is not impeded.

The second component (190) can alternately be formed with a BE frame (15) and can be delivered via a cylindrical dilation balloon (588) or an expandable mechanical devices that can enlarge to form a larger configuration that would expand out a BE stent-valve. The BE second component (190) can have a second component concave region (206) that fits the first component concave region (211) of the first component (200). The BE second component (190) can be expanded under large inflation pressures or expansion forces such that the BE stent frame (15) of the second component (190) is deformed plastically around the limiting cable (225) of the first component (200) to cause a frictional and geometrical fit with the first component (200).

Figure 25:
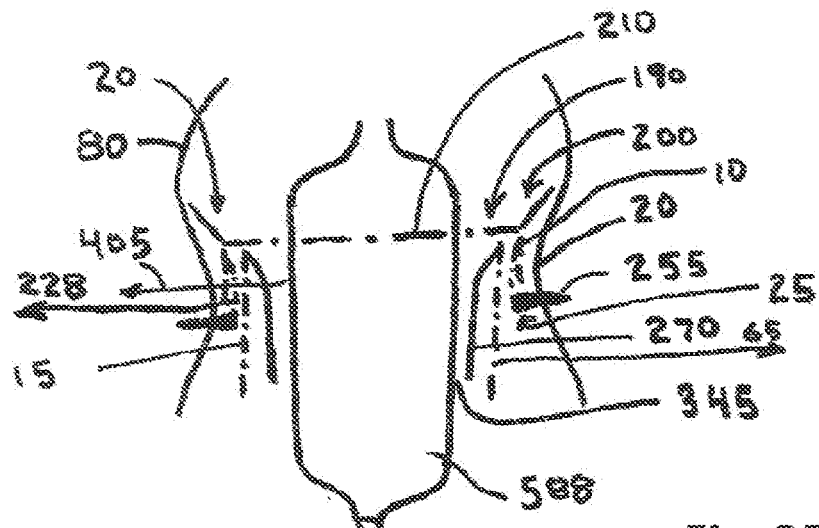
FIG. 25 is a sectional view of a balloon expandable second component placed within the open central lumen of a first component or support frame; a cylindrical dilation balloon expands the second component into contact with the support frame.
Figure 26A:
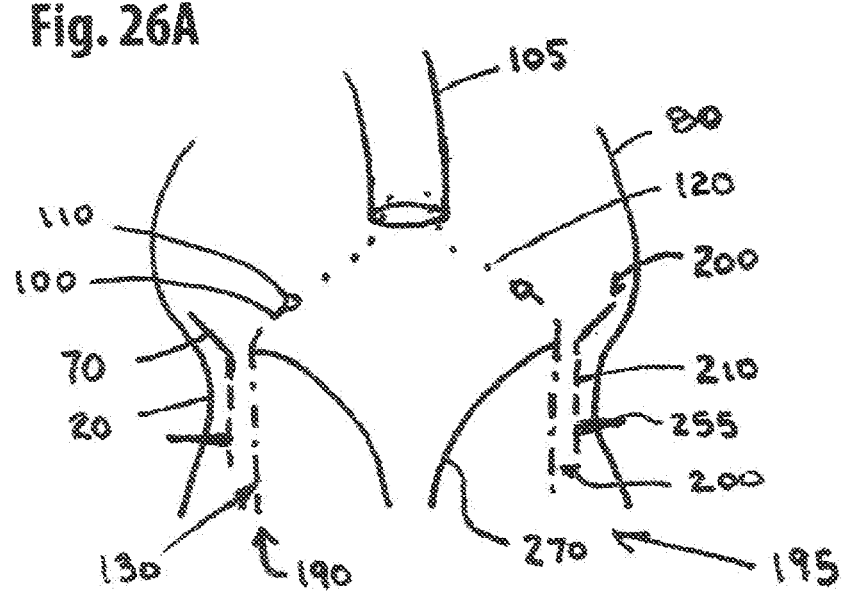
FIG. 26A is a sectional view of self-expanding second component being placed within the open central lumen of a first component or support frame; recapture struts are still attached to the valve frame of the second component.
Figure 26B:
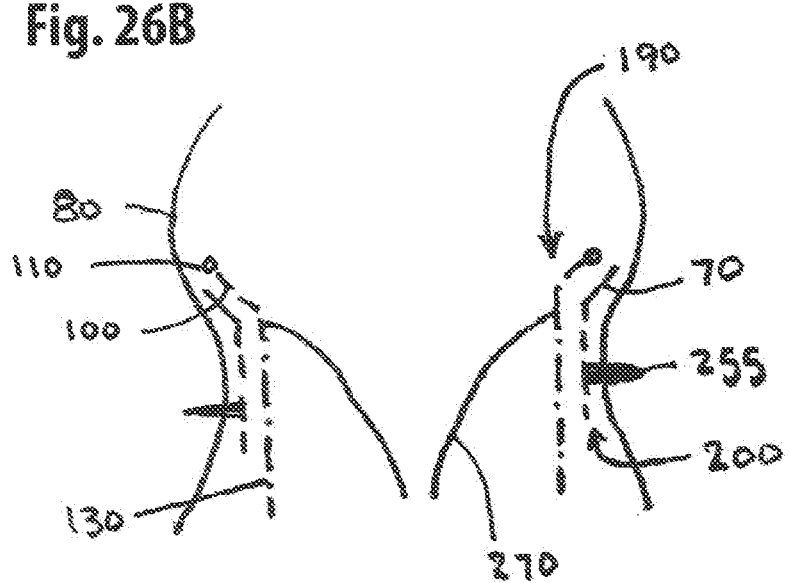
FIG. 26B is a sectional view of self-expanding second component that has been placed within the open central lumen of a first component or support frame and had its recapture struts released.

The BE stent-valve frame (15) can be delivered such that the stent frame (15) of the second component (190) of the dual member stent-valve is positioned adjacent the waist (10) of the first component (200) as shown in FIG. 25. A cylindrically-shaped dilation balloon (588) located on the luminal side (345) of the stent-valve frame (15) can apply an outward frame expansion force (405) to the frame (15) of the BE second component (190) stent valve into intimate contact with the waist (10) of the first component (200). The dilation balloon can also help to further apply an outward radial force (228) onto the barbs (25) to force the barb tips (255) outwards further into the annulus (20) or tissues of the heart valve. The limiting cables (210) located along a frame perimeter (375) of the first component (200) act to prevent over-expansion of the second component (190) to a diameter that could stretch the mitral annulus (20) potential causing injury to the patient. The limiting cables (210) also provide limit to the frame perimeter (375) that the first component (200) can attain thereby allowing the second component (190) to expand with a maximal frame outward force (65) that ensures maximal frictional contact between the second component (190) and the first component (200) thereby reducing the likelihood of migration of the second component (190) with respect to the first component (200), without the risk of over-expansion of the first component (200). The limiting cable of the first component (200) also allows the second component (190) to be expanded and deformed (by a dilation balloon, for example) such that the second component (190) forms a narrow waist (10) region adjacent to the limiting cable of the first component (200) such that the second component waist (205) of the second component (190) has an hour-glass shape that fits via a geometrical lock with the first component (200). Geometrically shaped waist (10) regions for the first and second component (190) can also help to ensure that undesirable axial movement of the second component (190) are prevented For the embodiment where the second component (190) has a SE stent-valve frame, the SE second component (190) is delivered via an external delivery sheath (105) that holds the second component (190) into a non-expanded configuration and delivers the second component (190) to a location adjacent the native mitral apparatus such that the frame waist (10) of the second component (190) is located adjacent the frame waist (10) of the first component (200) as shown in FIGS. 26A and 26B. Recapture struts (100) can be attached to the waist (10) or upper bulb (70) of the second component (190) (see FIG. 26A); the recapture struts (100) can attach to holding features (110) located at the upstream end; the holding features (110) allow control fibers (120) to be looped through them and extend through the delivery sheath (105) to the proximal end of the delivery sheath outside of the body. The control fibers (120) allow the second component (190) to be retrieved or repositioned as described in earlier embodiment presented in the present patent application such as the embodiment presented in FIG. 1A. The second component (190) is released from the external sheath and expands outward into contact with the first component (200) as shown in FIG. 26B. Frictional forces hold the second component (190) from migration with respect to the first component (200); geometrically shaped waist (10) regions or curved waist (40) regions for the first component (200) and second component (190) also assist in preventing migration of the second component (190). Release of a SE stent-valve is provided by a pushing member contained within the delivery sheath (105) as is known in the industry for delivery of SE stented devices.

The replacement leaflet (270) for the present invention can be formed from tissues taken from animal pericardium, xenograft heart valve, allograft heart valve, or other tissue or collagen materials. Alternately, the replacement leaflets (270) can be formed from a thin layer of polymeric material such an expanded polytetrafluoroethylene (ePTFE), Dacron film, polymeric woven, braided, or knitted material. Often a polymeric material that is exposed to continued stress will tend to creep, therefore many of the polymeric films and some of the tissue or collagen materials used for valve leaflets will need to be supported by fibers or thin films made from stronger materials that will not creep under stress. Such stronger support fibers and films include Dacron fibers, thin multifilament metal fibers, thin metal films such as Nitinol films and other materials of similarly high tensile strength and low creep; such films and fibers can have diameters and thickness of 0.001 inches (range 0.0003-0.002 inches) and can be very flexible.

Figure 27A:
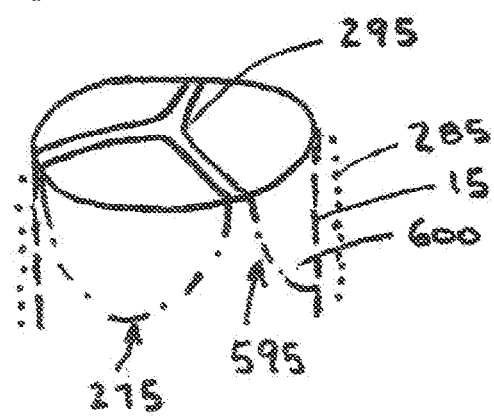
FIG. 27A is a perspective view of the semi lunar leaflets showing the crown-shaped attachment to the wall structure of the frame.
Figure 27B:
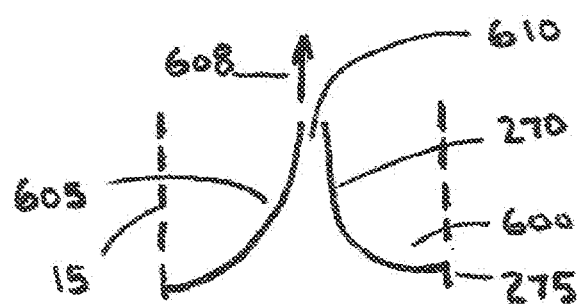
FIG. 27B is a plan view of valve leaflets showing pockets that are created as the leaflets form leaflet coaptation.
Figure 27C:
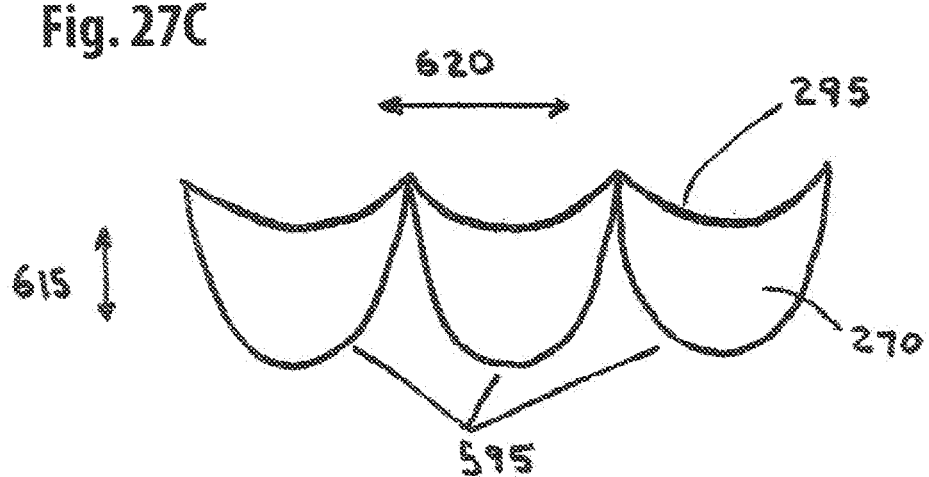
FIG. 27C is a plan view of valve leaflets splayed out showing the crown-shaped attached edge.

The semi-lunar valve leaflets of the present invention are attached to the wall of a cylindrical stent frame in a crown-shape attachment (595) path as shown in FIG. 27A. The free edge (295) of the valve leaflet comes into direct contact with a neighboring leaflet and a portion of the valve leaflet coapts with the neighboring leaflet. A leaflet pocket (600) is formed in the leaflet between the leaflet downstream surface (605) and the stent frame (15) as shown in FIG. 27B. Downstream (608) flow of blood through this valve is shown in an upward direction with blood flow leaving through the free edges (295). The leaflet pocket changes shape as the leaflet moves from an open configuration with leaflets positioned adjacent or near the wall of the stent frame (15) to a closed configuration as shown in FIGS. 27A and 27B. The leaflet pocket allows the leaflets to coapt over a coaptation surface (610) during systole when the leaflets are closed and neighboring leaflet surfaces near the free edges (270) contact each other for an axial distance of 3 mm (range 1-6 mm) forming leaflet coaptation; blood flow via a directed flow and via a recirculation pattern over the coaptation surface of the leaflets during diastole ensures that thrombus does not develop on the surfaces of the leaflets. The leaflets flex via extension in both the leaflet axial direction (615) and the circumferential direction (620) (see FIG. 27C) as they move from an open position to a closed position.

The leaflet support fibers extending circumferentially can provide the required circumferential strength with minimal strain of less than 10%; axial support fibers provide more flexing and strain (i.e., 15%) to form the valve leaflet pockets and assist in leaflet coaptation. Leaflet support fibers can be attached to the leaflets to allow leaflet expansion to occur in a controlled manner, also support fibers can provide a location by which the leaflets can be attached to the stent frame (15) of the present invention, further support fibers strengthen the free edge of the leaflets to prevent the free edge from encountering irreversible stretching. An embodiment for three semi-lunar leaflets that are found as replacement leaflets (270) in the present stent-valve assembly is shown in a splayed-out manner in FIG. 27C. The crown-shaped leaflet attachment (275) path for three leaflets is shown; the crown shaped path is intended to be attached to the stent frame; the semi-lunar valve can be formed with two or four leaflets, instead of three, for example, without deviating from the present invention.

Figure 28A:
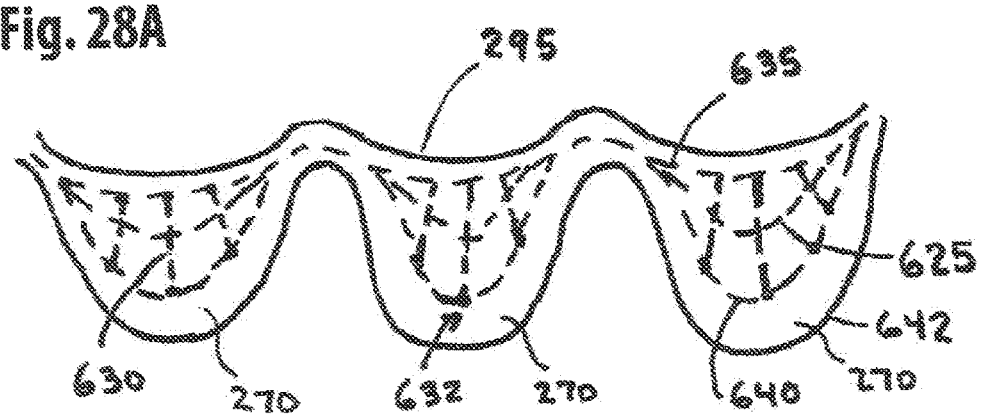
FIG. 28A is a plan view of valve leaflets showing the presence of axial and circumferential fibers attached to the leaflet surface to provide strength, control the leaflet compliance, and provide fibers to attach the leaflets to the frame.
Figure 28B:
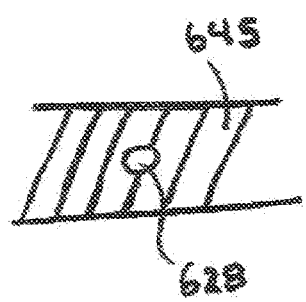
FIG. 28B is a sectional view through the thickness of a leaflet showing a fiber embedded within a polymer film.
Figure 28D:
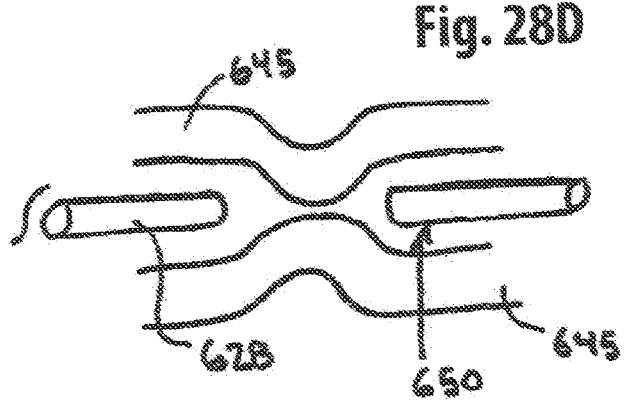
FIG. 28D is a perspective view of semilunar leaflets formed with axial fibers and circumferential fibers being attached to a frame of a stent valve.

One embodiment for the semi-lunar replacement leaflets (270) of the present invention is shown in FIG. 28A. The leaflets are formed from a polymeric film that is formed via either a film casting process, an extrusion process, or other film forming process. In this embodiment fibers (628) formed from Dacron, Nitinol, or stainless steel, for example, are embedded within the polymer matrix of the leaflet polymeric film, such as polyurethane, for example, as shown in FIGS. 28A and 28B. The fiber can also be attached to collagen matrix material or tissue surfaces used to form the leaflets, the fibers can also be attached to tissue valve leaflets via adhesives, sutures, or other bonding methods. The fibers include circumferentially oriented fibers (625) and axially oriented fibers (630). A free-edge fiber (635) can extend along or near the free edges (295) of the leaflets in a circumferential direction; an attachment-edge fiber (640) can extend along the attached edge (642) of the leaflets in a circumferential direction. One or more axial fibers can extend from the free-edge fiber to the attachment-edge fiber; axial fibers can be attached to free-edge fibers or attachment-edge fibers at fiber attachment sites (632) via brazing, soldering, welding, adhesives, swaging, thermal bonding, solvent bonding, knotting, or other bonding methods. The circumferentially oriented fibers and axially oriented fibers can be embedded within the polyurethane, collagen, or tissue matrix; the polymer or tissue matrix can be solvent cast or thermally cast around the fibers as shown in FIG. 28B forming a polymeric film (645) that can be used as a valve replacement leaflet. Alternately, two separate films of polyurethane or tissue matrix can be placed onto each side of the fibers and heated to thermally bond the two film layers together or bonded together via adhesives, solvent bonding, or other bonding method thereby forming a sandwiched fiber (650) as shown in FIG. 28D; the sandwiched fiber film is used as a replacement leaflet material.

Figure 28C:
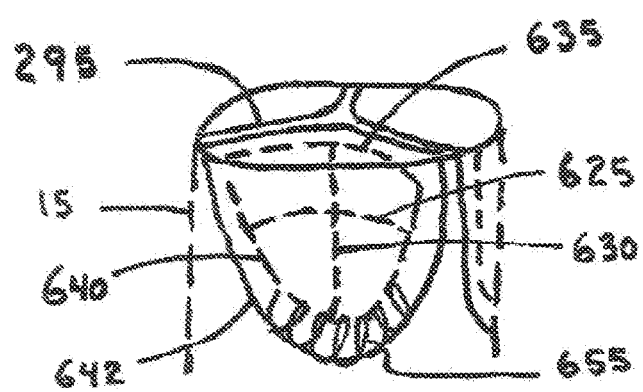
FIG. 28C is a sectional view through the thickness of a leaflet showing a fiber embedded or sandwiched between two polymer films.

The polymer or tissue matrix and fiber composite leaflets can then be attached to the stent frame (15) via a variety of methods. Sutures (655), for example can be used to sew the attachment-edge fiber to the stent frame (15) as shown in FIG. 28C. Alternately, the polymer used as the leaflet film can be used also as a covering (285) for the stent frame; the leaflet can be joined to the stent frame (15) via polymer to polymer bonding methods which include thermal bonding, solvent bonding, adhesive bonding, and other forms of bonding. The leaflet can also be contiguous with the covering (285) that is attached to the stent-valve frame.

Figure 29A:
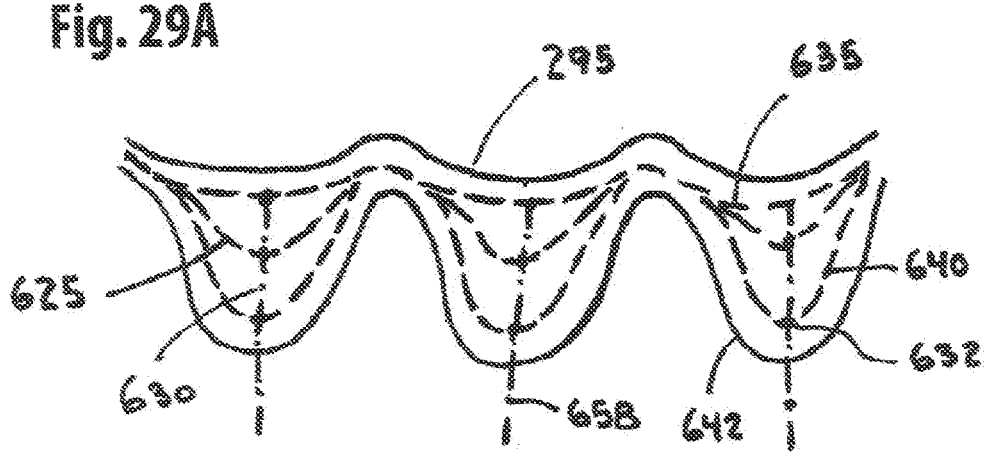
FIG. 29A is a plan view of a valve leaflets showing the presence of axial and circumferential fibers that extend within or are attached to the leaflets and have fiber extensions that allow attachment to the frame of the stent valve.
Figure 29B:
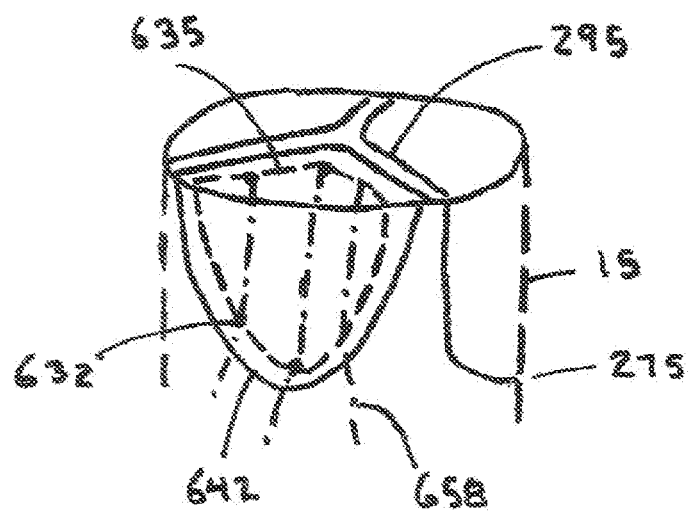
FIG. 29B is a perspective view of valve leaflets being attached to a frame via fiber extension that are embedded or attached to the leaflets.

Another embodiment for attaching the polymer and fiber composite leaflets to the stent frame (15) is shown in FIGS. 29A and 29B. In this embodiment the axial fibers are allowed to extend beyond the attached-edge fiber as shown in FIG. 29A. The axial fiber extensions can then be attached directly to the stent frame (15) via brazing, welding, swaging, adhesive bonding or other bonding methods available. The axial fibers can alternately be formed to be contiguous with the stent frame.

Figure 30:
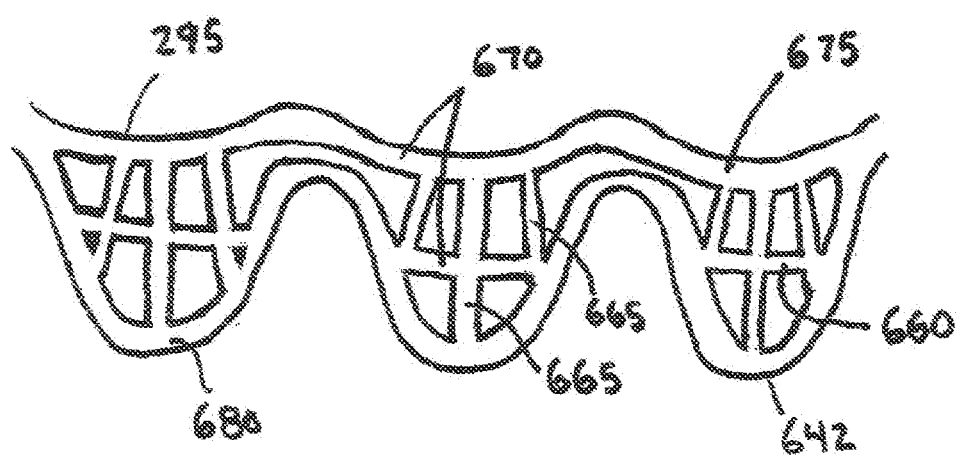
FIG. 30 is a plan view of valve leaflets having a thin film of a metal embedded within or attached to the surface of the leaflets to provide strength, compliance control, and a means for attachment.

A thin film (660) of Nitinol or other metal can be cut via laser, electric discharge method (EDM) or other methods to form a leaflet frame as shown in FIG. 30. The leaflet frame can have axial members (665) and circumferential members (670); the circumferential members can extend along the free edge forming free-edge members and along the attached edge forming attached-edge members; axial members can extend from the free-edge members to the attached-edge members. The leaflet frame can be embedded within a polymer matrix as described earlier for the fiber supported leaflet, alternately the leaflet frame can be sandwiched between to polymer films via thermal, solvent, adhesive, other bonding method used to bond two films together. The leaflet frame can be attached to the stent frame (15) via sutures, adhesive bonding, thermal bonding, welding, brazing, soldering, or other methods. Alternately, the leaflet frame can be contiguously formed along with the stent-valve frame (15).

Figure 31A:
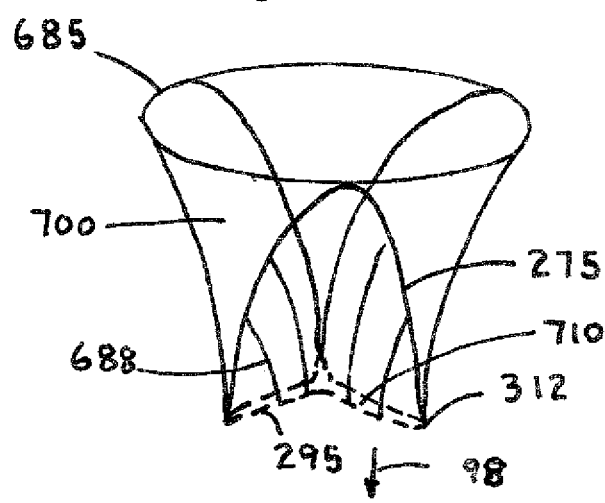
FIG. 31A is a perspective view of a mitral valve used for surgical replacement with the leaflets in a closed configuration.
Figure 31B:
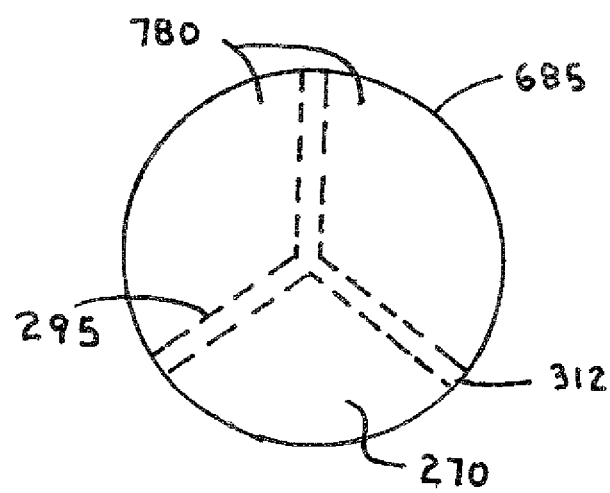
FIG. 31B is a sectional view of the replacement mitral valve showing the leaflets and leaflet free edges in a closed configuration.
Figure 31C:
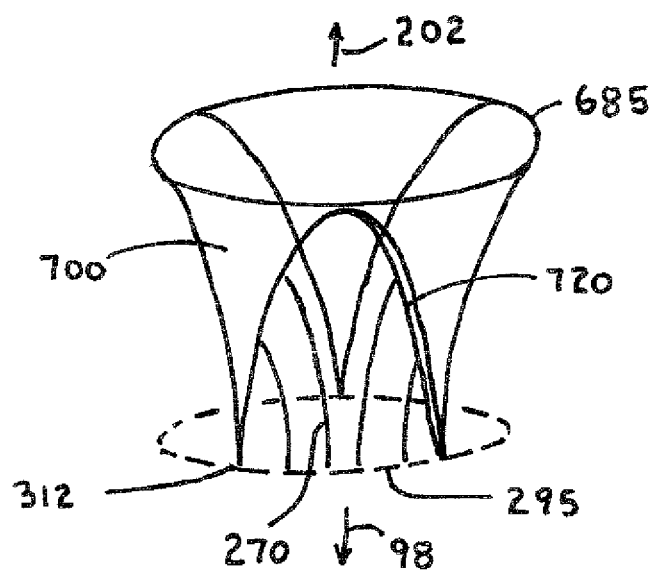
FIG. 31C is a perspective view of a mitral valve used for surgical replacement with the leaflets in an open configuration.
Figure 31D:
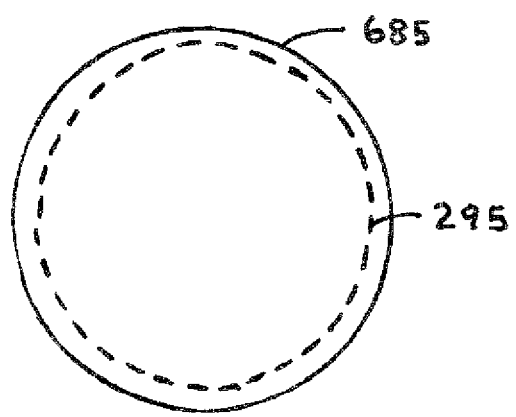
FIG. 31D is a sectional view of a transcatheter mitral valve replacement (TMVR) device showing the leaflets and leaflet free edges in an open configuration.

FIGS. 31A-31D show a surgical replacement valve of prior art with a surgical securement band (865) that can be sewn to the annulus (20) of the heart after the native heart valve leaflets (790) have been surgically removed. Three posts (700) (note: 2-4 posts can alternately be used to support 2-4 surgical leaflets (688) respectively) are attached to the surgical securement band (865) and extend downstream (98) to support three surgical leaflets (688). Each post (700) attaches to the commissures (312) of two neighboring leaflets (780). The replacement leaflets (270) attach to the posts (700) along a crown-shaped attachment path (275). The leaflet free edges (295) coapt together forming a leaflet coaptation (710) in a closed configuration as shown in FIGS. 31A and 31B, and the surgical leaflets (688) are shown in an open configuration in FIGS. 31C and 31D with the leaflet free edges (295) forming a circular shape. The posts (700) are impervious to blood flow across the post wall (720) thereby providing this surgical valve with an ability to direct blood flow downstream (98) and preventing blood flow upstream (202). The post does not prevent direct contact of the native leaflets nor the left ventricular lateral wall from interfering with the function of the replacement leaflets of a transcatheter mitral valve replacement device.

FIGS. 32A-32D show a prior art transcatheter stent-valve having a cylindrically-shaped stent frame (192) that extends from the upstream end (730) at the nadirs (280) of the leaflet attachments to the stent-valve frame surface (868) to the downstream end (740) at the location of the commissures (312) of the replacement leaflets (270). The leaflet attachment nadir (280) is the location along the crown-shaped attachment path (275) that is tangent or parallel with the upstream end (730) of the stent-valve frame (192). The stent-valve frame (192) can extend further upstream (202) than the nadirs (280) and can extend downstream (98) further than the commissures (312) without affecting the present invention. Three replacement leaflets (270) are attached to the stent frame (192) along a crown-shaped attachment path (275). The leaflet free edges (295) of neighboring leaflets (780) are coapted forming a leaflet coaptation (710) in a closed configuration in FIG. 32A; the replacement leaflets (270) are in an open configuration in FIG. 32B forming a generally circular shape. Each leaflet has a leaflet central surface (795) that forms a leaflet coaptation (710) with neighboring leaflets (780) near the central axis (45) of the stent-valve frame (192).

Stent-valves used for transcatheter valve replacement have a covering (285) attached to the stent-valve frame (192) in regions extending from the upstream end (730) (at the nadir (280) of the leaflet attachment) to the downstream end (740) of the stent-valve frame (192) (at the location of the commissures (312) of the replacement leaflets (270). The covering (285) prevents retrograde flow from going from the downstream end (740) to the upstream end (730) when the replacement leaflets (270) are in a closed configuration and prevents flow from travelling across the surface of the stent-valve frame wall (750) at locations where the covering (285) is attached to the stent-valve frame (192); the covering (285) may also assist in preventing perivalvular leaks. The covering (285) can be a thin fabric that lies against the stent-valve frame (192) or it can form an umbrella-like shape, folded shape, or pillow-like shape, or other skirt-shaped form that can help to prevent perivalvular leak around the outside (880) of the stent-valve frame (192).

Figure 32A:
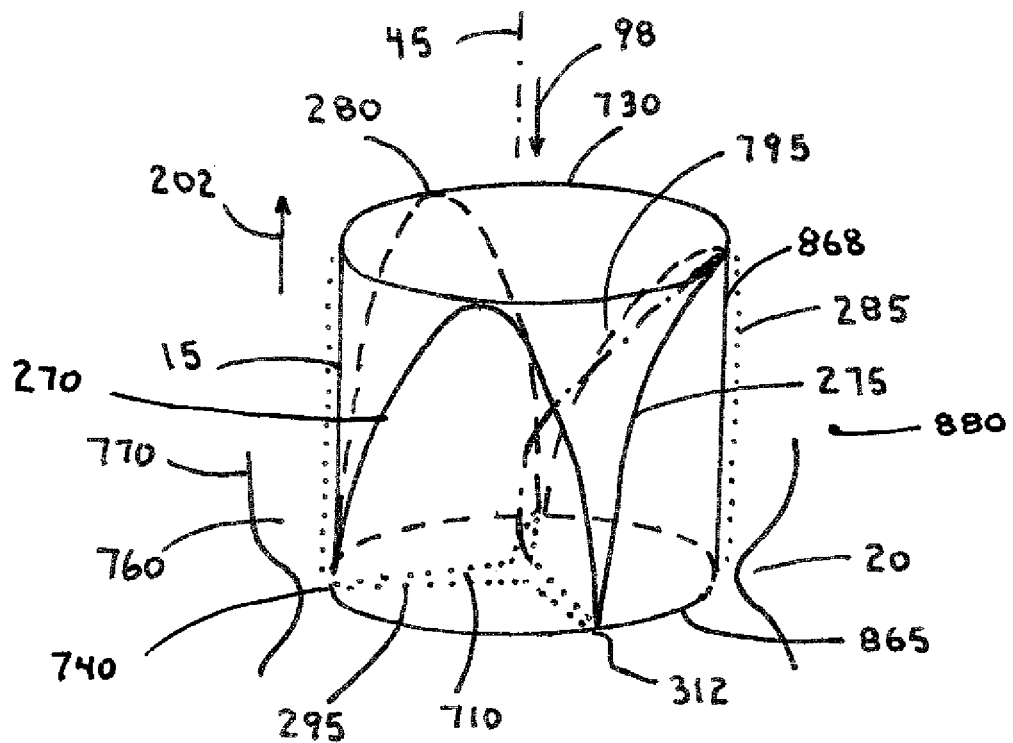
FIG. 32A is a perspective view of a prior art transcatheter mitral valve replacement (TMVR) device with leaflets in a closed configuration.
Figure 32B:
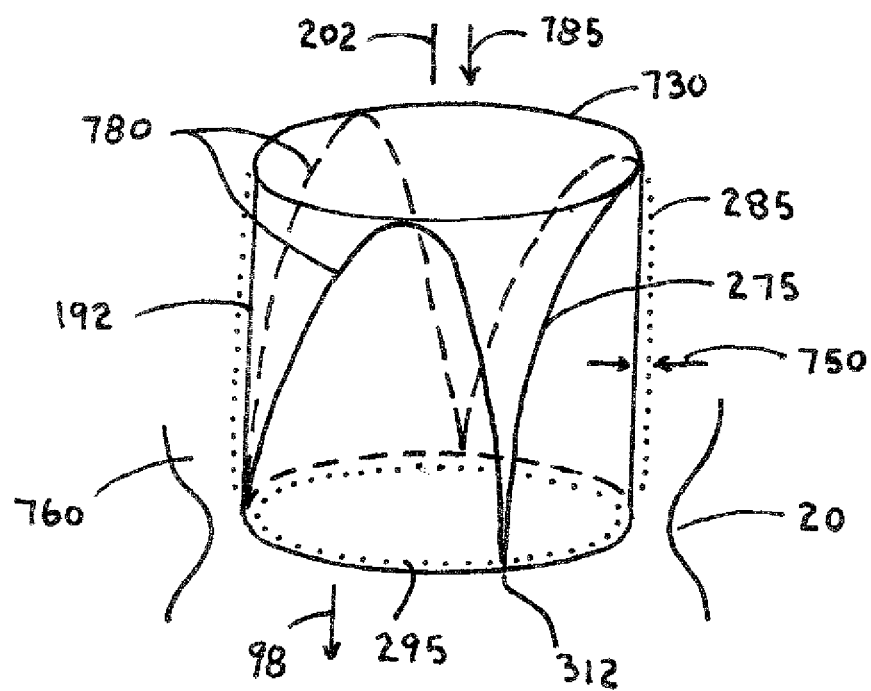
FIG. 32B is a perspective view of a prior art TMVR device with leaflets in an open configuration.

The stent-valve frame (192) is formed from a stent structure similar to a vascular stent used in angioplasty; the open stent structure requires that the covering (285) be attached to the stent-valve frame (192) to prevent blood flow across the stent wall. When the stent-valve is positioned such that the downstream end (740) of the stent-valve frame (192) which can form a securement band is secured to a heart annulus (20) as shown in FIG. 32A of the native valve (or other securement ring or location such as the base of native leaflets, for example), a stagnation region (760) is created between the native lumen wall (770) or tissue chamber wall (such as the left atrium (80) (LA), for example, for a mitral stent-valve replacement) and the covered stent-valve. A securement plane can be formed, for example, which intersects with and is coplanar with the downstream end (740) of the stent-valve frame (192); the downstream end (740) makes contact with the annulus (20) located outside (880) of the stent-valve frame (192) to hold the stent-valve frame (192) via friction, for example, to hold the stent-valve frame (192) from migration and to assist in preventing perivalvular leak due to the covering attached to the stent-valve frame (192). The fluid contained within this stagnation region (760) is required to flow in an upstream (202) direction to reach the upstream end (730) of the stent-valve frame (192) where the fluid can then flow downstream (98) and flow in an antegrade direction (785) through the lumen of the stent-valve frame (15) and out of the stent-valve with the replacement leaflets (270) in an open configuration. This stagnation region (760) can result in the formation of thromboemboli that can migrate into the blood stream and can lead to the formation of a stroke.

Figure 32C:
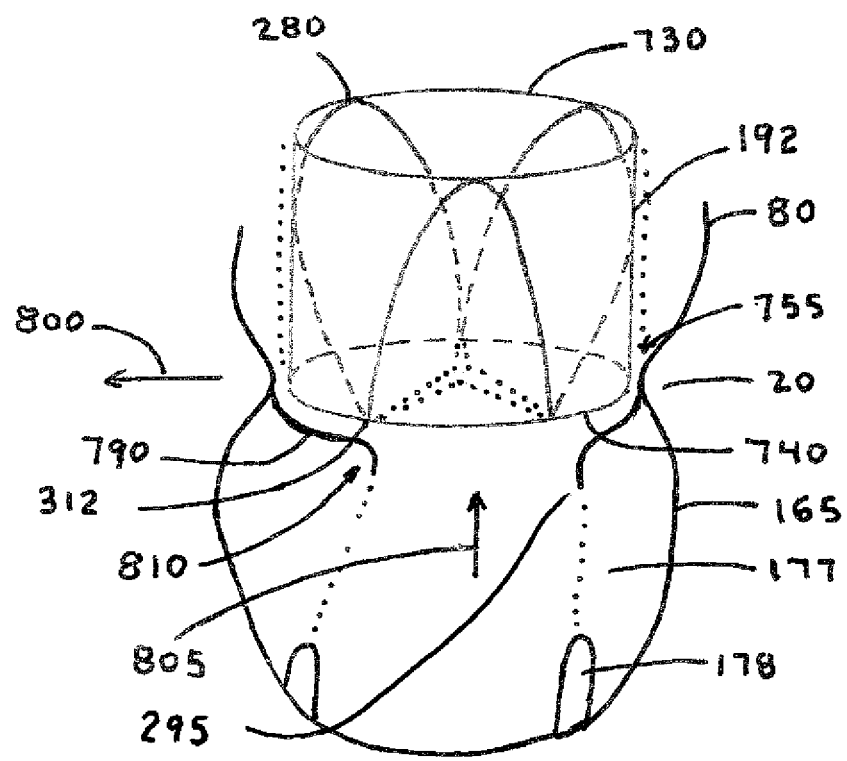
FIG. 32C is a perspective view of a prior art TMVR device that is positioned in the left atrium above the mitral annulus with regions of blood stagnation and thrombus formation.

As shown in FIG. 32C, if the stent-valve frame (192) is locate substantially within the left atrium (LA) (80) with very little (i.e., less than 5 mm) or none of the stent-valve frame (192) extending axially into the left ventricle (LV) (165), then a native valve leaflet that is prone to prolapse can overhang or extend into the downstream end (740) of the stent-valve frame (192). The cordae tendineae (177) normally attach the native leaflet free edges (295) to the papillary muscles (178) to prevent such overhang. However with improper anatomy such overhang of the native leaflet can interfere with the function of the replacement leaflets (270), can block blood flow in a retrograde direction (805) from initiating closure of the replacement leaflets (270) at the initiation of systole, and can cause regions of stagnation that can lead to thrombosis and formation of thromboemboli. Extension of downstream end (740) of the stent-valve frame (192) into the LV (165) is necessary to provide contact with the native mitral leaflet and push the native leaflet (790) outwards (800) such that the native leaflet cannot cause leaflet overhang (810) at the downstream end (740) of the stent-valve frame (192).

Figure 32D:
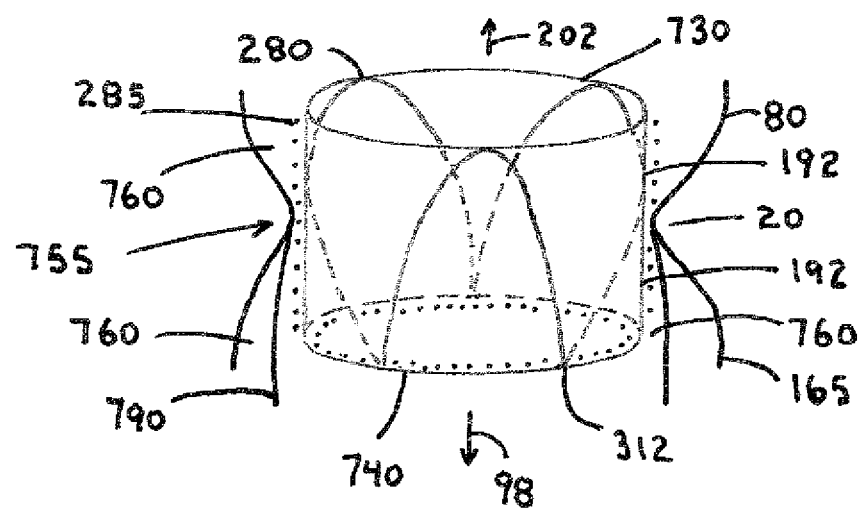
FIG. 32D is a perspective view of a prior art TMVR device that is positioned in both the left atrium and the left ventricle straddling the mitral annulus and having regions of blood stagnation and potential thrombo emboli formation.

The covered stent-valve frame can be located such that a portion of the stent-valve frame (192) that is covered is located above the securement location (755) or annulus (20) and a portion of the stent-valve frame (192) is located below the securement location (755) or annulus (20) as shown in FIG. 32D. The amount or volume of stagnation region (760) formed upstream (202) of the securement location (755) is reduced by locating some of the covered stent-valve downstream of the securement location (755). The stagnation region (760) still will allow blood to thrombose and lead to potential formation of thromboemboli. Also, a stagnation region (760) exists in the LV (165) between the native leaflets (790) and the covered stent-valve region. This stagnation region (760) can also contribute to thrombosis and formation of thromboemboli.

Figure 33A:
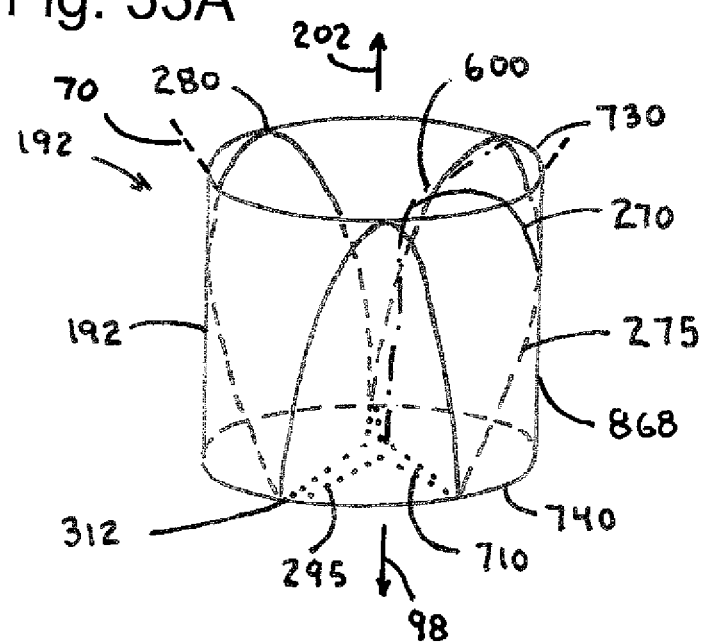
FIG. 33A is a perspective view of a cylindrically shaped stent-valve frame component of a two-component system with leaflets in a closed configuration and forming a leaflet pocket.
Figure 33B:
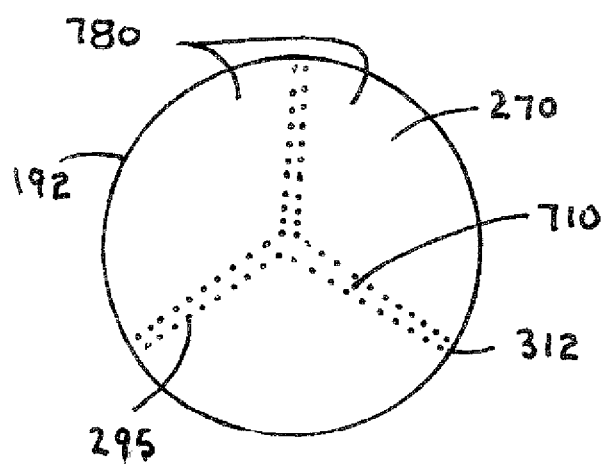
FIG. 33B is a sectional view of a stent-valve frame component showing the leaflets in a closed configuration.
Figure 33C:
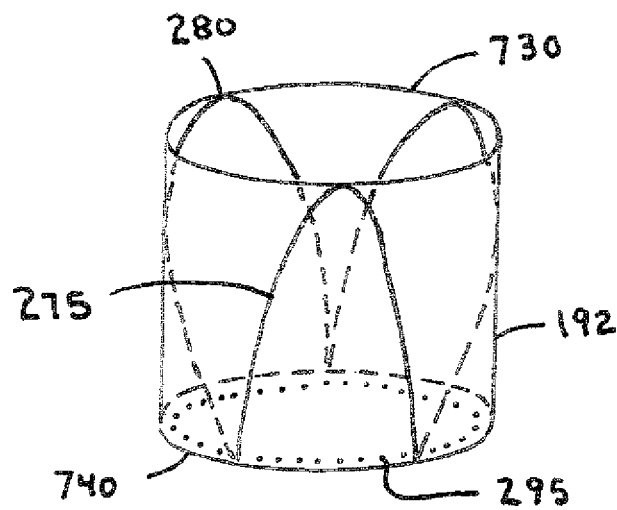
FIG. 33C is a perspective view of a cylindrically shaped stent-valve frame component showing leaflets in an open configuration.
Figure 33F:
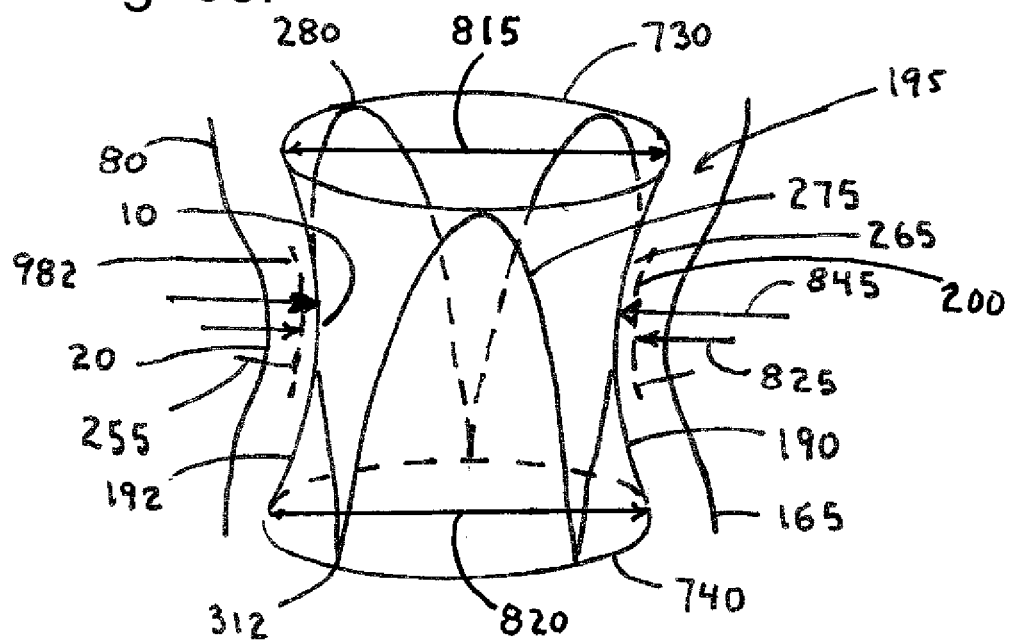
FIG. 33F is a perspective view of a dual member stent valve having a second component stent-valve frame having an hour-glass shape.
Figure 33D:
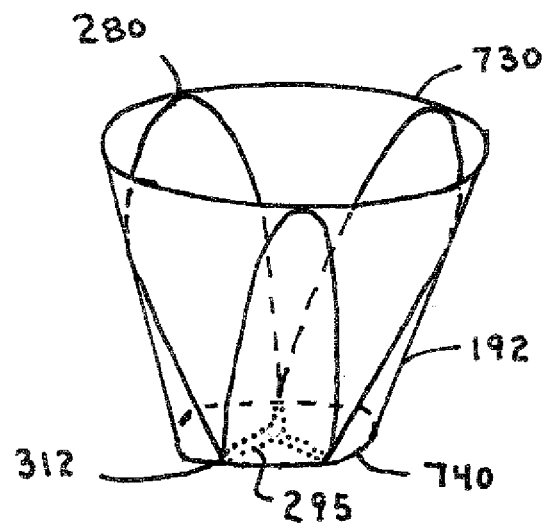
FIG. 33D is a perspective view of a frustum-shaped stent-valve frame component with the small diameter at the downstream end.
Figure 33E:
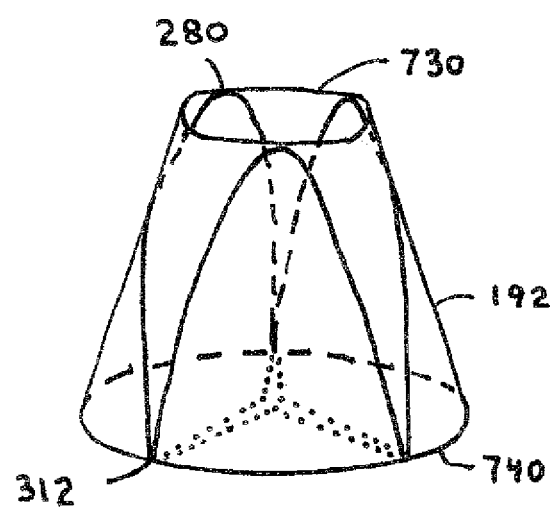
FIG. 33E is a perspective view of a frustum-shaped stent-valve frame component with the small diameter at the upstream end.
Figure 33G:
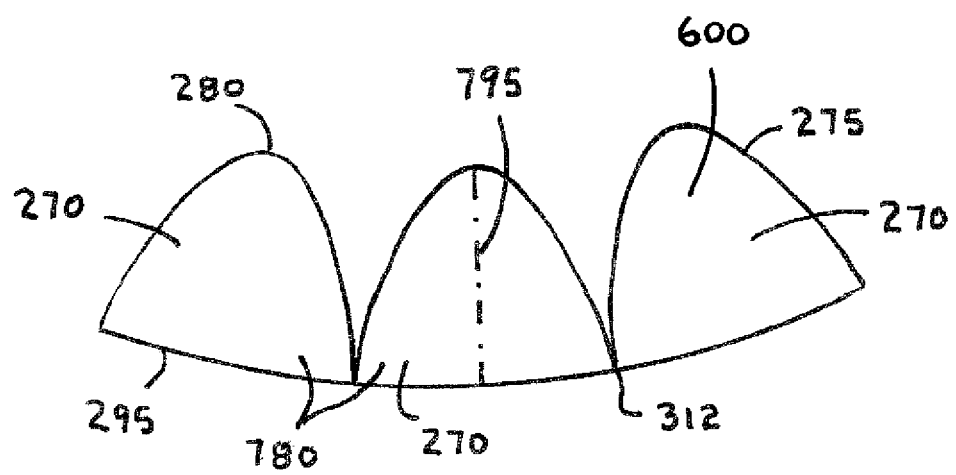
FIG. 33G shows three mitral valve leaflets and their commissures.
Figure 33H:
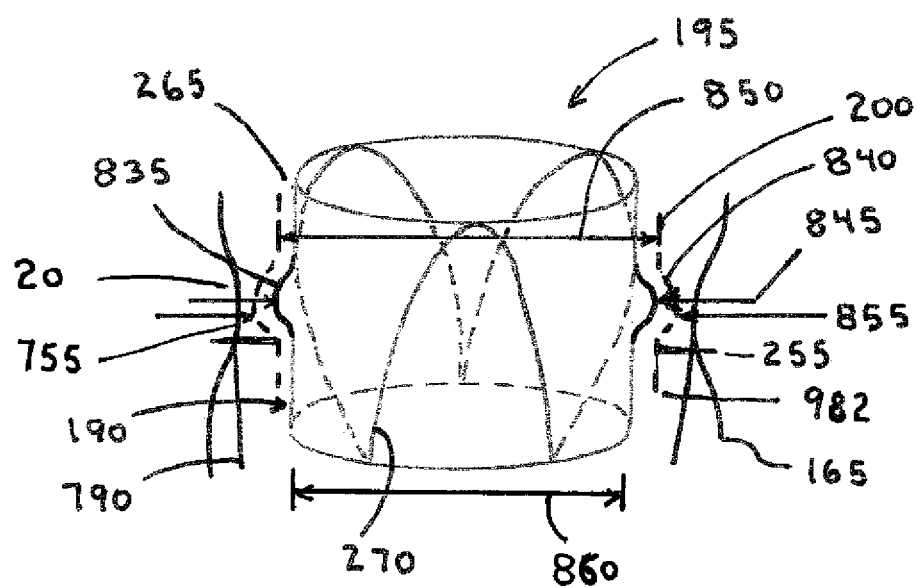
FIG. 33H is a perspective view of a dual member stent valve showing the first component locking to the second stent-valve component via convex locking regions.

The stent-valve component (190) (i.e., second component (190) of the two component system (195) described in earlier embodiments) of the present invention is shown in FIGS. 33A-33G. The stent-valve frame (192) can have a cylindrical shape as shown in FIG. 33A, a frustum shape where the upstream end (730) is of a larger diameter than the downstream end (740) (FIG. 33D), a frustum shape where the upstream end (730) is of a smaller diameter than the downstream end (740) (FIG. 33E), or other geometrical shape such as shown in FIG. 33F, for example, showing a dual member stent valve (195) having a larger upstream end diameter (815) and a larger downstream end diameter (820) than the smaller second component locking region diameter (845) such as a waist region diameter that geometrically fits with a first component locking region diameter (825), for example; the stent-valve frame (192) has an hour-glass shape. The smaller diameter waist diameter forms a second component concave waist that can be used to form a geometric fit or a geometrical lock of the second component (190) or stent-valve component (190) of the present embodiment to the concave waist region (or other geometrical locking shape) of a first component (200) of the present invention as described in previous embodiments. Alternately, as shown in FIG. 33H the dual member stent-valve (195) has the second component (190) or stent-valve component (190) having a convex geometrical region that is able to lock within a convex geometrical region found in the first component frame (982).

As shown in FIGS. 33A and 33B, the stent-valve frame (192) has three replacement leaflets (270) attached to the stent-frame surface (868) along a crown shaped attachment path (275). The present invention can also include only two replacement leaflets (270) or as many as four replacement leaflets (270). The crown-shaped attachment path (275) extends from the upstream end (730) of the stent-valve frame (192) where the nadir (280) of the attachment path (275) is in contact with the upstream end (730) of the stent-valve frame (192); the crown-shaped attachment path (275) extends to the leaflet commissures (312) which are located at the downstream end (740) of the stent-valve frame (192). The leaflet attachment nadir (280) is the location along the crown-shaped attachment path (275) that is tangent with the upstream end (730) of the stent-valve frame (192). A leaflet pocket (600) is formed in each of the replacement leaflets (270) as they each bow inwards at the leaflet nadir (280) at the upstream end (730) of the leaflet; each leaflet forms a leaflet coaptation (710) with other leaflets at the downstream end (740) to block off blood flow toward the upstream end (730) during systole.

The stent-valve frame (192) can extend further upstream (202) than the upstream end (730) and can extend further downstream (98) than the downstream end (740) of the stent-valve frame (192) if desired. An upper bulb (70), as discussed in other embodiments, can be attached to the upstream end (730) or intermediate between the upstream end (730) and downstream end (740) of the stent-valve frame (192) to assist the operator with positioning of the stent-valve frame (192) and assist in blocking perivalvular leaks as described in previous embodiments of the present invention. The upper bulb (70) can extend outwards (800) at an angle with respect to the axial direction of the stent-valve frame (192) as described in earlier embodiments. Similarly, a lower bulb, as discussed in other embodiments, can be attached to the downstream end (740) or intermediate between the upstream end (730) and downstream end (740) of the stent-valve frame (192) to assist in locking the stent-valve frame (192) onto a securement ring (755). The securement ring (755) or securement location (755) can be a native valve annulus (20), native valve leaflets, or a first component (200) that has been placed into the heart valve tissues prior to placing the stent-valve frame (192) of this embodiment.

Figure 33J:
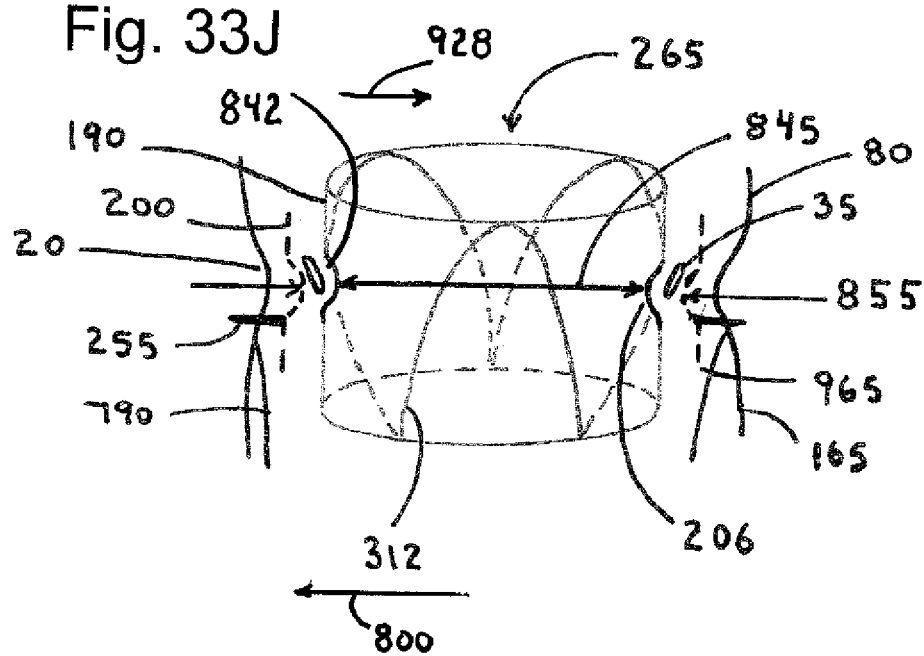
FIG. 33J is a perspective view of a dual member stent valve showing the first component locking to the second stent-valve component via concave locking regions.

An alternate system for attachment of the second component (190) or stent-valve component (190) to the first component (200) is shown in FIG. 33J. In this embodiment, the torus balloon (35) that is attached to the first component (200) is inflated with an inflation medium that is retained within the torus balloon (35) by a one-way flapper valve (540) (as shown earlier in FIG. 14, for example) located in the torus balloon (35) that prohibits exit of the inflation medium from the balloon. The inflation medium can include, for example, saline, polymer gels, curable polymers that form a solid or crosslinked structure, or other inflation medium examples. The torus balloon (35) forms a ring that extends inward (928) towards the central lumen (265) of the first component (200). The inflated torus balloon (35) forms a first component (200) locking region with a geometrical shape or first component concave region (211) that will lock with a second component stent-valve locking region having a second component concave locking region (206). The locking of the torus balloon (35) with the second component (190) concave region (206) via geometrical matching shape will prevent the second component (190) or stent-valve component (190) from migrating toward the LA (80) or toward the LV and will also assist in forming a leak-tight seal between the stent-valve component (190) and the torus balloon (35). The first component (200) locking region diameter (855) is larger than the second component cylindrical diameter (860) and matches the second component locking region diameter (845) such that a geometrical system lock (842) is formed.

As shown in FIGS. 33F, 33H, and 33J the concave region, convex region, or torus balloon (35) can extend inwards (928) in some embodiments toward the central lumen (265) of the first component (200) to form a first component locking region diameter (855) that ranges from 25-35 mm. Other portions of the first component (200) such as the first component downstream end (740) are able to extend outwards (800) to make contact with the mitral valve annulus (20) which can have diameters ranging from 30 to over 50 mm. Thus the second component (190) can have a second component locking region diameter (845) of approximately 25-35 mm to fit snugly against the locking region diameter (855) of first component (200). The number of sizes for the second component (190) to accommodate the varying diameters for the mitral valve annulus (20) can thereby be reduced to two or three sizes and thereby reduce device cost and complexity.

The replacement leaflets (270) have a bowed leaflet surface that forms a leaflet pocket (600) (as described earlier) that serves to allow blood flow to enter the leaflet pocket and assist in closure and coaptation of one leaflet with a neighboring leaflet. The free edges (295) of the leaflets (270) coapt forming a leaflet coaptation (710) when the leaflets (270) are in a closed configuration that prevents retrograde flow as shown in FIGS. 33A and 33B. During antegrade flow the leaflets (270) are in an open configuration as shown in FIG. 33C; the leaflet free edges (295) are near or in contact with the stent-valve frame (192) at the downstream end (740) of the stent-valve frame (192). FIG. 33G shows the three leaflets (270) splayed out and lying approximately flat as the leaflet pocket (600) is allowed to form an approximately flattened shape. The leaflet has a crown-shaped attachment path (275) that extends from the nadirs (280) to the commissures (312). The leaflet free edges (295) have central coaptation regions that come close or come into contact with other central coaptation regions located on other leaflets (270). Each of the three leaflets (270) can be individual entities that are attached separately to the stent-valve frame (192) if desired or they can be formed from a single sheet of tissue material, for example.

As shown in FIG. 33H is a two component system (195) of the present invention. The first component (200) is held to the surrounding tissues or annulus (20) via barb tips (255) that extend into the tissue. The second component (190) has a second component convex region (835) that locks into the first component convex region (840) via forming matching geometrical shapes that lock together forming a system lock (842) that holds the first component (190) via friction or geometrical fit. The second component locking region diameter (845) is larger than the first component cylindrical diameter (850) and matching the first component locking region diameter (855) at a location axially adjacent to the first component locking region.

Figure 34A:
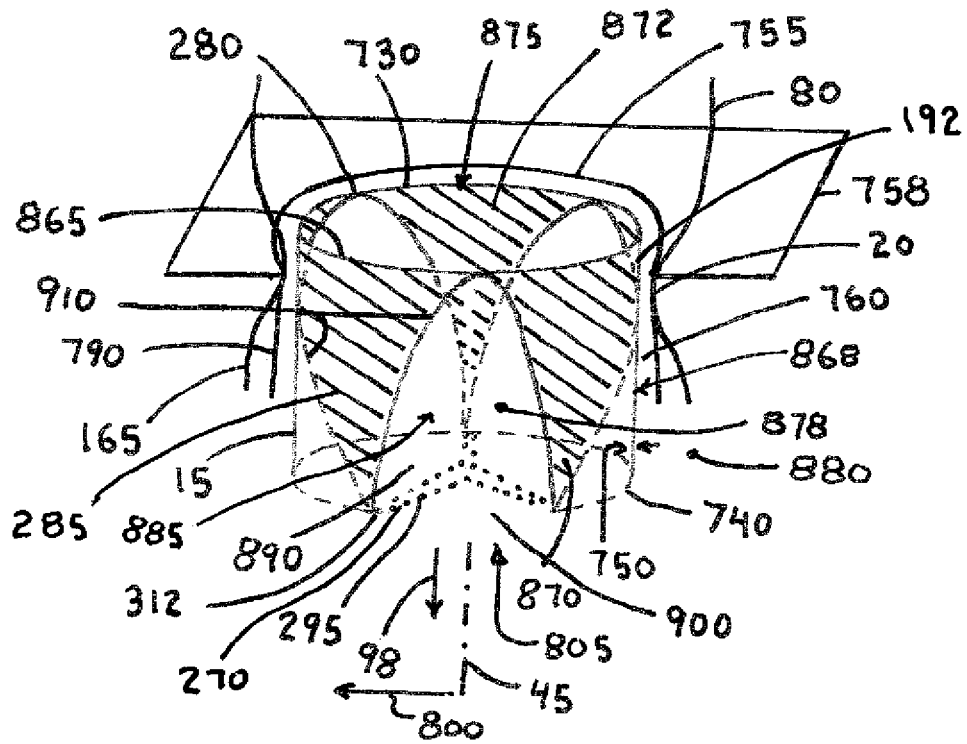
FIG. 34A is a perspective view of a stent-valve frame mounted below the annular plane either attached to the annulus or attached to first component frame; an open stent-valve frame surface is located radially adjacent to the replacement leaflets.
Figure 34B:
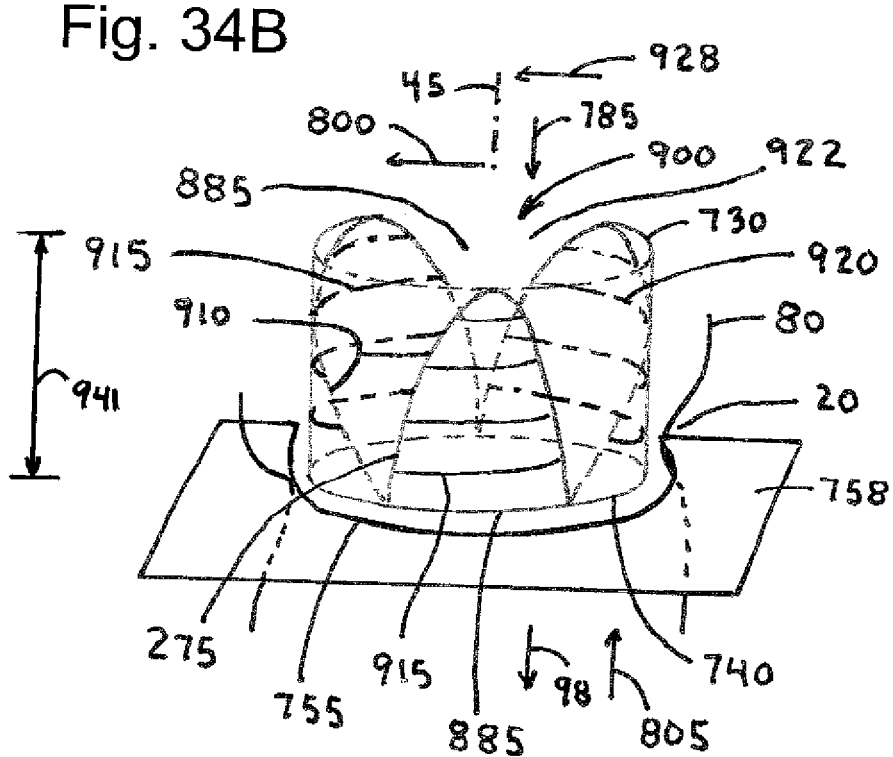
FIG. 34B is a perspective view of a stent-valve frame mounted above the annular plane either attached to the annulus or attached to first component frame; an open stent-valve frame surface is located radially adjacent to the spacing between neighboring leaflets.
Figure 34C:
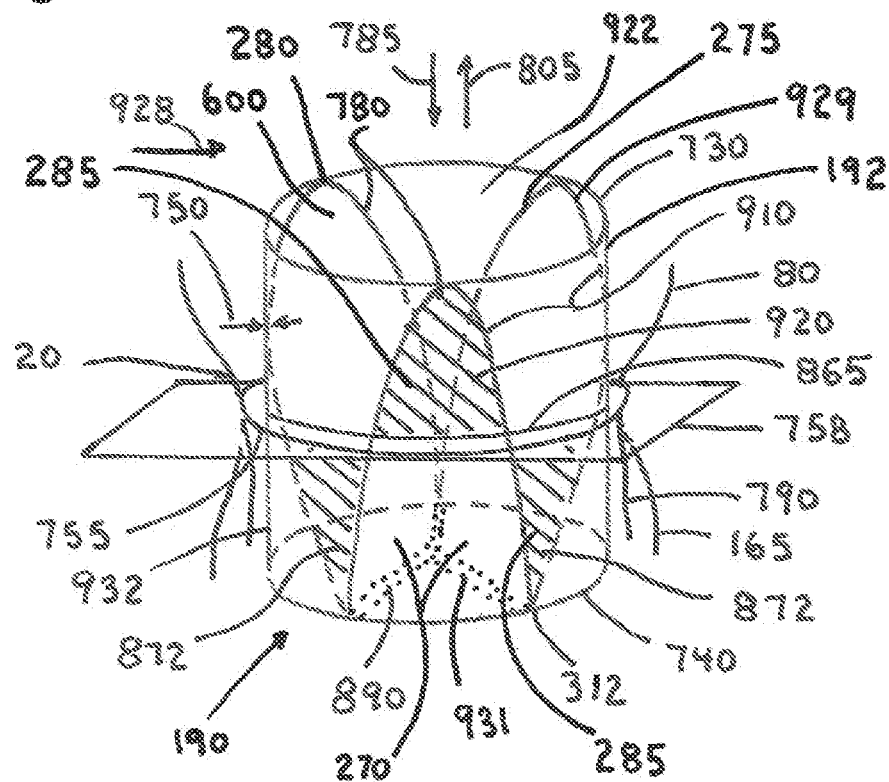
FIG. 34C is a perspective view of a stent-valve frame mounted such that it straddles the annular plane; the stent-valve frame surface has open surface both above and below the annular plane to reduce blood stagnation and thrombus formation.

FIGS. 34A-34C show embodiments of the present invention having a securement band (865) of the stent-valve frame (192) that forms an attachment to a securement ring (755); the securement ring (755) can be a native valve annulus (20), for example, for a single component system, or can be a stent-like structure found in a first component (200) of a stent-valve system; the securement ring (755) can be a limiting cable (225), for example, found attached to the first component (200) as shown in other embodiments. The securement band (865) is a portion of the stent-valve frame (192) that extends around the perimeter of the stent-valve frame (192) and is adapted to make sealing contact with the securement ring (755) and form a frictional or geometrical fit with the securement ring (755) and the securement band (865); the securement band (865) can be located at or near the upstream end (730) of the stent-valve frame (192) as shown in FIG. 34A, located at or near the downstream end (740) of the stent-valve frame (192) as shown in FIG. 34B, or located intermediate between the upstream end (730) and the downstream end (740) of the stent-valve frame (192) as shown in FIG. 34C. As shown in FIG. 34C the stent-valve frame (192) and the replacement leaflets (270) straddle the securement band (865) extending both upstream and downstream of the securement band (865). The securement band (865) extends around the perimeter of the stent-valve frame (192) making frictional or geometrical contact with a securement ring (755); the securement ring (755) can contain the annulus (20) or other structure of the first component that can serve as a continuous ring. A securement plane that contains the securement band (865) can also contains the structural elements that are placed into apposition with the securement band; the securement band (865) is held securely to the securement ring (755) via frictional fit or geometrical fit to prevent the first component (200) from migrational movement and provide a seal with the securement ring (755) that prevents fluid leakage between the securement band (865) and the securement ring (755). Such structural elements for the securement ring (755) can include the native annulus (20) or a fixed ring of the first component (200) such as the limiting cable, for example, as described earlier. The securement band (865) is contained within the securement plane that is perpendicular to the central axis (45) of the stent valve frame (192).

Referring to FIG. 34A, the securement band (865) of stent-valve frame (192) is placed into contact with the securement ring (755) such as the native valve annulus (20) or a closed ring (such as the limiting cable (225)) of a first component (200) that is placed into the native heart tissue prior to placing the stent-valve frame (192) (the stent-valve frame and replacement leaflets (270) being equivalent to a second component (190)) of the present embodiment); the closed ring can be another member that is attached to the native heart valve tissues such as a closed ring of an existing mechanical heart valve, for example. The securement band (865) is a portion of the stent-valve frame (192) that is expanded into contact, sutured into contact, forms a friction fit, forms a geometrical fit, or forms any form of locking fit, or is otherwise attached to the securement ring (755). The securement band (865) can be formed by expanding a portion of the stent-valve frame (192) into contact with the native valve annulus (20) or into contact with the closed ring of a first component (200), for example. The securement band (865) can be a SE stent region or a BE region of the stent-valve frame (192) that forms a contact with the surrounding native tissue or contact with an element of a first component (200) (i.e., the first component (200) being implanted prior to placement of the stent-valve second component (190) of the present embodiment) and forms a resistance to fluid flow or a blockage for leakage of blood or fluid around the stent-valve frame (192) between the stent-valve frame (192) and the surrounding tissues or between the stent-valve frame (192) and the first component (200) member.

The replacement leaflets (270) are attached to the stent-valve frame (192), as described earlier along a crown-shaped attachment path (275) that extends from the nadir (280) located at or near the upstream end (730) to the leaflet commissures (312) located at or near the downstream end (740) of the stent-valve frame (192). It is noted, that alternately the stent-valve frame (192) can extend upstream (202) from the nadirs (280) and can extend downstream (98) from the commissures (312) and remain within the scope of the present invention. The leaflet attachment nadir (280) is the location along the crown-shaped attachment path (275) that is tangent or parallel with the upstream end (730) of the stent-valve frame (192). The commissures (312) identify the junction of the leaflet with the downstream end (740) of the stent-valve frame (192) and also identify a contact point for one leaflet with a neighboring leaflet along the downstream end (740) of the stent-valve frame (192). To prevent leakage of fluid through the stent-valve frame wall (750) in a retrograde direction (805), the region of the stent-valve frame surface (868) located from the nadir (280) of one leaflet to the nadir (280) of a neighboring leaflet at the upstream end (730) and extending downstream (98) to the commissures (312) made between those two leaflets (270) is formed with a closed inter-leaflet frame surface (870); the closed inter-leaflet frame surface (870) extends between two neighboring attachment path portions (910) of the crown-shaped attachment paths (275) of two neighboring leaflets (780). A closed surface (875) does not allow fluid flow across the wall of the stent-valve frame wall (750) from inside (878) to outside (880) of the stent-valve frame (192). A covering (285) attached to the stent-valve frame (192) can be used to form a closed surface (875). This closed surface (875) will be referred to as the closed inter-leaflet frame surface (870) since it is located on the frame surface (868) and is located between two neighboring leaflets (780); this closed surface (875) will be referred to as a closed downsteam-planar inter-leaflet frame surface (872) since the closed surface (875) shown in this embodiment is located downstream (98) of the securement plane (755); hence in this embodiment zero percent of the second component frame (192) extends into the LA (80). The closed inter-leaflet frame surface (870) is similar to the posts (700) described earlier for the surgical valve and which prevents fluid flow across the surgical valve posts (700).

The stent-valve frame surface (868) located between the crown-shaped attachment path (275) of a single replacement leaflet from that leaflet's nadir (280) to the downsteam end of the stent-valve frame (192) is formed from an open mesh stent frame (similar to a vascular stent without a covering) that provides passage of blood or fluid across the stent-valve frame wall (750) and is hence referred to as an open surface (885). This open surface (885) portion of the stent-valve frame surface (868) will be referred to as an open downsteam-planar intra-leaflet frame surface (890) since it is located adjacent to and radially outward from a single valve leaflet and is located along the stent-valve frame surface (868). The open downstream-planar intra-leaflet frame surface (890) allows direct access of blood in the LV (165) between the native leaflet and the stent-valve frame (192); blood will flow radially outwards through this open surface (885) and impact directly onto the native tissues surrounding the stent-valve frame (192) thereby reducing the opportunity for a stagnation region (760) of blood in the LV (165) between the native leaflets (790) and the stent-valve frame (192) and thereby removing the potential for harmful thromboemboli formation and release to the brain. The open downstream-planar intra-leaflet surface also allows a small amount of blood to flow in a retrograde direction (805) across the atrial surface of the native leaflet tissue at the initiation of systole and radially inwards from the native tissue surrounding the stent-valve frame (192) to the inside (878) of the stent-valve frame (192) to help close the replacement leaflets (270). The open downstream-planar intra-leaflet surface also prevents leaflet overhang of the native leaflets from interfering with the function of the replacement leaflets.

As shown in FIG. 34A the leaflet free edges (295) are shown in a closed configuration. This embodiment will not allow retrograde flow occur from the downstream end (740) to the upstream end (730) as long as the securement band (865) is able to form a leak-free seal with the securement ring (755) via frictional fit due to the outwards expansion forces of the first component (200) or via a geometrical fit between the first component (200) and the second component (190). The closed inter-leaflet frame surface (870) can be formed by attaching a polymeric film, a polymeric weave, or other fabric to the stent-valve frame (192) at a location between neighboring leaflets (780) and extending to the common commissure for the two neighboring leaflets (780) as described for the closed inter-leaflet frame surface (870). The attachment of the fabric to the stent-valve frame (192) can be via adhesives, suturing, thermal bonding, solvent bonding, polymer bonding or any other method that achieves a seal that prevents fluid leakage across the stent-valve frame wall (750). Thus the inter-leaflet frame surface below the securement band (865) is a closed inter-leaflet frame surface (870) and the intra-leaflet frame surface below the securement band (865) is an open intra-leaflet frame surface. Any of the intra-leaflet frame surfaces that extend above the securement plane (758) (as described in further embodiments) would be required to be closed frame surfaces (875). In some instances the fabric located along the closed surface of the stent-valve frame (192) can be contiguous with or attached to the replacement leaflet material along the crown shaped attachment path of the replacement leaflet extending from the leaflet nadir to the leaflet commissures.

The open downstream-planar intra-leaflet frame surface (890) can be formed from a stent-like structure without a covering (285) that allows blood to travel through the stent-valve frame wall (750). The open intra-leaflet frame surface can make contact with the native leaflets (790) and serve to hold the native leaflets (790) outwards (800) such that the native leaflets (790) cannot make contact with the replacement leaflets (270) or overhang the downstream end (740) of the stent-valve. Also, blood can flow freely through the open frame surface (885) of the stent-like structure of the stent-valve frame (192). Alternately, the open downstream-planar intra-leaflet frame structure can be completely eliminated or removed forming a completely open surface (900) such that blood flow through this open region does not make contact with any stent-like structure.

FIG. 34B shows an embodiment of the present invention that allows the stent-valve frame (192) from the upstream end (730) to the downstream end (740) to be located, for example, in the LA (80) and having the securement of the stent-valve frame (192) located near or at the downstream end (740) of the stent-valve frame (192) to the securement ring (755) such as a heart annulus (20) or a region of a first component (200) (of a two component stent-valve system, for example) that is implanted prior to placing the stent-valve frame (192) of the present embodiment as a second component (190), for example. In this embodiment 100% of the stent-valve frame length (941) extends into the LA (80) and zero percent extends into the LV (165). Locating the stent-valve frame (192) such that up to 85% (range 15-85%) of the second component frame length (941) extends into the left atrium will ensure that impingement of the stent-valve frame (192) onto the native anterior mitral valve leaflet or onto the left ventricular outflow tract does not occur, but still the stent-valve frame (192) will prevent overhang of the native leaflets onto the replacement leaflets (270).

In this embodiment the closed surface (875) of the stent-valve frame (192) is located within the boundaries formed by the crown-shaped attachment path (275) of a single replacement leaflet (270) to the stent-valve frame (192) from a leaflet nadir (280) to the downstream end (740) of the stent-valve frame (192) and extending from one commissure of that leaflet to the other commissure of that leaflet. This closed surface (875) will be referred to as the closed intra-leaflet frame surface (915) since the surface is located on the frame surface (868) and is adjacent to and located radially outward (800) from a single leaflet. For a stent-valve having three replacement leaflets (270), for example, there will be three closed upstream-planar intra-leaflet frame surfaces (920) as shown in FIG. 34B. The frame surface upstream (202) of the securement band (865) and located between the attachments of two neighboring leaflets (780) (i.e., the open upstream-planar inter-leaflet frame surface (922)) is an open surface (885); this open frame surface (885) extends between two neighboring attachment path portions (910) of the crown-shaped attachment path (275) of two neighboring leaflets (780). The attachment path portions extend from the nadir (280) of a leaflet to the securement band (865). An open frame surface (885) allows blood or fluid to travel freely across the stent-valve wall from outside (880) to inside (878), for example, from the chamber of the LA into the stent-valve. The open upstream-planar inter-leaflet frame surface (922) is an open frame surface (885) formed, for example, of an open strut structure found in vascular stent without a covering (285) that allows for fluid flow across the open strut structure of the stent frame (192). As fluid attempts to flow in a retrograde direction (805) with the valve leaflets (270) in an closed configuration, the closed upstream-planar intra-leaflet frame surface (920) will prevent blood or fluid from travelling in a retrograde direction (805) from the downstream end (740) and out of the upstream end (730) of the stent-valve frame (192) or through the stent-valve frame wall (750) as the retrograde fluid is trapped in the three pockets formed by the native leaflets and the closed upstream-planar intra-leaflet frame surface (920).

The upstream-planar inter-leaflet frame structure (925) can be formed from a stent-like structure without a covering (285) that allows blood to pass freely through the stent-valve wall without measurable resistance to blood flow. Alternately, the upstream-planar frame surface (925) can be formed by providing a completely open surface (900) that does not contain any stent-like frame structure at all and the stent-valve frame (192) has been eliminated in this region having a completely open surface (900).

The open upstream-planar inter-leaflet frame surface (922) located upstream (202) to the securement band (865) provides an open surface (885) or completely open surface (900) for blood or fluid to flow in an antegrade direction (785) or inward direction (928) across the stent-valve frame wall (750) and through the open replacement leaflets (270) and downstream (98) from the downstream end (740) of the stent-valve frame (192). This open upstream-planar inter-leaflet frame surface (922) located above the securement plane (758) will provide a direct path for blood flow or fluid flow in an antegrade or lateral direction from a region above the securement plane (758) across the stent-valve wall without generating a stagnation region (760) caused by existing covered stent-valves. Existing covered stent valves require blood or fluid located between the native chamber and the stent valve above the securement plane (758) or securement band (865) to flow in a retrograde direction (805) in order to enter into the upstream end (730) of a covered stent-valve frame (192). The three pockets formed by the replacement leaflets and the closed upstream-planar intra-leaflet frame surface can be formed by attaching the replacement leaflet to the covering that is located along the closed surface areas of the stent-valve frame (192); the attachment extending along the crown shaped leaflet attachment path (275) (see FIG. 34). The formation of such pockets can allow the elimination of the stent frame structure entirely from a portion of the stent-valve frame (192) located upstream of the securement band thereby reducing the profile of the second component (190). The presence of a stent frame upstream of the securement band provides structural stability to the replacement leaflets to prevent leaflet deformation during antegrade blood flow.

FIG. 34C shows an embodiment having the securement plane (758) or securement band (865) located intermediate between the upstream end (730) and the downstream end (740) of the stent-valve frame (192). In this embodiment, the stent-valve frame (192) can be extended less into the LV (165) and more into the LA (80) for those patients that have an LVOT anatomy that would not tolerate potential obstruction of the LVOT caused by placing 1-2 cm of stent-valve stent axial length adjacent to the native mitral anterior leaflet and pushing the leaflet towards the LVOT. The portion of the frame surface (868) located upstream (202) of the securement band (865) or securement plane (758) will be referred to as the upstream-planar frame portion (930) and is attached to an upstream-planar leaflet portion (929) and the portion of the frame surface (868) located downsteam of the securement plane (758) or securement band (865) and is attached to a downstream-planar leaflet portion (931) will be referred to as the downstream-planar frame portion (932). In this embodiment the intra-leaflet frame surface (i.e., the frame surface located between the crown-shaped attachment of a single leaflet) located above the securement plane (758) is a closed upstream-planar intra-leaflet frame surface (920), and does not allow fluid to pass through the stent-valve frame wall (750); this surface is a closed upstream-planar intra-leaflet frame surface (920).

In one embodiment the closed upstream-planar intra-leaflet frame surface (920) has a covering (285) attached to the frame surface at a location radially adjacent and outwards from the replacement leaflets and following along the crown-shaped leaflet attachment path (275) and is attached to the stent-valve frame (192). In an alternate embodiment a portion of the stent-valve frame (192) can be eliminated or absent from the upstream-planar frame surface upstream of the securement band (865). A leaflet pocket (600) can be formed by attaching a fabric to the replacement leaflet (270) along the crown-shaped portion of the replacement leaflet (270) that extends from the leaflet nadir (280) to each of the commissures (312) for the replacement leaflet (270). It is noted however, that the presence of a frame structure in the upstream-planar frame structure region will provide strength and structural integrity to the replacement leaflet along the leaflet attachment path (275) and will prevent the replacement leaflet (270) from deforming improperly during antegrade flow and provide structural strength to the replacement leaflet during retrograde blood flow.

The downstream-planar intra-leaflet frame surface (935) (i.e., the frame surface located between the crown-shaped attachment of a single leaflet) located downsteam of the securement plane (758) is an open frame surface (885) (as shown in FIG. 34C) that allows fluid to pass through the stent-valve frame wall (750) radially outwards and into direct contact with the native tissues that surround the stent-valve frame (192); this downstream-planar intra-leaflet frame surface (935) as shown in FIG. 34C is an open downstream-planar intra-leaflet frame surface (890) since fluid can pass freely across the stent-valve frame surface or stent-valve frame wall (750) in this region. This open downstream-planar intra-leaflet frame surface (890) allows direct blood flow to enter into the stent-valve via a radially inward direction between the native leaflets (790) and the stent-valve without requiring blood entrance from the downstream end (740) of the stent-valve during the initiation of ventricular contraction at the beginning of systole. Thus, blood stagnation regions (760) between the native leaflets (790) and the stent-valve frame (192) are minimized. Additionally, during antegrade blood flow through the stent-valve during diastole or LV (165) relaxation, blood can exit radially outwards through the open downstream-planar intra-leaflet frame surface (890) and impinge directly onto surrounding tissues with a radial direction that will ensure that stagnation between the native leaflets (790) and the stent-valve frame (192) is minimized.

It is noted that this open downstream-planar intra-leaflet frame surface (890) can, in an alternate embodiment, be a closed frame surface (875) (i.e., a closed downstream-planar intra-leaflet frame surface) if it is desired or more easily manufactured with a covering (285), for example; the stent-valve will still function to direct antegrade flow from the upstream end (730) to the downstream end (740) and will block retrograde flow from the downstream end (740) to the upstream end (730) of the stent-valve. A closed downstream-planar intra-leaflet frame surface would not provide the advantage (to reduce stagnation between the native leaflets and the stent-valve frame) described above for the open downstream-planar intra-leaflet frame surface (890).

In the embodiment of FIG. 34C the open upstream-planar inter-leaflet frame surface (922) upstream (202) of the securement plane (758) (i.e., the frame surface located between the crown-shaped attachment of two neighboring leaflets (780) and extending from the nadirs (280) of those two neighboring leaflets (780) to the securement band (865)) is an open frame surface (885) that allows fluid to pass freely through the stent-valve frame wall (750); this open frame surface (885) is referred to as the open upstream-planar inter-leaflet frame surface (922). The nadirs (280) of the replacement leaflets are located at the upstream end of the stent-valve frame to provide the stent-valve frame (192) with the shortest axial length possible and thereby provide an enhanced capability for the stent-valve frame (192) to be delivered via transcatheter delivery across the atrial septum and bend with the smallest radius of curvature to allow such delivery. The open upstream-planar inter-leaflet frame surface (922) is contained between neighboring attachment path portions (910) of the crown-shaped attachment path (275) of two neighboring leaflets (780). It is this open upstream-planar inter-leaflet frame surface (922) that allows blood or fluid to enter the stent-valve across the stent-valve frame wall (750) upstream (202) of the securement band (865) in an antegrade and an inward direction (928) without generating a stagnation region (760) as found in existing prior art devices. Existing prior art devices require the blood or fluid to undergo a retrograde directionality (805) of flow to enter into the upstream end (730) of the stent-valve frame (192) thereby resulting in fluid stagnation and leading to potential formation of thromboemboli.

The closed downstream-planar inter-leaflet frame surface (872) downstream (98) of the securement band (865) (i.e., the frame surface located between neighboring attachment path portions (910) of the crown-shaped attachment of two neighboring leaflets (780) and extending from the securement band (865) to the commissures (312) of those two neighboring leaflets (780) located at the downstream end (740) of the frame) is a close frame surface that prevents fluid from passing through the stent-valve frame wall (750); this closed frame surface (875) is referred to as the closed downstream-planar inter-leaflet frame surface (872). It is the closed upstream-planar intra-leaflet frame surface (920) and the closed downstream-planar inter-leaflet frame surface (872) that prevents retrograde blood or fluid to pass across the stent-valve frame wall (750) with the leaflets (270) in a closed configuration; this stent-valve structure allows the stent-valve of the present invention to function to direct blood flow in an antegrade direction (785) and prohibit blood flow in a retrograde direction (805).

It is noted that the open frame surfaces (885) of this embodiment can be formed from an open stent-like structure without a covering (285) that allow blood to pass through the stent frame wall (750). Alternately, the open frame surface (885) found either upstream-planar or downstream-planar can be formed without any stent frame structure in these open surface regions and thereby form a completely open surface (900) as presented earlier. For the case where the device is used to treat a patient having native leaflet prolapse, the presence of an open frame surface (885) but still having a frame present along the entire perimeter of the frame that extends into the LV but no covering along the entire perimeter of the frame that extends into the LV will prohibit impingement of the native leaflet onto the downstream end (740) of the stent-valve and prevent native leaflet overhang (810) at the location near the downstream end (740) of the stent-valve.

The stent-valve frame portion that extends into the LA can be formed with a cylindrical shape, a frustum shape, or other curved shape, if desired. The frustum shape as described in FIGS. 33D-33F can be of a smaller diameter at its upstream end to prevent contact of the upstream end with the wall of the LA. Alternately the stent-valve frame can have the larger diameter of a frustum located at the upstream end of the stent-valve frame (192) to assist with placement and locking of the stent-valve frame (192) into the securement ring (755). The structural elements of the stent-valve frame (192) and replacement leaflets (270) described in FIGS. 34A-34H can be equally applied to other embodiments of the present invention.

Figure 34D:
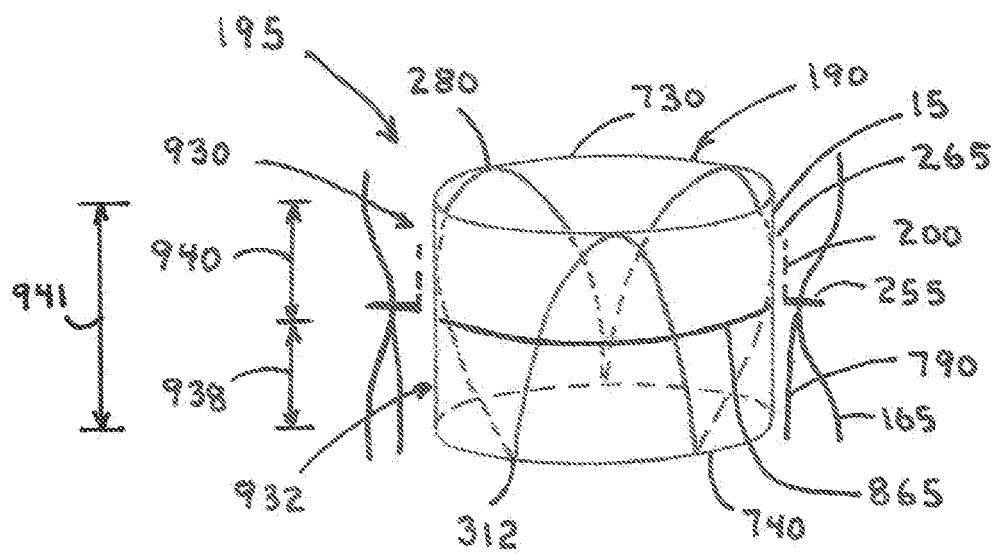
FIG. 34D shows a dual member stent-valve system having the first component located above the annulus and having the second stent-valve component straddling the annulus and locking to the first component.
Figure 34E:
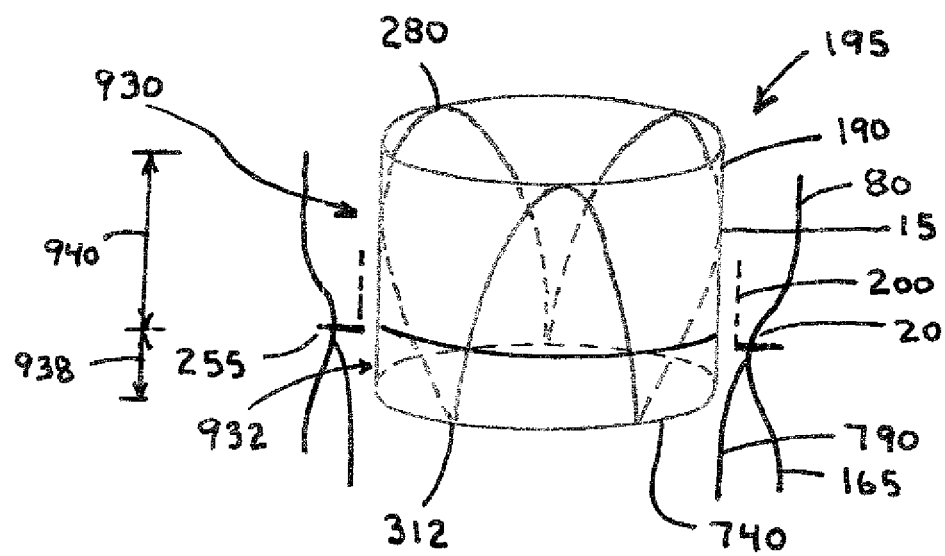
FIG. 34E shows a dual member stent-valve system having the second stent-valve component primarily above the annulus but having some stent-valve component frame below the annulus to prevent native leaflet overhang.
Figure 34F:
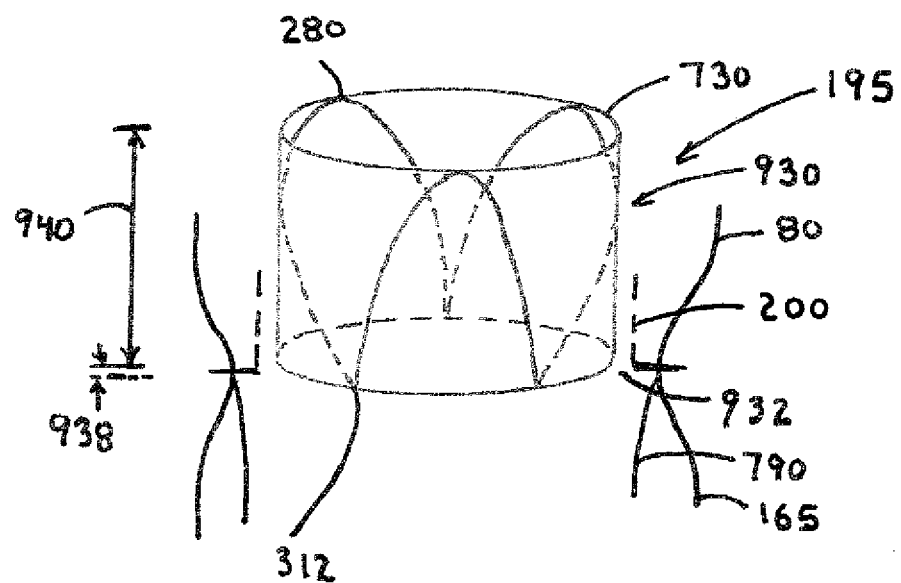
FIG. 34F shows a dual member stent-valve system having the second stent-valve component located above the annulus and locking to the first component.

FIGS. 34D-34F show embodiments of dual member stent—valve (195) positioned with various depths of the second component (190) extending into the LV. FIG. 34D shows the second component (190) or stent-valve component (190) of the present invention located within the central lumen (265) of a first component (200) that has been attached to the mitral valve annulus (20). The second component (190) is positioned such that the downstream-planar frame portion (932) is located within the LV (165) and is in contact with the native valve leaflets (790) pushing them outwards (800) such that the native leaflets (790) are not allowed to prolapse or overhang the downstream end (740) of the stent-valve. The downstream-planar frame length (938) extending downstream (98) from the securement band (865) to the commissures (312) is 7-15 mm. The upstream-planar frame portion (930) has an upstream-planar frame length (940) extending upstream (202) from the securement band (865) to the nadirs (280) that is 7-15 mm. In this embodiment that straddles the mitral annulus (20) or securement plane (758) at least 35% of the second component frame length (941) (range 35-65%) extends into the LA. The downstream planar frame portion (938) ranges from 35-65% of the second component frame length (941). This embodiment which straddles the mitral annulus (20) provides a balance of a short downstream-planar frame length (938) that will not contribute to LVOT obstruction and will not impact upon the wall of the LA which can lead to the formation of atrial fibrillation, and the downstream-planar frame length (938) will prohibit overhang of the native leaflets (790) into contact with the replacement leaflet function and can interfere with blood flow across the downstream end (740) of the stent-valve frame (192).

FIG. 34E shows the second component (190) of the present invention located within the central lumen (265) of a first component (200) that has been attached to the mitral valve annulus (20). The second component (190) is positioned such that the downstream-planar frame portion (932) is located within the LV (165) and is in contact with the native valve leaflets (790); the downstream-planar frame portion (932) has a downstream planar frame length (938) that is at least 15% (range 15-55%) of the second component frame length (941) and at least 45% of the second component frame length (941) extends into the LA (i.e., the downstream planar frame portion ranges from 15-55% of the second component frame length (941)) may push the native leaflets (790) outwards (800) with less outward displacement than that shown in FIG. 34D; some native leaflet prolapse can occur, and the native leaflets (790) may be able to overhang the downstream end (740) of the stent-valve to a lesser extent than that shown in FIG. 34B. The downstream-planar frame length (938) extending downstream (98) from the attachment band to the commissures (312) is 5-8 mm. The upstream-planar frame length (940) extending upstream (202) from the attachment band to the nadirs (280) is 12-18 mm. The greater upstream-planar length (i.e., greater than that shown and described for FIG. 34D) can cause impingement of the stent-valve frame (192) upon the wall of the LA (80) resulting in potential for formation of atrial fibrillation.

FIG. 34F shows the second component (190) of the present invention located within the central lumen (265) of a first component (200) that has been attached to the mitral valve annulus (20). The second component (190) is positioned such that the upstream-planar frame portion (930) is located primarily within the LA. The percentage of the stent-valve component frame (192) that extends into the LV (165) can be zero percent. Little contact is made between the downstream-planar frame portion (932) of the stent-valve frame (192) with the native valve leaflets (790) thereby allowing the native leaflet to prolapse or overhang the downstream end (740) of the stent-valve. The downstream-planar frame length (938) extending downstream (98) from the attachment band to the commissures (312) is 0-5 mm. The upstream-planar frame length (940) extending upstream (202) from the attachment band to the nadirs (280) is 15-22 mm.

Figure 34G:
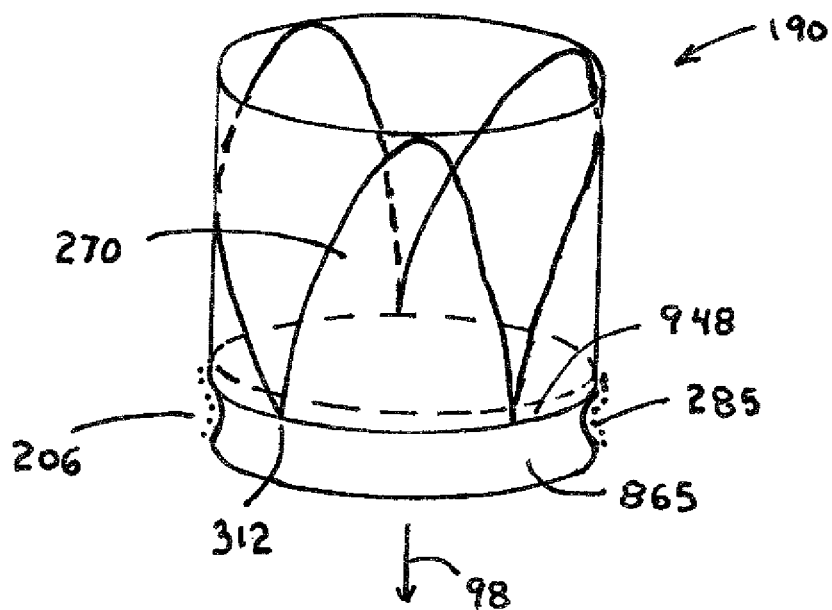
FIG. 34G is a perspective view of the second component stent-valve having a second component concave region located downstream of the commissures such that the replacement leaflets are located entirely within the left atrium.

FIG. 34G shows the second component (190) having a securement band (865) located downstream (98) of the replacement leaflet commissures (312). As shown, the second component concave region (206) is intended to be placed adjacent to a securement ring or a valve annulus. It is understood that a second component convex region or other geometrical locking shape can be used to form a geometrical lock or frictional lock with the securement ring or limiting cable of the first component. The securement band (865) has a covering (285) attached to its surface around its perimeter. The covering may extend to the overlap band-ring region (948) to ensure that leakage of blood cannot occur near the junction of the commissures (312) and the securement band (865). In this embodiment, the replacement leaflets (270) are located entirely within the LA.

Figure 34H:
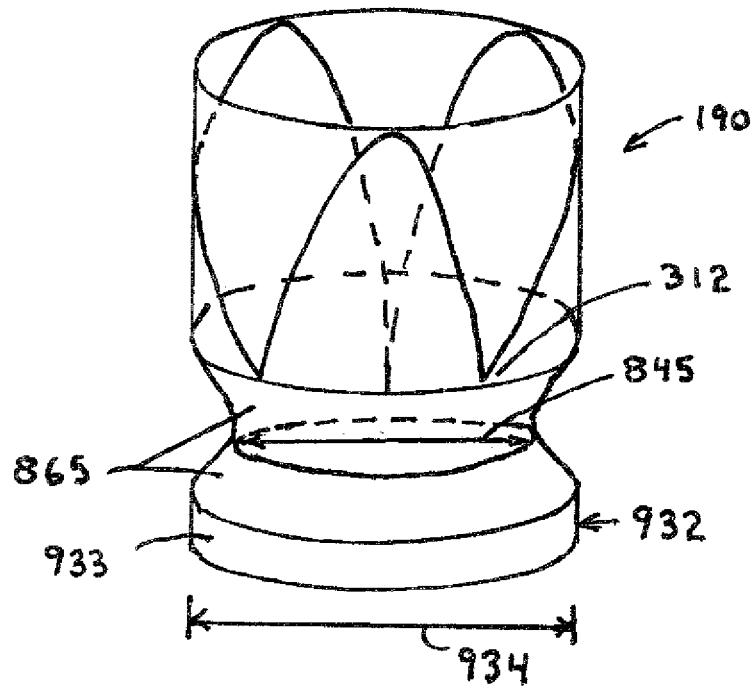
FIG. 34H is a perspective view of the second component having a downstream frame component located downstream of the securement band.

FIG. 34H shows a second component (190) having a securement band located downstream of the replacement leaflet commissures (312) similar to that shown in FIG. 34G. The securement band is intended to geometrically or frictionally lock with the securement ring or limiting cable of the first component. A downstream-planar frame portion (932) has a downsteam frame enlargement (933) that provides a larger downstream frame diameter (934) than the second component locking region diameter (845). The larger downstream frame diameter (934) is able to make contact with the native leaflets below the native leaflet rim to assist in preventing upstream migration of the second component and also thereby preventing migration of the first component to which the second component has formed a geometrical lock. In this embodiment, the replacement leaflets (270) are located entirely within the LA.

Figure 35A:
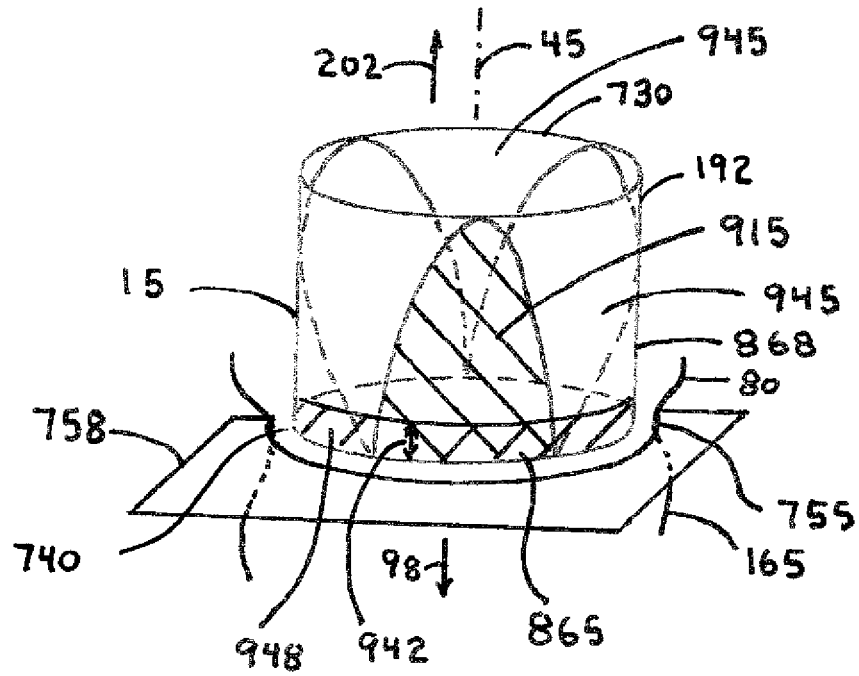
FIG. 35A is a perspective view of a stent-valve component located above the annular plane and positioned into the left atrium; the stent-valve component having a securement band that attaches to the annular plane.
Figure 35B:
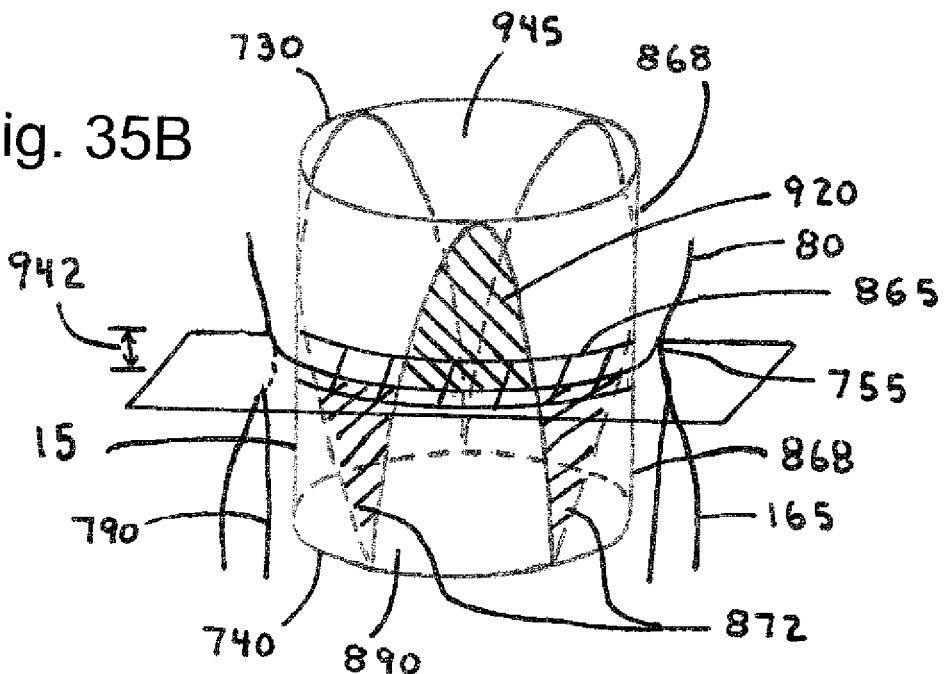
FIG. 35B is a perspective view of a stent-valve component located straddling the annular plane and positioned into both the left atrium and left ventricle; the stent-valve component having a securement band that attaches to the annular plane.

The securement plane (758) can be the planar region, saddle-shaped region, or D-shaped region, or round region, or oval region that contains a securement ring (755) and intersects to make contact with the securement band (865) of the stent-valve frame (192), for example. The securement ring (755) can be a closed ring of a first component (200) member that is delivered prior to the second component (190) that is described in the present embodiment, for example, to which the stent-valve frame (192) is being secured as shown in FIGS. 35A and 35B. A securement band (865) located on the stent-valve surface extends along the perimeter of the stent-valve frame surface such that the securement band (865) is perpendicular to the central axis (45) of the stent-valve frame (192). The securement band (865) forms a tight seal with the securement ring (755) such that fluid cannot leak between the outside (880) of the stent-valve frame (192) and the securement ring (755) associated with the native tissue (or a first component (200), for example) outside (880) of the stent-valve frame (192). The securement band (865) has a securement band height (942) in the axial direction of the stent-valve. This securement band height (942) can range from less than 1 mm to over 10 mm. The securement band (865) has a securement band height (942) that allows for an overlap band-ring region (948) for a closed frame surface (875) to extend upstream (202) or downstream (98) beyond the securement plane (758) and thereby ensure a leak-free seal across the frame surface near the securement plane (758) and assists in preventing fluid leakage between the stent-valve frame surface and the surrounding tissues or an initially placed first component (200). As shown in FIG. 35B, the stent-valve frame (192) has the securement band (865) between the upstream end (730) and the downstream end (740), for example; a portion of the upstream-planar inter-leaflet frame surface (945) located above the securement band (865) (also see FIG. 34C) can be covered with a covering (285) which includes the securement band (865) that prevents flow across the stent-valve frame wall (750) in order to improve the seal that is made between the securement band (865) and the securement ring (755). As shown in FIG. 35A, a securement band (865) having a securement band height (942) is secured to the securement ring (755); the securement band (865) is located near the downstream end (740) of the stent-valve frame (192). The securement band height (942) provides a securement band-ring overlap that assists in preventing leakage of fluid between the stent-valve frame (192) and the surrounding tissues (or first component (200)) and preventing fluid leakage across the stent-valve frame (192) in a region that is intended to have a closed stent-valve surface.

It is further understood that in some embodiments the covered surface of the stent-frame can extend beyond the specific crown-shaped attachment path (275), if desired, to ensure that a tight seal is made, for example, between a closed surface (875) and a replacement leaflet, for example, or a closed surface (875) and a securement band (865), for example.

FIGS. 36A and 36B show a stent-valve frame (192) with the downstream end (740) located adjacent to the securement ring (755); the securement band (865) is aligned with the securement ring (755). FIG. 36A shows how blocked fluid flow (950) is blocked from crossing over the stent-valve frame surface by having a closed upstream-planar intra-leaflet frame surface (920). In FIG. 36A the replacement valve leaflets (270) are in a closed configuration and blood flow in a retrograde direction (805) is being stopped by the closed leaflets (270) and by the closed upstream-planar intra-leaflet frame surface (920). In FIG. 36B the valve leaflets (270) are open and antegrade fluid flow (952) in an antegrade direction (785); inward fluid flow (955) traveling radially inward (928) is allowed to travel across the open upstream-planar inter-leaflet frame surface (922) and into the central lumen (265) of the stent-valve and flow downstream (98) from the downstream end (740) of the stent-valve.

FIGS. 37A-37B show the stent-valve frame (192) positioned such that the securement band (865) is located intermediate from the upstream end (730) and the downstream end (740) of the stent-valve frame (192). FIG. 37A shows the leaflets (270) in a closed configuration and retrograde blood flow is blocked from crossing the stent-valve frame surface at the initiation of systole by the closed upstream-planar intra-leaflet frame surface (920). The closed downstream-planar inter-leaflet frame surface (872) prevents fluid flow from passing from inside (878) to outside (880) across the stent-valve frame surface. The open downstream-planar intra-leaflet frame surface (890) allows initial systolic blood flow (960) to travel inwards (928) and in a retrograde direction (805) at the initiation of systole to assist in closing the replacement leaflets (270) and also to provide blood flow between the native leaflets (790) and the stent-valve frame (192) to minimize blood stagnation and prevent the formation of thromboemboli. The leaflet central surface (795) that forms a pocket extends to the central coaptation site (958).

FIG. 37B shows the replacement leaflets (270) in an open configuration. Blood flow in an antegrade direction (785) and inward fluid flow (955) occurs through the open upstream-planar inter-leaflet frame surface (922) from outside (880) the stent-valve to inside (878) the stent-valve and extends downstream (98) from the downstream end (740) of the stent-valve. As the antegrade blood flow travels downstream (98) of the securement band (865), the antegrade blood flow can travel in a radially outward direction (800) and exit through the open downstream-planar intra-leaflet frame surface (890); this blood flow will travel radially outwards from the stent-valve frame (192) and impinge directly onto the native tissues such as the native leaflets (790) ensuring that blood stagnation does not occur in the LV (165) between the stent-valve frame (192) and the native leaflets (790).

Figure 38A:
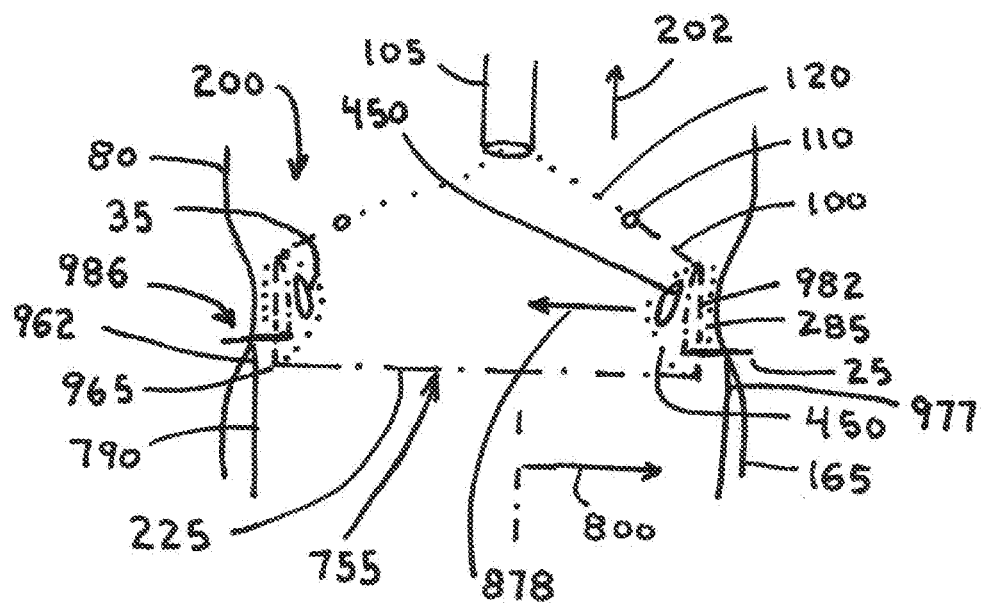
FIG. 38A is a plan view of the first component of a dual member system; the first component is being positioned adjacent to the mitral annulus while being held by control fibers and recapture struts that are held by the delivery sheath.
Figure 38B:
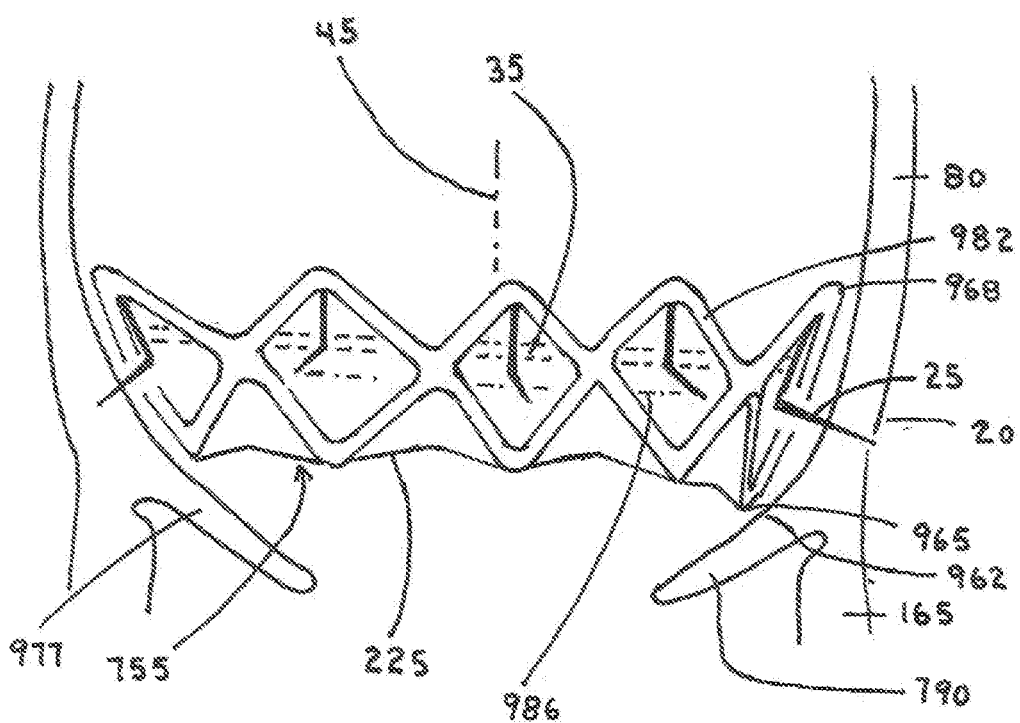
FIG. 38B is a plan view of a first component frame placed above the native leaflets and having the barbs in an activated configuration.

FIGS. 38A and 38B show an embodiment for the first component (200) of the stent-valve system of the present invention; much of this embodiment has been described in previous embodiments. The first component frame (982) is positioned such that the barbs (25) of the first component (200) penetrate into the mitral annulus (20), for example. As the barbs (25) are activated, they penetrate through the covering (285) and extend into the surrounding tissues. It is noted that the covering (285) for the first component frame (982) can be located inside (878) of the barbs) 25) such that the barbs (25) can extend outwards upon activation without interacting with or penetrating through the covering (285). The first component frame distal end (965) is in contact with the native leaflet shoulder (962) of the native mitral valve leaflets (790) to provide for ease of positioning of the first component (200). The leaflet shoulder (962) is transition corner of the native leaflet rim (977) where the native leaflet (790) curves from the plane of the annulus toward the LV; the leaflet rim (977) being the continuous portion of the native leaflet that extends around and attaches to the perimeter of the annulus having net yet formed individual native anterior and posterior mitral leaflets. The native mitral valve leaflets (790) are able to function normally while the first component (200) is being delivered such that the fixation ring (986) of the first component (200) is adjacent to the mitral annulus (20). The first component (200) proximal end (968) is attached to recapture struts (100) (shown in FIG. 38A) that contain a holding feature (110) such as a ring located at the upstream end (730) of the recapture struts (100); control fibers (120) can form a loop through the rings; the control fibers (120) then extend into the delivery sheath (105). The control fibers (120) allow the first component (200) to be held, repositioned, or retracted into the delivery sheath (105) prior to activation of the barbs (25) as described in earlier embodiments. Upon determination that the first component (200) is located properly, the torus balloon (35) is inflated with saline to activate the barbs (25) outward into the mitral annulus (20) upstream (202) and adjacent to or touching the native mitral valve leaflets (790). A backing element (450) can be located to the inside (878) of the torus balloon (35) to ensure that the inflation forces of the torus balloon (35) cause the barbs (25) to become activated by pushing the barbs (25) outwards (800). A limiting cable (225) can be located along the perimeter of the first component frame (982) to provide a closed ring into which a second component (190) (i.e., the stent-valve frame (192) that contains the replacement leaflets (270)) can be expanded and held via friction fit, geometrical shape fit, or other locking mechanism including the locking features as described in earlier embodiments. The stent limiting cable (225) can be formed and included within the stent configuration to limit the stent from expansion beyond a preset amount; the stent limiting cable (225) can serve as a securement ring (755) to form the closed ring structure. A flexible strut or flexible element of the stent-like structure of the first component frame can act as a limiting cable (225) by connecting the hinge regions of a zig-zag stent structure, and prevent the zig-zag structure (335), for example, from opening beyond a specified perimeter. This flexible strut or cable can be formed, for example, via a laser machining operation that is used to laser cut the zig-zag shape of the first component stent frame (982).

FIG. 38B shows one embodiment for a first component frame structure (982) formed with a closed cell structure. The first component frame (982) is shown, for example, with a conical or frustum shape with the smaller diameter distal end (965) of the frustum being positioned adjacent to the native leaflet shoulder (962). The barbs (25) are shown in an activated configuration after being pushed outwards into the mitral annulus via the torus balloon (35). The first component frame (982) could equally well have been configured with an open cell structure.

Figure 39A:
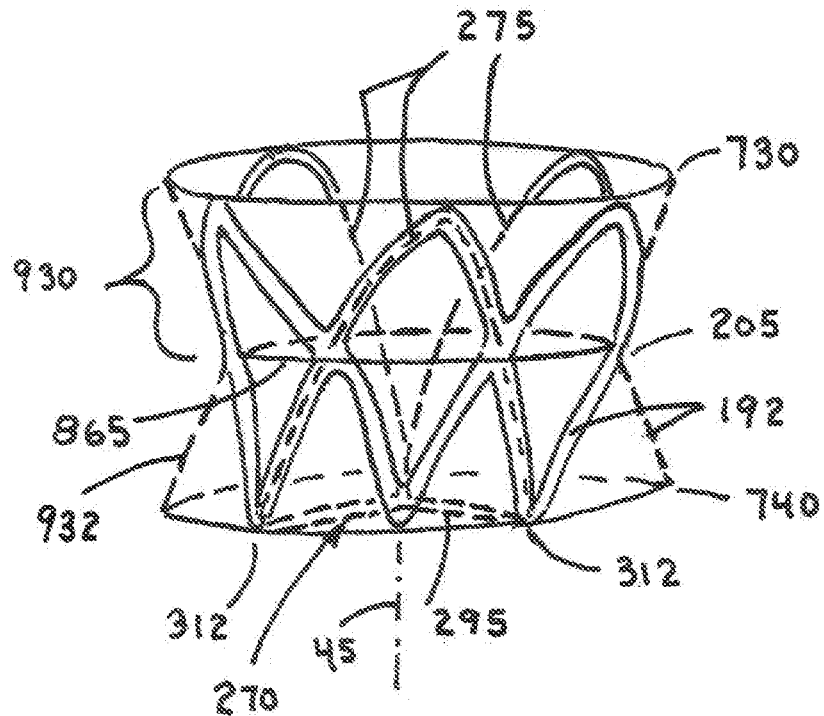
FIG. 39A is a perspective view of a second component stent-valve frame having an hour-glass shape with a waist that is narrower than an upstream portion and a downstream portion.

FIG. 39A shows a second component frame (192) having a generally hour-glass shape having a securement band (865) located between the upstream end (730) and the downstream end (740) and having a smaller diameter waist (205) than the upstream end (730) and the downstream end (740).

The upstream-planar frame portion (930) forms a conical (or frustum) shape that can match the conical shape of the first component frame presented in FIG. 38B and thereby will automatically align the central axis (45) of the second component frame (192) with the central axis of the first component frame (982) when the two components are brought together to form a two-component stent-valve system. The second component frame (192) can be formed from a closed cell structure as shown in FIG. 39A or can be formed from an open cell structure. The crown-shaped attachment (275) of the replacement leaflets (270) follow a crown-shaped pattern of the structural Nitinol struts or elements of the second component frame (192). Portions of the surface of the second component frame (192) can be covered, open, or completely open as described in other embodiments of the present invention.

Figure 39B:
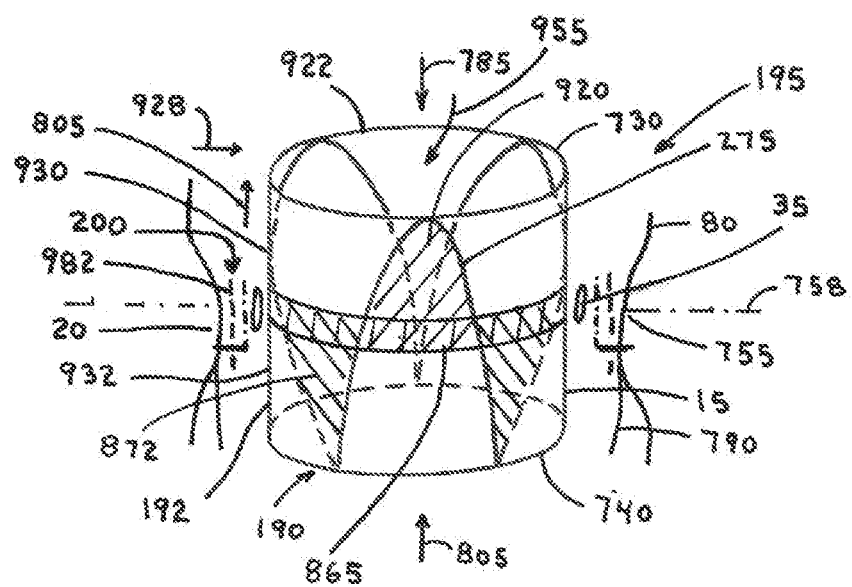
FIG. 39B is a perspective view of a dual member stent-valve system having a first component attached to the annulus and having a second stent-valve component positioned such that it straddles the annulus and straddles the first component.
Figure 39C:
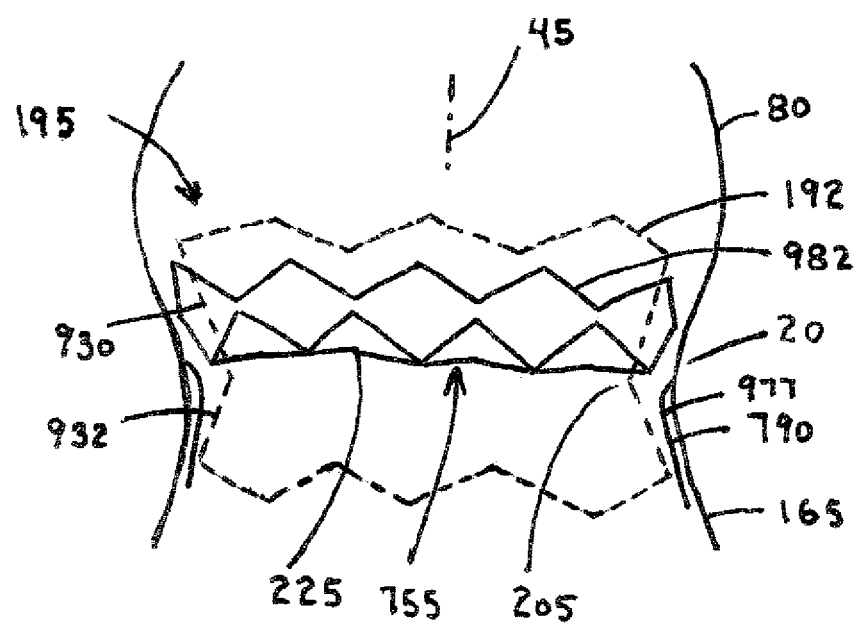
FIG. 39C is a plan view of a dual member stent-valve with the second component forming a geometrical fit with the first component via a conical shape that aligns and axial positions the two components relative to each other.

FIGS. 39B and 39C show the dual member stent-valve (195) or two-component stent-valve system having the second component (190) of the present invention or stent-valve frame (192) being placed within the inside (878) or central lumen (265) of the first component (200) and held to the first component via a system lock (842). The system lock (842) can be a friction fit between the first component frame (982) and the second component frame (192) as shown in FIG. 39B or a geometrical fit as shown in FIG. 39C. The second component (190) is placed such that the downstream end (740) of the stent-valve frame (192) is downstream of the mitral annulus (20). The securement band (865) is located intermediate between the upstream end (730) and the downstream end (740) of the stent-valve frame (192). Placing the second component (190) with an upstream-planar frame portion (930) of the stent-valve frame (192) located in the LA allows an advantage that less of the downstream-planar frame portion (932) of the second component (190) stent-valve frame (192) extends downstream (98) of the securement ring (755) which can be the limiting cable (225) and securement plane (758); thus the stent-valve frame (192) is less likely to impinge upon the LVOT and less likely to push the native leaflets (790) into the LVOT. The open upstream-planar inter-leaflet frame surface (922) allows inward blood flow (955) from the LA (80) to travel in an antegrade and inward direction (928) through the stent-valve frame wall (750). Fluid flow is not required to flow in a retrograde direction (805) within the LA to enter into the upstream end (730) of the stent-valve frame (192) as found in existing stent-valve devices that cause stagnation and resultant thromboemboli. Fluid can flow radially outwards out of the open downstream-planar intra-leaflet frame surface (890) and impinge directly onto the native tissues such as the native leaflets to wash their atrial surface and prevent thrombus formation. The stent-valve frame (192) of the second component (190) can lock to the first component (200) via a friction fit, geometric fit, or other locking mechanism to hold the first component (200) to the second component (190) via a system lock (842).

The contact of the downstream end (740) of the stent-valve on the native leaflets (790) will act to prevent the native leaflets (790) from overhanging into the downsteam end of the stent-valve frame (192) which could impair replacement leaflet function and can cause stagnation regions (760) leading to thrombus formation. The first component (200) and second component (190) can have concave geometrical structures in their waists or in other regions (as shown in other embodiments) along their length to assist with locating the first component (200) within the second component (190) and locking them together to form a system lock (842). Alternately, the torus balloon (35) can be inflated not only to activate the barbs (25) of the first component (200) but also to serve as a locking ring to which a concave region of the second component (190) can form a geometrical lock as the SE stent frame of the second component (190) expands outwards (800) into contact with the first component (200) to form a system lock (842). The downstream-planar frame portion (932) of the stent-valve will help to prevent the native leaflets (790) from prolapsing into the replacement stent-valve.

The torus balloon (35) can be inflated with a fluid or gel, for example, that is retained within the torus balloon via a flapper valve; the torus balloon can serve to hold the stent-valve frame (192) of the second component (190) from migration and also provide a seal that will prevent leakage between the first component (200) and the second component (190) as the second component (190) expands outwards into contact with the torus balloon (35). The inflated torus balloon allows the second component (190) to require a significantly smaller diameter than the first component frame (982) that is located radially adjacent to the annulus (20) and require a smaller number of second component diametric sizes to accommodate the large range of patient annulus diameters. The torus balloon (35) of the first component (200) also allows movement of the mitral annulus identified from systolic and diastolic motion to be absorbed by the torus balloon and not transferred to the second component (190). The second component (190) can thereby retain a more consistent shape such as a round shape, for example, due to the ability of the torus balloon (35) to deform and comply with shape changes that occur during contraction and relaxation of the heart and annulus (20).

FIG. 39C shows an embodiment of the first component frame (982) that has been attached to the mitral annulus as presented in FIG. 38B and located on the LA side of the native leaflets (790) such that native leaflet function is not affected. The second component frame (192) has been delivered within the lumen of the first component frame and released such that the second component waist (205) is located adjacent to and in contact with the limiting cable (225) of the first component frame (982). The upstream-planar frame portion (930) of the stent-valve frame (192) has a conical shape that fits within the conical shape of the first component frame (982) such that the first component frame (982) is axially aligned with the second component frame (192) due to the cone-in-cone geometrical fit. The second component waist (205) will orient itself in an axial direction (i.e., along the direction of the central axis (45)) to be positioned adjacent to the limiting cable (225) which forms a securement ring (755) with a closed ring configuration. The downstream-planar frame portion (932) can push outwards a small amount onto the native leaflet rim (977) or on the LV side of the native leaflet rim (977) to assist in holding the dual-member stent-valve (195) from migrating toward the LA. The downstream planar frame portion (932) should not push the anterior native leaflet towards the LVOT which can obstruct blood flow in the LVOT.

Figure 40:
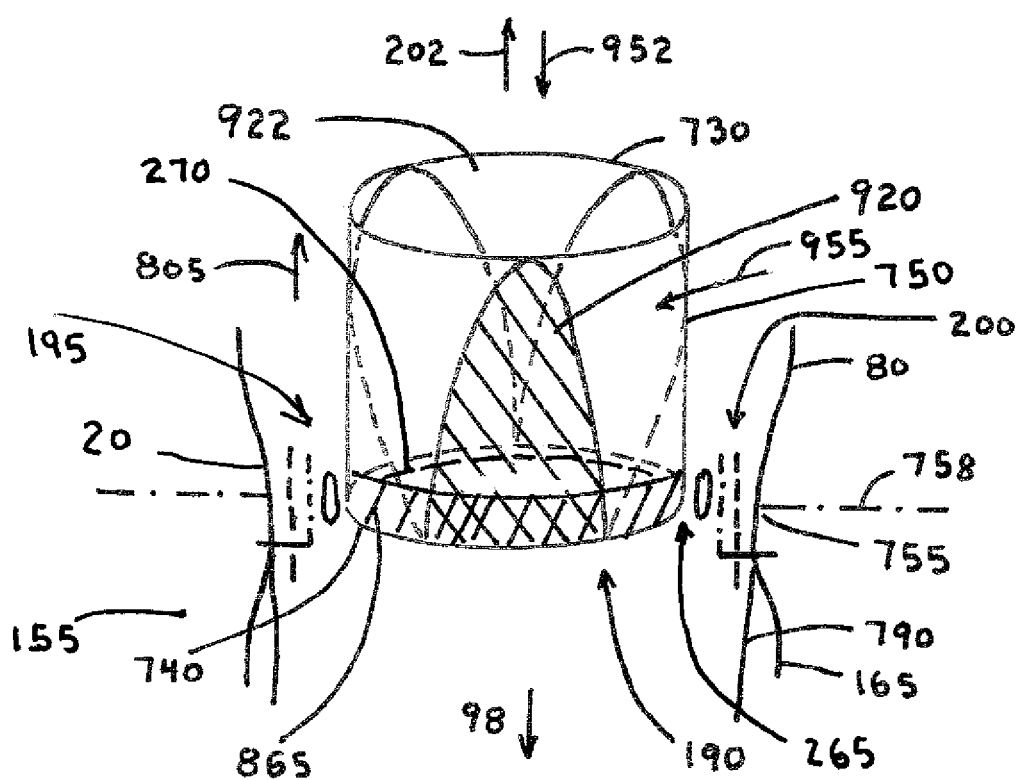
FIG. 40 is a perspective view of a dual member stent-valve system having a first component attached to the annulus and having a second stent-valve component positioned above the mitral annulus and primarily above the first component.

FIG. 40 shows the dual member stent-valve (195) of the present invention having the second component (190) of the present invention being placed within the inside (878) or central lumen (265) of the first component (200). The second component (190) is placed such that the downstream end (740) of the stent-valve frame (192) is upstream (202) of the native mitral valve leaflets (790) thereby placing the securement band (865) near or at the downstream end (740) of the stent-valve frame (192) and adjacent to the securement ring (755), heart annulus (20), or heart tissue. The second component (190) is placed with all or nearly all of the stent-valve frame (192) located in the LA (80) with the advantage that none or almost none of the second component (190) stent-valve frame (192) extends downstream (98) of the securement ring (755) (such as the mitral annulus (20), for example). The stent-valve frame (192) cannot impinge upon the LVOT (155) and cannot push the native leaflets (790) into the LVOT since the stent-valve frame (192) does not extend downstream (98) beyond the mitral annulus (20), for example. The open upstream-planar inter-leaflet frame surface (922) allows antegrade blood flow (952) or inward blood flow (955) to travel from the LA (80) through the stent-valve frame wall (750) and travel downstream (98) through the open replacement leaflets (270) and out of the stent-valve into the LV (165) located downstream (98) of the stent-valve downstream end (740). Fluid flow from the LA (80) is not required to flow in a retrograde direction (805) to enter into the upstream end (730) of the stent-valve frame (192) as found in existing stent-valve devices that cause stagnation and resultant thromboemboli. This embodiment is well suited to the patient that does not have native leaflets (790) that could potentially prolapse toward the LA.

Figure 41A:
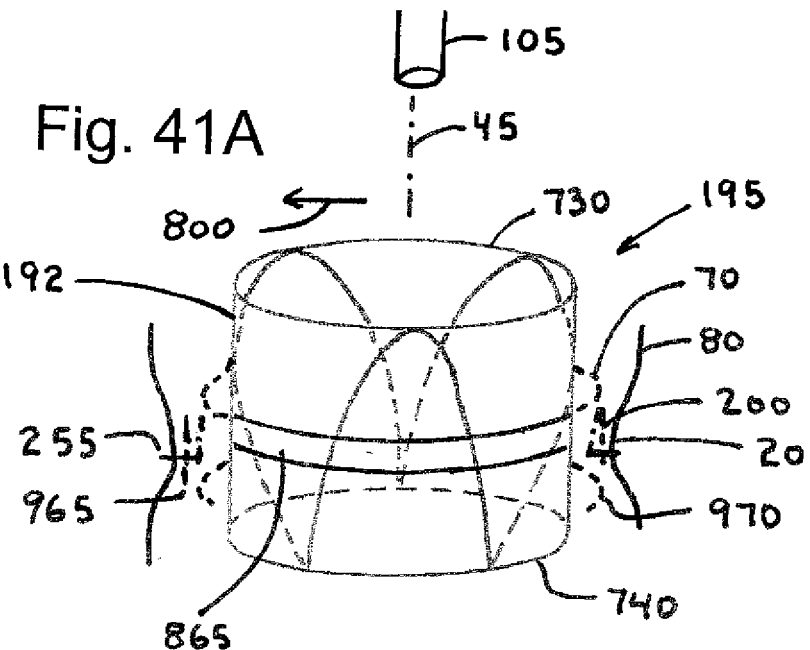
FIG. 41A is a perspective view of a dual member stent-valve having a second stent-valve component with an upper bulb and a lower bulb that locks above and below the first component and holds the second component such that it straddles the mitral annulus.
Figure 41B:
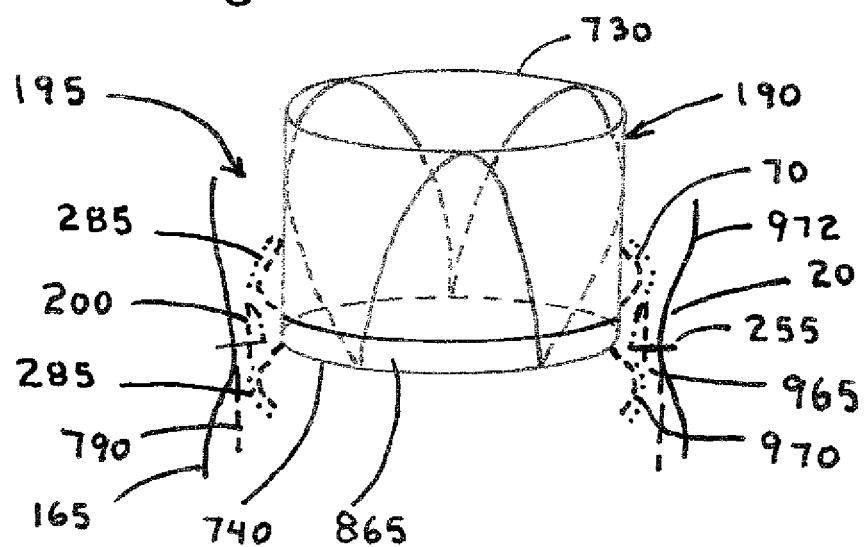
FIG. 41B is a perspective view of a dual member stent-valve having a second stent-valve component with an upper bulb and a lower bulb that locks above and below the first component and holds the second component above the mitral annulus.

FIGS. 41A and 41B show dual member stent-valve systems (195) of the present invention having the stent-valve frame (192) or second component (190) of a two component system (195) for heart valve replacement of the present invention. In FIG. 41A the securement band (865) is located intermediate between the upstream end (730) and the downstream end (740) of the stent-valve frame (192); in FIG. 41B, the securement band (865) is located at the downstream end (740) of the stent-valve frame (192). The stent-valve frame (192) can have an upper bulb (70) attached along the perimeter of the stent-valve frame (192) at a location adjacent to or upstream (202) of the securement band (865). The upper bulb (70) extends outwards (800) toward the upstream end (730) at an angle (range 90-45 degrees from the frame axial direction. The upper bulb (70) helps with positioning of the stent-valve frame (192) such that the upper bulb (70) rests upon the left atrial surface of the mitral leaflet, for example or the upper bulb (70) is positioned just upstream (202) of the native mitral valve leaflet shoulder (962) adjacent to the LA wall (972). Also, the upper bulb (70) can have a covering (285) attached to its surface to assist with preventing perivalvular leaks that can form between the outside (880) of the stent-valve frame (192) and the native tissues or first component (200) member that is located on the outside (880) of the stent-valve frame (192). The barb tip (255) is able to penetrate through the covering (285) and into the annulus (20) as the barb tip (255) is activated. The upper bulb (70) is able to rest in a configuration adjacent to the stent-valve frame (192) as the stent-valve frame (192) is being delivered within the delivery sheath (105). The upper bulb (70) is constructed of Nitinol such that release of the stent-valve frame (192) from the delivery sheath (105) allows the upper bulb (70) to spring outwards (800) into the configuration shown in FIG. 41A. The upper bulb (70) can be withdrawn along with the stent-valve frame (192) into the delivery sheath (105) to allow the stent-valve frame (192) to be repositioned or removed if necessary.

The stent-valve frame (192) can have a lower bulb (970) attached along the perimeter of the stent-valve frame (192) at a location adjacent to or downstream (98) of the securement band (865). The lower bulb (970) extends outwards (800) toward the downstream end (740) at an angle (range 90-45 degrees from the frame axial direction. The lower bulb helps to lock and prevent migration of the stent-valve frame (192) via geometric shape around the first component distal end (965) when the stent-valve frame (192) is being placed subsequent to placement of a first component (200). The lower bulb alternately can lock onto the native mitral valve leaflets (790) or lock downstream (98) of the native mitral valve shoulder (962) or native leaflet rim to prevent migration of the stent-valve toward the left atrium (80) Also, the lower bulb can have a covering (285) attached to its surface to assist with preventing perivalvular leaks that can form between the outside (880) of the stent-valve frame (192) and the native tissues, native leaflets (790), or first component (200) member that is located on the outside (880) of the stent-valve frame (192). The lower bulb is also constructed of Nitinol such that it has a smaller diameter configuration during delivery within the delivery sheath (105); the lower bulb can be withdrawn back into the delivery sheath (105) following its release from the delivery sheath (105).

Figure 42A:
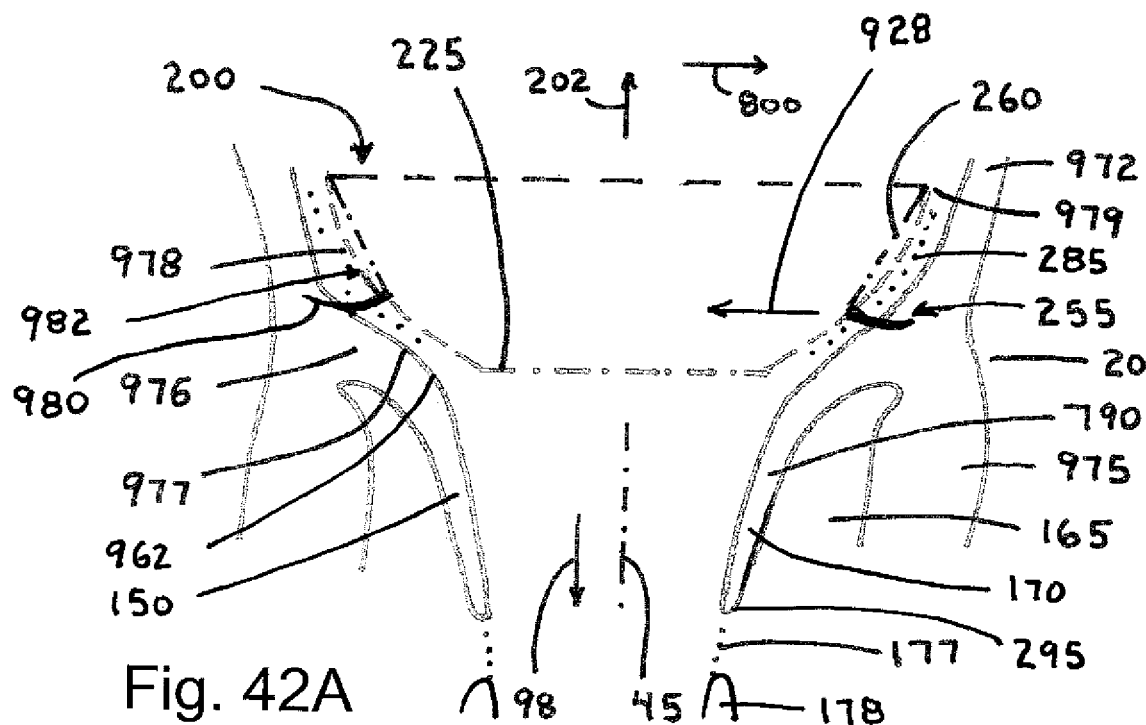
FIG. 42A is a plan view of the first component attached to the mitral annulus via barbs that have been activated by a torus balloon.

FIG. 42A shows the mitral valve annulus (20) with the left atrial wall (972) (of the left atrium (80) (LA)) extending upstream (202) of the mitral annulus (20) and the left ventricular wall (975) (of the left ventricle (165) (LV)) extending downstream (98) of the annulus (20). The native mitral leaflet is attached to the mitral valve annulus (20) at the native mitral leaflet base (976) at the junction of the left atrium (80) with the left ventricle (165). A mitral leaflet rim (977) extends around the perimeter of the mitral valve annulus (20) forming a continuous perimeter of leaflet tissue. The mitral leaflet rim (977) forms a mitral leaflet shoulder (962) that forms a perimeter of the leaflet rim at a location where the leaflet tissue is divided to form a native anterior mitral leaflet (150) and a native posterior mitral leaflet (170). Two mitral valve leaflets (790) extend downstream (98) from the mitral valve rim; each mitral valve leaflet is attached at their free edges (295) via cordae tendineae (177) to papillary muscles (178) that are contiguous with the left ventricular wall. The cordae tendineae (177) prevent the mitral leaflets (790) from prolapsing into the LA (80) during systolic contraction of the LV (165) which can result in mitral regurgitation with consequential negative sequellae.

Figure 42B:
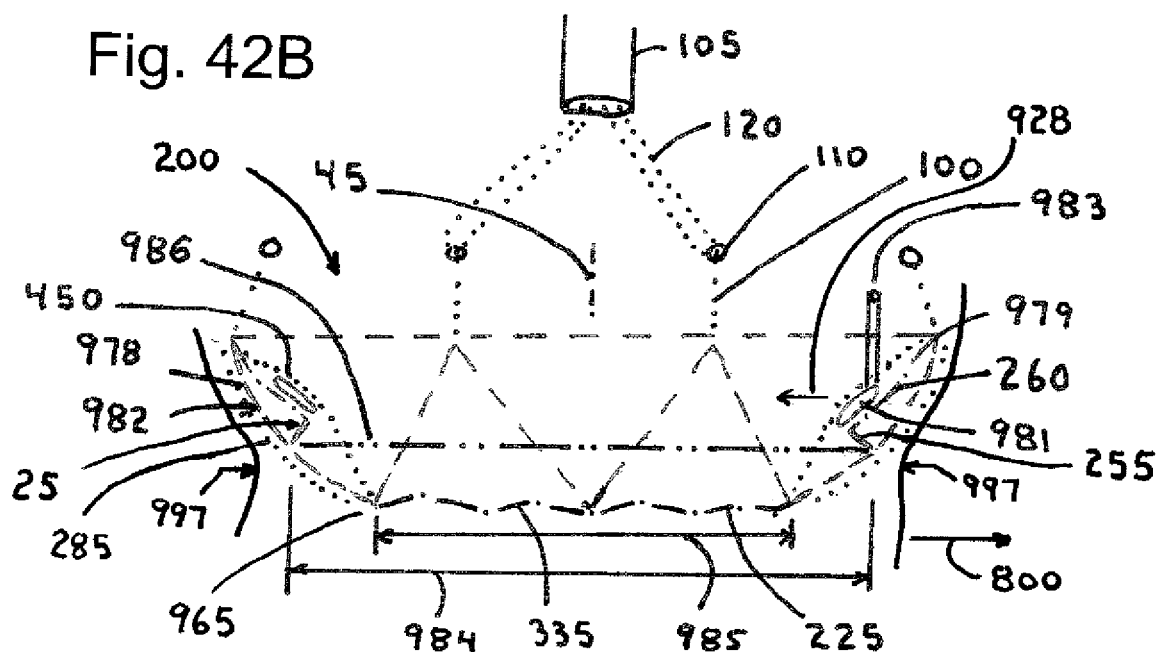
FIG. 42B is a plan view of the first component positioned adjacent to the mitral annulus prior to activation of barbs by a torus balloon; a limiting cable that is contiguous with the stent-valve frame restricts further expansion of the first component frame.

An embodiment of the first component (200) of the present invention is shown in FIGS. 42A and 42B to demonstrate one potential position of the first component (200) relative to the surrounding mitral valve tissues. The structure of the first component (200) can also be found in other embodiment drawings for the first component (200). The first component frame (982) is allowed to expand elastically outward such that it is placed into contact with a portion of the native mitral leaflet near the native leaflet base (976); the first component frame (982) extends inwardly (928) from the native leaflet base (976) along the native leaflet rim (977); the upstream frame region (978) of the first component frame (982) extends upstream (202) and radially outwards (800) along a portion of the LA wall (972); this first component upstream frame region (978) can form a flange-shaped portion that extends outwards (800) at an angle with respect to the central axis (45), or can extend upstream (202) in the direction of the central axis (45) (30-90 degrees from the direction of the central axis (45)). A barb strut (260) is attached to the first component frame (982); the barb strut (260) has a balloon-expandable (BE) barb hinge (979) that allows the barb strut (260) to undergo a plastic deformation if it is exposed to a deformation force (such as from the torus balloon (35) of the present invention, for example) that causes the barb strut (260) to be pivoted along the barb hinge (979). A barb tip (255) located at one end of the barb strut (260) is shown in an activated configuration having the barb tip (255) embedded into the mitral valve annulus (20) or surrounding tissues of the mitral valve. The barb tip (255) holds the first component (200) securely to the mitral valve surrounding tissues and prevents migration of the first component frame (982) upstream (202) towards the LA (80) and also assist in stabilizing the first component (200) from migration downstream (98) towards the LV (165). The barb tips (255) are able to penetrate through the covering (285) to extend into the surrounding tissues during activation of the barb tips (255). Alternately, the covering (285) can be located inwards (928) of the barb strut (260) or inwards (928) of the activating torus balloon (981) while being attached to the upstream end and downstream end of the first component frame (982) such that the covering does not interfere with the barbs (25) or require penetration by the barbs (25) through the covering (285) during activation of the barbs (25). All or a portion of the first component frame (982) can have a covering (285) attached to the frame surface to help ensure that perivalvular leakage or leakage of blood through the first component frame (982) does not occur; the covering (285) is formed from a thin fabric including Dacron and expanded polytetrafluoroethylene (ePTFE) and other fabrics which will prevent blood flow through the fabric. The barb tip (255) can be straight and extend for a distance of 3 mm (range 1.5-6 mm) or the barb can have a barb tip (255) that forms an arc and has a curved barb tip (980); the curved barb tip (980) can arc in an upstream (202) direction such that the curved barb tip (980) forms a stable configuration within the LA wall (972) or other native tissues to prevent migration of the first component (200) upstream (202), for example. Alternately, the curved barb (980) can arc in a downstream direction (98).

As shown in FIG. 42B, an activating torus balloon (981) is located along the perimeter of the first component frame (982) on the inward (928) side of the barb strut (260). A plurality of backing elements are located on an inward-facing (928) surface of the activating torus balloon (981) at locations radially inward (928) from each of the barb struts (260) to provide backing support to the activating torus balloon (981) such that balloon inflation will cause the activating torus balloon (981) to push the barb strut (260) outwards (800). The backing elements (450) are attached to the first component frame (982) at attachment sites that will provide tension to the backing elements during inflation of the activating torus balloon (981) and allow the torus balloon to transfer its inflation pressure outwards (800) to activate the barbs (25). The activating torus balloon (981) can be inflated via an inflation port (983) to cause activation of the barbs (25) in an outward direction to place the barb tips (255) into the surrounding mitral tissue. An inflation port (983) connected to the activating torus balloon (981) extends into and throughout a delivery sheath (105) and further extends outside (880) of the patient such that an operator can inflate the activating torus balloon (981) after the first component (200) has been placed via elastic expansion of the first component frame (982) into intimate contact with the mitral valve annulus (20).

Recapture members (100) (described also in previous embodiments) that are attached to the first component (200) allow the first component frame (982) to be released from a delivery sheath (105) and placed into contact with the mitral annulus (20), but still can be repositioned within the mitral surrounding tissues or removed by withdrawing the first component frame (982) back into a delivery sheath (105). The recapture members (100) can be permanently affixed or contiguous with the first component frame (982). A plurality of control fibers (120) can be temporarily attached or looped through a holding feature (110) such as a ring that is attached to the upstream end (730) of the first component frame (982) or the upstream end (730) of the recapture struts (100); one end of the control fibers (120) can be released from the first component frame (982) once positioning of the first component frame (982) has been deemed acceptable by the operator, and the control fibers can be removed from the body.

A limiting cable (225) is located along the perimeter of the first component frame (982); the limiting cable (225) can be formed into the strut structure of the first component frame (982) such that thin flexible limiting struts, for example, formed as a zig-zag structure (335) into the first component frame (982) reach a geometrical configuration (via opening the zig-zag structure (335) into a linear configuration that can no longer extend in circumferential length) that extends around the perimeter of the first component frame (982) and forms a closed ring that is unable to extend to a larger perimeter and thereby limit the perimeter of the first component (200). The limiting cable (225) prevents the first component frame (982) from applying a continued outward force onto the mitral annulus (20) due to the elastic character of the SE Nitinol frame once the stent-valve frame (192) has reached a specified limiting diameter controlled by the limiting cable (225). The limiting cable (225) also provides a fixed ring structure into which a second component (190), such as a stent-valve can be placed and held via a friction fit to the first component (200) or via a geometrical shape that locks the second component (190) to the first component (200). The limiting cable (225) can have a smaller limiting cable diameter (985) than the mitral valve annulus diameter and smaller than a fixation ring diameter (984), the fixation ring diameter (984) being the diameter of a fixation ring (986) of the first component frame (982) at a location where the barb tips (255) are entering the mitral valve annulus (20). The smaller limiting cable diameter (985) (smaller than the fixation ring diameter (984) for one embodiment) allows a smaller diameter for a second component (190) stent-valve to be locked into the first component (200) forming a system lock (8) at the location of the limiting cable. Thus for patients with widely varying and enlarged annulus diameters (997), fewer sizes (i.e., fewer diameter-based stent-valve frames (15)) for the second component (190) are needed to cover a large range of annulus diameters (997) found in patients with annulus diameters (997) ranging from 25 to over 55 mm in diameter. The limiting cable (225) can be 10 mm smaller in diameter (range 2-30 mm smaller in diameter) than the mitral annulus diameter (997) or fixation ring diameter (984). Also, the profile for the second component (190) stent-valve will be reduced due to the smaller limiting cable diameter (985). The benefit of a reduced profile will allow the present device to be delivered by the greatly preferred transseptal atrial approach rather than via the more patient-risky apical access.

The first component frame (982) can be formed from a hinge and strut structure (such as described in FIGS. 50A-50C, for example) that is able to conform to the oval or saddle shape of the mitral annulus, thereby providing improved contact of the first component frame (982) with the mitral annulus. The improved contact will provide improved attachment of the barbs with the surrounding mitral tissues along the entire perimeter of the oval annulus; also, improved contact will reduce likelihood for perivalvular leaks located at the small radius of curvature portions of the oval annulus. The limiting cable (225) located near the first component distal end (965) provides a closed ring into which the second component frame (192) can be delivered and expanded to form a friction fit or geometrical fit such that it locks with the limiting cable as the second component frame (192) expands outward to form a round shape. The round shape of the second component frame (192) provides the second component frame with the benefit of not requiring orientation around the circumferential direction and the round shape helps to provide improved leaflet symmetry and durability. Thus the first component proximal end (968) forms an oval shape to conform to the oval annulus and the first component distal end (965) has a round shape to provide a closed ring that matches the rounded shape of the second component frame (192). A covering (285) attached to the surface of the first component frame (982) ensures that leakage of blood cannot occur across the wall of the first component frame (982).

Alternately, the limiting can have a limiting cable diameter (985) that is equal to the diameter of the mitral valve annulus (20) or fixation ring diameter (984) such that the second component (190) can enter within the perimeter of the limiting cable (225), the limiting cable diameter (985) being the diameter of a circle having the same perimeter as the limiting cable (225). The limiting cable (225) can be located at the first component distal end (965) or located at the position of the first component fixation ring (986).

Figure 43A:
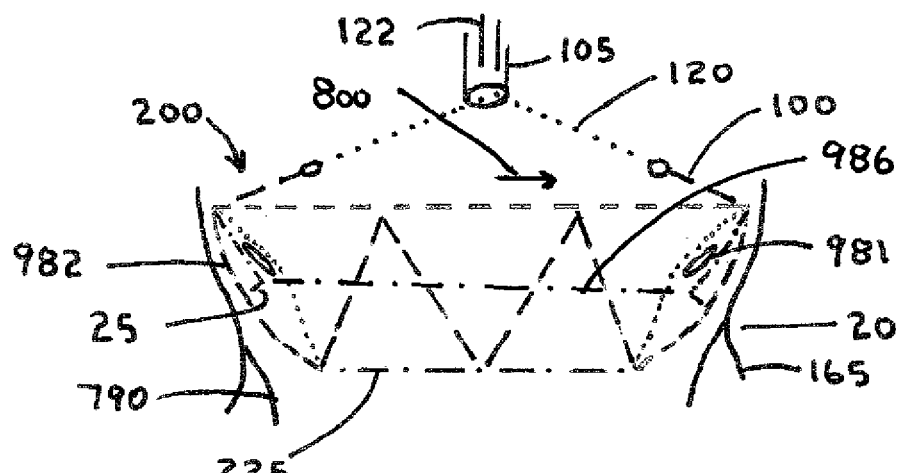
FIG. 43A is a plan view of the first component positioned adjacent to the mitral annulus and extending to a smaller diameter than the mitral annulus at the distal end of the first component frame due to the limiting cable.
Figure 43B:
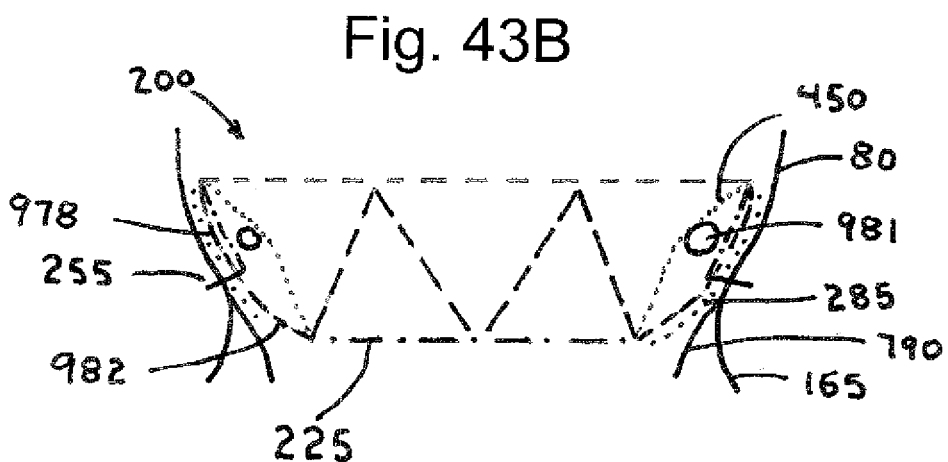
FIG. 43B is a plan view of the first component adjacent to the mitral annulus and having barb tips activated via a torus balloon into the surrounding mitral tissues.

FIGS. 43A and 43B show the delivery method for the first component (200) to the mitral valve surrounding tissues. The first component (200) is delivered to the site of the mitral annulus (20) via a delivery sheath (105); the first component (200) is expelled from the delivery sheath (105) using a pusher member (122) or other means used in the medical device industry. The first component (200) expands outwards (800) via SE elastic stored energy of the Nitinol or other elastic metal frame and comes into contact with the mitral annulus (20). The first component (200) is being held by control fibers (120) that extent into the delivery sheath (105) as shown in FIG. 43A. The control fibers (120) are temporarily attached or looped though a holding feature (110) such as a ring located in the upstream end (730) of the recapture struts (100) or the first component frame (982). Once the physician determines that the position of the first component (200) is acceptable; the operator is able to reposition the first component (200) or remove the first component (200) back into the delivery sheath (105) using the control fibers (120) that extend to the proximal end of the delivery sheath (105). After the position for the first component (200) has been established (i.e., the fixation ring (986) is located adjacent to the leaflet base or mitral valve annulus (20)), the activating torus balloon (981) is inflated to push the barb tips (255) outwards (800) into the surrounding mitral valve tissues as shown in FIG. 43B. The barb tips (255) are able to penetrate through the covering (285) and extend into the surrounding tissues. The position of the first component (200) is stabilized during barb activation via the control fibers (120) and recapture members (100). The control fibers (120) can be removed or recapture members (100) can be released from the delivery sheath (105) to deliver the first component (200) to the mitral valve surrounding tissues as shown in FIG. 43B. A covering (285) is attached to all or a portion of the first component frame (982). The covering (285) assists in making a good seal between the first component frame (982) and the surrounding tissues to prevent perivalvular leaks, particularly after the surrounding tissues have had a chance to ingrow into the micro-pores of the covering (285) material. The penetration of fibrous tissues into the pores of the covering (285) assists in stabilizing the first component (200) from axial migration towards the LV (165) or LA (80).

Figure 44A:
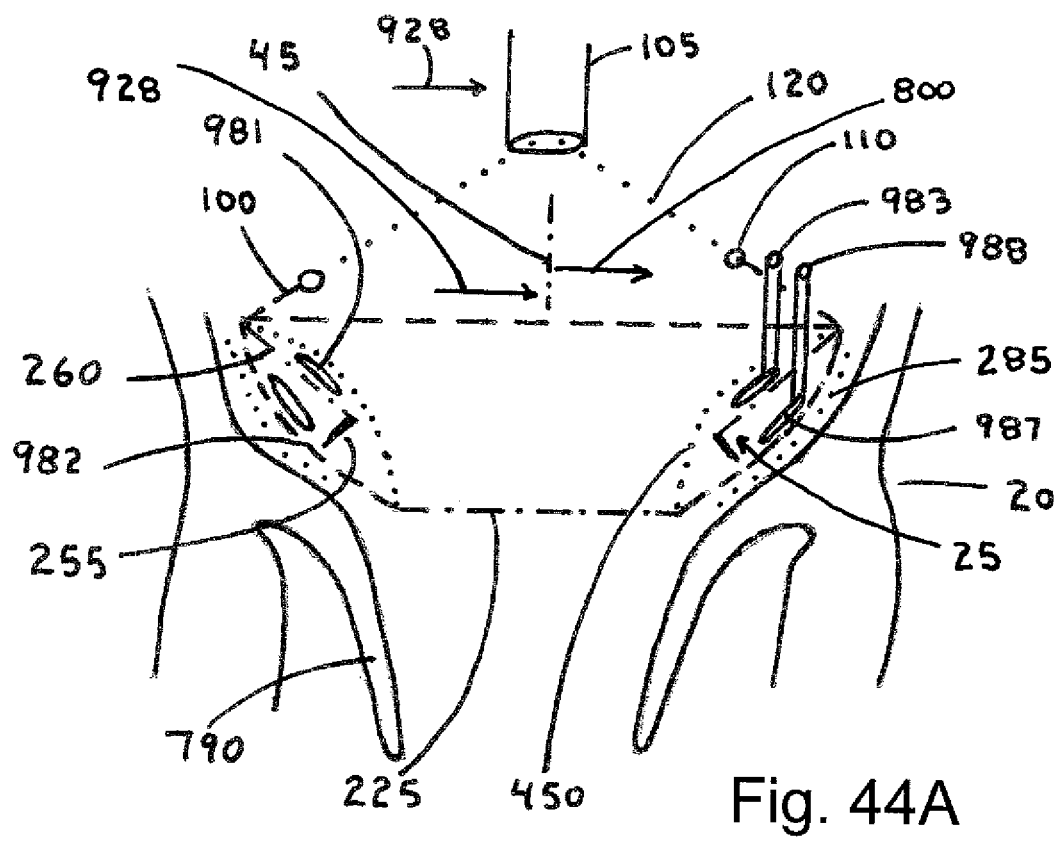
Figure 44B:
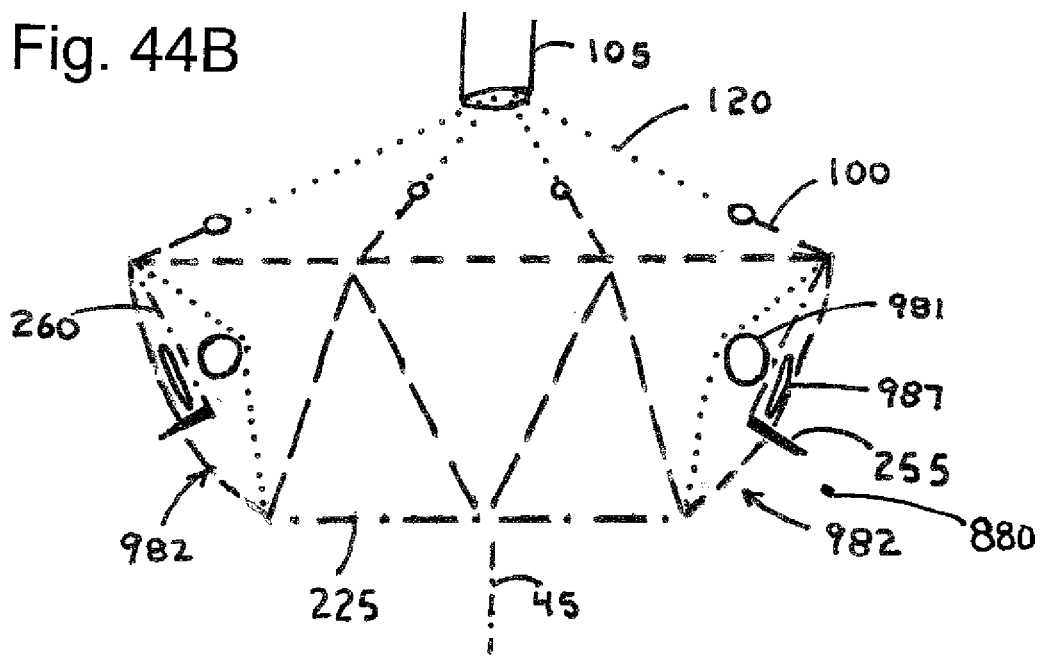
Figure 44C:
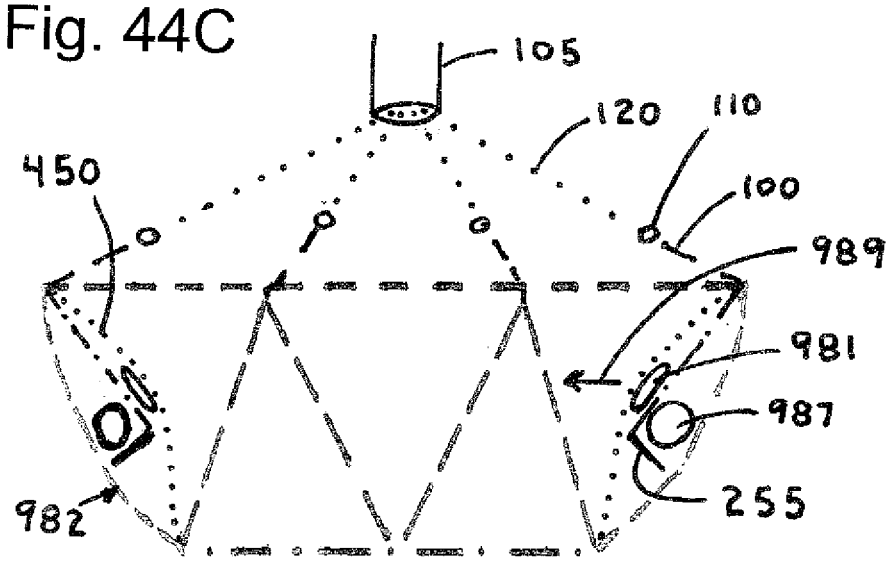

FIGS. 44A to 44C shown an embodiment for the first component (200) that is repositionable and removable even after the activating torus balloon (981) has been inflated to activate the barbs (25) outward into the surrounding tissues. The structural elements of this embodiment are the same as described in the previous embodiment shown in FIG. 42A and in other embodiments except with the addition of a deactivating torus balloon (987). The deactivating torus balloon (987) is attached along the perimeter of the first component frame (982) along the inward surface of the first component frame (982). The struts or structural stent elements of the first component frame (982) provide support to the outward surface of the deactivating torus balloon (987). The deactivating torus balloon (987) can be attached along the insides surface of the first component frame (982) around the perimeter of the first component frame (982). The deactivating torus balloon (987) has a deactivating torus balloon inflation port (988) that allows the deactivating torus balloon (987) to be inflated independently from the activating torus balloon (981).

As shown in FIG. 44A the first component frame (982) has been partially released from a delivery sheath (105) and has expanded outwards (800) (relative to the central axis (45)) via SE character of the first component frame (982) to a diameter that makes contact with the mitral annulus (20). The first component (200) is being held by control fibers (120) that are temporarily attached to recapture members (100), the recapture members (100) being attached or contiguous with the upstream end (730) of the first component (200). The control fibers (120) extend into a delivery sheath (105) such that the first component (200) can be withdrawn back into the delivery sheath (105) by application of tension to the recapture members (100) and control fibers (120). The activating torus balloon (981) which is located inwards (928) from the barb struts (260) is noninflated; the deactivating torus balloon (987) located outwards (800) of the barb struts (260) is also noninflated. A covering (285) is attached to all or a portion of the first component frame (982) to provide an improved seal between the first component frame (982) and the surrounding tissues; the improved seal assists with preventing perivalvular leak and helps to provide stabilization against frame migration as surrounding tissues integrate into the pores of the covering (285). The barb tips (255) are able to penetrate through the covering (285) during activation of the barb tips (255).

As shown in FIG. 44B, the activating torus balloon (981) has been inflated to activate the barbs (25) outwards (800) placing the barb strut (260) into contact with the uninflated deactivating torus balloon (987) and applying an outward force to the barb strut (260) to place the barb tip (255) to the outside (880) of the first component frame (982) and into the mitral valve surrounding tissues. If the operator does not approve of the positioning of the first component (200) relative to the annulus (20), for example, the activating torus balloon (981) can be deflated via application of vacuum or via disconnecting the activating torus balloon inflation port (983) to allow the inflation fluid to leak out of the inflation port (983) of the activation torus balloon. The deactivating torus balloon (987) can then be inflated to push the barb struts (260) inwards (928) as shown in FIG. 44C. The inward force (989) supplied by the deactivating torus balloon (987)

is supported by the first component frame (982) which is in contact with the outward-facing surface (on the outwards (800) side of the deactivating torus balloon (987)) of the deactivating torus balloon (987). The barb tips (255) will then move inwards (928) to a location inwards (928) of the first component frame (982) and the barbs (25) will then be in an inactive configuration. The first component frame (982) can then be repositioned or removed using the control fibers (120) placed under tension to pull the first component (200) back into the delivery sheath (105).

Other methods of deactivating the barbs (25) are anticipated. For example, the barb strut (260) can easily be bonded to the activating torus balloon (981) using standard bonding methods. Following inflation of the activating torus balloon (981) and activation of the barbs (25), the activating torus balloon (981) could then be exposed to a vacuum to pull the barb strut (260) inwards (928) and cause the barb tip (255) to be removed from the surrounding mitral valve tissue, and the barb to become deactivated. This alternate embodiment would require that the backing member (450) be formed from a rigid material such as a rigid metal and the activating torus balloon (981) would be bonded to the backing member (450) using standard bonding methods. The backing member (450) would provide the support that would allow a vacuum contained within the activating torus balloon (981) to pull the barb strut (260) inwards (928) such that the barb is no longer activated. The activating torus balloon (981) in this alternate embodiment would serve as both an activating torus balloon (981) and a deactivating torus balloon (987).

Figure 45:
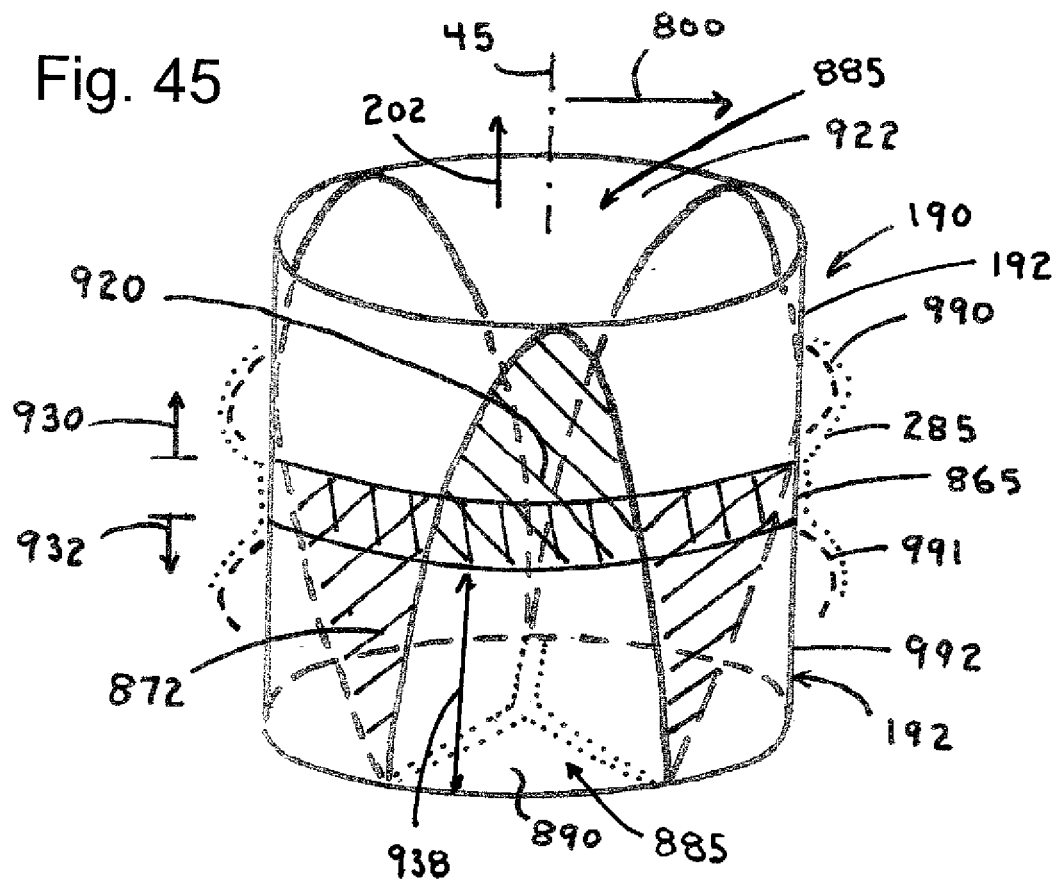

FIG. 45 shows an embodiment for the second component (190) or stent-valve component (190) of the two component system (195) of the present invention. The stent-valve frame (192) of this embodiment has a generally cylindrical stent frame body (992) with a supra-securement locking feature (990) located upstream (202) of the securement band (865) and an infra-securement locking feature (991) located downstream (98) of the securement band (865). The stent-valve frame (192) has a securement band (865) that has a covering (285) attached along a perimeter of the stent-valve frame (192); the securement band (865) is intended to be located axially along the stent-valve frame (192) such that it is in contact with and radially inward (928) from the limiting cable (225) of the first component (200) or other locking feature or geometric locking shape formed into the first component frame (982) that forms a system lock (842). A tight friction fit between the securement band (865) and the limiting cable (225) ensures that blood is unable to leak between these two components. A supra securement locking feature is attached to the stent-valve frame (192); the supra-securement locking feature (990) extends outwards (800) from the stent-valve frame body (992) and makes contact with the upstream frame region (978) of the first component frame (982); the feature extends outwards (800) from the stent-valve frame body (992) by approximately 3 mm (range 1-6 mm). The supra-securement locking feature (990) can have, but is not required to have, a covering (285) attached to all or a portion of its surface. An open supra-securement locking feature (990) can allow for blood flow through the stent-valve frame wall (750) without creating blood stagnation regions (760). The infra-securement locking feature (991) is intended to be placed downstream (98) of the limiting cable (225) of the first component (200) or other locking feature or geometric locking shape found in the first component frame (982). The infra-securement locking feature (991) will prevent movement of the second component (190) or stent-valve component (190) in a retrograde direction (805) toward the LA. The infra-securement locking feature (991) can extend around the entire perimeter of the first component (200). Alternately, the infra-securement locking feature (991) can extend along only a portion of the perimeter of the second component (190); a portion of the first component frame (192) perimeter that faces the native anterior leaflet may not be preferable to contain the infra-securement band locking feature to avoid pushing the native anterior leaflet toward the LVOT.

The second component (190) of this embodiment is intended to straddle the mitral annulus (20) and thereby contains an upstream-planar frame portion (930) or supra-securement band portion (930) that extends into the LA (80) and a downstream-planar frame portion (932) or infra-securement band portion (932) that extends into the LV. The downstream-planar frame portion (932) that extends into the LV (165) has a downstream-planar frame length (938) of 10 mm (range 5-15 mm) such that the stent-valve frame (192) does not extend into the LVOT and does not push the anterior native mitral leaflet into the LVOT. The stent-valve frame (192) does extend far enough into the LV (165) to ensure that the native mitral leaflets (790) cannot overhang the downstream end (740) of the stent-valve frame (192). The stent-valve frame (192) is open (without a covering (285)) in the open downstream-planar intra-leaflet frame surface (890); the open surface (885) allows blood to flow between the stent-valve frame (192) and the luminal surface of the native leaflets thereby preventing blood stagnation and potential thrombosis in this region. The stent-valve frame surface is covered in the closed downstream-planar inter-leaflet frame surface (872) to prevent blood from an retrograde flow path without proper valve control from the downstream end (740) to the upstream end (730) of the stent-valve frame (192). The upstream-planar frame portion (930) has an open surface (885) (i.e., no covering (285)) in the open upstream-planar inter-leaflet frame surface (922); this allows direct blood flow from the LA (80) into the lumen of the stent-valve frame (192) without requiring entry into the upstream end (730) of the stent-valve frame (192); this prevents regions of blood stagnation in the LA. The upstream-planar frame portion (930) has a closed upstream-planar intra-leaflet frame surface (920). The supra-securement band and infra-securement band locking feature can have a covering (285) attached to all or a portion of each of the locking features to provide an improved seal with the surrounding tissues and to assist with prevention of perivalvular leak.

Figure 46A:
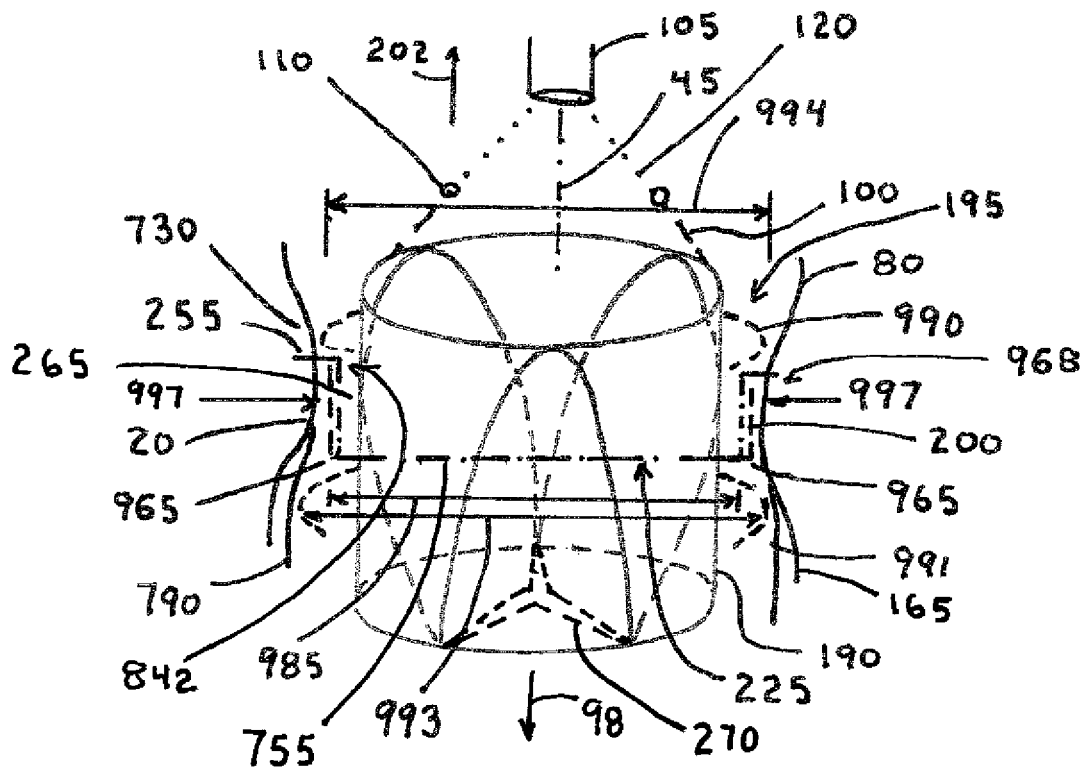
Figure 46B:
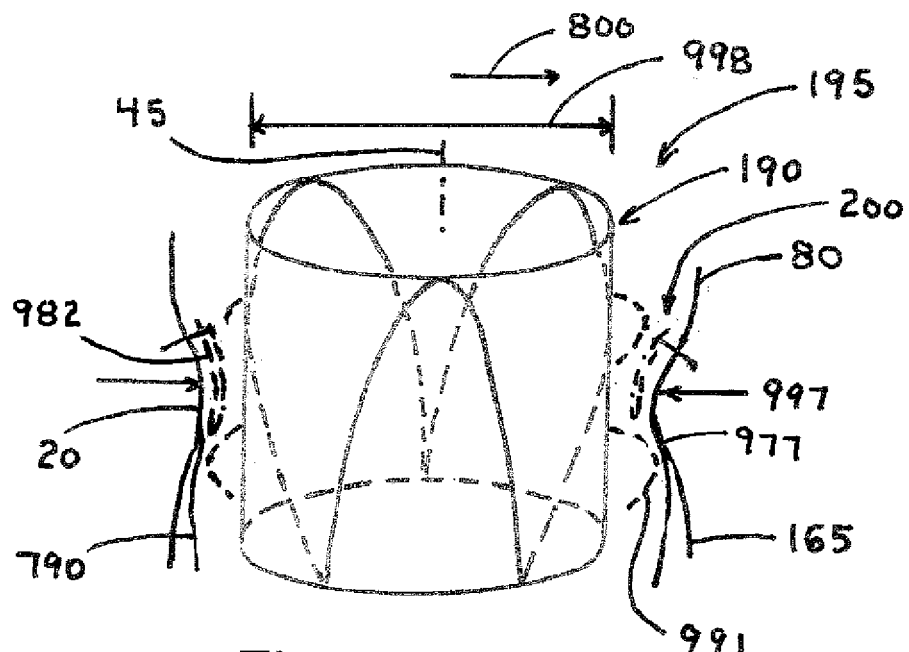

FIGS. 46A and 46B show the delivery of the second component (190) of a dual member stent-valve (195) having the second component (190) placed into the central lumen (265) of the first component (200) and locking the second component (190) to the first component (200) to form a system lock (842). As shown in FIG. 46A, the first component (200) has been delivered to the mitral annulus (20) and has been attached to the mitral annulus (20) via activation of the barb tips (255) into the surrounding mitral tissues. The first component stent frame (982) extends downstream (98) from the location that the barb tips (255) extend through the stent frame; the first component (200) extends further inwards (928) to a diameter that is less than the mitral annulus diameter (997). The limiting cable diameter (985) can be 10 mm less (range 2-30 mm less) than the diameter of the mitral annulus (20). The limiting cable (225) that extends around the perimeter of the first component (200) can be located, for example, at the distal end (965) of the first component (200) as shown in FIG. 46A such that the limiting cable diameter (985) is less than the mitral annulus diameter (997) and can serve, for example, as a closed securement ring (755) onto which the second component (190) can be locked via geometrical shape fit or via friction fit. The mitral annulus diameter (997), stent frame diameter, limiting cable diameter (985), securement band diameter (999), and other device component diameters that are used in the present specification represent the diameter of a circle that has a perimeter of the mitral annulus (20), perimeter of the stent frame, or perimeter of the limiting cable (225), respectively, for example. It is noted that the limiting cable diameter (985) can be as large as the diameter of the mitral annulus (20) such that the second component (190) is able to be delivered within the closed ring formed by the limiting cable (225).

The barb tips (255) have been activated and extend through the first component frame (982) into the surrounding mitral valve tissue at a location near the base of the mitral valve leaflets (790). The barb tip (255) extends approximately 3 mm (range 1.5-6 mm) into the surrounding tissues such that barb tip (255) does not allow for migration of the first component (200) and does not extend too far into the tissue to interfere with the circumflex artery or extend into the aortic artery luminal space. The first component (200) can be placed without requiring orientation around the angular direction with respect to the central axis (45) of the mitral annulus (20). The first component stent frame (982) extends from a first component distal end (965) having a location nearest to the LV (165) to a location upstream (202) toward the LA (80) and outwards (800) at an angle of 20 degrees (range of 90 to zero degrees; shown best in FIGS. 44A-44C) with respect to the central axis (45) of the first component (200) along the shoulder or rim of the mitral leaflets (790); the first component frame (982) extends further upstream (202) and outwards (800) upstream (202) of the native leaflets (790) at an angle of 20 degrees (range zero to 80 degrees) with respect to the central axis (45) of the first component (200)) along a portion of the left atrial wall to the first component (200) proximal end (968) (see FIGS. 44A-44C).

The second component (190) is delivered via a delivery sheath (105) as shown in FIG. 46A. The second component (190) is partially released from the delivery sheath (105) and allowed to expand under elastic SE stent stored energy to a location such that the infra-securement locking feature (991) is released and can be positioned downstream (98) of the securements ring (such as the limiting cable (225)) of the first component (200). The infra-securement locking feature (991) extends outwards (800) to a infra-securement locking feature diameter (993) that is larger than the limiting cable diameter (985) by 4 mm (range 2-10 mm). The delivery sheath (105) can then be retracted proximally while holding position of the stent-valve to release the supra-securement locking feature (990) above the securement ring (755) (such as the annulus (20), for example) or limiting cable (225) of the first component (200). The supra-securement locking feature (990) has a supra-securement locking feature diameter (994) that is 4 mm (range 2-10 mm) larger than the limiting cable diameter (985) or geometric locking feature of the first component frame (982). The stent-valve can be pushed downstream (98) via compression to the delivery sheath (105) or tension to the delivery sheath (105) to ensure that the stent-valve is locked onto both sides of the securement ring (755) of the first component (200) via the locking features of the second component (190) as shown in FIG. 46A.

The second component (190) is still attached to the delivery sheath (105) via control fibers (120) which are temporarily attached or looped through holding features (110) located at the upstream end (730) of recapture struts (100) or upstream end (730) of the second component (190); the control fibers (120) extend into the delivery sheath (105) and allow the operator to pull the second component (190) back into the delivery sheath (105) if the second component (190) or stent-valve component (190) is not acceptably positioned across the mitral valve annulus (20). Upon verification that the second component (190) is functioning properly and the position is proper, the control fibers (120) can be removed and the recapture members (100) can be released from the delivery sheath (105) to fully release the second component (190) as shown in FIG. 46B. The infra-securement locking feature diameter (993) is larger than the limiting cable diameter (985) to ensure that the second component (190) is locked into the first component (200) via geometrical constraints and is unable to migrate toward the LA. The infra-securement locking feature (991) can be located downstream (98) of the annulus (20) or downstream (98) of the native leaflet rim. The infra-securement locking feature (991) diameter can be larger than the annulus diameter (997) or native leaflet rim (977) and can push outwards (800) against the native leaflet at a location downstream of the native leaflet rim (977) in the LV (165) to further prevent the second component (190) from migrating toward the LA (80) as shown in FIG. 46B. The infra-securement band locking feature can extend around the entire perimeter of the first component (200) or alternately, along only a portion of the perimeter of the first component (200) to avoid pushing the native anterior leaflet into the LVOT.

The infra-securement locking feature diameter (993) can be 4 mm (range 0-6 mm) larger than the annulus diameter (997). Since the first component (200) and second component (190) are locked together via the locking features located upstream (202) and downstream (98) of the limiting cable (225) to form a system lock (842), the first component (200) is also prevented from migrating toward the LA (80) due to the infra-securement locking feature (991). The infra-securement locking feature (991) thereby reduces the axial force exerted by the LV pressure that acts to push the mitral valve system towards the LA; the axial force transmitted onto the barbs (25) of the first component (200) is thereby reduced, reducing the likelihood of dehiscence from the barbs (25) due to micro movement which can occur relative to the surrounding tissues during each cycle of the beating heart. The barbs (25) of the first component (200) can then be allowed to form an improved healing response with the surrounding tissues without the likelihood for inflammatory response due to relative movement between the barb tip (255) and the surrounding tissues. To further reduce the chances for inflammation at this site the barb tips (255) can be coated with a biocompatible material such as a microporous polyurethane, porous Dacron, or other microporous, fibrous, or biocompatible material that provides for cellular attachment, cellular incorporation, or favorable cellular healing.

One feature of the present invention relates to limiting the number of sizes needed for the first or second component (190) to meet the varying diameters for mitral valve annulus (20) found in patients. By providing a limiting cable (225) with a smaller limiting cable diameter that the mitral annulus (20), the number of sizes for the second component (190) can be reduced since the second component (190) is sized to fit frictionally or geometrically within the closed ring provided by the limiting cable (225).

Another feature of the present invention is that the first component frame (982) can be formed of a hinge and strut structure such as that show in FIGS. 50A-50C, for example.

The hinge and strut structure of the first component can conform to an oval or saddle shaped annulus in the region of the first component frame (982) that is adjacent to the annulus. The first component frame (982) can be very conformable to form a rounded shape at the location of the limiting cable near the first component distal end (965). Thus the compliant portion of the first component frame (982) adjacent to the annulus makes full apposition with the oval annulus to allow the barbs to embed themselves into the surrounding mitral tissue along the entire perimeter of the mitral annulus, and also, the full apposition will prevent the formation of perivalvular leaks on the outside of the first component frame (982) between the first component frame (982) and the native mitral tissues. The first component frame (982) near the first component distal end (965) can have a rounded shape in its expanded configuration. The limiting cable is further forced into a round shape by the expansion forces of the second component frame (192) into the region of the limiting cable; the limiting cable serves as a closed ring into which the second component frame (192) is locked via frictional forces or via geometrical shape features found in the first component frame (982) and second component frame (192).

Figure 46C:
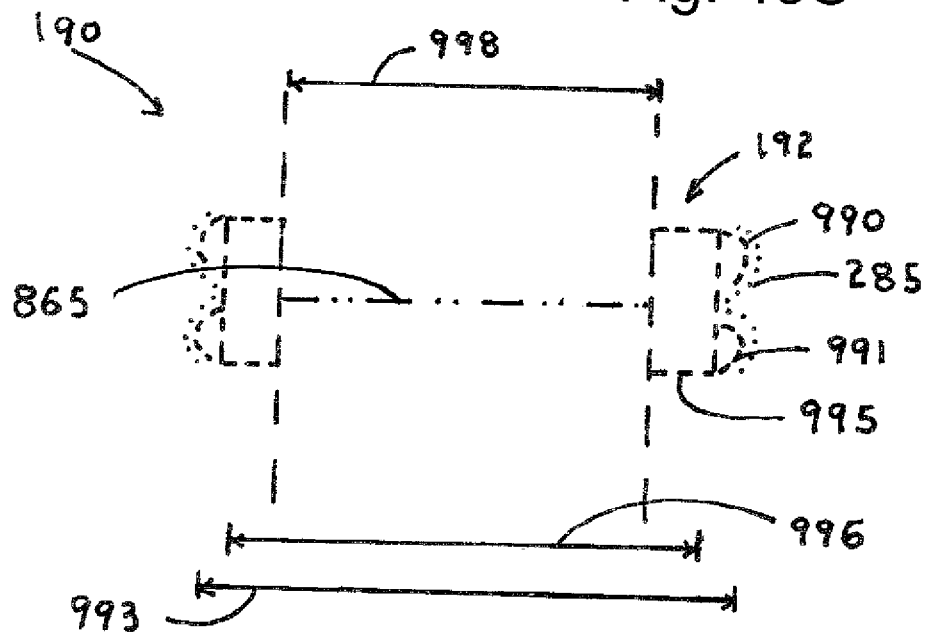

The use of such a limiting cable diameter (985) that is smaller than the annulus diameter or first component diameter at a location adjacent to the mitral annulus can create within the second component (190) a greater challenge to have an infra-securement locking feature diameter (993) larger than the mitral annulus (20) and still be withdrawn back into the delivery sheath (105) for possible repositioning or removal. An embodiment intended to address this concern is shown in FIG. 46C. In this embodiment a frame extension (995) is attached to the outside (880) of the stent frame of the second component (190) in the region of the stent frame upstream (202) and downstream (98) of the securement band (865) such that the supra-securement locking feature (990) and infra-securement locking feature (991) are attached to the frame extension (995). The frame extension (995) has a frame extension diameter (996) that extends outwards (800) to fit snugly with friction within the closed ring of the limiting cable (225) found in the first component (200) or securement ring. The limiting cable diameter (985) can be approximately equal to the mitral annulus diameter (997). The frame extension diameter (996) is 6 mm (range 5-30 mm) larger in diameter than the stent-valve frame body diameter (998) that contains the replacement leaflets (270). The supra-securement locking feature (990) and infra-securement locking feature (991) extend outwards (800) from the stent-valve frame (192) by 4 mm (range 2-10 mm) on each side of the stent-valve frame (192).

Figure 46D:
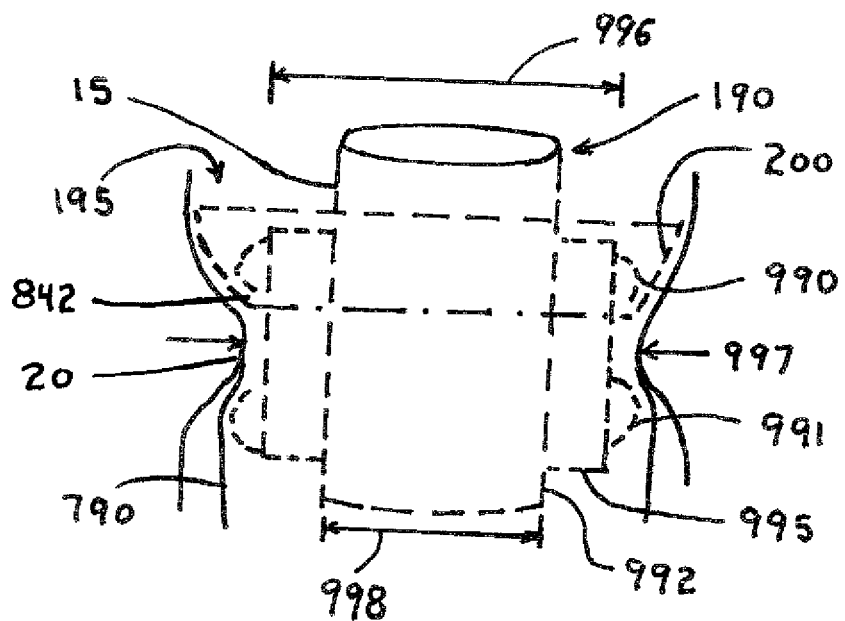

As shown in FIG. 46D, when the second component (190) is placed within and locked within the first component (200) forming a system lock (842), the infra-securement locking feature (991) is able to push outwards (800) onto the native leaflet (790) downstream (98) of the mitral annulus (20) thereby providing additional assistance against upstream (202) migration. The stent-valve frame body (992) that houses the leaflets (270) can have a stent-valve body diameter that is 5-30 mm smaller than the mitral annulus (20) thereby allowing a lesser number of sizes for the stent-valve frame body (992) and leaflet subcomponent; the stent-valve frame body (992) can be combined via a permanent attachment or an attachment that can be locked in place via a secondary step with a frame extension (995) to form the stent-valve frame (192) and meet the varied patient's mitral valve annulus diameters (997). The stent-valve frame (192) can have a stent-valve frame diameter that is 10 mm smaller (range 2-30 mm smaller) than the mitral annulus diameter (997) thereby reducing the profile for the stent-valve frame (192).

Several designs are contemplated for the stent valve extension. The extension can take the form, for example of an outer stent that place over and attached to the stent-valve frame (192). Alternately, the frame extension (995) can be comprised of metal arms or paddles that extend outwards (800) from the second component stent frame (192) to a diameter that is larger than the stent-valve frame (192).

Figure 47A:
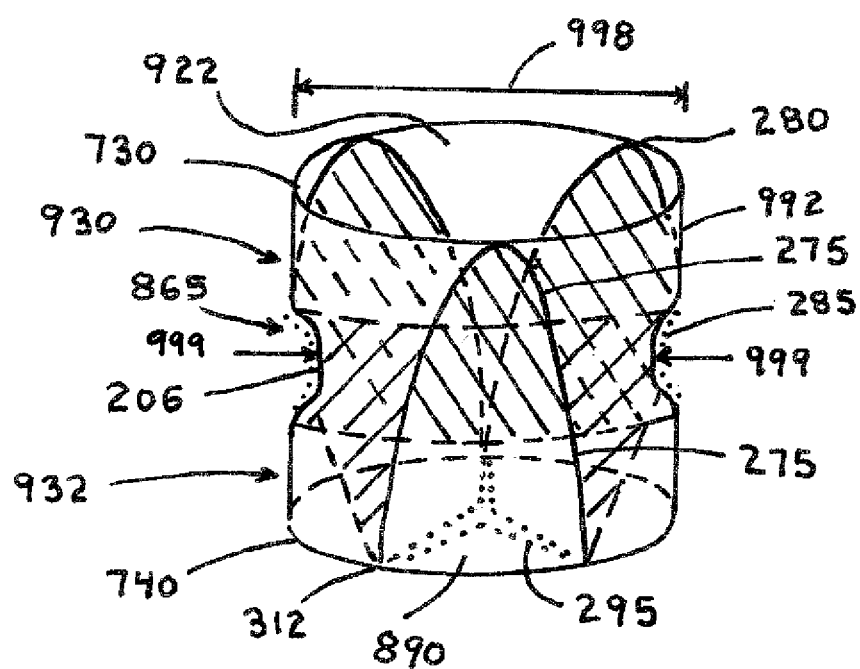

Other means of locking the second component (190) to the first component (200) are anticipated. The second component stent frame can be formed. for example, with a concave securement band (865) having a second component concave region (206) as shown in FIG. 47A. The second component concave region (206) has a covering (285) attached to it and forms a reduced diameter region having a securement band diameter (999) 3 mm (range 1-5 mm) smaller than the stent-valve frame body diameter (998). The second component (190) is delivered via a delivery catheter as shown in FIG. 47B and released in a manner that places the securement band (865) axially adjacent to the securement ring (755) or limiting cable (225) of the first component (200). The second component (190) is held via control fibers (120) which are temporarily attached or looped through holding features attached to recapture struts (100) which are either attached to the upstream end (730) of the first component (200) or are themselves frame elements of the first component (200). The control fibers (120) can be placed under tension by the operator at the proximal end of the delivery sheath (105) to provide for repositioning and removal of the second component (190) if required by the operator. Upon achieving a locking of the securement band (865) of the second component (190) adjacent to the securement ring (755) or limiting cable (225) of the first component (200) forming a system lock (842), the second component (190) is fully released as shown in FIG. 47C to form the dual member stent-valve (195).

Figure 47D:
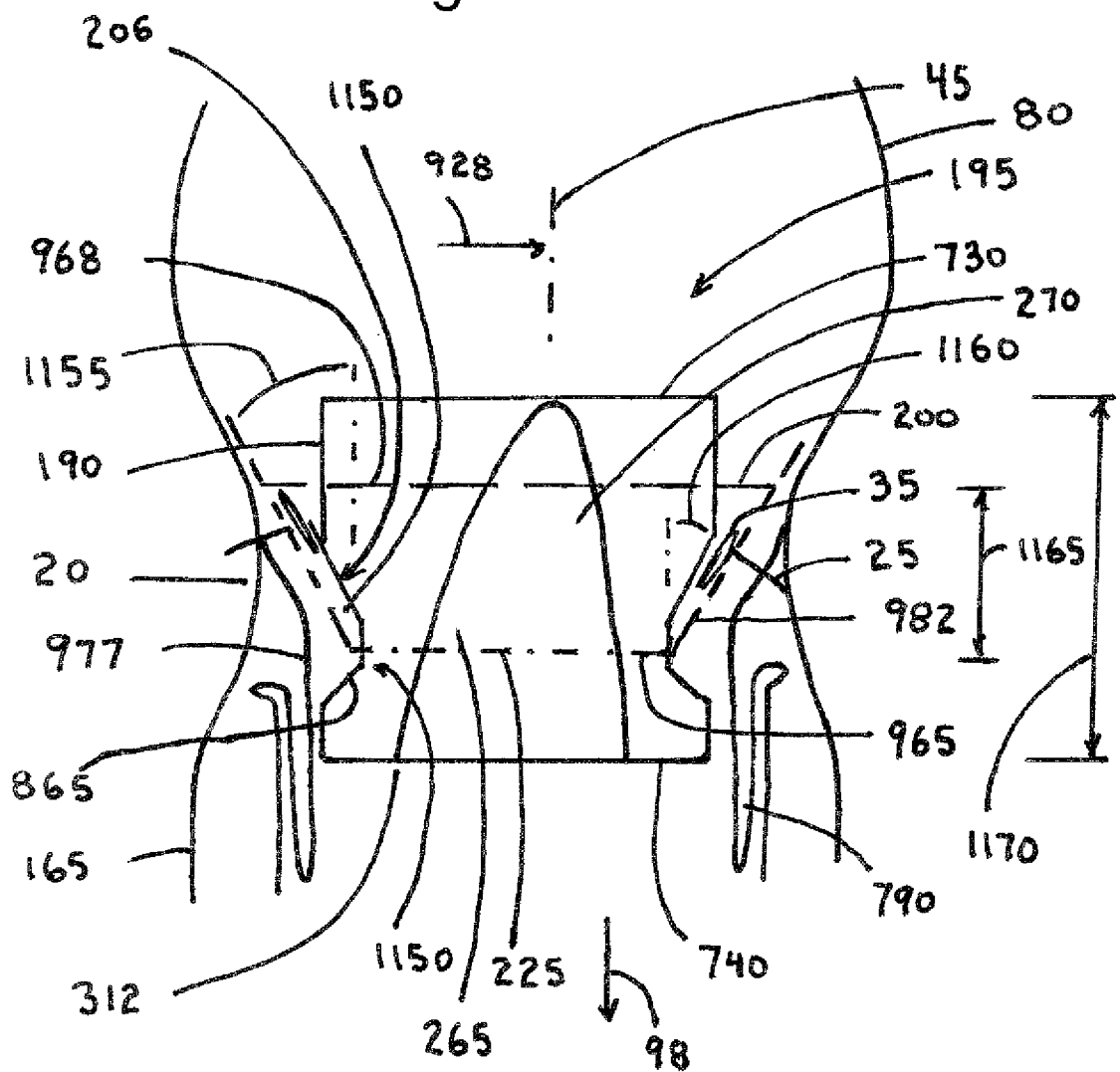

A dual-member stent-valve (195) is shown in FIG. 47D having a geometrical lock (1150) to lock the first component (200) to the second component (190). The first component (200) is attached to the mitral annulus (20) via barbs (25) that have been activated via a torus balloon (35). The first component is delivered to place the first component distal end (965) into contact with the native leaflet rim (977) and allowed to expand and conform to the oval or D-shaped annulus prior to activation of the barbs. The first component frame (982) is formed with a frame structure that allows it to conform into small radius of curvature bends found in the D-shaped mitral annulus. The first component frame (982) can be formed with hinge and strut dimensions that provide for increased outward expansion force and increased bending characteristics than standard stent structures as described later in the specification. The inflation of the torus balloon (35) provides support to the first component frame (982) to ensure that expansion forces supplied by the torus balloon are transferred outwards to drive the barbs (25) into the surrounding tissues and the first component frame cannot move inwards (928) toward the axis (45) of the first component frame (982). The first component frame (982) has a first component angle (1155) that is 35 degrees (range 20-75 degrees) off of the axis (45) and has a smaller first component frame diameter at the first component distal end (965) than the first component frame diameter at the first component proximal end (968). A limiting cable (225) extends around the perimeter of the first component frame (982) and can be located near the first component distal end (965) as shown in FIG. 47D.

The second component (190) can have a second component concave region (206) located intermediate between the second component upstream end (730) and the second component downstream end (740) as shown in FIG. 47D. The second component concave region (206) can have a rounded shape, can form a V-shaped divot, or any other geometrical shape that is able to form a geometrical lock with the first component. As shown in FIG. 47D, the second component concave region (206) has a second component angle (1160) of 35 degrees (range 20-75 degrees) off of the axis (45) such that it matches the first component angle (1155) and forming a tight fit or geometrical lock (1150) between the second component (190) and the first component (200). The second component (190) is allowed to expand into the lumen of the first component (200) such that the second component concave region (206) locks both upstream and downstream (98) of the limiting cable (225) found on the first component forming a geometrical lock (1150) that prevents migration of the second component (190) with respect to the first component (200). The first component angle (1155) and the second component angle (1160) form a cone-in-cone alignment of the second component (190) with the first component (200) along the axis (45), and also position the second component (190) axially such that the second component concave region (206) is positioned to lock both upstream and downstream (98) of the limiting cable (225).

Other embodiments are anticipated having the second component concave locking region (206) or geometrical lock (1150) located at various locations along the second component frame (192) as described earlier in this specification. The geometrical lock (1150) can be formed via convex regions of the first component (200) and second component (190) or other geometrical or mechanical locking mechanisms used to hold a cylindrical or frustum-shaped first frame from migrated in an axial direction with respect to a cylindrical or frustum-shaped second frame that is located within the central lumen (265) of the first frame. It is anticipated that the first component axial length (1165) is 13 mm (range 8-25 mm). The second component axial length (1170) can be 21 mm (range 15-35 mm), for example, and can have 16 mm, for example, (range 15%-100% of the second component axial length (1170)) extending into the LA (80). It is anticipated that 6 mm (range 3-15 mm) of the second component axial length (1170) extends into the LV (165) to prevent the native leaflets (790) from interfering with the function of the replacement leaflets (270).

FIG. 47E shows a structure for the second component frame (192) for the second component (190) of the present invention. The second component frame (192) can have a zig-zag structure with an upstream end (740) and a downstream end (730). The replacement leaflets are attached to the second component frame (192) along a generally crown-shaped leaflet attachment (275) found in the second component frame (192). Attached to the upstream end (730) are recapture struts (100) that are more compliant than the second component frame body (992) and provide a transitional amount of flexibility to allow the second component frame (192) to be withdrawn into the delivery sheath. The recapture struts (100) are more flexible to allow ease of entry into the delivery sheath during withdrawal of the second component (190) into the delivery sheath if it is necessary to reposition or remove the second component from its delivered location within the central lumen of the first component. The recapture struts (100) have holding features (110) such as eyelets, for example, that allow control fibers to be looped through the eyelets; control for holding and releasing of the recapture struts can be performed by the operator by releasing one end of the control fiber, for example, to allow the second component to be released completely from the delivery sheath.

One embodiment for the first component (200) includes two barb rings to hold the stent frame against the surrounding tissues and prevent migration of the first component (200) upstream (202) towards the LA (80) as shown in FIG. 48. The stent frame has an upstream barb ring (1000) that contain a plurality (range 8-32) of upstream barb struts (1005) located along the perimeter of the first component frame (982) and are attached to the first component proximal end (968) of the stent frame via upstream hinges (1010). The upstream barb struts (1005) attach to upstream barb tips (1015) that can be activated such that they penetrate into the surrounding tissues at or near the mitral valve annulus (20). An upstream activating torus balloon (1020) extends around and is attached to the perimeter of the stent frame and makes contact with the upstream barb struts (1005) such that inflation of the upstream torus balloon causes the upstream barbs (25) to become activated as shown in FIG. 48. The stent frame also has a downstream barb ring (1025) that contain a plurality (range 8-32) of downstream barb struts (1030) that are attached along a perimeter of the first component distal end (965) of the stent frame via downstream hinges (1035). The downstream barb struts (1030) attach to downstream barb tips (1040) that can be activated such that they penetrate into the surrounding tissues at or near the mitral valve annulus (20) or into the rim of the mitral valve leaflets (790). A downstream activating torus balloon (1045) extends around the perimeter of the stent frame and makes contact with the downstream barb struts (1030) such that inflation of the downstream torus balloon causes the upstream barbs (25) to become activated as shown in FIG. 48. The upstream barb ring (1000) and downstream barb ring (1025) can be attached to the first component frame (982) such that the upstream barb tips (1015) and downstream barb tips are curved barb tips and the curved barb tips can penetrate the surrounding valve tissues to form a clam-shell configuration such that the arcs of the barb tips are directed toward each other to grab the valve tissues securely when the barbs are activated.

The upstream torus balloon can have a separate upstream inflation port (1050) and the downstream torus balloon can have a downstream torus balloon inflation port (1055) such that the upstream torus balloon and the downstream torus balloon can each be inflated independently via separate and independent balloon ports located at the catheter manifold outside of the patient's body and interfacing with the delivery catheter. Alternately a single inflation port (983) can be used to inflate both the upstream activating torus balloon (1020) and downstream activating torus balloon (1045) at the same time if desired. The upstream inflation port (1050) and downstream inflation port (1055) are removably attached to the torus balloons via a threaded connection (525) or other junction connection (488) as described in earlier embodiments of the present invention. A single backing element can extend from the stent proximal end (968) to the stent distal end (965) along the inward side (928) (toward the central axis (45)) of the two torus balloons to provide support to the torus balloons such that inflation of the torus balloons exerts an outward force against the barb struts to activate the barb tips (255) to a region outside (880) of the stent frame and into the surrounding tissues. The presence of two barb rings provides and additional number of barbs (25) such that 32 barbs (25) (range 16-64 barbs) are located along the perimeter of the stent frame to ensure that migration toward the LA (80) does not occur.

The present invention includes a plurality of barbs that are attached along the perimeter of the first component frame (982), and the barbs are activated via inflation of one or more torus balloons to push the barb tips (255) into the mitral annulus (20). It is understood that patients can have mitral annular calcium (MAC) deposits along the perimeter of the mitral annulus. Penetration of the barb tips into the MAC tissue may be inconsistent thereby reducing the number of barb tips that are acting to hold the first component frame against the mitral annulus to prevent migration of the first component frame (982) toward the LA (80) or toward the LV (165). To improve the penetration of the barb tips (255) into the annular tissue in the presence of MAC the torus balloon is exposed to a pulsating pressure that transfers its force to the barbs such that the barbs can penetrate the hard calcified tissues. The torus balloon can initially be inflated to a pressure of 5 atm (range 1-20 atm) to cause the barb tips to extend to the outside (880) of the first component frame (982). The inflation pressure to the torus balloon is then pulsed at a location of the catheter manifold located outside of the patient's body. The pulsed pressure is transmitted via an inflation tube to the inflation port (983) located near the torus balloon. The inflation pressure is pulsed at a frequency of 10 Hertz (range 1-30 Hz) by using a positive displacement pump such as a piston pump that is placed in fluid communication with the syringe or other inflation device that the operator is using to inflate the torus balloon. The inflation pressure can be pulsed such that a pressure differential at the torus balloon is varied by 5 atm (range 1-20 atm) at 10 Hz, for example. The torus balloon internal pressure can vary, for example during each pulsed cycle from zero to 5 atm to cause the barb tips to cycle their way through the calcified plaque.

In addition to providing a device system for treatment of functional mitral regurgitation, as well as forms of primary mitral regurgitation, the first component frame (982) of the first component (200) of the present invention can be used (without the need of the second stent-valve component of the present stent-valve invention, for example) to treat degenerative mitral regurgitation which often presents with a flailed native leaflet (1060) as shown in FIG. 49A. The native leaflet can extend toward the LA (80) side of the mitral annulus (20) providing the native leaflets (790) with a lack of full coaptation and resulting in a flow path for blood from the LV (165) back to the LA (80) during systole. One embodiment for the first component (200) of the present invention is shown in FIG. 49B. In this embodiment the first component frame (982) has been delivered on the LA (80) side of the native leaflets (790) and mitral annulus (20) as described in previous embodiments. The barb tips (255) have been activated via an inflated torus balloon that extends around and is attached to the perimeter of the stent frame as described in previous embodiments. The barb tips (255) extend into the mitral annulus tissue (20), the native leaflet base (976), the native leaflet rim (977), or other surrounding tissues of the mitral valve. The first component frame (982) extends to a first component distal end (965) with a frame distal end diameter (1065). The frame distal end diameter (1065) is 10 mm smaller (range 5-30 mm smaller) than the mitral annulus diameter (997). The downstream frame region (1070) that extends downstream (98) from the location of the barb tips (255) provides support to the native leaflets (790) to prevent the native leaflets (790) from everting towards or into the LA (80) as shown in FIG. 49B. The downstream frame region (1070) can be rounded or curved near the first component distal end (965) to prevent contact abrasion of the native leaflet with the stent frame as the native leaflets (790) make contact with the downstream frame region (1070) during each contraction of the LV.

As described previously in this specification, the mitral annulus (20) has a saddle shape that when viewed from the top or from the LA (80) side looks like an oval shape. Often standard stented valves including transcatheter aortic valve replacement (TAVR) devices, and other devices with stent frames have difficulty making contact around the perimeter of an oval-shape annulus (20) and leakage can occur around the stented frame in regions where the oval has its smallest radius of curvature. Often stent-valve frames are formed by cutting a stent pattern or structure out of a Nitinol tube; also stent frames can be formed from zig-zag structure (335) from one or more Nitinol wires. Such stent manufacturing methods often result in stent frames that are of a continuous dimension in the radial dimension of the stent frame wall. These standard stent frame structures have limitations in their effectiveness to function effectively to form a close apposition along the entire perimeter of an oval annulus. If the standard stent structure is formed from a smaller caliber of Nitinol wire or has a smaller radial dimension in order to conform to the oval shape, then the stent structure may not apply enough of an outward expansion force against the annulus (20) to provide good apposition of the stent frame with the surrounding tissues and prevent stent frame migration or perivalvular leak. If the standard stent structure is constructed with a larger caliber of Nitinol wire or with a larger radial dimension, then the stent structure will not bend into the small radius curves of the oval shape and will not conform uniformly along the perimeter of the annulus (20).

Embodiments of the present invention for either the first component frame (982) or second component frame (192) may be comprised of hinges (1072) and struts (1074) (as shown in FIGS. 50A-50C); the frame structure (1075) of the first component (200) and frame structure (1075) of the second component (190) has a hinge radial dimension (1080) extending in the radial direction (1082) that is greater than a strut radial dimension (1085) and a hinge width (1090) that is smaller than a strut width (1095); this is fully described in US patent entitled, Intravascular Hinge Stent, with U.S. Pat. No. 8,585,751 which is made reference to and is herein incorporated fully within the present patent application.

In one embodiment the frame structure (1075) of the first component (200) or second component (190) is formed from Nitinol (or other elastic metal or polymer) that has been machined via laser and mechanical machining as shown in FIGS. 50A-50C. As shown in FIG. 50A the hinge length (1100) is greater than the hinge width (1090); the hinge length (1100) provides the frame structure (1075) with a self-expanding character without undergoing plastic deformation; the hinge length (1100) can be 0.015 inches (range 0.010 to 0.060 inches). The hinge width (1090) allows full hinge (1072) expansion deformation without exposing the hinge (1072) to plastic deformation; the hinge width (1090) is 0.004 inches (range 0.003-0.006 inches). The hinge radial dimension (1080) is greater than the strut radial dimension (1085); the hinge radial dimension (1080) provides the expansion force that pushes the frame structure (1075) outwards (800) against the annulus (20) during expansion deformation. The hinge radial dimension (1080) can be larger than the radial dimension of a standard frame structure to provide even greater outward expansion force than can be obtained with a standard frame structure having the same ability to conform with apposition against the perimeter of an annulus (20). The hinge radial dimension can be 0.005 inches (range 0.004-0.010 inches).

As shown in FIG. 50B the frame structure (1075) is in an unexpanded configuration and the hinges (1072) are able to expand outwards in a circumferential direction (1105) elastically within the mitral annulus to cause the mitral annulus to place the frame structure (1075) into contact with the mitral annulus and to reduce some of the oval shape of the mitral annulus. The hinge radial dimension (1080) prevents bending of the hinge (1072) in the radial direction, but the strut (1074) is able to provide all of the bending necessary to make full contact of the frame structure (1075) with the small radius of curvature portion of an oval annulus (20).

The strut radial dimension (1085) is smaller than the hinge radial dimension (1080) such that the strut (1074) is able to bend easily around the small radius curve of an oval annulus (20). The strut radial dimension (1085) can be smaller than the radial dimension of a standard stent frame structure such that the strut (1074) can bend easier than a standard frame structure and provide full contact along the perimeter of the annulus (20), even in the smaller radius of curvature portion of an oval annulus (20). The strut radial dimension (1085) can be 0.003 inches (range 0.002-0.005 for a conforming elastic strut). The strut width (1095) is greater than the hinge width (1090) such that the strut (1074) does not bend in the circumferential direction (1105) as the hinge (1072) expansion forces cause the hinge (1072) to open and cause struts (1074) to align along a circumferential direction (1105) with the stent frame in an expanded configuration as shown in FIG. 50C. The strut width (1095) can be 0.005 inches (range 0.004-0.010 inches).

The result for this embodiment for the frame structure (1075) for the first component (200) is that the first component (200) (as described in other embodiments) will make full contact along the perimeter of first component frame (982) with the annulus (20) prior to activation of the barbs (25). The first component frame (982) that is formed with the hinge and strut frame structure (1075) will not require circumferential orientation during its placement within the oval annulus; the frame structure (1075) will conform to the oval annulus independent of its circumferential orientation. The large outward expansion force applied by the hinges (1072) allows the barbs (25) to push outwards (800) and embed themselves into the surrounding tissues along the entire perimeter of the first component frame (982); the frame structure (1075) supplying the force necessary for the torus balloon to push against to cause the barbs (25) to become activated. In addition, the apposition of the first component frame (982) with the oval shape of the annulus will help to reduce locations for perivalvular leak in regions where the oval makes smaller radius of curvature bends at the long axis ends of the oval. The structure for the first component frame can include a generally rounded or circular configuration in the region of the first component frame (982) near the first component distal end (965). Delivery of the second component into the rounded or circular first component distal end (965) provides a locking of the first component frame (892) to the second component frame (192) to form the system lock (842) while maintaining the second component frame (192) in a rounded configuration (i.e., circular cross sectional shape) to help maintain optimal replacement leaflet coaptation and provide for replacement leaflet durability.

Another embodiment for the frame structure (1075) for the first component frame (982) or second component frame (192) as just described for FIGS. 50A-50C can be altered such that the strut radial dimension (1085) is not so thin that it bends easily around a small radius of curvature bend found in an oval annulus (20) but instead forms the oval annulus (20) into a round annulus (20) (i.e., a round cross-sectional shape when viewed from above the annulus; the strut radial dimension (1085) is more similar to the radial dimension of a standard stent structure. The other aspects of the hinge (1072) and strut (1074) construction are the same as previously described. In this embodiment, the larger hinge radial dimension (1080) (i.e., larger than a standard stent frame radial thickness) frame structure (1075) is able to expand the oval annulus (20) outwards (800) into a round cross-sectional shape prior to activation of the barbs (25) found in the first component frame (982). Also, this embodiment of the frame structure (1075) can be used in the second component frame to provide a round expanded configuration. The round configuration of the second component (190) will provide the replacement leaflets (270) with a uniform shape that will provide optimal leaflet coaptation (710) and allow for improved leaflet durability.

The dual member stent valve (195) of the present invention as well as embodiments of the single component stent-valve configurations are able to conform to an oval or saddle shaped mitral annulus for attachment to the mitral tissues and still provide a round securement band or cylindrical shape to the stent-valve component (190) or leaflet-containing portion of the stent-valve frame. In one embodiment as shown in FIG. 51A the first component frame (982) has an upstream region (978) that conforms well to the oval mitral annulus (20) and has an oval first component cross-section (1110). The structure of the first component frame (982) can be the hinge and strut structure described in FIGS. 50A-50C or can be any other stent frame structure used in forming vascular stents or stent-valves. The limiting cable (225) of the first component (200) that is located near the first component distal end (965) forms a closed ring that can serve as a landing zone for locating the securement band (865) of the second component (190). The first component downstream frame region (1070) and the limiting cable (225) can be formed with a round cross-sectional shape or can form a round cross-sectional shape upon delivery of a second component frame (192) into the first component frame (982). The limiting cable (225) can have a limiting cable diameter (985) that is smaller than the first component frame diameter at a location where the barb (25) penetrates into the surrounding native tissues. A round second component cross-section (1115) is formed into the second component frame (192). The round second component cross-section (1115) provides improved replacement leaflet function without centro-valvular leakage and provides for improved leaflet durability. The second component diameter (1140) of the round second component cross-section (1115) can have a smaller second component diameter (1140) than the effective diameter (i.e., diameter of a circle with the same perimeter) associated with a perimeter of the oval annulus or perimeter of the first component frame (192) at a location adjacent to the annulus (20). The second component diameter (1140) can be equal to the limiting cable diameter (985). Thus the profile of the second component frame (982) can be smaller than if it matched the effective diameter of the annulus. Also, the same second component diameter (1140) can be used to fit within and lock by forming a system lock (842) into a variety of first component sizes which are intended to conform to a variety of annulus oval shapes and oval annulus perimeters. Thus the number of sizes for the second component to serve a variety of annulus diameters and annulus perimeters will be reduced.

Alternately, the stent-valve devices of the present invention can be configured such that the first component frame (982) has enough outward expansion force to cause the mitral annulus (20) to become rounded or nearly round with a round first component cross-section (1120) as shown in FIG. 51B. Placement of the second component frame (192) into the lumen of the first component frame (982) provides a round second component cross-section (1115). The second component frame (192) can be placed such that it locks via friction or geometrical fit with the first component frame (982) at or near the limiting cable (225) to form a system lock (842). The limiting cable can have a limiting cable diameter (985) that confers or provides a smaller second component diameter (1140) than the effective diameter of the first component frame (982) at a location adjacent to the annulus (20).

Further alternately, as shown in FIG. 51C the first component frame (982) can conform well to the oval annulus thereby forming an oval first component cross-section (1110) prior to delivery of the second component (190). After the second component (190) has been delivered into the lumen of the first component (200) as shown in FIG. 51D, the second component frame (192) has enough outward expansion force to form the first component frame (982) into a round first component cross-section (1120), and also provide a round second component cross-section (1115). The second component diameter (1140) can be approximately equal to (or less than) the first component frame diameter (1145) at a location adjacent to the annulus (20).

In yet another embodiment the first component frame (982) conforms to the oval annulus forming an oval first component cross-section (1110). Upon delivery of the second component (190) into the lumen of the first component frame (982), the second component frame (192) expands out to meet the minor axis (1125) of the oval first component cross-section (1110). The second component frame forms a round second component cross-section (1120) but with a second component reduced diameter (1130) that is equal to the minor axis distance (1125) of the oval first component cross-section (1110). A flange (1135) attached to the second component frame (192) ensures that blood cannot leak between the first component frame (982) and the second component frame (192). The flange (1135) can be comprised of the infra securement band locking frame (991), supra securement band locking frame, the upper bulb (70), covering, or other portion of the second component frame (192) or other feature capable of blocking blood flow or blood leakage between the first component (200) and the second component (190). The smaller second component reduced diameter (1130) (i.e., smaller than the effective diameter of the first component frame (982) at a location adjacent to the annulus (20)) provides this embodiment with a lower profile for the second component and a reduced number of sizes for the second component (190) that are required to meet the needs of the varied patient annulus sizes, annulus diameters, and annulus perimeters.

Similar reference names and reference numbers used throughout this specification can be applied to all other embodiments found in the specification. Various structural elements described throughout this specification can be applied to other embodiments within the specification and are thereby understood to be included in the present invention.

The invention claimed is:

1. A stent-valve device for transcatheter implantation into native valvular tissues of a heart, said stent-valve device configured to direct bloodflow in a downstream direction through the native valvular tissues and to prohibit bloodflow in an upstream direction, said stent-valve device being deliverable in a smaller diameter configuration and expandable out to a larger diameter configuration, said stent-valve device comprising;

A. a stent-valve frame having an axial length that extends from an upstream end to a downstream end, wherein said downstream end is able to extend within a heart ventricle and said upstream end is able to extend within a heart atrium, said stent-valve frame configured to direct blood flow from said upstream end to said downstream end, said stent-valve frame having two or more replacement leaflets attached thereto, B. each of said replacement leaflets being attached to said stent-valve frame along a crown-shaped attachment path, said crown-shaped attachment path extending from a leaflet first commissure located at said downstream end to a leaflet nadir located at said upstream end to a leaflet second commissure located at said downstream end, C. said stent-valve frame having a covering attached thereto, said covering preventing blood flow through said stent-valve frame in a radial direction, D. a securement band comprising a covering attached along a portion of said stent-valve frame located around a perimeter of said stent-valve frame between said upstream end and said downstream end, wherein said securement band is able to secure said stent-valve device to prevent migration of said stent-valve frame relative to the native tissues and to prevent blood flow across said stent-valve frame, E. said stent-valve frame having a downstream open frame surface located on said stent-valve frame downstream of said securement band, said downstream open frame surface being bounded by said crown-shaped attachment path extending from said leaflet first commissure to said securement band and further extending along said crown-shaped attachment path from said securement band to said leaflet second commissure, and even further extending circumferentially back to said leaflet first commissure, said downstream open frame surface being free of said covering and configured to allow bloodflow radially outwards through said downstream open frame surface, F. said stent-valve frame having an upstream closed frame surface having said covering attached to said stent-valve frame upstream of said securement band, said upstream closed frame surface being bounded by said crown-shaped attachment path located upstream of said securement band extending from a first leaflet nadir downstream to said securement band and further extending circumferentially along said securement band and extending back to said first leaflet nadir.

2. The stent-valve device of claim 1 wherein said stent-valve frame has an upstream open frame surface that is free of said covering located on said stent-valve frame upstream of said securement band, said upstream open frame surface extending between two neighboring of said crown-shaped attachment paths belonging to two neighboring of said replacement leaflets, said upstream open frame surface being bounded by said crown-shaped attachment path extending from a first leaflet nadir of a first replacement leaflet to said securement band, and further extending from said securement band along said crown-shaped attachment path of a second replacement leaflet to a second leaflet nadir of said second replacement leaflet, and even further extending circumferentially back to said first leaflet nadir, said upstream open frame surface being configured to allow radially and inwardly directed blood flow through said upstream open frame surface.

3. The stent-valve device of claim 2 wherein said stent-valve frame comprises an upstream completely open surface at said upstream open frame surface, such that said upstream completely open surface is devoid of said stent-valve frame within the boundaries of said upstream open frame surface; said upstream completely open surface allowing radial blood flow therethrough.

4. A stent-valve device of claim 1 wherein said covering is attached to said securement band and is configured to prevent said upstream closed frame surface from fluid leakage across said stent-valve frame at the native valvular tissues of the heart.

5. A stent-valve device of claim 1 wherein said stent-valve frame has an upstream length extending from said upstream end to said securement band, and said stent-valve frame has a stent-valve component length extending from said upstream end to said downstream end, said upstream length comprising from 15% to 55% of said stent-valve component length.

6. A stent-valve device of claim 1 wherein said stent-valve frame has an upstream length extending from said upstream end to said securement band, and said stent-valve frame has a stent-valve component length extending from said upstream end to said downstream end, said upstream length comprising from 35% to 65% of said stent-valve component length.

7. The stent-valve device of claim 1 wherein said stent-valve frame comprises a downstream completely open surface at said downstream open frame surface, such that said downstream completely open surface is devoid of said stent-valve frame within the boundaries of said downstream open frame surface, said downstream completely open surface allowing radial blood flow therethrough.

8. The stent-valve device of claim 1 wherein said securement band is configured to contact and attach to a heart annulus or other structures located within the native valvular tissues of the heart.

9. The stent-valve device of claim 1 further comprising a support component having an expandable support component frame, said expandable support component frame being configured to be attached to the native valvular tissues of the heart, said support component being configured to hold said stent-valve frame within said support component via frictional or geometrical fit.

10. The stent-valve device of claim 9 wherein said expandable support component frame has a limiting cable extending along a perimeter of said expandable support component frame, said limiting cable limiting the perimeter of said expandable support component frame in an expanded configuration.

11. The stent-valve device of claim 10 wherein said stent-valve frame has a stent-valve frame diameter in said larger diameter configuration that is equal to a diameter of said limiting cable.

12. The stent-valve device of claim 1 further comprising a support component having an expandable support component frame; said expandable support component frame being configured to be attached to the native valvular tissues of the heart; said expandable support component frame having a closed ring structure that cannot expand beyond a specified perimeter, said securement band being configured to contact said closed ring structure.

13. The stent-valve device of claim 1 wherein said upstream end of said stent-valve frame has a larger diameter than said downstream end.

14. The stent-valve device of claim 1 wherein said stent-valve frame has a concave region located between said upstream end and said downsteam end, said concave region configured to prevent movement of said stent-valve frame relative to the native valvular tissues of the heart.

15. The stent-valve device of claim 1 wherein said stent-valve frame has a round stent-valve frame cross section in said larger diameter configuration, said round stent-valve frame cross-section providing said replacement leaflets with a greater durability.

16. A stent-valve device for transcatheter implantation into native valvular tissues of a heart from a heart atrium to a heart ventricle, said stent-valve device being deliverable in a smaller diameter configuration and expandable out to a larger diameter configuration, said stent-valve device comprising;
A. a stent-valve frame having an axial length that extends from an upstream end to a downstream end, said stent-valve frame having a ventricular portion able to extend within the heart ventricle and having an atrial portion able to extend within the heart atrium, said stent-valve frame having two or more replacement leaflets attached thereto,
B. each of said replacement leaflets being attached to said stent-valve frame along a crown-shaped leaflet attachment path, said crown-shaped attachment path extending from a leaflet first commissure at said downstream end to a leaflet nadir at said upstream end, and further extending to a leaflet second commissure at said downstream end,
C. said stent-valve frame having a covering attached thereto, said covering preventing blood flow through said stent-valve frame in a radial direction,
D. a securement band located around a perimeter of said stent-valve frame positioned between said upstream end and said downstream end, said securement band comprising a covering attached to said stent-valve frame, wherein said securement band is configured to provide a seal with the native tissues and prevent said stent-valve frame from migrating relative to the native valvular tissues,
E. said stent-valve frame having an atrial open frame surface in said atrial portion extending between two neighboring of said leaflet attachment paths, said atrial open frame surface extending from a first leaflet nadir of a first replacement leaflet to said securement band and further extending to a second leaflet nadir of a second neighboring replacement leaflet, said atrial open frame surface being free of said covering and configured to allow blood flow through a wall of said stent-valve frame in a radial direction.

17. The stent-valve device of claim 16 wherein said stent-valve frame comprises an atrial completely open surface at said atrial open frame surface, such that said atrial completely open surface is devoid of said stent-valve frame within the boundaries of said atrial open frame surface, said atrial completely open surface configured to allow radial blood flow therethrough with said stent-valve frame.

18. A stent-valve device for transcatheter implantation into native valvular tissues of a heart, said stent-valve device configured to direct blood flow in a downstream direction through the native valvular tissues and to prohibit blood flow in an upstream direction, said stent-valve device being deliverable in a smaller diameter configuration and expandable out to a larger diameter configuration, said stent-valve device comprising;

A. a stent-valve frame having a downstream end able to extend within a heart ventricle and having an upstream end able to extend within a heart atrium, said stent-valve frame configured to direct blood flow from said upstream end to said downstream end, said stent-valve frame having two or more replacement leaflets attached thereto, B. each of said replacement leaflets being attached to said stent-valve frame along a crown-shaped attachment path, said crown-shaped attachment path extending from a leaflet first commissure located at said downstream end to a leaflet nadir located at said upstream end to a leaflet second commissure located at said downstream end, C. said stent-valve frame having a covering attached thereto, said covering preventing blood flow through said stent-valve frame in a radial direction, D. a securement band extending around a perimeter of said stent-valve frame between said upstream end and said downstream end, said securement band comprising a covering attached to said stent-valve frame, said securement band configured to secure said stent-valve device to the native tissues of the heart valve to hold said-stent-valve frame from migration and able to provide a seal to prevent blood flow across said stent-valve frame in the region of the native valvular tissues of the heart, E. said stent-valve frame having a downstream open frame surface located on said stent-valve frame downstream of said securement band, said downstream open frame surface being bounded by said crown-shaped attachment path extending from said leaflet first commissure to said securement band and further extending along said crown-shaped attachment path from said securement band to said leaflet second commissure, and even further extending circumferentially back to said leaflet first commissure, said downstream open frame surface being free of said covering and configured to direct blood flow radially outwards through said downstream open frame surface, F. said stent-valve frame having an upstream closed frame surface having said covering located on said stent-valve frame upstream of said securement band, said upstream closed frame surface being bounded by said crown-shaped attachment path extending from a first leaflet nadir downstream to said securement band and further extending circumferentially along said securement band and extending back to said first leaflet nadir, G. said stent-valve frame having an upstream open frame surface being free of said covering located on said stent-valve frame upstream of said securement band, said upstream open frame surface extending between two neighboring of said crown-shaped attachment paths belonging to two neighboring of said replacement leaflets, said upstream open frame surface being bounded by said crown-shaped attachment path extending from a first leaflet nadir of a first replacement leaflet to said securement band, and further extending from said securement band along said crown-shaped attachment path of a second replacement leaflet to a second leaflet nadir of said second replacement leaflet, and even further extending circumferentially back to said first leaflet nadir, said upstream open frame surface being free of a covering and configured to allow radially and inwardly directed blood flow through said upstream open frame surface.

19. The stent-valve device of claim 18 wherein said covering is attached to said securement band and is configured to prevent said upstream closed frame surface from fluid leakage across said stent-valve frame at the native valvular tissues of the heart.

* * * * *